United States Patent
Hsieh et al.

(10) Patent No.: US 10,081,799 B2
(45) Date of Patent: *Sep. 25, 2018

(54) FUSION POLYMERASE AND METHOD FOR USING THE SAME

(71) Applicant: New England Biolabs, Inc., Ipswich, MA (US)

(72) Inventors: Pei-Chung Hsieh, Topsfield, MA (US); Luo Sun, Hamilton, MA (US); Thomas C. Evans, Jr., Topsfield, MA (US); Theodore B. Davis, Boxford, MA (US); Andrew Gardner, Manchester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/432,031

(22) Filed: Feb. 14, 2017

(65) Prior Publication Data

US 2017/0152493 A1 Jun. 1, 2017

Related U.S. Application Data

(63) Continuation of application No. 15/046,166, filed on Feb. 17, 2016, now Pat. No. 9,963,687, which is a continuation-in-part of application No. 14/837,820, filed on Aug. 27, 2015, now Pat. No. 9,447,445.

(60) Provisional application No. 62/193,168, filed on Jul. 16, 2015, provisional application No. 62/189,599, filed on Jul. 7, 2015, provisional application No. 62/042,527, filed on Aug. 27, 2014.

(51) Int. Cl.
| | |
|---|---|
| C12N 9/12 | (2006.01) |
| C12N 9/96 | (2006.01) |
| C12N 9/22 | (2006.01) |
| C12N 15/10 | (2006.01) |
| C12P 19/34 | (2006.01) |
| C12N 15/64 | (2006.01) |
| C12N 15/66 | (2006.01) |
| C12N 9/20 | (2006.01) |

(52) U.S. Cl.
CPC ............ *C12N 9/1252* (2013.01); *C12N 9/20* (2013.01); *C12N 9/22* (2013.01); *C12N 9/96* (2013.01); *C12N 15/1027* (2013.01); *C12N 15/1031* (2013.01); *C12N 15/64* (2013.01); *C12N 15/66* (2013.01); *C12P 19/34* (2013.01); *C12Y 207/07007* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 8,476,045 B2 * | 7/2013 | Wang | ................... | C07K 14/195 435/194 |
| 9,447,445 B2 * | 9/2016 | Hsieh | ................... | C12N 9/1252 |
| 2008/0227159 A1 * | 9/2008 | Hogrefe | ............... | C12N 9/1252 435/91.2 |
| 2010/0035768 A1 * | 2/2010 | Gibson | ................. | C12N 15/10 506/17 |
| 2014/0220577 A1 | 8/2014 | Wang et al. | | |

OTHER PUBLICATIONS

WP_013748330.1 (NCBI Reference Sequence, *Pyrococcus* sp. NA2 DNA polymerase, GI:503513858, priority to May 27, 2013) (Year: 2013).*
WP_011011764.1 (NCBI Reference Sequence, Pyrococcus DNA-binding protein, priority to Jul. 18, 2013) (Year: 2013).*
Doherty et al. (1996) The helix-hairpin-helix DNA-binding motif: a structural basis for non-sequence-specific recognition of DNA. Nucleic Acids Research, 24(13):2488-2497 (Year: 1996).*
Choli, et al., Isolation, characterization and microsequence analysis of a small basic methylated DNA-binding protein from the Archaebacterium, Sulfolobus solfataricus, Biochim Biophys Acta, 1988, 950 (2):193-203.
McAfee, et al., Gene Cloning, Expression, and Characterization of the Sac7 Proteins from the Hyperthermophile Sulfolobus acidocaldarius, Biochemistry, 1995, 34 (31):10063-10077.
Pavlov, et al., Helix-hairpin-helix motifs confer salt resistance and processivity on chimeric DNA polymerases, Proc. Natl. Acad. Sci., 2002, 99 (21):13510-13515.
Bedford, et al., The thioredoxin binding domain of bacteriophage T7 DNA polymerase confers processivity on *Escherichia coli* DNA polymerase I, Proc. Natl. Acad. Sci., 1997, 94 479-484.
Zuccola, et al., The Crystal Structure of an Unusual Processivity Factor, Herpes Simplex Virus UL42, Bound to the C Terminus of Its Cognate Polymerase, Molecular Cell, 2000, 5 (2):267-278.
Shamoo, et al., Building a Replisome from Interacting Pieces: Sliding Clamp Complexed to a Peptide from DNA Polymerase and a Polymerase Editing Complex, Cell, 1999, 99 (2):155-166.
Wang, et al., A novel strategy to engineer DNA polymerases for enhanced processivity and improved performance in vitro, Nucleic Acids Research, 2004, 32 (3):1197-1207.
Halford, et al., How do site-specific DNA-binding proteins find their targets?, Nucleic Acids Research, 2004, 32 (10):3040-3052.
Schleif, DNA Binding by Proteins, Science, 1988, 241, 1182-1187.

* cited by examiner

*Primary Examiner* — Neil P Hammell
(74) *Attorney, Agent, or Firm* — New England Biolabs, Inc; Harriet M. Strimpel

(57) ABSTRACT

This disclosure provides, among other things, a composition comprising: comprising a fusion protein comprising: (a) a DNA polymerase; and (b) a heterologous sequence-specific DNA binding domain. A method for copying a DNA template, as well as a kit for performing the same, are also described.

36 Claims, 30 Drawing Sheets

Specification includes a Sequence Listing.

FAM-primer ①  blocking oligo ②
5' FAM-CGCCAGGGTTTTCCCAGTCACGAC(SEQ ID NO:30)           GCCAAGCTTGCATGCCTGCAGGTCGAC (SEQ ID NO:31)
3' GCGGTCCCAAAGGGTCAGTGCTGCTGCAACATTTGCTGTGCCGGTTCACGGTTCGAACGTACGGACGTCCAGCTG (SEQ ID NO:32)

FIG. 1A

Sequence of Single-stranded oligo:
ATCTTGTGGAAGGAAGAAACACCGGGAAGAACCTCTTCCAAGAGTTTTAGAGCTAGAAATAGCAAGTT (SEQ ID NO:28)
Double-stranded vector used: GeneArt® CRISPR Nuclease Vector with OFP Reporter Kit Catalog number: A21174
FIG. 8A
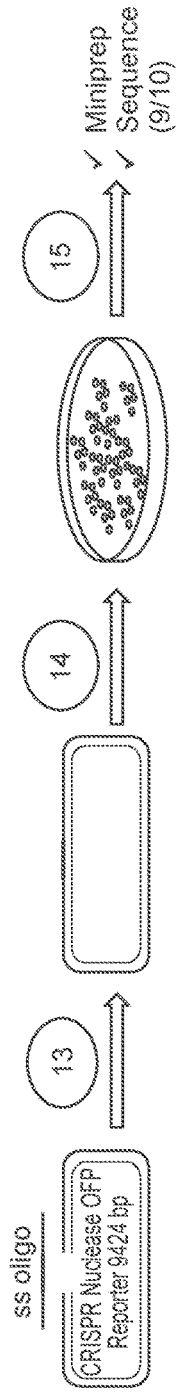
FIG. 8B
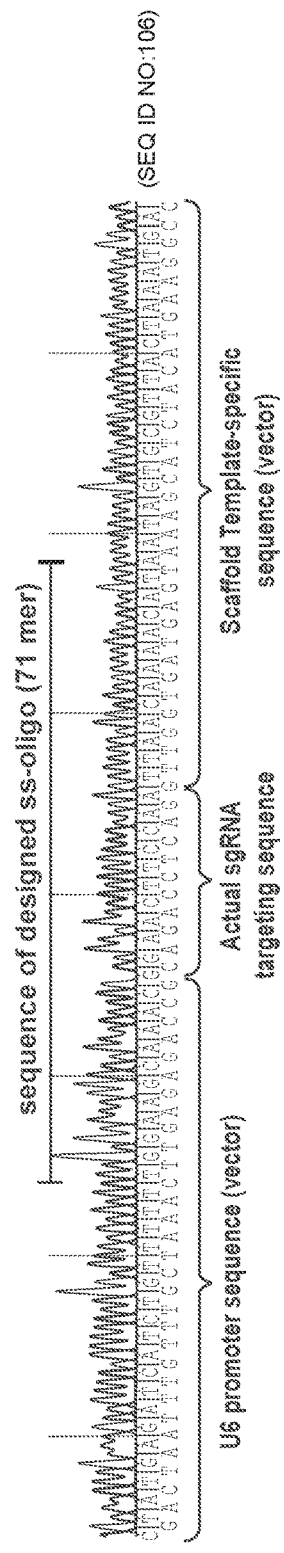
FIG. 8C Sequence of single stranded oligo containing degenerate bases:
ATCTTGTGTGAAAGGACGAAACACGNNNNNNNNNNNNNNNNNNNNGTTTTAGAGCTAGAAATAGCAAGTT (SEQ ID NO:29)
Double-stranded vector used: GeneArt® CRISPR Nuclease Vector with OFP Reporter Kit Catalog number: A21174
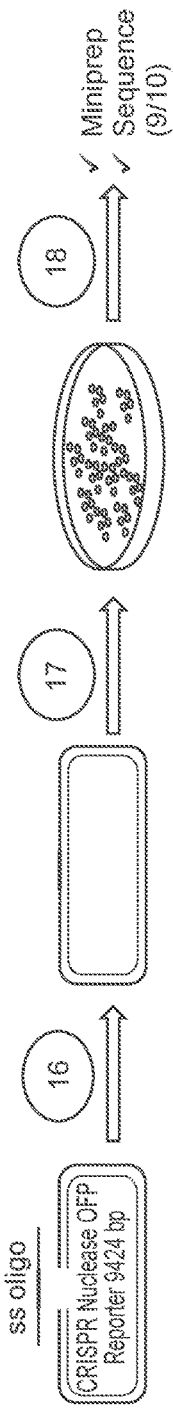
FIG. 9A
FIG. 9B
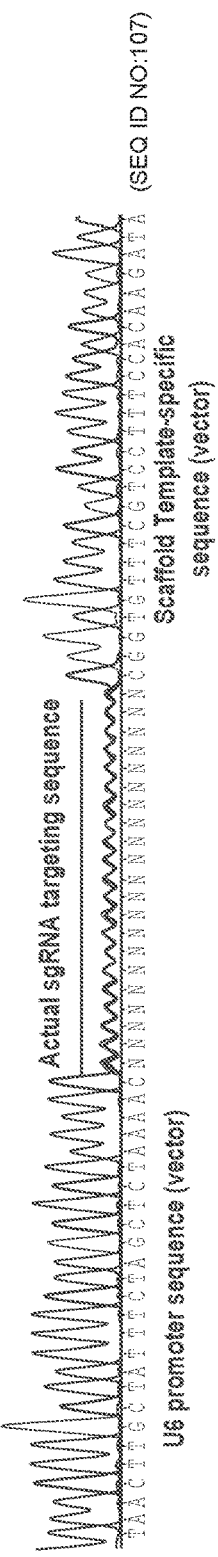
FIG. 9C

DNA binding domains from Archaea Pyrococcus Furiosus

BD-51
MKTFLTEQQIKVLMLRAKGYKQSEIAKILGTSRANVSILEKRAMEKIEKARNTLLLWEQINSKVIVEIKAGEDIFSIPEKFFKKADKVGVKVPYSTAEIITFLVEHAPVE
DRLAKRDFVLFLDSKNKLRIGDCLVIEEIKED (SEQ ID NO:56)

BE-52
MPITKVTRNYQJITIPAEIRKALGIKEGELLEVRLENGKIIIERLKKERKTLKLGKKLTLEEIEKAIEEGMKQCMQ (SEQ ID NO:57)

BD-54
TKIEILRLLKEREMYAYEIWSLLGKPLKYQAVHQHIKELLELGLVEQAYRKGKRVYYKITEKGLRILQNFEDLENI (SEQ ID NO:58)

BD-62
MNTGAQGVSEMSRMKIISVQLPQSLIHGLDALVKRGIYPNRSEAIRVAIRELLKKELYKEEIQEEIPEYVVK (SEQ ID NO:59)

BD-67
NNCECMVVKEKLYTVKQASEILGVHPKTIQKWDREGKIKTVRTPGGRRRIPESEIKRLLGISEEK (SEQ ID NO:61)

BD-71
MLKDSAPKRKILEELRKGETVSGDYLASKLGVSRVAIWKHIRELKELGYGIIADKKGYKLVYEPKKPYPWE (SEQ ID NO:62)

BD-74
MIDERDKIILEILEKDARTPFTEIAKKLGISETAVRKRVKALEEKGIIEGYTIKINPKKLGYSLVTITGVDTKPEKLFEVAEKLKE (SEQ ID NO:63)

BD-75
MEIDDLDRKILSLLIEDSRLSYREIAKKLNVAVGTIYNRIKKLEDMGVIQQGFTVKLNYEKLGYELTAIIGIKAQGKK (SEQ ID NO: 64)

BD-81
EMLWMYILKLLKDRPMYAYEIRNELKRFGFEPATVSSYVVLYRLEEGGYVSSEWHESEAGRPSRKYYRLTEKGEKLLEKGIETIEDVLNMLKS (SEQ ID NO:65)

BD-82
MKVSKATASKVLRSLENKGIVERERRGKTYLVRLTNKGLELLEEISKAGKELDEKIFAEMSVDERIVL (SEQ ID NO:66)

BD-85
SEDYMLQNRRKVLAKVLELLNYNPKALNISELARMFGVSRDTIYNDIQQIIKNVEV (SEQ ID NO:67)

BD-86
SKEISRFLKVISNPIRYGILKMLNDRWMCVCLISEALEIDQTLVSHHIRILKELDLLEERKEGKLRFYRTNKEKLREYLEKVLEDFNHGTSKGS (SEQ ID NO:68)

BD-88
MCRRDVMIISDPKQIKALSDPTRVKILELLRYHPMTVSEISRVIGKDKSTIYRHIKALEEAGLVEEVEKIGNETVYGR (SEQ ID NO:69)

BD-89
MEPVEFKLNQKGIKSILPTMEAEIMEYMWEIKEATAGEVYEYMKTKYPEIRRSTVSILMNRLCERGLLKRRMEKGKGGIRYVVSITTREEFERKVVEKIIESLMM
NFREATFAYLSKINKK (SEQ ID NO:70)

BD-91
MKKSNLDLLILLAKAGGIEKEILTTSRELSKMLNVSPQTIVRWLEDLEKDGLIKKSESRKGTLVTITEEGVKFLEKLHEELSDALYR (SEQ ID NO:71)

FIG. 11A

DNA binding domains from Archaea Pyrococcus Furiosus

BBD-92
MEIPPEISHALSEIGFTKYEILTYWTLLVVGPSTAKEISTKSGIPYNRVYDTISSLKLRGFVTEIEGTPKVVAAYSPRIAFFRFKKELEDIMKKLEIEL
NNVKK (SEQ ID NO:72)

BD-93
IINPQARLTPLELEILEIIKQKKSITTEIKEILSERRKSEYPLSLVSEYISRLERKGYVKKIAKGRKKFVEALI (SEQ ID NO:73)

BD-94
GIDVVIPEIKHDPIARDIVKILFDLRRANVSQIARELKGRRGKASRNTVRKKLKELELKGVVKEVPGERGSVYTLSREVVKKWLDLIGIPINLL
(SEQ ID NO:74)

BD-97
MTKRVKVITDPEVIKVMLEDTRRKILQLLRNREMTISQLSEILGKMPQTIYHHIEKLKEAGLVEVKR (SEQ ID NO:75)

BD-98
MEEIKEIMKSHTLGNPVRLGIMIYLFPRRRAPFSHIQKALDLTPGNLDSHIKVLEKHGFVRTYKVIADRPRTMVEITDYGMEETRKFLSHLK
TVIDAIHF (SEQ ID NO:76)

BD-100
MGEELNRLLDVLGNETRRRILFLLTKRPYFVSELSRELGVGQKAVLEHLRILEEAGLIESRVEKIPRGRPRKYYMIKKGLRLEILLTPTLFGSEM
YEAK (SEQ ID NO:77)

BD-102
MRRMDKVDLQLIKILSQNSRLTYRELAEMLGTTRQRVARKVDKLKLKLGIIRKFTIIPNLEK (SEQ ID NO:78)

BD-105
MGRDKKNTALLDIARDIGGDEAVEVVKALEKKGEATDEELAELTGVRVNTVRKILYALYDAKLATFRRVRDDETGWYYYWRIDTKRLPEVI
RTRKLQELEKLK (SEQ ID NO:108)

BD-109
GRKVRTQQNEILNLNEKEKAVLRAILEHGGEIKQEDLPELVGYSRPTISKVIQELENKGLIKREKSGKTFVVKIERKIKLD (SEQ ID NO:79)

FIG. 11B

DNA binding domains from Bacteria Thermotoga Maritima

BD-02 KSLQRFLRRNTTSIKHLSEITGVARNRLSDILNGKTQKIRGETLRKIAKAFEKSNILSF (SEQ ID NO:80)
BD-03 DVIQRIKEKYDEFTNAEKKIADTILSDPKGIIESSISDLSEKAGVSEASVVKFYKKLGLNSFQQFKVLLAQSISRAPLEIVYEDVSSEDDTKTITEKIFKATVRAI (SEQ ID NO:81)
BD-04 KIRDKILNVYTQFSPAERKVADYVLERPDDVIHYSITEFAKIVGVSETTIHRMIKKLDFEGYQAFKIALARELSGLEETIERRDFIDEEIDILRRLKDTLD (SEQ ID NO:82)
BD-06 MRGTVKWFDSKKGYGFITMENGEDIFVHWSAIQMDGFKTLRENETVEFEVQKGTKGPQAVNVRPVR (SEQ ID NO:109)
BD-07 KRRPTINDVAKLAGVSISTVSRYLKDPSQVSEKLGERIREAIKKLGYKPNKIAQGLRTGD (SEQ ID NO:83)
Bd-08 MASIKDVAKLAGVSIATVSRVINGYNNVSEETRKKVIDAIRKLNYHPVVAVKGAVLKR (SEQ ID NO:84)
BD-09 MKKKYVTIRDIAEKAGVSINTVSRALNNKPDISEETRRKILKIAQELGYVKNATASSLRSK (SEQ ID NO:85)
BD-11 MPTIEDVAKLAGVSIATVSRVINGSGYVSEKTRYKVVWKAIEELGYKPEISAKLLASKG (SEQ ID NO:86)
BD-12 MRIGEKLRKLRLSRGLTQEELAERTDLSRSFISQLESDKTSPSIDTLERILEALGTDLKHF (SEQ ID NO:87)
Bd-14 MHMKTVRQERLKSIVRILERSKEPVSGAQLAEELSVSRQVIVQDIAYLRSLGYNIVATPRGYVLAGG (SEQ ID NO:88)
BD-16 MNTLKKAFEILDFIVKNPGDVSVSEIAEKFNMSVSNAYKYMVVLEEKGFVLRKKDKRYVPGYKLIEYGSFVLRRF (SEQ ID NO:89)
Bd-17 MRRLNRKNINEALKKLNDRQRKVLYCIVREYIENKKPVSSQRVLEVSNIEFSSATIRNDMKKLEYLGYIVQPHTSAGRIPTDKGLRFYYEEMLKISKE (SEQ ID NO:110)

FIG. 13A

DNA binding domains from Bacteria Thermotoga Maritima

BD-18
MKISKKRRQELIRKIIHEKKISNQFQIVEELKKYGIKAVQPTVARDLKEIGAVKIMDESGNYVYKLLDETPVIDPWKELKR (SEQ ID NO:90)
BD-22
MPKSVRAENISRILKRIMKSPVSRVELAEELGLTKTTVGEIAKIFLEKGIVEEKDSPKGVGRPTKSL (SEQ ID NO:111)
BD-23
MHKKLNPKSMKRENKKMVLRYLIESGPHSRVEIARKTGLAQSAIWRIIEELVNEGLVEEKGTATGRRRKAVTYGPTRSFITS (SEQ ID NO:91)
BD-24
MPSPLLRRENKIKILRYILKNGKTTRNQLASNLNLAHSTLSYIIDELLDEGFLVFEEIKKKRGRPYQILSVNPEKFTAI (SEQ ID NO:92)
BD-30
MKEERLKEILDIVDRNGFISMKDLQEQLGVSMITVRRDVAELVKRNLVKKVHGGIRKVNYFEKETDFMKRLSINREAKE (SEQ ID NO:93)
BD-32
MFTMRSEYALRLMIVMAKEYGNYLSMTEILEKAKQSVPREFAEKILVTLKAGLVKTRRGKSGGYMLSRPPKEIKVSEIVFLLDRKSKVFFDMPGC
PDELDCVIRALWKRVENEIEKILSGVTLEDLVREQEEKMKQ (SEQ ID NO:94)
BD-37
MRDTKGHLKFLVLHIIISQQPSHGYYIMKKISQIIGAEPPSPGALYPILSSLRKQKYIETYNEGKRKVVRLTDKGRKYLEEHKEEIKKALDFAERF (SEQ
ID NO:95)
BD-43
MRHRGGRGFRGWWLASTILLLVAEKPSHGYELAERLAEFGIEIPGIGHMGNIYRVLADLEESGFLSTEWDTTVSPPRKIYRITPQGKLYLREILRSLE
DMKRRIETLEERIKRVLQEE (SEQ ID NO:96)
BD-44
ITALNYLKEHFNESVNMKRLAEMVGMSVSTFYQNFKILTGMTPLQYQKKLRLCEARKLLMAGSDVTTAAYQVGYESLSQFSREYKRFFGVSPSQD
AKKLKEEPYTRILY (SEQ ID NO:112)
BD-45
MLSKRDAILKAAVEVFGKKGYDRATTDEIAEKAGVAKGLIFHYFKNKEELYYQAVMSVTEKLQKEFENFL (SEQ ID NO:97)

FIG. 13B

Sequences for fusions of DNA polymerase SP-17 (DNA polymerase family B)
with binding domains SP-07, 08 and 98

SP-17-BD07
MIKAWLLDVDYVTENDRAVIRLWCKDDKGVFVAYDRNFLPYFYVIGCKAEDVMKVKRTNEGIITPLKVEEIEAKSLGKPIKALKVTRHPQHVFKLREEIKKFAEVREADIPFAYRYLIDKDLACM
DGIEIEPIAVKEGVLRAYEVRSVRRVEKKGFPDLKIIAFDCEMLAQFMPDPEKDFIIALAVCGDFEEVLHGDERDILRRFVSIIKEQDPDIIVGYNQDNFDWPYVKKRAEKFGIRLDIGRDRSEIS
FRGGRPKIAGRLNVDLYDIALKIPDVKIKTLKVAEFLGAKVEEEDIEGRDIYKCWMRGEKEKVFKHVLNDVLTTYRLALELLPMHYELSRMIRLPLDDVARLGRGKQVDYFLLSEAKKINEIAPNP
PEIEESYEGAFVLEPARGLHENVACLDFASMYPSIMINFNISPDTLVKGECEDCYVAPEVGHKFRKSPDGFFKRILKMLIEKRREMKRQMKELDPDSEDYKLLDIKQQTLKVLTNSFYGYTGWNLAR
WYCRECAEATTAWGRYFIKRAVKIAESMGFEVLYGDTDSLFIKKNKLNLKDLEKECLKLIDVISKELPIQLEIDEFYKAIFFVEKKRYAGLTDDDRIVVKGLEVRRGDWCELAKRVQREVIEIIRE
RNPDKALKFVKNVIEEIKEGKFKLEDYVIYKGLTKKPDKYESKQAHVKAALRAMEMGIYYPIGTKVGFVIVKGGGSISDRAYPIELIEEFDGENLKIRTPSGIMVKKLDKDYYIDHQIIPAVMRLLE
RFGYTEASLKTTIQKTLFDFTGFGGGGKRRPTINDVAKLAGVSHSTVSRYLKDPSQVSEKLGERIREAHKLGYKPNKIAQGLRTGD (SEQ ID NO:113)

SP-17-BD08
MIKAWLLDVDYVTENDRAVIRLWCKDDKGVFVAYDRNFLPYFYVIGCKAEDVMKVKRTNEGIITPLKVEEIEAKSLGKPIKALKVTRHPQHVFKLREEIKKFAEVREADIPFAYRYLIDKDLAC
MDGIEIEPIAVKEGVLRAYEVRSVRRVEKKGFPDLKIIAFDCEMLAQFMPDPEKDFIIALAVCGDFEEVLHGDERDILRRFVSIIKEQDPDIIVGYNQDNFDWPYVKKRAEKFGIRLDIGRDRSE
ISFRGGRPKIAGRLNVDLYDIALKIPDVKIKTLKVAEFLGAKVEEEDIEGRDIYKCWMRGEKEKVFKHVLNDVLTTYRLALELLPMHYELSRMIRLPLDDVARLGRGKQVDYFLLSEAKKINEIA
PNPPEIEESYEGAFVLEPARGLHENVACLDFASMYPSIMINFNISPDTLVKGECEDCYVAPEVGHKFRKSPDGFFKRILKMLIEKRREMKRQMKELDPDSEDYKLLDIKQQTLKVLTNSFYGYTGW
NLARWYCRECAEATTAWGRYFIKRAVKIAESMGFEVLYGDTDSLFIKKNKLNLKDLEKECLKLIDVISKELPIQLEIDEFYKAIFFVEKKRYAGLTDDDRIVVKGLEVRRGDWCELAKRVQREVIE
IIRERNPDKALKFVKNVIEEIKEGKFKLEDYVIYKGLTKKPDKYESKQAHVKAALRAMEMGIYYPIGTKVGFVIVKGGGSISDRAYPIELIEEFDGENLKIRTPSGIMVKKLDKDYYIDHQIIPA
VMRLERFGYTEASLKTTIQKTLFDFTGTGGGGASKDVAKLAGVSHSTVSRVINEGYNNVSEETRKKVIDAIRKLNYHPYYAVKGAVLKR (SEQ ID NO:114)

SP-17-BD98
MIKAWLLDVDYVTENDRAVIRLWCKDDKGVFVAYDRNFLPYFYVIGCKAEDVMKVKRTNEGIITPLKVEEIEAKSLGKPIKALKVTRHPQHVFKLREEIKKFAEVREADIPFAYRYLIDKDLAC
MDGIEIEPIAVKEGVLRAYEVRSVRRVEKKGFPDLKIIAFDCEMLAQFMPDPEKDFIIALAVCGDFEEVLHGDERDILRRFVSIIKEQDPDIIVGYNQDNFDWPYVKKRAEKFGIRLDIGRDRSE
ISFRGGRPKIAGRLNVDLYDIALKIPDVKIKTLKVAEFLGAKVEEEDIEGRDIYKCWMRGEKEKVFKHVLNDVLTTYRLALELLPMHYELSRMIRLPLDDVARLGRGKQVDYFLLSEAKKINEIA
PNPPEIEESYEGAFVLEPARGLHENVACLDFASMYPSIMINFNISPDTLVKGECEDCYVAPEVGHKFRKSPDGFFKRILKMLIEKRREMKRQMKELDPDSEDYKLLDIKQQTLKVLTNSFYGYTGW
NLARWYCRECAEATTAWGRYFIKRAVKIAESMGFEVLYGDTDSLFIKKNKLNLKDLEKECLKLIDVISKELPIQLEIDEFYKAIFFVEKKRYAGLTDDDRIVVKGLEVRRGDWCELAKRVQREVIE
IILRERNPDKALKFVKNVIEEIKEGKFKLEDYVIYKGLTKKPDKYESKQAHVKAALRAMEMGIYYPIGTKVGFVIVKGGGSISDRAYPIELIEEFDGENLKIRTPSGIMVKKLDKDYYIDHQIIPA
VMRLERFGYTEASLKTTIQKTLFDFTGTGGGGEEIKEIMKSHTLGNPVRLGIMIYLFPRRRAPFSHIQKALDLTPGNLDSHIKVLEKHGFVRTYKVIADRPRTMVEHDYGMEETRKFLSHLKTVIDAHF (SEQ ID
NO:115)

FIG. 16

Sequences for fusions of DNA polymerase SP-04 (DNA polymerase family A)
with binding domains SP-07, 02 and 98

SP-04-BD07

MARLFLDGTALAYRAYYALDRSLSTSTGIPTNATYGVARMLVRFIKDHIIVGKDYVAVAFDKKAATFRHKLLETYKAQRPKTPDLLQQLPYIKKLVEALGMKVLEVEGYEADDIIATLAVKGLPLFDEIFVTGDKDMLQLVNEKIK
VWRIVKGISDLELYDAQKVKEKYGVEPQQIPDLLALTGDEIDNIPGVTGIGEKTAVQLLEKYKDLEDHLNHVRELPQKVRKALLRDRENAILSKKLAHETNVPIEINWEELRYQGYDREKLLPLLKELEFASIMKELQLYEESEPVGYRI
VKDLVEFEKLIEKLRESPSFAIDLETSSLDPFCDLDVGISVSFKPKEAYYIPLHHRNAQNLDEKEVLKKLKEILEDPGAKIVGQNLKFDYKVLMVKGVEPVPPHFDTMIAAYLLEPNEKKFNLDDLALKFLGYKMTSYQELMSFSSPLFG
FSFADVPVEKAANVSCEDADITYRLYKHLSLKLHEADLENVFYKIEMPLVSVLARMELNGVVDTEFLKKLSEEYGKKLEELAEEIYRIAGEPFNINSPKQVSRILFEKLGIKPRGKTTKTGDYSTRIEVLEELAGEHEIPPLILEYRKIQKLKS
TYIDALPKMVNPKTGRIHASFNQTGTATGRLSSSDPNLQNLPTKSEEGKEIRKAIVPQDPNWMWIVSADYSQIELRILAHLSGDENLLKAFEEGIDVHTLTASRIFNVKPEEVTEEMRRAGKMVNFSIHYGVTPYGLSVRLGVPVKEA
EKMIVNYFVLYPKVRDYIQRVVSEAEKGVVRTLFGRKRDIPQLMARDRNTQAEGERIAINTPIQGTAADIIKLAMIEIDRELKERKMRSKMHQVHDELVFEVPDEEKDALVELVKDRMTNVVKLSVPLEVDVTIGKTWSGIGGG
GKRRPTINDVAKLAGVSISTVSRYLKDPSQVSEKLGERIREAIKKLGYKPNKIAQGLRTGD (SEQ ID NO:116)

SP-04-BD02

MIRAWLLDVDYVTENDRAVIRLMCKDDKGVFVAYDRNFLPYFYVIGCKAEDVMKVVRFNEGFITPLKVERIEAKSLGKPIKALKVYTRHPQHVPKLREFIKKFAEVREADIPFAYRYLIDKDLACMDG
IEIEPIAVVEGVLRAYEVRASVRRVEKKGFPDLKILAFPDCEMLAQFMPDPEKDPIIALAVRCGDFEEVLIIGDERDILRRFVSIIKEQPDIIVGYNQDNFDWPYVKRAEKFGIRLLDIGRDSEISFRGG
RPKLAGRLNVDLYDLALKLPDVKLKTLKKVAEFLGAKVEEEDIEGRDIYKCMRGEEKVFKHVLNDVLTTYRLALELLPMHYELSRMIRLPLDDVARLGRGKQVDYFLLSEAKKINEARPNPEIEES
YEGAFVLEPARGLHENVACLDFASMYPSIMINFNISPTLVKGECEDCYAPEVGHKFPKSPDGFFKRILMLIEKREMRQMKELDPDSEDYKLLDIKQTLKVLTNSFYGYTGWNLARWYCRECAE
ATTAWGRYTKRAVKIAESMGFEVLYGDTDSIFTKKNKLNLKDLEKECLKLLIDVISKELPIQLEIDEFYKALFFVEKKRYAGLTDDRIVVKGLEVRRGDWCELAKRVQREVIEIILREENPDKALKFV
KNVFEEINFGKFKLEDYVLYKGLTKKPDKYESKQAHVKAALRAMEMGLYYPIGTKVGFVIVKGGGSISDRAYPIELIEEFDGENLKRTPSGIMVKKIBKDYYIDHQIIPAVMRILERFGYTEASLKTT
IQKTLFDTTGTGGGKSLQRFLRRNTTSIKHLSEITGVARNRLSDHLMGKTQKIRGETLRKIAKAFEKSNHLSF (SEQ ID NO:117)

SP-04-BD98

MARLFLDGTALAYRAYYALDRSLSTSTGIPTNATYGVARMLVRFIKDHIIVGKDYVAVAFDKKAATFRHKLLETYKAQRPKTPDLLQQLPYIKKLVEALGMKVLEVEGYEADDIIATLAVKGLPLFDEIFVTGDKDMLQLVNEKIK
VWRIVKGISDLELYDAQKVKEKYGVEPQQIPDLLALTGDEIDNIPGVTGIGEKTAVQLLEKYKDLEDHLNHVRELPQKVRKALLRDRENAILSKKLAHETNVPIEINWEELRYQGYDREKLLPLLKELEFASIMKELQLYEESEPVGYRI
VKDLVEFEKLIEKLRESPSFAIDLETSSLDPFCDLDVGISVSFKPKEAYYIPLHHRNAQNLDEKEVLKKLKEILEDPGAKIVGQNLKFDYKVLMVKGVEPVPPHFDTMIAAYLLEPNEKKFNLDDLALKFLGYKMTSYQELMSFSSPLFG
FSFADVPVEKAANVSCEDADITYRLYKHLSLKLHEADLENVFYKIEMPLVSVLARMELNGVVDTEFLKKLSEEYGKKLEELAEEIYRIAGEPFNINSPKQVSRILFEKLGIKPRGKTTKTGDYSTRIEVLEELAGEHEIPPLILEYRKIQKLKS
TYIDALPKMVNPKTGRIHASFNQTGTATGRLSSSDPNLQNLPTKSEEGKEIRKAIVPQDPNWMWIVSADYSQIELRILAHLSGDENLLKAFEEGIDVHTLTASRIFNVKPEEVTEEMRRAGKMVNFSIHYGVTPYGLSVRLGVPVKEA
EKMIVNYFVLYPKVRDYIQRVVSEAEKGVVRTLFGRKRDIPQLMARDRNTQAEGERIAINTPIQGTAADIIKLAMIEIDRELKERKMRSKMHQVHDELVFEVPDEEKDALVELVKDRMTNVVKLSVPLEVDVTIGKTWSGIGGG
GEEKEIMKSHTLGNPVRLGIMIYLFPRRRAPESHIQKALDLTPGNLDSHIKVLEKHGFVRTYKVIADRPRTIMVEHDYGMEETRKFLSHLKTVIDAIHF (SEQ ID NO:118)

FIG. 17

Sequences for fusions of DNA polymerase SP-61 (DNA polymerase family B)
with binding domains BD-07, 09, 23, 62, 93 and 109

SP-61-BD07

MEGWILLDADYITAEDGRAVVRLWCKDFDGNTFVVYDRNFQPYFYAFKNGLSKEDIEKIVVKSREGVIKPFKVEEVRRKVFGKEVEVFKIYAYHPQHVPKLREELKKITEVREADIPFAYRYLIDKDLACMDGIRVE
GKVREERGLKVIDAEHVERFEIPLPEPKVLAFDCEMLTELGMPDPEKDKIIHGVKCGDFEEHTGNEREILLRFVEIIKEQDPDVIVGYNQDNFDWPYIRKRAEKLSVKLNIGRDGSEISFRGGRPKIAGRLNVDLYDIA
MKLDVKVKTLENVAEFLGRKVELADIEAKDIYKRWTSGDKESVLKYSKQDVLNTYFIAEELLPMHYELSRMIRPTDDVARIGRGKQVDWFLLSEAYKIGEIAPNPAEVEESYEGAFVLEPSRGLHKNVVCLDFAS
MYPSIMIAYNISPDTYVFGKCDDCYVAPEVGHKFRKHPDGFFKRILKMLIEKRREIKNQMKSLDRNSREYLLLNIKQQTLKILTNSFYGYTGWSGARWYCRQCAEATTAWGRHLIKSAVEIAKKLGFEVLYGDTD
SIFVKKGNLSLEKIRGEVEKLIEEISEKFPVQIEVDEYYKTIFFVEKKRYAGLTEDGILVVKGLEVRRGDWCELAKEVQKKVIEHLKEENPEKAAEYVRKVINDIKSGKVKLEDVVIYKGLTKRPDKYESKQAHVKAALRA
MELGIVYNVGSKVGFVVVEGAGNVGDRAYPIDLIEEFDGENLVIRTRSGSIVKKLDKDYYINHQIIPSVLRILERFGYNEASLKGATQKTLDAFW
GTGGGGKRRPTINDVAKLAGVSISTVSRYLKDPSQVSEKLGERIREAHKKLGYKPNKIAQGLRTGD (SEQ ID NO:119)

SP-61-BD09

MEGWILLDADYITAEDGRAVVRLWCKDFDGNTFVVYDRNFQPYFYAFKNGLSKEDIEKIVVKSREGVIKPFKVEEVRRKVFGKEVEVFKIYAYHPQHVPKLREELKKITEVREADIPFAYRYLIDKDLACMDGIRVEGKV
REERGLKVIDAEHVERFEIPLPEPKVLAFDCEMLTELGMPDPEKDKIIHGVKCGDFEEHTGNEREILLRFVEIIKEQDPDVIVGYNQDNFDWPYIRKRAEKLSVKLNIGRDGSEISFRGGRPKIAGRLNVDLYDIAMKLDV
KVKTLENVAEFLGRKVELADIEAKDIYKRWTSGDKESVLKYSKQDVLNTYFIAEELLPMHYELSRMIRPTDDVARIGRGKQVDWFLLSEAYKIGEIAPNPAEVEESYEGAFVLEPSRGLHKNVVCLDFASMYPSIMIAY
NISPDTYVFGKCDDCYVAPEVGHKFRKHPDGFFKRILKMLIEKRREIKNQMKSLDRNSREYLLLNIKQQTLKILTNSFYGYTGWSGARWYCRQCAEATTAWGRHLIKSAVEIAKKLGFEVLYGDTDSIFVKKGNLSLEKI
RGEVEKLIEEISEKFPVQIEVDEYYKTIFFVEKKRYAGLTEDGILVVKGLEVRRGDWCELAKEVQKKVIEHLKEENPEKAAEYVRKVINDIKSGKVKLEDVVIYKGLTKRPDKYESKQAHVKAALRAMELGIVYNVGSKVGF
VVVEGAGNVGDRAYPIDLIEEFDGENLVIRTRSGSIVKKLDKDYYINHQIIPSVLRILERFGYNEASLKGATQKTLDAFW
GTGGGGKKKYVTIRDJAEKAGVSINTVSRALNNMKPDISEETRRKILKIAQELGYVKNATASSLRSK (SEQ ID NO:120)

SP-61-BD23

MEGWILLDADYITAEDGRAVVRLWCKDFDGNTFVVYDRNFQPYFYAFKNGLSKEDIEKIVVKSREGVIKPFKVEEVRRKVFGKEVEVFKIYAYHPQHVPKLREELKKITEVREADIPFAYRYLIDKDLACMDGIRVEGK
VREERGLKVIDAEHVERFEIPLPEPKVLAFDCEMLTELGMPDPEKDKIIHGVKCGDFEEHTGNEREILLRFVEIIKEQDPDVIVGYNQDNFDWPYIRKRAEKLSVKLNIGRDGSEISFRGGRPKIAGRLNVDLYDIAMKL
DVKVKTLENVAEFLGRKVELADIEAKDIYKRWTSGDKESVLKYSKQDVLNTYFIAEELLPMHYELSRMIRPTDDVARIGRGKQVDWFLLSEAYKIGEIAPNPAEVEESYEGAFVLEPSRGLHKNVVCLDFASMYPSI
MIAYNISPDTYVFGKCDDCYVAPEVGHKFRKHPDGFFKRILKMLIEKRREIKNQMKSLDRNSREYLLLNIKQQTLKILTNSFYGYTGWSGARWYCRQCAEATTAWGRHLIKSAVEIAKKLGFEVLYGDTDSIFVKKG
NLSLEKIRGEVEKLIEEISEKFPVQIEVDEYYKTIFFVEKKRYAGLTEDGILVVKGLEVRRGDWCELAKEVQKKVIEHLKEENPEKAAEYVRKVINDIKSGKVKLEDVVIYKGLTKRPDKYESKQAHVKAALRAMELGIVYN
VGSKVGFVVVEGAGNVGDRAYPIDLIEEFDGENLVIRTRSGSIVKKLDKDYYINHQIIPSVLRILERFGYNEASLKGATQKTLDAFW
GTGGGGHKKLNPKSMKRENKKMVLRYLIESGPHSRVEIARKTGLAQSAIWRIHEELVNEGLVEEKGTATGRRRKAVTYGPTRSEHTS (SEQ ID NO:121)

FIG. 18A

Sequences for fusions of DNA polymerase SP-61 (DNA polymerase family B)
with binding domains BD-07, 09, 23, 62, 93 and 109

SP-61-BD62

MEGWLLDADYITAEDGRAVVRLWCKDFDGNTFVVYDRNFCQPYFYAFKNGLSKEDIEKIVVKSREGVIKPFKVEEVRRKVFGKEVEVFKIYAYHPQHVPKLREELKKITEVREADIPFAYRYLIDKDLACMDGIRVEGKVREERGLKVID
AEHVEREIPLPEPKVLAFDCEMLTELGMPDPEKDKIIIIGVKCGDFEEIITGNEREIILRFVEIIKEQDPDVIVGYNQDNFDWPYIRKRAEKLSVKLNIGRDGSEISFRGGRPKIAGRLNVDLYDIAMKLDVKVKTLENVAEFLGRKVELA
DIEAKDIYKRWTSGDKESVLKYSKQDVLNTYFIAEELLPMHYELSRMIRPTDDVARIGRGKQVDWFLLSEAYKIGEIAPNPAEVEESYEGAFVLEPSRGLHKNVVCLDFASMYPSIMIAYNISPDTYVFGKCDDCYVAPEVGHKFRKH
PDGFFKRILKMLIEKRREIKNQMKSLDRNSREYLLLNIKQQTLKILTNSFYGYTGWSSGARWYCRQCAEATTAWGRHLIKSAVEIAKKLGFEVLYGDTDSIFVKKGNLSLEKIRGEVEKLIEEISEKFPVQJEVDEYYKTIFFVEKKRYAGLITE
DGILVVKGLEVRRGDWCELAKEVQKKVIEIILKEENPEKAAEYVRKVINDIKSGKVKLEDVVIYKGLTKRPDKYESKQAHVKAALRAMELGIVYNVGSKVGFVVEGAGNVGDRAYPIDLIEEFDGENLVIRTRSGSIVKKLDKDYYINH
QIIPSVLRILERFGYNEASLKGATQKTLDAFWGTGGGGNTGAQGVSEMSRMKIISVQLPQSLIHGLDALVKRGIYPNRSEAIRVAIRELLIKKELYKEEIQEEIPEYVVK (SEQ ID NO:122)

SP-61-BD93

MEGWLLDADYITAEDGRAVVRLWCKDFDGNTFVVYDRNFCQPYFYAFKNGLSKEDIEKIVVKSREGVIKPFKVEEVRRKVFGKEVEVFKIYAYHPQHVPKLREELKKITEVREADIPFAYRYLIDKDLACMDGIRVEGKVREERGLKVI
DAEHVEREIPLPEPKVLAFDCEMLTELGMPDPEKDKIIIIGVKCGDFEEIITGNEREIILRFVEIIKEQDPDVIVGYNQDNFDWPYIRKRAEKLSVKLNIGRDGSEISFRGGRPKIAGRLNVDLYDIAMKLDVKVKTLENVAEFLGRKVE
LADIEAKDIYKRWTSGDKESVLKYSKQDVLNTYFIAEELLPMHYELSRMIRPTDDVARIGRGKQVDWFLLSEAYKIGEIAPNPAEVEESYEGAFVLEPSRGLHKNVVCLDFASMYPSIMIAYNISPDTYVFGKCDDCYVAPEVGHKF
RKHPDGFFKRILKMLIEKRREIKNQMKSLDRNSREYLLLNIKQQTLKILTNSFYGYTGWSSGARWYCRQCAEATTAWGRHLIKSAVEIAKKLGFEVLYGDTDSIFVKKGNLSLEKIRGEVEKLIEEISEKFPVQJEVDEYYKTIFFVEKKRY
AGLTEDGILVVKGLEVRRGDWCELAKEVQKKVIEIILKEENPEKAAEYVRKVINDIKSGKVKLEDVVIYKGLTKRPDKYESKQAHVKAALRAMELGIVYNVGSKVGFVVEGAGNVGDRAYPIDLIEEFDGENLVIRTRSGSIVKKLDK
DYYINHQIIPSVLRILERFGYNEASLKGATQKTLDAFWGTGGGGIHNPQARLTPLELEHEHQKSITITEIKEILSERRKSEYPLSLVSEYISRLERKGYVKKIAKGRKFVEALI (SEQ ID NO:123)

SP-61-BD109

MEGWLLDADYITAEDGRAVVRLWCKDFDGNTFVVYDRNFCQPYFYAFKNGLSKEDIEKIVVKSREGVIKPFKVEEVRRKVFGKEVEVFKIYAYHPQHVPKLREELKKITEVREADIPFAYRYLIDKDLACMDGIRVEGKVREERGLKVI
DAEHVEREIPLPEPKVLAFDCEMLTELGMPDPEKDKIIIIGVKCGDFEEIITGNEREIILRFVEIIKEQDPDVIVGYNQDNFDWPYIRKRAEKLSVKLNIGRDGSEISFRGGRPKIAGRLNVDLYDIAMKLDVKVKTLENVAEFLGRKVE
LADIEAKDIYKRWTSGDKESVLKYSKQDVLNTYFIAEELLPMHYELSRMIRPTDDVARIGRGKQVDWFLLSEAYKIGEIAPNPAEVEESYEGAFVLEPSRGLHKNVVCLDFASMYPSIMIAYNISPDTYVFGKCDDCYVAPEVGHKF
RKHPDGFFKRILKMLIEKRREIKNQMKSLDRNSREYLLLNIKQQTLKILTNSFYGYTGWSSGARWYCRQCAEATTAWGRHLIKSAVEIAKKLGFEVLYGDTDSIFVKKGNLSLEKIRGEVEKLIEEISEKFPVQJEVDEYYKTIFFVEKKRY
AGLTEDGILVVKGLEVRRGDWCELAKEVQKKVIEIILKEENPEKAAEYVRKVINDIKSGKVKLEDVVIYKGLTKRPDKYESKQAHVKAALRAMELGIVYNVGSKVGFVVEGAGNVGDRAYPIDLIEEFDGENLVIRTRSGSIVKKLDK
DYYINHQIIPSVLRILERFGYNEASLKGATQKTLDAFWGTGGGGGGRKVRTQQNEIILNLLNEKEKAVLRAILLEHGGEIKQEDLPELVGYSRPTISKVIQELENKGLIKREKSGKTFVVKIERKIKLD (SEQ ID NO:124)

FIG. 18B

Sequences for fusions of DNA polymerase 49 (DNA polymerase family B) with binding domains BD-07, 09, 23, 62, 93 and 109

SP-49-BD07
MILDADYITEDGKPIHRLFKKENGRFKVEYDRNFRPYIYALLKDDSAIDDVRKITSERHGKVVRVIDVEKVKKKFLGRPIEVVKLYFEHPQDVPAMRDKIREHPAVIDIFEYDIPFAKRYLIDKGLIPMEGNEELTFLAVDIETLY HEGEEFGKGPIIMISYADEEGAKVITWKKIDLPYVEVVANEREMIKRLIKVIREKDPDVIITYNGDNFDFPYLLKRAEKLGMKLPLGRDNSEPKMQRLGDSLAVEIKGRIHFDLFPVIRRTINLPTYTLEAVYEAIFGKQKEKVY PHEIAEAWETGKGLERVAKYSMEDAKVTYELGKEFFPMEAQLARLVGQPLWDVSRSSTGNLVEWYLLRKAYERNELAPNKPDEREYERRLRESYEGGYVKEPERGLWEGIVSLDFRSLYPSIIITHNVSPDTLNKEGCGEY DEAPEVGHRFCKDFPGFIPSLLGSLLEERQKIKKRMKESKDPVERKLLDYRQRAIKILANSFYGYYGYAKARWYCKECAESVTAWGRQYIELVRRELEERGFKVLYIDTDGLYATIPGEKNWEEIKRRALEFVNYINSKLPGILE LEYEGGFYTRGFFVTKKKYALIDEEGKIVTRGLEIVRRDWSEIAKETQAKVLEALLKHGNVEEAVKIVKEVTEKLSNYEIPVEKLVIYEQITRPLNEYKAIGPHVAVAKRLAAKGIKIKPGMVIGYVVLRGDGPISKRAIAIEEFDGK KHKYDAEYYIENQVLPAVERILKAFGYKREDLRWQKTKQVGLGAWLKVKKSGTGGGKRRPTINDVAKLAGVSISTVSRYLKDPSQVSEKLGENIREAIKILGYKPNKIAQGLRTGD (SEQ ID NO:125)

SP-49-BD09
MILDADYITEDGKPIHRLFKKENGRFKVEYDRNFRPYIYALLKDDSAIDDVRKITSERHGKVVRVIDVEKVKKKFLGRPIEVVKLYFEHPQDVPAMRDKIREHPAVIDIFEYDIPFAKRYLIDKGLIPMEGNEELTFLAVDIETLY HEGEEFGKGPIIMISYADEEGAKVITWKKIDLPYVEVVANEREMIKRLIKVIREKDPDVIITYNGDNFDFPYLLKRAEKLGMKLPLGRDNSEPKMQRLGDSLAVEIKGRIHFDLFPVIRRTINLPTYTLEAVYEAIFGKQKEKVY PHEIAEAWETGKGLERVAKYSMEDAKVTYELGKEFFPMEAQLARLVGQPLWDVSRSSTGNLVEWYLLRKAYERNELAPNKPDEREYERRLRESYEGGYVKEPERGLWEGIVSLDFRSLYPSIIITHNVSPDTLNKEGCGEY DEAPEVGHRFCKDFPGFIPSLLGSLLEERQKIKKRMKESKDPVERKLLDYRQRAIKILANSFYGYYGYAKARWYCKECAESVTAWGRQYIELVRRELEERGFKVLYIDTDGLYATIPGEKNWEEIKRRALEFVNYINSKLPGILE LEYEGGFYTRGFFVTKKKYALIDEEGKIVTRGLEIVRRDWSEIAKETQAKVLEALLKHGNVEEAVKIVKEVTEKLSNYEIPVEKLVIYEQITRPLNEYKAIGPHVAVAKRLAAKGIKIKPGMVIGYVVLRGDGPISKRAIAIEEFDGKK HKYDAEYYIENQVLPAVERILKAFGYKREDLRWQKTKQVGLGAWLKVKKSGTGGGCKKKYVTIRDIAEKAGVSINTVSRALNNKPDISEETRKKILKIAQELGYVKNATASSLRSK (SEQ ID NO:126)

SP-49-BD23
MILDADYITEDGKPIHRLFKKENGRFKVEYDRNFRPYIYALLKDDSAIDDVRKITSERHGKVVRVIDVEKVKKKFLGRPIEVVKLYFEHPQDVPAMRDKIREHPAVIDIFEYDIPFAKRYLIDKGLIPMEGNEELTFLAVDIETLY HEGEEFGKGPIIMISYADEEGAKVITWKKIDLPYVEVVANEREMIKRLIKVIREKDPDVIITYNGDNFDFPYLLKRAEKLGMKLPLGRDNSEPKMQRLGDSLAVEIKGRIHFDLFPVIRRTINLPTYTLEAVYEAIFGKQKEKVY PHEIAEAWETGKGLERVAKYSMEDAKVTYELGKEFFPMEAQLARLVGQPLWDVSRSSTGNLVEWYLLRKAYERNELAPNKPDEREYERRLRESYEGGYVKEPERGLWEGIVSLDFRSLYPSIIITHNVSPDTLNKEGCGEY DEAPEVGHRFCKDFPGFIPSLLGSLLEERQKIKKRMKESKDPVERKLLDYRQRAIKILANSFYGYYGYAKARWYCKECAESVTAWGRQYIELVRRELEERGFKVLYIDTDGLYATIPGEKNWEEIKRRALEFVNYINSKLPGILE LEYEGGFYTRGFFVTKKKYALIDEEGKIVTRGLEIVRRDWSEIAKETQAKVLEALLKHGNVEEAVKIVKEVTEKLSNYEIPVEKLVIYEQITRPLNEYKAIGPHVAVAKRLAAKGIKIKPGMVIGYVVLRGDGPISKRAIAIEEFDGKK HKYDAEYYIENQVLPAVERILKAFGYKREDLRWQKTKQVGLGAWLKVKKSGTGGGHKKLNPKSMKRENKKMVLRYLIESGPHSRVEJARKTGLAQSAIWRIIEELVNEGLVEEKGTATGRRRKAVTYGPTRSFITS (SEQ ID NO:127)

FIG. 19A

Sequences for fusions of DNA polymerase 49 (DNA polymerase family B) with binding domains BD-07, 09, 23, 62, 93 and 109

SP-49-BD62

MILDADYITEDGKPIIRLFKKENGRFKVEYDRNFRPYIYALLKDDSAIDDVRKITSERHGKVVRVIDVEKVKKKFLGRPIEVWKLYFEHPQDVPAMRDKIREHPAVIDIFEYDIPFAKRYLIDKGLIPMEGNEELTFLAVDIETLYHEG EEFGKGPIIMISYADEEGAKVITWKKIDLPYVEVVANEREMIKRLIRVIREKDPDVHTYNGDNFDFPYLLKRAEKLGMKLPLGRDNSEPKMQRLGDSLAVEIKGRIHFDLFPVIRRTINLPTYTLEAVYEAIFGKQKEKVYPHEIAEA WETGKGLERVAKYSMEDAKVTYELGKEFFPMEAQLARLVGQPLWDVSRSSTGNLVEWYLLRKAYERNELAPNKPDEREYERRLRESYEGGYVKEPERGLWEGIVSLDFRSLYPSIIHTHNVSPDTLNKEGCGEYDEAPEVGHR FCKDFPGFIPSLLGSLLEERQKIKKRMKESKDPVERKLLDYRQRAIKILANSFYGYGYAKARWYCKECAESVTAWGRQYIELVRRELEERGFKVLYIDTDGLYATIPGEKNWEEIKRRALEFVNYINSKLPGILELEYEGFYTRGFFV TKKKYALIDEEGKIVTRGLEIVRRDWSEIAKETQAKVLEAILKHGNVEEAVKIVKEVTEKLSNYEIPVEKLVIYEQJTRPLNEYKAIGPHVAVAKRLAAKGIKIKPGMVIGYVVLRGDGPISKRAIAIEEFDGKKHKYDAEYYIENQVLP AVERILKAFGYKREDLRWQKTKQVGLGAWLKVKKS GTGGGGNTGAQGVSEMSRMAKIISVQLPQSLIHGLDALVKRGIYPNRSEAIRVAIRELLKKELYKEEJQEEPEYVVK (SEQ ID NO:128)

SP-49-BD93

MILDADYITEDGKPIIRLFKKENGRFKVEYDRNFRPYIYALLKDDSAIDDVRKITSERHGKVVRVIDVEKVKKKFLGRPIEVWKLYFEHPQDVPAMRDKIREHPAVIDIFEYDIPFAKRYLIDKGLIPMEGNEELTFLAVDIETLYHEG EEFGKGPIIMISYADEEGAKVITWKKIDLPYVEVVANEREMIKRLIRVIREKDPDVHTYNGDNFDFPYLLKRAEKLGMKLPLGRDNSEPKMQRLGDSLAVEIKGRIHFDLFPVIRRTINLPTYTLEAVYEAIFGKQKEKVYPHEIAEA WETGKGLERVAKYSMEDAKVTYELGKEFFPMEAQLARLVGQPLWDVSRSSTGNLVEWYLLRKAYERNELAPNKPDEREYERRLRESYEGGYVKEPERGLWEGIVSLDFRSLYPSIIHTHNVSPDTLNKEGCGEYDEAPEVGHR FCKDFPGFIPSLLGSLLEERQKIKKRMKESKDPVERKLLDYRQRAIKILANSFYGYGYAKARWYCKECAESVTAWGRQYIELVRRELEERGFKVLYIDTDGLYATIPGEKNWEEIKRRALEFVNYINSKLPGILELEYEGFYTRGFFV TKKKYALIDEEGKIVTRGLEIVRRDWSEIAKETQAKVLEAILKHGNVEEAVKIVKEVTEKLSNYEIPVEKLVIYEQJTRPLNEYKAIGPHVAVAKRLAAKGIKIKPGAVIGYVVLRGDGPISKRAIAIEEFDGKKHKYDAEYYIENQVLP AVERILKAFGYKREDLRWQKTKQVGLGAWLKVKKS GTGGGGHMPQARLTPLELEILEHKQKKSITITEIKELSERRKSEYPLSLVSEYISRLERKGYVKKIAKGRKKFVEALI (SEQ ID NO:129)

SP-49-BD109

MILDADYITEDGKPIIRLFKKENGRFKVEYDRNFRPYIYALLKDDSAIDDVRKITSERHGKVVRVIDVEKVKKKFLGRPIEVWKLYFEHPQDVPAMRDKIREHPAVIDIFEYDIPFAKRYLIDKGLIPMEGNEELTFLAVDIETLYHEGE EFGKGPIIMISYADEEGAKVITWKKIDLPYVEVVANEREMIKRLIRVIREKDPDVHTYNGDNFDFPYLLKRAEKLGMKLPLGRDNSEPKMQRLGDSLAVEIKGRIHFDLFPVIRRTINLPTYTLEAVYEAIFGKQKEKVYPHEIAEAW ETGKGLERVAKYSMEDAKVTYELGKEFFPMEAQLARLVGQPLWDVSRSSTGNLVEWYLLRKAYERNELAPNKPDEREYERRLRESYEGGYVKEPERGLWEGIVSLDFRSLYPSIIHTHNVSPDTLNKEGCGEYDEAPEVGHRFCK DFPGFIPSLLGSLLEERQKIKKRMKESKDPVERKLLDYRQRAIKILANSFYGYGYAKARWYCKECAESVTAWGRQYIELVRRELEERGFKVLYIDTDGLYATIPGEKNWEEIKRRALEFVNYINSKLPGILELEYEGFYTRGFFVTK KYALIDEEGKIVTRGLEIVRRDWSEIAKETQAKVLEAILKHGNVEEAVKIVKEVTEKLSNYEIPVEKLVIYEQJTRPLNEYKAIGPHVAVAKRLAAKGIKIKPGMAVIGYVVLRGDGPISKRAIAIEEFDGKKHKYDAEYYIENQVLPAVE RILKAFGYKREDLRWQKTKQVGLGAWLKVKKS GTGGGGRKVRTQQNEHLNLNEKEKAVLRAILEHGGEHKQEDLPELVGYSRPTISKVIQELENKGLIKREKSGKTFVVKIERKIKLD (SEQ ID NO:130)

FIG. 19B

FUSION POLYMERASE AND METHOD FOR USING THE SAME

CROSS-REFERENCE

This application is a continuation of U.S. Ser. No. 15/046,166, filed on Feb. 17, 2016 which is a continuation-in-part of U.S. Pat. No. 9,447,445, issued on Sep. 20, 2016, which claims the benefit of U.S. provisional application Ser. No. 62/042,527, filed Aug. 27, 2014, 62/189,599, filed Jul. 7, 2015 and 62/193,168, filed on Jul. 16, 2015, which applications are incorporated by reference herein.

BACKGROUND

DNA polymerases are widely used in in vitro applications. In particular, use of thermostable polymerases has revolutionized modern molecular biology. The processivity of a DNA polymerase, i.e., the length of product generated by the enzyme per binding event, is an important factor in many in vitro reactions. For example, in a PCR reaction or an in vitro sequence assembly reaction, the length of a product is largely determined by the proofreading activity and the processivity of the DNA polymerase used. Increasing the processivity of a DNA polymerase can, in theory, allow one to copy and/or amplify a template (particularly a longer template) more efficiently altering the fidelity of the polymerase. However, in practice, increasing the processivity of a DNA polymerase does not always have the desired effect because the proofreading activity of the polymerase may counteract any positive effects conferred by the increase in processivity.

One way to increase the processivity of a DNA polymerase involves adding Sso7d, a non-specific DNA binding protein, onto the polymerase (Wang et al, Nuc. Acids Res. 2004 32: 1197-1207). Because Sso7d binds DNA non-specifically, it is thought that the addition of the domain helps anchor the polymerase to its template, thereby stabilizing the interaction between the polymerase and the template.

SUMMARY

As will be described in greater detail below, the performance of many DNA polymerases can be unexpectedly increased by the addition of a sequence-specific DNA binding domain (e.g., the DNA binding domain of a transcription factor) to the N- or C-terminus of the polymerase. This increase in performance is believed to be unexpected because where a sequence-specific DNA binding domain preferentially binds to a specific sequence, it would not be expected to help the DNA polymerase to remain bound to its template. Indeed, an effect opposite to the desired one would be expected to occur, namely that the sequence-specific DNA binding domain would anchor the polymerase only to target sequences and prevent it from moving.

This disclosure provides, among other things, a composition comprising a fusion protein comprising: (a) a DNA polymerase; and (b) the DNA binding domain of a heterologous sequence-specific DNA binding domain. In some embodiments, the fusion protein may exhibit increased processivity relative to the polymerase of (a) in the absence of the DNA binding domain of (b). The sequence-specific DNA binding domain is C-terminal or N-terminal of the polymerase. In some embodiments, the DNA polymerase is a type A polymerase whereas on other embodiments, the DNA polymerase may be a type B polymerase. In some embodiments, the sequence-specific DNA binding domain may a helix-loop-helix, ribbon-helix-helix, helix-turn-helix, winged helix, or homeodomain structure. In some embodiments, the sequence-specific DNA binding domain may be from a transcriptional activator. In some embodiments, the sequence-specific DNA binding domain may be at least 90% identical to a DNA binding domain of a naturally occurring transcription factor.

In some embodiments, the polymerase may have proofreading activity. In some embodiments, the polymerase may at least 90% identical to a wild type polymerase, e.g., a bacterial or archaebacterial polymerase such as a wild type *Pyrococcus* or *Thermococcus* polymerase. In some embodiments, the polymerase may thermostable. In some embodiments, the sequence-specific DNA binding domain may be thermostable.

Also provided herein, among other things, is a kit comprising: (a) a composition comprising a fusion protein, as summarized above; and (b) a reaction buffer. In some embodiments, the composition may comprise glycerol. In some embodiments, the buffer may be in concentrated form.

Also described herein, among other things, is a method comprising: combining a DNA template with nucleotides and a composition comprising a fusion protein, as summarized above, to produce a reaction mix; and copying the DNA template. In some embodiments, the DNA template may be a plurality of overlapping primers. In some embodiments, the reaction mix may comprise a plurality of primers and genomic DNA. The copying step may done using isothermal conditions or thermocycling, for example.

This disclosure also provides, among other things, a composition comprising: i. a 5' exonuclease; ii. a strand-displacing polymerase; iii. a single strand (ss) DNA binding protein; and, iv. a non-naturally occurring buffering agent, wherein the composition does not comprise a crowding agent and/or a non-strand-displacing polymerase. The composition can be employed to assemble polynucleotides into a synthon. Embodiments of the composition optionally contain a ligase depending on whether assembly is performed for purposes of cloning in a bacterial cell that would contain its own ligase or whether assembly is performed for purposes which do not include a cloning step in bacteria.

Previously described assembly methods required a non-strand displacing polymerases and evolved to additionally require a crowding agent (see for example U.S. Pat. No. 8,968,999). Contrary to the prior teachings, present embodiments demonstrate that a strand displacing polymerase has advantages over a non-strand displacing polymerase when used with a 5'-3' exonuclease. This combination has a preference for including a ss binding protein over a crowding agent which is the reverse over prior art teachings which assert that use of crowding agents are four fold more effective than alternatives including the use of a single stand binding protein. Present embodiments provide compositions, methods and kits that provide increased efficiency of assembly and cloning of functional genes and synthons from oligonucleotides and polynucleotides including ds and/or ss nucleic acid molecules in a single step method and/or in a single reaction vessel. These embodiments do not rely on crowding agents nor do they require non-strand displacing polymerases for filling in gaps that are present after two molecules anneal. For example, when a 5'-3' exonuclease that acts upon ds DNA generates a 3' ss DNA overhang that can anneal effectively with a 3' ss DNA overhang from another molecule, the strand-displacing polymerase can fill-in gaps left after the molecules anneal. A combination of activities of the strand-displacing DNA polymerase and the 5'-3' exonuclease results in a duplex synthon containing a nick at or near the site of joining. This nick can be sealed in vitro by a ligase or in vivo by an endogenous cellular ligase. Additionally, the inclusion of a ss DNA binding protein in the reaction mixture enables efficient assembly of relatively low concentrations of nucleic acid fragments, thereby providing a cost saving without loss of efficiency or loss of accuracy of joining.

In some embodiments of the compositions, the strand-displacing polymerase is a Family B polymerase. A strand displacing polymerase should preferably have strand-displacing activity that is greater than that observed with Phusion® polymerase (Thermo Fisher, Waltham, Mass.) (which is generally described as non-strand displacing) under the same reaction conditions (for example, using an assay such as described in FIG. 1A-1E. In the present compositions, methods and kits the strand displacing polymerase is utilized primarily for its strand displacing activity. In some embodiments, the strand-displacing polymerase may be non-naturally occurring, for example, the strand-displacing polymerase may be a mutant. Examples of mutants include polymerases having one or more amino acid substitutions, non-naturally occurring polymerases may alternatively or in addition be fusion proteins with a moiety having an unrelated amino acid sequence where the fusion polymerase is not encountered in nature. Preferably the strand displacing polymerase is stable at 50° C. or above and may thus be referred to as a thermostable strand displacing polymerase. In some cases, the strand-displacing polymerase is a fusion polymerase having an unrelated or heterologous DNA binding domain. In some embodiments, the polymerase moiety may have an amino acid sequence that is at least 90% or 95%, or 98% or 99% identical to SEQ ID NO:102. In another embodiment, the polymerase may have an amino acid sequence that is at least 90% or 95% or 98% or 99% or 100% identical to SEQ ID NO:1 preferably at least 90%. In another embodiment, the polymerase may have an amino acid sequence that is at least 90% or 95% or 98% or 99% or 100% identical to any of SEQ ID NO:33-55 preferably at least 90%. In some embodiments, the DNA binding domain moiety may have an amino acid sequence that is at least 90% or 95%, or 98% or 99% identical to SEQ ID NO:2. In another embodiment, the polymerase may have an amino acid sequence that is at least 90% or 95% or 98% or 99% or 100% identical to any of SEQ ID NOs:1, 3, 56-96 or 102, preferably at least 90%. In other embodiments, any of the polymerase domain moieties described herein may be combined with any of the DNA binding domains described herein provided that that the Polymerase moiety and the DNA binding domain are heterologous. For example, in other embodiments, the fusion protein may have an amino acid sequence that has at least 90% or 95% or 99% or 100% identity with SEQ ID NO:1 and SEQ ID NO:2, preferably at least 90%. In other embodiments, the fusion protein may have at least 90% or 95% or 98% or 99% or 100% sequence identity to SEQ ID NO:3 preferably at least 90%. The strand-displacing polymerase may or may not have a 3'-5' exonuclease activity. Where strand displacing polymerases have 3'-5' exonuclease activity, polynucleotide joining may be optimized by balancing 3'-5' exonuclease activity, 5'-3' polymerization activity and strand displacement activity using the conditions that include those exemplified herein. The efficacy and accuracy of the assembly can be confirmed using the assay described herein (see for example, FIGS. 3A and 3B). In some embodiments, the polymerase is not Phusion, 9° N, Pfu or Vent, or a polymerase that has an amino acid sequence that is at least 90% identical to Phusion or wild type 9° N, Pfu or Vent. In some embodiments, the polymerase is thermostable, i.e., active at a temperature of at least 40° C. or at least 50° C. degrees. In contrast to strand-displacing polymerases, some polymerases such as Taq DNA polymerase, degrade an encountered downstream strand via a 5'→3' exonuclease activity. This activity is utilized for nick translation protocols. Hence Taq DNA polymerase is not included in the definition of strand displacing polymerases.

An assay to determine efficiency and accuracy of synthon formation is described in the examples and shown in FIG. 3A-3B. The designed assembled fragments encode the lacI and lacZ proteins, which yield a blue colony if DNA fragments are assembled correctly. Thus, the number of "blue" colonies from an overnight plate denotes both efficiency and accuracy of assembly. In the absence of a blue color, efficient assembly may occur but errors at the joining/extension region prevents expression. When synthons are assembled and then cloned into a host cell, efficiency and accuracy of synthon formation translates into a confidence that each clone will contain the accurately assembled synthon. With this confidence, only one or a few duplicate clones need to be sequenced to confirm the presence of a synthon. This reduces the cost and inconvenience of sequencing clones that might contain errors. In one embodiment, at least 80% or alternatively at least 90% of clones will contain accurately assembled synthons.

In some embodiments, methods utilizing the compositions described herein are capable of yields that are substantially in excess of minimum requirements. For example, as many as 5,000 or 10,000 colonies can be produced in a single transformation event. If the purpose of assembly is to create a single example of a synthon rather than a library of synthons, then lower starting amounts of nucleic acid fragments and reagents can be used even below the ranges provided herein. Examples of concentration ranges suitable for use in an assembly mixture include the following: 0.02 nM-100 nM for DNA fragment or for example 0.2 nM-10 nM DNA may be added to the reagent mixture in a reaction vessel. In one embodiment, vector DNA is included at a ratio of 1:1 with the DNA fragments although higher or lower ratios can be used. A higher concentration of ss DNA may be preferred when compared with the concentration selected for ds DNA. The reagent mixture in the reaction vessel may further include 0.0004 U/µl-0.064 U/µl of the 5'-3' exonuclease (for example 0.0004 U/µl-0.01 U/µl); 0.5 U/µl-32 U/µl of an optional ligase (for example 1 U/µl-10 U/µl); 0.0025 U/µl-0.25 U/µl of the strand displacing polymerase (for example 0.005 U/µl-0.1 U/µl); and 0.001 µg/µl-0.1 µg/µl for the ss binding protein (for example 0.01 µg/µl-0.5 µg/µl) (units correspond with those specified by the manufacturer (New England Biolabs, Ipswich, Mass.)).

The amount of 5'-3' exonuclease can be further optimized according to the length of overlap of nucleic acid fragments and size of each fragment. For example, amounts of 5'-3' exonuclease may be increased within the range for nucleic acid fragments greater than 80 nucleotides in length. The absolute concentration of the strand displacing polymerase within the specified range is not critical.

A ss DNA binding protein for use in the composition may be E. coli recA, T7 gene 2.5 product, RedB (from phage lambda) or RecT (from Rac prophage), ET SSB (extreme thermostable single-stranded DNA binding protein) or a ss binding protein with 90% sequence identity to SEQ ID NO:100 although many other ss DNA binding proteins are known and could be used in the composition. The inclusion of a ss binding protein improves the efficiency of assembly particularly for nucleic acid fragments with longer overlap sequences (e.g. at least 20 nucleotides) than would be otherwise occur in the absence of ss binding protein as measured by colony number.

The optional ligase may be an NAD$^+$ dependent ligase such as Taq ligase or an ATP dependent ligase such as T4 ligase. However, for PCR, it is convenient to use an NAD$^+$ dependent ligase since ATP can inhibit Taq polymerase used in subsequent amplification of the synthon. Examples of a suitable ligase include a protein with at least 90% sequence identity to SEQ ID NO:101.

The 5'-3' exonuclease used here may be an enzyme that has a 5'-3' exonuclease activity as well as a ss endonuclease activity (see, for example, Garforth, et al., PNAS, 96, 38-43 (1999)). Examples of a 5'-3' exonuclease with exonuclease and ss endonuclease activity include T5 exonuclease, as well as homologs and variants thereof. In one example, the 5'-3' exonuclease has at least 90% amino acid sequence identity SEQ ID NO:98. There is no requirement to denature the 5'-3' exonuclease prior to joining the polynucleotides with the strand displacing polymerase. Hence the use of a thermostable 5'-3' exonuclease is described in the examples.

In some embodiments, the composition may further comprise dNTPs (i.e., a mixture of dGTP, dATP, dGTP and dTTP) and, in some embodiments, where T5 5'-3' exonuclease is used, the composition may further comprise potassium salt such as KCl (e.g., at a concentration in the range of 7 mM-150 mM).

In general, a method for producing a synthon is provided. In some embodiments, the method may include incubating an embodiment of the composition described herein that comprises a strand displacing polymerase as described herein and a 5'-3' exonuclease and optionally a ligase (if the reaction is in vitro or in vivo in a cell or organism that does not contain a ligase) and may also contain a ss binding protein, with a set of polynucleotides and/or oligonucleotides in which at least one or some of the members of the set have a sequence that overlaps with one or some other members of the set, under suitable reaction conditions. In some embodiments, the polynucleotides or oligonucleotides may be ds DNA, e.g., overlapping PCR products or overlapping restriction fragments. In other embodiments, the polynucleotides may be ss DNA or RNA. In some embodiments, the set of polynucleotides may comprise ss DNA or RNA. In some embodiments, the set of polynucleotides may comprise ds polynucleotides. In some embodiments, the set of polynucleotides may comprise at least one ds polynucleotide and at least one ss polynucleotide. In some embodiments, the set of polynucleotides may comprise a sub-population of polynucleotides that have identical sequences apart from a sub-sequence that varies between members of the sub-population. In other embodiments, the set of polynucleotides may comprise ss or ds polynucleotides or polynucleotides that have overlapping regions at their ends for purposes of joining but different internal sequences that form the synthon. Thus, in one embodiment of the method of the invention, the polynucleotides in the set of polynucleotides are ds; such as wherein the ds polynucleotides are overlapping PCR products or overlapping restriction fragments or assembled from ss polynucleotides In an alternative embodiment of the method of the invention, the synthon is assembled from polynucleotides in the set of polynucleotides that are ss. In a further alternative embodiment of the method of the invention, the synthon is assembled from a set of polynucleotides that comprises a mixture of at least one ds polynucleotide and at least one ss oligonucleotide. In embodiments of the method of the invention, the synthon is assembled from a set of polynucleotides that comprise a sub-population of polynucleotides that are identical to one another except for a sub-sequence that varies between the members of the sub-population.

Embodiments of the method may be used to produce a variety of synthons, including coding sequences, vectors, guide molecules for gene engineering and expression cassettes.

Prior to assembly, the initial ds polynucleotides may be in the range of 100 bases-30 kb in length, although polynucleotides outside of this range may be used in certain cases. For example, in some embodiments, individual fragment sizes can be as much as 20 kb-30 kb or longer or as short as 30 bases-500 bases. Moreover, in some embodiments, fragments of different sizes can be joined in the assembly reaction. In one example, long polynucleotides (e.g., fragments of 5 kb-20 kb in length) are joined to short polynucleotides (e.g., fragments of 100 bases-500 bases in length). Newly assembled synthons may be sequenced, either directly using single molecule sequencing methods or after cloning or amplification.

In one embodiment, the members of the set may contain overlapping sequences having a length less than 2 kb for example, in the range of 15-200 nucleotides for example, 20-100 nucleotides.

In one embodiment, a composition is provided where the composition has a 5'-3' exonuclease; a strand-displacing polymerase; and a buffer containing a potassium salt such as KCl in a concentration range of 7 mM-150 mM, for example, 20 mM-50 mM. A sodium salt (e.g., sodium chloride) in the range of 10 mM-100 mM such as 20 mM may also be used in addition to potassium salt. A ss binding protein may be included in the composition. In some embodiments, the composition does not contain a crowding agent such as polyethylene glycol (PEG), Ficoll, or dextran. In some embodiments, the composition does not contain a non-strand displacing polymerase. In another embodiment, polynucleotide and/or oligonucleotide fragments are included in the composition for forming a synthon.

In another embodiment of the method, a set of oligonucleotides may be joined using a composition that comprises a crowding agent such as polyethylene glycol (PEG), Ficoll, or dextran in addition to or instead of the ss binding protein and at least 7 mM potassium salt such as KCl together with a strand displacing polymerase and a 5'-3' exonuclease in the absence of a non-strand displacing polymerase. In one embodiment the potassium salt is at a concentration of less than 150 mM for example, 20 mM-50 mM.

Also provided is a kit for polynucleotide assembly, comprising: i. a 5'-3' exonuclease; ii. an optional ligase; iii a strand-displacing polymerase; and iv. a ss DNA binding protein. In certain embodiments, the kit may further comprise dNTPs and/or a buffering agent, for example. The components of the kit may be in separate containers (e.g. one or more different reaction tubes), or, the components of the kit may be in a single container. The components may be lyophilized or in solution or in part lyophilized and in part in solution. The components may be immobilized in part or in whole on a solid surface such as a bead or surface of a reaction chamber or may be in solution. The components may be added to target polynucleotides that may be in part or in whole, immobilized or in solution. In some embodiments, the kit may contain one or more mixtures of the components of the kit. In some embodiments, the kit does not contain a non-strand-displacing polymerase, or a crowding agent.

In one embodiment, a polymerase having at least 80%, 85%, 90% or 95% sequence identity with SEQ ID NO:1 is provided for the assembly mixture. In another embodiment, a polymerase having a binding domain having at least 80%, 85%, 90%, or 95% sequence identity with SEQ ID NO:2 is provided for the assembly mixture. In another embodiment, a polymerase having at least 80%, 85%, 90% or 95% sequence identity with SEQ ID NO:3 is provided for the assembly mixture. These compositions may be used in reaction conditions in which the polymerase is strand displacing. The compositions may be used in reaction conditions in which any 3' exonuclease activity associated with the polymerase activity is active.

The assembly reaction may occur using ss or ds nucleic acids. Any number of fragments e.g., 2, 3, 4, 5, 6, 7, 8, 9, 10, 11, 12, 13, 14, 15, 16, 17, 18, 19 or 20 or more fragments can be assembled. Chemically synthesized ss polynucleotides can be assembled into ds overlapping fragments and hybridized and ligated to the ends of linearized vectors to form synthons suitable for cloning. Alternatively, duplex fragments can be assembled into synthons and inserted into vectors for cloning or PCR or isothermal amplification (see for example, FIG. 2A-2C). ss nucleic acid fragments can also be directly inserted into vectors (see for example, FIG. 7) by hybridizing the nucleic acid fragment to the 3' ss end of a linearized ds vector. The ss nucleic acids may be assembled through overlapping complementary ends at the same time, before, or after the a ss nucleic acid fragment has hybridized to the 3' ss end of the linearized vector. Assembled fragments may be amplified by PCR or isothermal methods before insertion into vectors for cloning. The nucleic acid fragments may contain randomized nucleotide sequences or degenerate code enabling libraries to be formed that contain representative variants at each nucleotide position of the variable region. The random sequence may be positioned between a defined sequence at each end. In one embodiment, the random sequence positioned between defined sequences may be for hybridizing to a second nucleic acid fragment (such as a second ss genomic polynucleotide) or to a linearized vector end. In one example, the random sequence hybridizes to a target genomic sequence for guiding a Cas9 protein to a target nucleic acid for gene editing (see for example, FIG. 9A-9C). Thus, in accordance with this aspect of the invention, the method may be used to hybridize at least one member of a set of polynucleotides to a second nucleic acid fragment (such as a second ss genomic polynucleotide) or to a linearized vector end. For example, the method may be for hybridization of the at least one member of the set of polynucleotides to a target genomic sequence in order to guide a Cas endonuclease such as Cas9 to a target genomic nucleic acid in a method of gene editing.

In some embodiments, a method is provided for assembling a plurality of polynucleotides into a synthon, that includes: combining the plurality of polynucleotides with a composition comprising a 5'-3' exonuclease, a strand displacing polymerase, optionally a ligase, a ss binding protein and a buffer wherein each polynucleotide has a 3' ss terminal polynucleotide sequence on one strand that can be hybridized to a complementary ss complementary sequence on a second polynucleotide and can be joined to form a continuous duplex polynucleotide optionally under isothermal conditions in a single container. The synthon can further be joined at its ends to the ends of a linearized plasmid for amplification and/or cloning In some embodiments, the entire assembly method may be carried out as a "one-step" reaction (in a single tube, which does not have to be opened during after the reaction is started). In one example, the components are mixed together in a reaction vessel and incubated at a temperature of between 40° C. to 60° C. for a period of time, e.g., 5 minutes to 12 hours, thereby producing the synthon.

In one aspect, the method includes a step of strand displacement in the polynucleotides to be joined by a polymerase having at least 90% amino acid sequence identity with SEQ ID NO:1 or SEQ ID NO:102 and/or SEQ ID NO:2 or SEQ ID NO:3. In embodiments of the method, no additional steps of 3'-5' exonuclease chew back are required. Another aspect further comprises enhancing the efficiency of the assembly reaction by including a potassium salt at a minimum concentration of 7 mM in the reaction mixture where the potassium salt is exemplified by KCl.

In one aspect, a method is provided, wherein the polynucleotides contain a random sequence between defined sequence ends. In another aspect, the method further comprises screening the random sequences for hybridizing activity with a genomic DNA and identifying the random sequence with the hybridizing activity. In another aspect, the method comprises performing gene editing by transcribing the random sequences with hybridizing activity to form RNA and using the RNA for gene editing in the presence of a Cas endonuclease.

In one embodiment of the composition, kit, or method of the invention, the strand-displacing polymerase used in the composition, kit, or method of the invention may be non-naturally occurring, such as a mutant or fusion protein. In the composition, kit, or method of the invention, the non-natural strand-displacing fusion polymerase may be characterized by an amino acid composition of the polymerase moiety that is at least 90% or 95% or 99% or 100% identical to any of SEQ ID NOs: 33-55 or SEQ ID NO:1 or of the DNA binding moiety that is at least 90% or 95% or 99% or 100% identical to any of SEQ ID NOs: 56-98 or SEQ ID NO:2. In one embodiment, the polymerase moiety may have an amino acid sequence that has 90% or 95% or 98% or 99% amino acid sequence identity with SEQ ID NO:102 fused to a heterologous DNA binding moiety selected from a polypeptide that has at least 90% or 95% or 99% or 100% amino acid sequence identity to any of SEQ ID NOs: 56-98.

In general in one aspect, a preparation is provided that includes a composition having an amino acid sequence that has at least 90% sequence identity to SEQ ID NO:3. The preparation may further comprise a 5'-3' exonuclease, for example a T5 exonuclease. The preparation may further comprise a ss DNA binding protein, for example, an ET SSB, *E. coli* recA, T7 gene 2.5 product, phage lambda RedB or Rac prophage RecT, more particularly a thermostable ss binding protein such as ET SSB. The preparation may further comprise a ligase. In one aspect, a preparation including the composition may further comprise a ss binding domain and a 5-3' exonuclease, wherein the preparation does not comprise a crowding agent and/or a non-strand-displacing polymerase. The preparation may further include a potassium salt.

In one aspect, the preparation including the composition may further comprise a plurality of polynucleotides in a set wherein at least a polynucleotide in the set has a sequence that overlaps with another polynucleotide in the set; and wherein the polynucleotides are selected from: (i) ds polynucleotides; (ii) ss oligonucleotides; (iii) at least one ds polynucleotide and at least one ss oligonucleotide; and (iv) a subpopulation of polynucleotides that are otherwise identical to one another except for a sequence that varies between the members of the sub-population. In one aspect the set of polynucleotides has at least 3 members or at least 4 members or at least 5 members.

In general, a method for producing a synthon, that includes: incubating a composition of claim 1 further comprising a 5'-3' exonuclease and, optionally, a ligase and a ss DNA binding protein, with a plurality of polynucleotides that form a set, wherein members of the set have sequences that overlap under suitable reaction conditions; and joining at least two the polynucleotides to produce a synthon. In one aspect, the set of polynucleotides contains at least 3 members or at least 4 members or at least 5 members. In one aspect, the preparation further includes a ligase. In one aspect, the preparation, further includes a ss DNA binding protein. In one aspect, the polynucleotides are ds and the ds polynucleotides are overlapping PCR products, overlapping restriction fragments or assembled from ss oligonucleotides. In one aspect, the polynucleotides are ss oligonucleotides. In one aspect, the set of polynucleotides comprises at least one ds polynucleotide and at least one ss oligonucleotide.

In general, a kit is provided that includes a preparation according to claim 1 and a 5'-3' exonuclease such as for example T5 exonuclease. In one aspect, the kit may further include a ss binding protein. In another aspect, the kit may include a ligase. In another aspect, the kit may include a buffering agent. In one aspect, the kit does not include a crowding agent. In one aspect, the composition and the 5'-3' exonuclease are in the same vessel. In another aspect, the composition and the 5'-3' exonuclease are in different vessels optionally in buffers suitable for combining into a single vessel.

In general, a composition is provided for assembling a synthon, that includes: a 5'-3' exonuclease, which in one aspect has ss endonuclease activity, for example having 90% sequence identity with SEQ ID NO:98; a strand-displacing polymerase, including a Family B strand displacing polymerase that is preferably non-naturally occurring such as a mutant or a fusion protein derived from a naturally occurring polymerase that may additionally be thermostable; optionally a ss DNA binding protein, such as for example the ss DNA binding protein is ET SSB, E. coli recA, T7 gene 2.5 product, phage lambda RedB or Rac prophage RecT; and a non-naturally occurring buffering agent, wherein the composition does not comprise a crowding agent and/or a non strand-displacing polymerase. In one aspect, the composition further includes a ligase and/or a ss binding domain. In one aspect, the composition includes a set of at least two polynucleotides (a plurality of polynucleotides). In one aspect, the composition does not include a non-strand displacing polymerase. In another aspect, the composition does not include 9° N, Phusion, Vent or Pfu DNA polymerases.

In one aspect, the strand-displacing polymerase in the composition is a fusion protein wherein the polymerase moiety has an amino acid sequence that is at least 90% identical to SEQ ID NO:1 or SEQ ID NO:102, or any of SEQ ID NOs:33-55. For example, the fusion protein may have an amino acid sequence that is at least 90% identical to SEQ ID NO:1 or 102 and SEQ ID NO:2. For example, the strand-displacing polymerase may have at least 90% sequence identity to SEQ ID NO:3. In one aspect, the composition may include a potassium salt having a concentration of at least 7 mM. In one aspect, the composition may include a set of polynucleotides in which at least one polynucleotide in the set has a sequence that overlaps with another polynucleotide in the set; and wherein the polynucleotides are selected from: (i) ds polynucleotides; (ii) ss oligonucleotides; (iii) at least one ds polynucleotide and at least one ss oligonucleotide; and (iv) a subpopulation of polynucleotides that are otherwise identical to one another except for a sequence that varies between the members of the sub-population. In one aspect, at least one member of the set of polynucleotides contains a random sequence positioned between a defined sequence at each end for hybridizing to a second ss genomic polynucleotide where for example, the random sequence is ss and is capable of hybridizing to a target genomic sequence for guiding a Cas protein to a target genomic nucleic acid for gene editing.

In general, a method for forming a synthon, is provided that includes incubating any of the compositions described above that contain a set of polynucleotides having sequences that overlap under suitable reaction conditions; and joining at least some of the polynucleotides to other polynucleotides to produce a synthon. In one aspect of the method, all or a portion of the polynucleotides in the set are ds. In another aspect, the ds polynucleotides are overlapping PCR products; overlapping restriction fragments, or synthetic ds molecules assembled from complementary ss oligonucleotides where these oligonucleotides may have been made in a synthesizer. In one aspect, all or a portion of the polynucleotides in the set are ss oligonucleotides. In one aspect, the set of polynucleotides comprises at least one ds polynucleotide and at least one ss oligonucleotide. In one aspect, the set of polynucleotides comprises a subpopulation of polynucleotides that are otherwise identical to one another except for a sequence that varies between the members of the sub-population. In one aspect, the overlapping sequences of the polynucleotides are less than 2 kilobases in length. In one aspect of the method, the strand-displacing polymerase comprises an amino acid sequence that is at least 90% identical to any of SEQ ID NOs:1, 2, 3, 33-96, or 102. In one aspect of the method, at least one member of the set of polynucleotides contains a random sequence between defined sequence ends. Another aspect of the method includes screening the random sequences for hybridizing activity with a genomic DNA and identifying the random sequence with the hybridizing activity. Another aspect of the method includes performing gene editing by transcribing the random sequences with hybridizing activity to form RNA and using the RNA for gene editing in the presence of a Cas protein.

In general, a kit for polynucleotide assembly is provided that includes: a 5'-3' exonuclease; a strand-displacing polymerase; and optionally a ss DNA binding protein wherein the kit optionally does not comprise a crowding agent and/or a non-strand-displacing polymerase. In one aspect, the kit includes a ligase. In another aspect, the kit includes dNTPs. In another aspect, the kit includes a buffering agent. In another aspect, the individual components of the kit may be in the same or separate containers such as one or more different storage or reaction containers.

In general, a composition is provided that includes a polymerase fusion protein, wherein the polymerase fusion protein includes an amino acid sequence that is at least 90% identical to any of SEQ ID NOs:2, 56-96 and a heterologous polymerase domain. In one aspect, the polymerase fusion protein includes an amino acid sequence that is at least 90% identical to any of SEQ ID NO:2; and a heterologous polymerase domain.

In general, a composition is provided that includes a polymerase fusion protein is provided wherein the polymerase fusion protein includes a polymerase domain that has an amino acid sequence that is at least 90% identical to any of SEQ ID NOs:1, 33-55, or 102; and a heterologous DNA binding domain. In one aspect, the polymerase fusion protein, the polymerase domain that has an amino acid sequence that is at least 90% identical to SEQ ID NO:1; and a heterologous DNA binding domain. In one aspect, the polymerase fusion protein has a polymerase domain that has an amino acid sequence that is at least 90% identical to SEQ ID NO:102; and a heterologous DNA binding domain. In one aspect, the polymerase fusion protein has an amino acid sequence that is at least 90% identical to SEQ ID NO:3.

In one aspect, the compositions above further include a 5'-3' exonuclease such as T5 exonuclease. In one aspect, the composition further includes a single-strand DNA binding protein for example a single-strand binding protein selected from an ET SSB, E. coli recA, T7 gene 2.5 product, phage lambda RedB or Rac prophage RecT. In one aspect, the composition may include a ligase. In one aspect, the ligase is thermostable. In one aspect, the composition does not include a crowding agent and/or a non-strand-displacing polymerase. In another aspect, the composition further includes dNTPs. In another aspect, the composition further includes a potassium salt having a concentration of at least 7 mM. One aspect of the composition includes a set of polynucleotides wherein at least a polynucleotide in the set has a sequence that overlaps with another polynucleotide in the set; and wherein the polynucleotides are selected from: (i) ds polynucleotides; (ii) ss oligonucleotides; (iii) at least one ds polynucleotide and at least one ss oligonucleotide; and (iv) a subpopulation of polynucleotides that are otherwise identical to one another except for a sequence that varies between the members of the sub-population.

In general, a method is provided for producing a synthon, that includes incubating a set of polynucleotides where individual polynucleotides contain sequences that overlap with sequences in other polynucleotides, where the overlapping sequences of different polynucleotides are capable of cross-hybridizing under suitable reaction conditions, and where for example the overlapping region is less than 2 kilobases, with a composition comprising a polymerase characterized above, wherein the composition further includes a 5'-3' exonuclease and, optionally, a ligase and a ss DNA binding protein; and joining the polynucleotides to produce a synthon.

In different aspects, the composition includes a ligase; and/or a ss DNA binding protein. In another aspect, one or more polynucleotides in the set are ds, where the ds polynucleotides are PCR products, overlapping restriction fragments or assembled from ss oligonucleotides and/or one or more polynucleotides are ss oligonucleotides; and/or the set of polynucleotides includes at least one ds polynucleotide and at least one ss oligonucleotide.

In general, a kit for polynucleotide assembly is provided that includes a polymerase fusion protein, as described above and a 5'-3' exonuclease; and a ss DNA binding protein. In one aspect, the kit may include any or all of a ligase, dNTPs, and buffering agent where the components of the kit may be in the same vessel or in different vessels.

BRIEF DESCRIPTION OF THE FIGURES

The skilled artisan will understand that the drawings, described below, are for illustration purposes only. The drawings are not intended to limit the scope of the present teachings in any way.

FIG. 1A-1E shows how the assay described in Example 1 differentiates between a strand displacing and non-strand displacing polymerase. This assay confirms that T4 DNA polymerase is non-strand displacing and terminates synthesis of a template DNA at 44 nucleotides in length at a blocking oligonucleotide (2) (FIG. 1C) whereas Bst polymerase (FIG. 1D) and a non-natural polymerase (FIG. 1E) are strand displacing and can continue DNA synthesis of a FAM primer (1) by displacing the blocking oligonucleotide (27 nucleotides in length).

FIG. 1A shows the sequence and position of the primer (1) and a blocking oligonucleotide (2) on a DNA template used in the assay for the enzymes below.

FIG. 1B shows fluorescence observed in samples obtained after capillary electrophoresis where no enzyme was added and the starting material formed a peak at a position corresponding to 24 nucleotides of the FAM primer.

FIG. 1C shows the result of adding T4 DNA polymerase. The primer was extended to a final length of 44 nucleotides (24 nucleotides plus 20 nucleotides) but was terminated by the blocking oligonucleotide.

FIG. 1D shows that Bst DNA polymerase (large fragment) strand-displaces the blocking oligonucleotide and copies template by extending the primer to a total length of 72 nucleotides (24+20+27+dA).

FIG. 1E shows a family B strand displacing DNA polymerase which is a proof reading polymerase that strand displaces blocking oligonucleotides and copies template by extending the primer by 71 nucleotides (24+20+27).

FIG. 2A shows the incorporation of the amplicons of each of 5 fragments into 5 plasmids with ampicillin resistance markers. The 5 fragments were initially amplified with primers that generated amplicons which had overlapping regions as well as flanked by NotI restriction sites. The NotI cleavage produces sticky ends. NotI restriction (3) permitted release of each amplicon from the vectors. The restriction enzyme cleaved fragments have an 80 base pair overlap region (4) with the adjacent fragment. In FIG. 2C, the overlap between the first fragment and an adjacent reagent vector end and a last fragment and adjacent reagent vector end is 15-25 nucleotides, for example, 20 nucleotides, for convenience and cost reduction but this is not intended to be limiting.

FIG. 2B shows NotI cleaved optionally sequenced fragments (5) where the amplicon is retrieved from a vector and the 5' ends of Frag. 1 are SEQ ID NO:103 and 104 and of Frag. 2 top strand is SEQ ID NO:105. These fragments were then treated with an enzyme mixture that included T5/5'-3' exonuclease, DNA polymerase with 3'-5' exonuclease activity, a ss binding protein ET SSB (New England Biolabs, Ipswich, Mass.) and DNA ligase in a single reaction vessel (6)-(8). Although NotI is used here, other restriction endonucleases may be used for cleavage depending on convenience. Double digestion with two or more restriction endonucleases may be used. For example, double digestion of vector DNA with two restriction endonucleases has been found to reduce background from uncut vector. The overlapping ss DNA sequences hybridized to adjacent fragments. The T5 exonuclease chewed back a DNA strand from 5' to 3' on each fragment to expose a 3' ss region (6) which allowed the fragments to anneal together in the presence of ss binding protein (7). Removal of the 2 base flap was achieved by means of the 3'-5' exonuclease activity associated with a strand displacing polymerase followed by extension by the strand displacing polymerase to fill the gap in the assembled product (8). Any residual nick or 5' flap may be repaired by a ligase and/or T5 exonuclease.

FIG. 2C shows the 5 fragments (Frag. 1-Frag. 5) now joined in sequence and inserted into a second plasmid carrying chloramphenicol resistance gene (Cam) for transformation into a bacterial host.

FIG. 3A shows chloramphenicol only.

FIG. 3B shows chloramphenicol+IPTG+XgaI.

FIG. 8A-8C shows the workflow for bridging ds DNA by a short ss oligonucleotide. (The protocol is described in FIG. 7).

FIG. 8A provides an example of a sequence of a short ss oligonucleotide for integration into a ds DNA vector shown here as a CRISPR Nuclease Vector with OFP Reporter.

FIG. 8B shows the workflow starting with a ss oligonucleotide and a ds CRISPR Nuclease Vector (9424 bp) treated with 5'-3' exonuclease, strand displacing polymerase, a ligase and a ss binding protein (13) to produce a complete ds circular DNA. This DNA was transformed into competent cells (14). After an overnight incubation, the colonies were analyzed by a mini-prep and then the plasmids sequenced (15).

FIG. 8C shows the insert and adjacent sequences (SEQ ID NO:106) of U6 promoter sequence (vector) including the designed ss oligonucleotide (71mer), and scaffold template-specific sequence (vector). The ss oligonucleotide (71mer) including an overlap region of 25 nucleotides at each end (21 nucleotides of the target DNA in bold)) was properly integrated into the vector in host cells.

FIG. 9A-9C show that a similar workflow to that in FIG. 8B can be used for an ss oligonucleotide having degenerate bases between the overlapping ends. Again the starting sequence in FIG. 9A is shown above the workflow (FIG. 9B) and the Sanger-sequencing results from colonies from assembly pool is shown below (FIG. 9C) with the solid line referring to a pool of sgRNA targeting sequences. The sgRNA targeting sequence contained 21 variable nucleotide positions providing $4^{21}$ variants. The pool contained every possible variant and each variant was amenable to cloning reflecting the degeneracy of the sequence between the overlapping ends and the vector. FIG. 9A shows the sequence of a ss oligonucleotide containing degenerate bases (SEQ ID NO:29). The sgRNA targeting sequence of FIG. 9A was inserted between a U6 promoter sequence and a scaffold template specific sequence of the vector (16), transformed into host cells (17) and analyzed for synthons by miniprep and sequencing (18) as described above and herein. Sanger sequencing was performed on clones from the assembly pool. An example of a sequence is provided in FIG. 9C.

FIGS. 11A and 11B show the amino acid sequences from a variety of DNA binding domains from Pyrococcus furiosus, an Archaebacterium.

FIGS. 13A and 13B show the amino acid sequences from a variety of DNA binding domains from Thermotoga maritima, a thermophilic bacterium.

FIG. 16 shows the amino acid sequences of fusions of DNA polymerase SP-17 (DNA polymerase family B) with binding domains BD-07, 08 and 98.

FIG. 17 shows the amino acid sequences for fusions of DNA polymerase SP-04 (DNA polymerase family A) with binding domains BD-07, 02 and 98.

FIGS. 18A and 18B shows the amino acid sequences of fusions of DNA polymerase SP-61 (DNA polymerase family B) with binding domains BD-07, 09, 23, 62, 93 and 109.

FIGS. 19A and 19B shows the amino acid sequences for fusions of DNA polymerase SP-49 (DNA polymerase family B) with binding domains BD-07, 09, 23, 62, 93 and 109.

DESCRIPTION OF TERMS

Figure 1B:
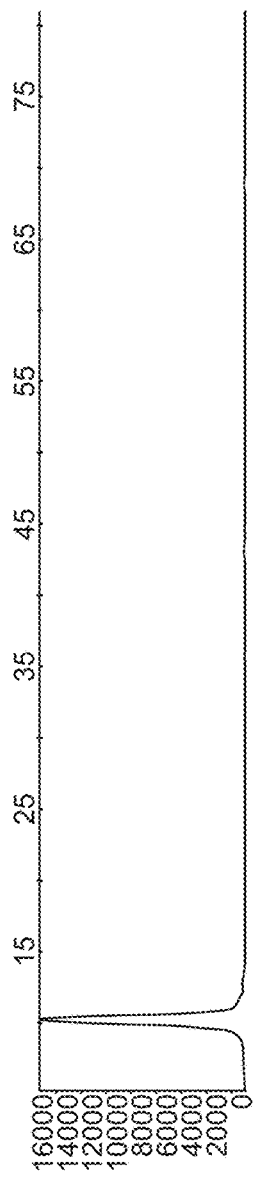

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "synthon" as used in the field of gene synthesis refers to a polynucleotide assembly. Polynucleotide assembly may include assembling overlapping fragments of a size that can be prepared on an oligonucleotide synthesizer which at the present time is generally 2000-3000 bases for each synthetic polynucleic acid. Alternatively, overlapping fragments may be obtained by PCR from naturally occurring nucleic acid to which adaptors have been attached to provide the overlapping sequences. For assembly purposes there is no limitation on the size of each fragment. Many fragments can be assembled end to end relying on overlapping sequences at the ends to enable constructs of any desirable length to be made accurately and efficiently. Preferably a synthon is a continuous longer polynucleotide that does not contain gaps or nicks that are formed from the assembly of shorter polynucleotides. The length of synthons resulting from assembly of nucleic acid fragments is not limited to any particular size however.

As used herein, the term "5'-3' exonuclease", refers to an exonuclease that degrades DNA from the 5' end, i.e., in the 5' to 3' direction. 5'-3' exonucleases of interest can remove nucleotides from the 5' end of a strand of ds DNA at a blunt end and, in certain embodiments, at a 3' and or 5' overhang. T5 exonuclease, lambda exonuclease and T7 exonuclease are examples of 5'-3' exonucleases. In certain embodiments, T5 exonuclease is preferred. T5 exonuclease additionally has a ss endonuclease activity.

As used herein, the term "ligase", refers to an enzyme that can covalently join a 3' end of a DNA molecule to a 5' end of another DNA molecule, particularly at a nick. Examples of ligases include T7 ligase, T4 DNA ligase, E. coli DNA ligase and Taq ligase, although many others are known and may be used herein.

As used herein, the term "strand-displacing polymerase", refers to a polymerase that is able to displace one or more nucleotides, such as at least 10 or 100 or more nucleotides that are downstream from the enzyme. Strand displacing polymerases can be differentiated from Phusion where the art recognized definition of Phusion is a non-strand displacing polymerase. In some embodiments, the strand displacing polymerase is stable and active at a temperature of at least 50° C. or at least 55° C. (including the strand displacing activity). Taq polymerase is a nick translating polymerase and, as such, is not a strand displacing polymerase.

As used herein, the term "single strand (ss) DNA binding protein", refers to proteins that bind to ss DNA and prevent premature annealing, protect the ss DNA from being digested by nucleases, and polymerases and/or remove secondary structure from the DNA to allow other enzymes to function effectively upon it. Inclusion of a ss binding protein in the compositions described herein is preferable to optimize the efficiency of synthon formation. Examples of ss DNA binding proteins are T4 gene 32 protein, E. coli SSB, T7 gp2.5 SSB, and phage phi29 SSB, and ET SSB although many others, e.g., RedB of lambda phage, RecT of Rac prophage and the sequences listed below, are known and may be used herein. A thermostable ss DNA binding protein that is stable at 50° C. may be used in some cases. Thus, in one embodiment of the composition, kit, or method of the invention, the ss DNA binding protein is T4 gene 32 protein, E. coli SSB, T7 gp2.5 SSB, phage phi29 SSB, ET SSB, RedB of lambda phage, or RecT of Rac prophage. In one embodiment, the ss DNA binding protein is ET SSB. In one embodiment of the composition, kit, or method of the invention, the ss DNA binding protein is thermostable (i.e. stable at 40° C.-60° C.).

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, 3-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

It may be desirable to use a strand displacing polymerase that has 3' exonuclease activity. While not wishing to be limited by theory, the 3' exonuclease activity is desirable to remove a flap sequence on the 3' end of a duplex where the flap sequence may be the result of enzyme cleavage to extract the target polynucleotide from the plasmid in which it is placed. This is the case when NotI is used as described in the examples. However, if a restriction endonuclease is used that creates a blunt end on the excised fragment, 3' exonuclease activity may not be required.

The 3' exonuclease activity can be routinely determined by using a standard DNA template and primers where the primers either have or do not have non-hybridized 3' nucleotides. If the polymerase has 3' exonuclease activity, an amplicon will be detected using either primer pair. If the polymerase lacks the 3' exonuclease activity, no amplicon will be detected using those primers having a non-hybridized 3' nucleotide.

As used herein, the term "potassium salt", refers to a salt of potassium including, but not limited to, KCl. The term "sodium salt", refers to a salt of sodium including, but not limited to, NaCl.

As used herein, the term "polynucleotide" encompasses oligonucleotides and refers to a nucleic acid of any length. Polynucleotides may be DNA or RNA. Polynucleotides may be ss or ds unless specified. Polynucleotides may be synthetic, for example, synthesized in a DNA synthesizer, or naturally occurring, for example, extracted from a natural source, or derived from cloned or amplified material. Polynucleotides referred to herein may contain modified bases.

As used herein, the term "set of polynucleotides", refers to a collection of at least 2 polynucleotides. In some embodiments, a set of polynucleotides may comprise at least 5, at least 10, at least 12 or at least 15 or more polynucleotides.

As used herein, the term "overlapping sequence", refers to a sequence that is complementary in two polynucleotides and where the overlapping sequence is ss, on one polynucleotide it can be hybridized to another overlapping complementary ss region on another polynucleotide. By way of example, the overlapping sequence may be complementary in at least 5, 10, 15, or more polynucleotides in a set of polynucleotides. An overlapping sequence may be at or close to (e.g., within about 5, 10, 20 nucleotides of) the 3' ends of two distinct molecules (e.g., the 3' ends of two ss oligonucleotides, or the 3' end of the top strand of first ds polynucleotide and the 3' end of the bottom strand of a second ds molecule), where, if the non-overlapping sequence is at the 3' ends then the non-overlapping sequence may be removed using a 3'-5' exonuclease activity of a polymerase. An overlapping sequence may vary in length and, in some cases, may be at least 12 nucleotides in length (e.g. at least 15, 20 or more nucleotides in length) and/or may be up 100 nucleotides in length (e.g., up to 50, up to 30, up to 20 or up to 15 nucleotides in length). Alternatively, overlapping sequences in the set of polynucleotides may be 2 kb or less, or 1 kb or less or less than 900 bases, 800 bases, 700 bases, 600 bases, 500 bases, 400 bases, 300 bases, 200 bases or 100 bases. Preferably the overlapping sequence length is in the range of 15 nucleotides-80 nucleotides for example up to 20, up to 25, up to 30, up to 35, up to 40, up to 45, up to 50, up to 55, up to 60, up to 65, up to 70, up to 75, or up to 80 nucleotides. The minimum length of the overlap may be defined by a Tm that is preferably equal to or greater than 48° C.

As used herein, the term "polynucleotide assembly", refers to a reaction in which two or more, four or more, six or more, eight or more, ten or more, 12 or more 15 or more polynucleotides, e.g., four or more polynucleotides are joined to another to make a longer polynucleotide. The product of a polynucleotide assembly reaction, i.e., the "assembled polynucleotide" or "synthon" in many embodiments should contain one copy of each of the overlapping sequences.

As used herein, the term "incubating under suitable reaction conditions", refers to maintaining a reaction a suitable temperature and time to achieve the desired results, i.e., polynucleotide assembly. Reaction conditions suitable for the enzymes and reagents used in the present method are known (e.g. as described in the Examples herein) and, as such, suitable reaction conditions for the present method can be readily determined. These reactions conditions may change depending on the enzymes used (e.g., depending on their optimum temperatures, etc.).

As used herein, the term "isothermal" refers to temperature conditions that do not require active modulation of temperature for assembly to occur. Insignificant variations in the temperature of a water bath or heating block are within the scope of the meaning of the term isothermal. By way of example, the term "isothermal", may refer to reaction conditions that do not require a heat denaturation step after the reaction has started. More specifically, isothermal methods do not involve thermocycling, i.e., cycling between a denaturation temperature of above 90° C. and an annealing/extension temperature. Isothermal conditions usually involve incubation at a temperature that is below 90° C. for a period of time (e.g., 5 minutes to 12 hours or more). In one embodiment, isothermal amplification reactions were performed at a temperature in the range of 30° C.-75° C., for example, 40° C.-60° C.

As used herein, the term "joining", refers to the production of covalent linkage between two sequences.

As used herein, the term "composition" refers to a combination of reagents that may contain other reagents, e.g., glycerol, salt, dNTPs, etc., in addition to those listed. A composition may be in any form, e.g., aqueous or lyophilized, and may be at any state (e.g., frozen or in liquid form).

As used herein a "vector" is a suitable DNA into which a fragment or a synthon may be integrated such that the engineered vector can be replicated in a host cell. A linearized vector may be created restriction endonuclease digestion of a circular vector or by PCR. The concentration of fragments and/or linearized vectors can be determined by gel electrophoresis or other means.

Any one or more of the proteins (e.g., the ligase, SSBP, 5'-3' exonuclease or polymerase, etc.) used herein may be temperature sensitive or thermostable where, as used herein, the term "temperature sensitive" refers to an enzyme that loses at least 95% of its activity after 10 minutes at a temperature of 65° C., and the term "thermostable" refers to an enzyme that retains at least 95% of its activity after 10 minutes at a temperature of 65° C.

The term "domain" refers to a structurally conserved part of a larger protein, the sequence and tertiary structure of which that can evolve, function, and exist independently of the rest of the protein. A "domain" can be transferred to another protein with the expectation that it will still function.

The term "sequence-specific DNA binding domain" refers to a domain that, based on its predicted tertiary structure and/or sequence identity to other proteins, is predicted to bind double stranded DNA in a sequence-specific manner. Sequence-specific DNA binding domains are commonly found in transcription factors, e.g., transcriptional activators or repressors. Sequence-specific DNA binding domains have much higher affinity (e.g., at least 1000× more affinity) for specific DNA sequences (which may be composed of a sequence of 4, 5, 6, 7 or 8 or more continuous or discontinuous nucleotides) and do not bind to all sequences with the same affinity. The sequence-specific DNA binding domain, when it is present in a longer protein, e.g., a transcription factor, is sufficient to anchor the protein at a particular nucleotide sequence in double stranded DNA, thereby allowing the longer protein to affect another process that is local to the binding site, e.g., activate transcription, inhibit transcription, effect recombination or transposition, etc. A sequence-specific DNA binding domain may have an amino acid sequence that is at least 80%, at least 90%, at least 95%, or at least 98%, identical to a naturally occurring sequence that based on its predicted tertiary structure and/or sequence identity to other proteins, is predicted to bind double stranded DNA in a sequence-specific manner.

The term "heterologous", when used in the context of a fusion protein that contains a first domain and a second "heterologous" second domain, refers to a combination of elements that are not usually found together naturally. In the context of a fusion protein, the two domains may be from different distinct proteins, which proteins may be from the same species (in which case the proteins may be expressed in the same cell) or different species.

DETAILED DESCRIPTION OF EMBODIMENTS

Before various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Fusion Proteins

In some embodiments, the fusion protein may be a fusion between a DNA polymerase and a sequence-specific DNA binding domain, where the sequence-specific DNA binding domain may be N-terminal or C-terminal to the DNA polymerase. In other words, the fusion protein has a polymerase domain and a heterologous sequence-specific DNA binding domain. The fusion protein has a polymerase activity and, as would be apparent, such a fusion protein does not exist in nature, i.e., is non-naturally occurring.

As noted above, the polymerase may be a family A polymerase or a family B polymerase. Family A polymerases, which includes bacterial, archaeal and bacteriophage polymerases, share significant similarity to *Escherichia coli* polymerase I and have an exonuclease activity, which is usually provided by the N-terminal portion of the protein. Family A polymerases are classed as being replicative polymerases or repair polymerases. The repair polymerases "proofread" the new strands created and rectify any mistakes in the base pairing. The replicative members of family A include the T7 DNA polymerase as well as the eukaryotic mitochondrial DNA polymerase γ. The repair polymerases include DNA pol I from *E. coli*, pol I from *Thermus aquaticus* and pol I from *Bacillus stearothermophilus*. Family B polymerases have six regions of similarity (numbered from I to VI). The most conserved region (I) includes a conserved tetrapeptide with two aspartate residues. Its function is not yet known, but it has been suggested that it may be involved in binding a magnesium ion. All sequences in the B family contain a characteristic DTDS motif, and possess many functional domains, including a 5'-3' elongation domain, a 3'-5' exonuclease domain, a DNA binding domain, and binding domains for both dNTP's and pyrophosphate. If the polymerase is a family A polymerase, then the DNA binding domain of a sequence-specific DNA binding protein can be N-terminal or C-terminal to the polymerase in the fusion protein. If the polymerase is a family B polymerase, then the DNA binding domain of a sequence-specific DNA binding protein can be N- or C-terminal to the polymerase in the fusion protein. In certain embodiments, the fusion protein may further comprise a flexible linker between the polymerase domain and the DNA binding domain. Several examples of fusion proteins that work are shown in FIGS. 16, 17, 18A, 18B, 19A and 19B. Further fusion proteins can be readily designed using these examples.

In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, Omni Klen Taq DNA polymerase series, Klen Taq DNA polymerase series, T7 DNA polymerase, and Tth DNA polymerase. In some embodiments, the DNA polymerase is Bst DNA polymerase. In other embodiments, the DNA polymerase is *E. coli* DNA polymerase I. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Bst polymerase, Tli polymerase, Pfu polymerase, Pfu turbo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, Therminator polymerase, phage Phi29 polymerase, and phage B103 polymerase. In some embodiments, the polymerase is KOD polymerase. In some embodiments, the polymerase is Therminator polymerase. In some embodiments, the polymerase is phage Phi29 DNA polymerase. In some embodiments the polymerase is phage B103 polymerase, including, for example, the variants disclosed in U.S. Patent Publication No. 2011/0014612 which is incorporated by reference herein.

In some embodiments, the amino acid sequence of the polymerase may be at least 90% identical to (e.g., at least 95% identical to, at least 98% identical to or at least 99% identical to) the amino acid sequence of a naturally occurring bacterial or archaebacterial polymerase such as a polymerase from *Pyrococcus* or *Thermococcus*. Exemplary archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase (New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Thermococcus* sp. NA1; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2, etc.

As would be apparent, the polymerase may be a thermostable polymerase, where the term "thermostable" refers to a polymerase that has an optimal activity at a temperature above 45° C., e.g., above 60° C. The polymerase may be strand-displacing, not strand displacing and, in certain embodiments it may or may not have a proofreading activity. Fusions of strand-displacing polymerases are of particular interest.

The sequence-specific DNA binding domain of the fusion protein should be capable of autonomously binding its target sequence as a discrete unit and may be obtained from any type of sequence-specific DNA binding protein, e.g., a transcription factor such as a transcriptional activator or transcriptional repressor or the like. As would be apparent, if the sequence-specific DNA binding domain is from a transcription factor, then other domains of the transcription factor (e.g., the transcriptional activation or repression domain) may not be in the fusion protein. In particular embodiments, the DNA binding domain may have a helix-loop-helix structure, a ribbon-helix-helix structure, helix-turn-helix structure (e.g., from the lambda or repressor and lacI), a winged helix structure or a homeodomain structure or the like. As for the polymerase, the amino acid sequence of the sequence-specific DNA binding domain may be at least 90% identical to (e.g., at least 95% identical to, at least 98% identical to or at least 99% identical to) the amino acid sequence of the DNA binding domain of a naturally occurring bacterial or archaebacterial transcription factor, e.g., from *Pyrocyoccus* or *Thermococcus* or any of the other species listed above or below. The sequence-specific DNA binding domain used should not be the DNA binding domain of a non-specific DNA binding protein, e.g., a topoisomerase, HMG protein, histone, gyrase, transposase or the DNA binding domain of Sso7D or an ortholog thereof (including Sac7d) or a variant thereof, as described in Choli (Biochim. Biophys. Acta 1988 950: 193-203), McAfee (Biochemistry 1995 34: 10063-10077) and Pavlov (Proc. Natl Acad. Sci. 2002 99 13510-13515). These proteins have no known sequence preference and are not transcription factors. Likewise, the DNA binding domain does not form a DNA sliding clamp structure, as described in thioredoxin and UL42 (see Bedford Proc. Natl Acad. 1997 Sci. USA, 94: 479-484; Zuccola, Mol. Cell 2000 5: 267-278; and Shamoo Cell 1999 99: 155-166).

In certain embodiments, the sequence-specific DNA binding domain of the fusion protein has a winged helix motif, which has a compact α/β structure that consists of two wings (W1 and W2), three α helices (H1, H2 and H3) and three β strands (S1, S2 and S3), arranged in order H1-S1-H2-H3-S2-W1-S3-W2. This domain is approximately 90-120 amino acids in length. The N-terminal half of the motif is believed to be helical, whereas the C-terminal half is believed to be composed of two of the three strands forming the twisted antiparallel β sheet and the two large loops or wings, W1 and W2. Wing W1 connects strands S2 and S3, and wing W2 extends from strand S3 to the C terminus of the DBD. HFH proteins are members of the helix-turn-helix (HTH) superfamily, but differ from canonical HTH proteins in the length of the 'turn' connecting helices H2 and H3. The DNA-recognition helix makes sequence-specific DNA contacts with the major groove of DNA, while the wings make different DNA contacts, often with the minor groove or the backbone of DNA. Several winged-helix proteins display an exposed patch of hydrophobic residues thought to mediate protein-protein interactions. Many proteins contain a winged helix DNA-binding domain, including transcriptional repressors (e.g., the biotin repressor, LexA repressor and the arginine repressor), transcription factors (e.g., the hepatocyte nuclear factor-3 protein, heat-shock transcription factor, and the general transcription factors TFIIE and TFIIF) and endonucleases (e.g., FokI and TnsA). Winged helix proteins are reviewed in Gajivala (Current Opinion in Structural Biology 2000 10: 110-116).

In some embodiments, the polymerase activity of the fusion protein has an improvement in one or more biochemical characteristics relative to the polymerase portion of the fusion protein on its own, i.e., in the absence of the DNA binding domain. The improved biochemical characteristic may be an increase in processivity, an increase in thermal stability, an increase in salt tolerance, an increase in tolerance to impurities or an increase in speed, an increase to amplify GC rich template, an increase in PCR DNA product specificity (e.g., an increase of at least 10%, an increase of at least 20%, an increase of at least 50%, an increase of at least 100% or an increase of at least 200%), without effecting the fidelity of the polymerase. In particular embodiments, the polymerase activity of the fusion protein has an improvement in PCR efficiency relative to the polymerase portion of the fusion protein on its own, i.e., in the absence of the DNA binding domain. Polymerase efficiency may be measured by measuring the amount of amplicon produced under a given set of thermocycling conditions, where the product may be at least 1 kb, at least 2 kb, at least 3 kb, at least 5 kb, at least 10 kb or at least 15 kb in length. In certain cases, the fusion protein may allow products to be amplified using a shorter extension time (e.g., a 10% shorter, a 20% shorter, a 50% shorter or an 80% shorter extension time), relative to the polymerase portion of the fusion protein on its own, i.e., in the absence of the sequence-specific DNA binding domain.

Methods

Also provided herein are a variety of methods that generally comprise combining a DNA template with nucleotides and a composition comprising a fusion protein, as described above, to produce a reaction mix, and incubating the reaction mix in order to copy the DNA template. As would be apparent, the reaction mix may contain, in some embodiments, one or more primers (e.g., a single primer, a random primer, a single or several pairs of PCR primers, or a set of overlapping oligonucleotides as described elsewhere herein). In some cases, the DNA template itself may be a plurality of overlapping primers. In other embodiments, the reaction mix may comprise a plurality of primers and genomic DNA (e.g., mammalian genomic DNA).

Depending on the desired result, the copying step may be done using isothermal conditions, (e.g., by incubating the reaction at one or more temperatures that are above 50° C., such as a temperature in the range of 60° C. to 75° C. In other embodiments, the copying may be done using thermocycling conditions, e.g., 8 to 50 cycles of an annealing temperature, an extension temperature, and a denaturation temperature. In some cases, the annealing temperature and the extension temperature may be the same. In some cases, the reaction mix may comprise a plurality of overlapping primers as well as other reagents (as described elsewhere herein), and the copying step may result in the assembly of a synthon. Synthon assembly is usually done using thermocycling conditions. In some cases, the copying may be done by PCR, in which case the reaction mix may contain one or more pairs of PCR primers. Depending on the desired application, the length of the amplicon or synthon produced by this method may vary greatly and, in some cases, may be 50 bp to 40 kb in length, e.g., 50 bp to 10 kb. In certain embodiments, the template may be genomic DNA.

Further compositions and methods are described below.

The sequences that overlap in the set of polynucleotides may be of any suitable length such as 2 kb or less, or 1 kb or less or less than 900 bases, 800 bases, 700 bases, 600 bases, 500 bases, 400 bases, 300 bases, 200 bases or 100 bases. The overlapping region may be as few as 8 nucleotides. Preferably the overlapping sequence length is in the range of 15 nucleotides-80 nucleotides for example up to 20, up to 25, up to 30, up to 35, up to 40, up to 45, up to 50, up to 55, up to 60, up to 65, up to 70, up to 75, or up to 80 nucleotides. For example, the minimum length of the overlap may be defined by a Tm that is preferably equal to or greater than 48° C.

Synthetic oligonucleotides and polynucleotides may contain errors created during their synthesis prior to their use in synthon assembly. To correct these errors prior to assembly, it is desirable to perform a mismatch repair step. To this end, various methods have been described to achieve mismatch repair of the synthetic nucleic acids prior to assembly. A population of synthetic nucleic acids may have random errors so that denaturation and renaturation of the preparation may reveal mismatches. Proteins that have been isolated from nature such as mutHLS, cel-1 nuclease, T7 endo 1, uvrD, T4 EndoVII, *E. coli* EndoV, (see U.S. Pat. No. 7,851,192 and U.S. Pat. No. 8,048,664) that can bind selectively to DNA duplexes containing mismatches; cleave nucleic acids at the mismatched bases and optionally replace with correct bases based on the nucleotide sequences of the templates.

Despite teaching in the art that a non-strand displacing polymerase must be utilized with a ss binding protein, 5'-3'-exonuclease and ligase to assemble fragments of DNA, it has been surprisingly shown herein that a strand displacing polymerase may be used under conditions where strand displacement occurs and that this is efficient at surprising low concentrations of starting polynucleotide fragments to effectively generate a single nucleic acid from a plurality of fragments.

Examples of strand displacing polymerases that may be used in embodiments of an assembly mixture, composition, kit, or method of the invention include members of family B polymerases, such as (but not limited to) any of those identified in Table 1 (SEQ ID NOs:33-55). In addition, fusions of such polymerases may be used, for example fusions between a plurality of polymerases and/or ss binding domains (such as shown in Table 2) (SEQ ID NOs: 56-97). In embodiments any of the polymerase moieties in Table 1 or proteins having at least 80%, 85%, 90%, 95% 98%, 99% or 100% amino acid sequence identity to any of these protein moieties in Table 1 may be fused at the N-terminal end or the C-terminal end to any of the DNA binding domains described in Table 2 or a protein moiety have at least 80%, 85%, 90%, 95% 98%, 99% or 100% amino acid sequence identity to any of the DNA binding moieties in Table 2 to form a strand displacing fusion polymerase for use herein. The DNA binding domain may optionally be fused to the N-terminal end or the C-terminal end of the polymerase.

Variants of other polymerases or novel isolates that are revealed to be strand displacing as determined by the assay provided herein (see for example, FIGS. 1A-1E and Example 1) may also be used. Sequences of the polymerases found from these sources are readily accessible through GenBank. Because of the high degree of conservation of strand displacing sequences, any variant having 80%, 85%, 90%, or 95% amino acid sequence identity with such wild type polymerases might be expected to have strand displacing properties that can be quickly and easily verified in the assay provided in Example 1 in a preselected buffer without undue experimentation.

In one embodiment, the reaction mixture, composition, kit, or method of the invention comprises or uses a strand displacing polymerase having at least 80%, 85%, 90%, 95%, 98%, 99% or 100% sequence identity with SEQ ID NO:1 or SEQ ID NO:102 (e.g. 100% sequence identity with SEQ ID NO:1 or SEQ ID NO:102). In another embodiment, the reaction mixture, composition, kit, or method of the invention comprises or uses a polymerase having a binding domain having at least 80%, 85%, 90%, 95%, 98%, 99% or 100% sequence identity with SEQ ID NO:2 (e.g. 100% sequence identity with SEQ ID NO:2). In another embodiment, the reaction mixture, composition, kit, or method of the invention comprises or uses a polymerase having at least 80%, 85%, 90%, 95%, 98%, 99% or 100% sequence identity with SEQ ID NO:1, or SEQ ID NO:102 and SEQ ID NO:2, or SEQ ID NO:3 or any of SEQ ID NOs:33-97 (e.g. 100% sequence identity with SEQ ID NO:1 or SEQ ID NO: 102, and SEQ ID NO:2 or SEQ ID NO:3 or any of SEQ ID NOs:33-97). These compositions may be used in reaction conditions in which the polymerase is strand displacing. The compositions may be used in reaction conditions in which any 3'-5' exonuclease activity associated with the polymerase activity is active. This may be helpful when a restriction enzyme is used in the reaction such as NotI. In this case, the 3'-5' exonuclease may remove a flap sequence on the 3' end of the duplex. However, if a restriction endonuclease is used that creates a blunt end on the excised fragment, 3'-5' exonuclease activity may not be required. The assembly reaction may be performed under isothermal conditions. In one embodiment the isothermal conditions are 50° C.

TABLE 1

Table of polymerases

| | | | |
|---|---|---|---|
| *Methanocaldococcus vulcanius* M7 | SP-13 | gi\|502573182 | SEQ ID NO: 33 |
| *Archaeoglobus fulgidus* DSM 4304 | SP-16 | gi\|499180464 | SEQ ID NO: 34 |
| *Archaeoglobus profundus* DSM 5631 | SP-17 | gi\|502704426 | SEQ ID NO: 35 |
| *Caldicellulosiruptor hydrothermalis* 108 | SP-19 | gi\|503168530 | SEQ ID NO: 36 |
| *Desulfurococcus mucosus* DSM 2162 | SP-27 | gi\|503328138 | SEQ ID NO: 37 |
| *Pyrolobus fumarii* | SP-29 | gi\|503791850 | SEQ ID NO: 38 |
| *Pyrobaculum oguniense* CH | SP-30 | gi\|379003208 | SEQ ID NO: 39 |
| *Staphylothermus marinus* F1 | SP-33 | gi\|500164563 | SEQ ID NO: 40 |
| *Pyrococcus yayaosii* CH1 | SP-42 | gi\|503672202 | SEQ ID NO: 41 |
| *Thermococcus* sp.AM4-del | SP-43 | gi\|503888003 | SEQ ID NO: 42 |
| *Thermococcus hydrothermalis* | SP-44 | gi\|17375628 | SEQ ID NO: 43 |
| *Thermococcus thioreducens* | SP-45 | gi\|117958105 | SEQ ID NO: 44 |
| *Thermococcus waiotapuensis* | SP-46 | gi\|378813034 | SEQ ID NO: 45 |
| *Thermococcus sibiricus* MM 739 | SP-47 | gi\|506329477 | SEQ ID NO: 46 |
| *Pyrococcus glycovorans* | SP-48 | gi\|7288074 | SEQ ID NO: 47 |
| *Pyrococcus* sp. NA2 | SP-49 | gi\|503513858 | SEQ ID NO: 48 |
| *Ferroglobus placidus* DSM 10642 | SP-61 | gi\|502730992 | SEQ ID NO: 49 |
| *Palaeococcus ferrophilus* DSM 13482 | SP-5 | gi\|851288004 | SEQ ID NO: 50 |
| *Thermococcus gammatolerans* EJ3 | SP-50 | gi\|506339349 | SEQ ID NO: 51 |
| *Thermococcus celericrescens* | SP-51 | gi\|332308985 | SEQ ID NO: 52 |
| *Vulcanisaeta distributa* DSM 14429 | SP-60 | gi\|503101260 | SEQ ID NO: 53 |
| *Methanopyrus kandleri* AV19 | SP-7 | gi\|20094475 | SEQ ID NO: 54 |
| *Thermoproteus neutrophilus* V24Sta | SP-9 | gi\|171185774 | SEQ ID NO: 55 |

TABLE 2

| DNA binding proteins | | | |
|---|---|---|---|
| DNA-binding protein Tfx | BD-51 | gi\|499321160 | SEQ ID NO: 56 |
| AbrB/MazE/MraZ-like | BD-52 | gi\|499321199 | SEQ ID NO: 57 |
| "Winged helix" DNA-binding domain | BD-54 | gi\|499322061 | SEQ ID NO: 58 |
| Ribbon-helix-helix protein, copG family | BD-62 | gi\|499321149 | SEQ ID NO: 59 |
| lambda repressor-like DNA-binding domains | BD-63 | gi\|499322443 | SEQ ID NO: 60 |
| Resolvase-like | BD-67 | gi\|499322676 | SEQ ID NO: 61 |
| "Winged helix" DNA-binding domain | BD-71 | gi\|499322676 | SEQ ID NO: 62 |
| "Winged helix" DNA-binding domain | BD-74 | gi\|499322255 | SEQ ID NO: 63 |
| "Winged helix" DNA-binding domain | BD-75 | gi\|499322388 | SEQ ID NO: 64 |
| "Winged helix" DNA-binding domain | BD-81 | gi\|499322131 | SEQ ID NO: 65 |
| "Winged helix" DNA-binding domain | BD-82 | gi\|499321342 | SEQ ID NO: 66 |
| "Winged helix" DNA-binding domain | BD-85 | gi\|499321130 | SEQ ID NO: 67 |
| "Winged helix" DNA-binding domain | BD-86 | gi\|499322705 | SEQ ID NO: 68 |
| "Winged helix" DNA-binding domain | BD-88 | gi\|499320855 | SEQ ID NO: 69 |
| "Winged helix" DNA-binding domain | BD-89 | gi\|499322250 | SEQ ID NO: 70 |
| "Winged helix" DNA-binding domain | BD-91 | gi\|499321633 | SEQ ID NO: 71 |
| "Winged helix" DNA-binding domain | BD-92 | gi\|490170077 | SEQ ID NO: 72 |
| "Winged helix" DNA-binding domain | BD-93 | gi\|499321272 | SEQ ID NO: 73 |
| "Winged helix" DNA-binding domain | BD-94 | gi\|499320919 | SEQ ID NO: 74 |
| "Winged helix" DNA-binding domain | BD-97 | gi\|499320853 | SEQ ID NO: 75 |
| "Winged helix" DNA-binding domain | BD-98 | gi\|499321734 | SEQ ID NO: 76 |
| "Winged helix" DNA-binding domain | BD-100 | gi\|499322439 | SEQ ID NO: 77 |
| "Winged helix" DNA-binding domain | BD-102 | gi\|499322707 | SEQ ID NO: 78 |
| "Winged helix" DNA-binding domain | BD-109 | gi\|499321112 | SEQ ID NO: 79 |
| HCP-like | BD-02 | gi\|351675391 | SEQ ID NO: 80 |
| Helix-turn-helix domain, rpiR family | BD-03 | gi\|500479591 | SEQ ID NO: 81 |
| Helix-turn-helix domain, rpiR family | BD-04 | gi\|15643984 | SEQ ID NO: 82 |
| Bacterial regulatory proteins, lacI family | BD-07 | gi\|15643711 | SEQ ID NO: 83 |
| Bacterial regulatory proteins, lacI family | BD-08 | gi\|15643974 | SEQ ID NO: 84 |
| Bacterial regulatory proteins, lacI family | BD-09 | gi\|15643956 | SEQ ID NO: 85 |
| Bacterial regulatory proteins, lacI family | BD-11 | gi\|500480095 | SEQ ID NO: 86 |
| lambda repressor-like DNA-binding domains | BD-12 | gi\|15643421 | SEQ ID NO: 87 |
| "Winged helix" DNA-binding domain | BD-14 | gi\|15644350 | SEQ ID NO: 88 |
| "Winged helix" DNA-binding domain | BD-16 | gi\|24159093 | SEQ ID NO: 89 |
| "Winged helix" DNA-binding domain | BD-18 | gi\|15643139 | SEQ ID NO: 90 |
| "Winged helix" DNA-binding domain | BD-23 | gi\|15642807 | SEQ ID NO: 91 |
| "Winged helix" DNA-binding domain | BD-24 | gi\|15643159 | SEQ ID NO: 92 |
| "Winged helix" DNA-binding domain | BD-30 | gi\|15643333 | SEQ ID NO: 93 |
| "Winged helix" DNA-binding domain | BD-32 | gi\|15643055 | SEQ ID NO: 94 |
| "Winged helix" DNA-binding domain | BD-37 | gi\|15643827 | SEQ ID NO: 95 |
| "Winged helix" DNA-binding domain | BD-43 | gi\|15643699 | SEQ ID NO: 96 |
| Homeodomain-like | BD-45 | gi\|15643788 | SEQ ID NO: 97 |

In an embodiment of the invention, the reaction mixture, composition, kit or method may include or use a 5'-3' exonuclease such as T5/5'-3'-exonuclease that is temperature sensitive and can be inactivated by raising the temperature above 50° C. In one embodiment, the 5'-3' exonuclease has exonuclease activity and ss endonuclease activity. In some embodiments, a reaction mixture may further include a ligase for example, an $NAD^+$ requiring ligase and/or a thermostable ligase, for example Taq ligase. In preferred embodiments, the reaction mixture may include a ss binding protein. The ss binding protein may be thermostable for example, ET SSB. The assembly reaction may be performed under isothermal conditions.

In certain embodiments, the use of a ligase is optional. For example, where an assembled fragment is introduced directly into a vector for transformation of a host cell, a ligase is not required as the host cell such as E. coli may be capable of repairing nicks in vivo. However, if the assembled fragment is amplified for purposes of confirming correct assembly prior to transformation, it is desirable to use a ligase to close nicks and enable a polymerase to amplify the entire target DNA.

Cloning of individual fragments may use chemically synthesized polynucleotide fragments with sequences obtained from any database or publication where the polynucleotide fragments have overlapping sequences. These can be cloned in a plasmid by inserting the polynucleotide into a site in the plasmid adjacent to restriction enzyme sites suitable for excision of the inserted polynucleotide.

Any plasmid may be used. The present examples utilize the commercially available pACYC184 that contains the chloramphenicol gene as a selectable marker. Any selectable marker may be used in place of chloramphenicol resistance gene. Similarly a specific recognition site for any cleavage enzyme capable of specifically cleaving at the ends of the oligonucleotide to generate either staggered ends or blunt ends may be selected where the specific cleavage site does not occur in the fragments of interest in addition to the engineered position adjacent to the ends of the fragment of interest. In the present examples, the recognition site for the eight base cutter NotI (CGCCGGCG) that produces staggered ends has been introduced adjacent to the polynucleotide of interest by means of DNA synthesis. However, this site may be present in a plasmid of choice or added to the synthetic oligonucleotide of interest by a primer for amplification. Examples of specific cleavage enzymes include restriction endonucleases and homing endonucleases.

Once the oligonucleotide or DNA fragment of interest has been chemically synthesized cloned or amplified from an existing DNA and cloned into a vector with a selectable marker, it is excised preferably by enzyme cleavage. The fragments or oligonucleotides that have been synthesized or amplified so as to incorporate overlapping sequence with an adjacent fragment or oligonucleotide to which it is intended to be joined are then assembled in an assembly reaction.

Under the hybridization conditions selected, the 5'-3' exonuclease in the reaction mixture (for example, at a concentration in the range of 0.004-0.016 U/µl) chews back any ss region at the 5' end of the fragment or oligonucleotide and continues to chew back through the region of overlapping sequences and may continue further continues for a limited distance (for example, at least 100 bases) to provide a 3' ss region (see for example, FIGS. 2A-2C and 7). At the same time, the strand-displacing polymerase as defined by the assay in FIGS. 1A-1E and Example 1 (for example, at a concentration in the range of 0.005 U/µl-0.5 U/µl) repairs the gap remaining between the hybridized ds region and any residual ss region. Since the polymerase is strand-displacing, it may displace additional downstream sequences to form an ss flap. However, T5 exonuclease ss endonuclease activity will remove this flap and any associated nick may be repaired by a ligase (for example, at a concentration in the range of 0.001 U/µl-20 U/µl).

Once fragments are assembled into a larger piece of DNA which are cloned in colonies of host cells under selective pressure, the DNA from these colonies can be rescued from the vectors and again assembled with other fragments and transformed into host cells thus expanding the size of the DNA many times. The host cell may be a competent bacterial cell or may be a yeast cell or other eukaryotic cell.

Figure 5:
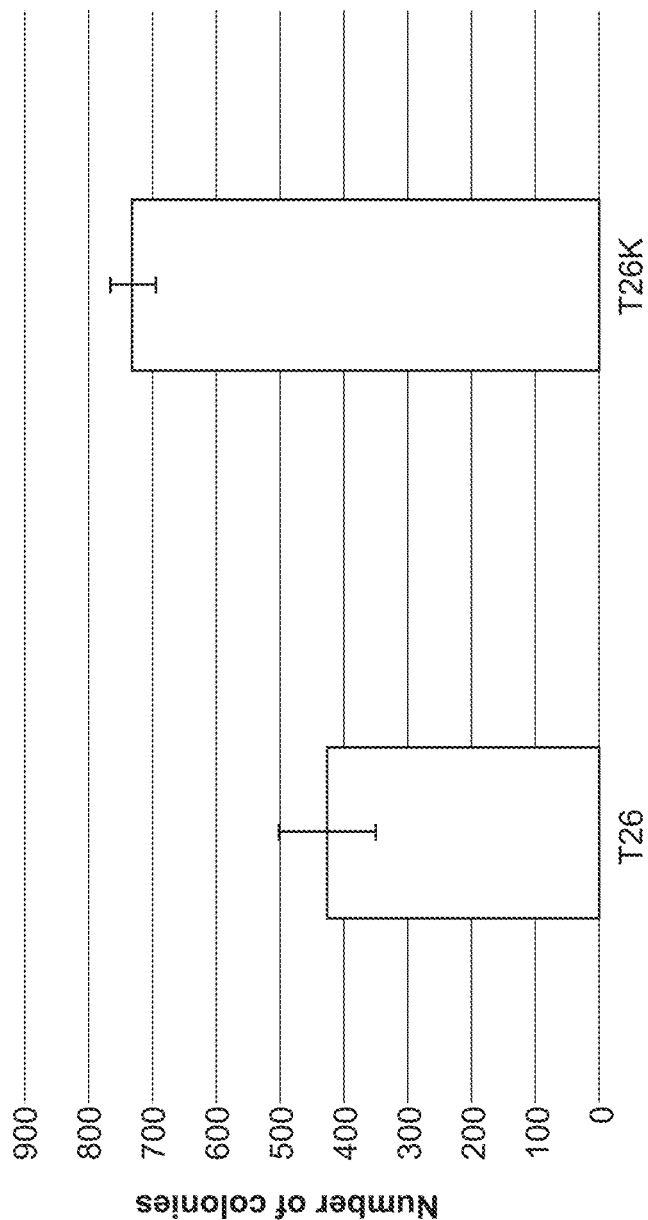
FIG. 5 shows the effect of KCl in the assembly mix as determined by the number of colonies. The increase in accuracy/efficiency of assembly using a strand displacing polymerase in an assembly mix is demonstrated using an increased concentration of KCl in the buffer. The histogram on the left (T26) does not contain KCl whereas the histogram on the right (T26K) contains 25 mM KCl showing a 1.5 fold enhancement of efficiency. This improvement occurs regardless of the assembly condition. A similar relative enhancement of efficiency is expected if PEG or other crowding agent were used in the absence of ss binding protein.
Figure 6:
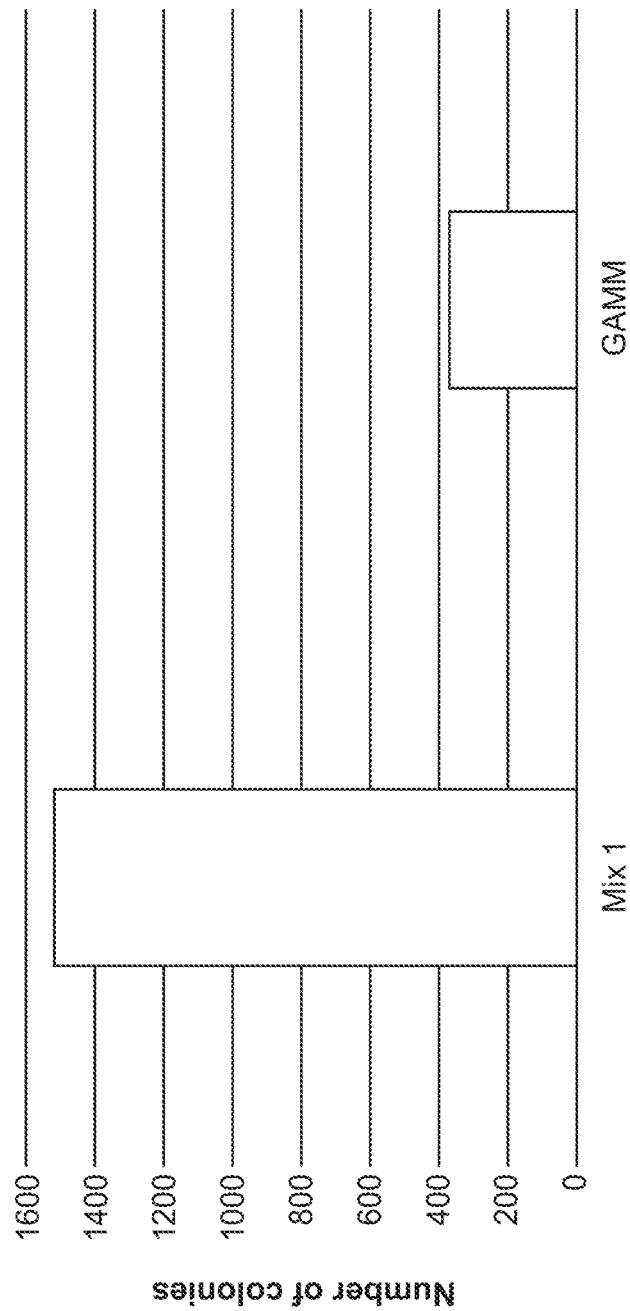
FIG. 6 shows a comparison between the mixture described in Example 2 (Strand displacing polymerase/ss binding protein/5'-3' exonuclease/ligase)(Mix1) and the commercial Gibson Assembly® Mix (GAMM) (non-strand displacing polymerase and polyethylene glycol) (Synthetic Genomics, La Jolla, Calif./New England Biolabs, Ipswich, Mass.) following the protocol provided by the manufacturer. Mix 1 results in significantly higher efficiencies of DNA assembly and transformation.
Figure 7:
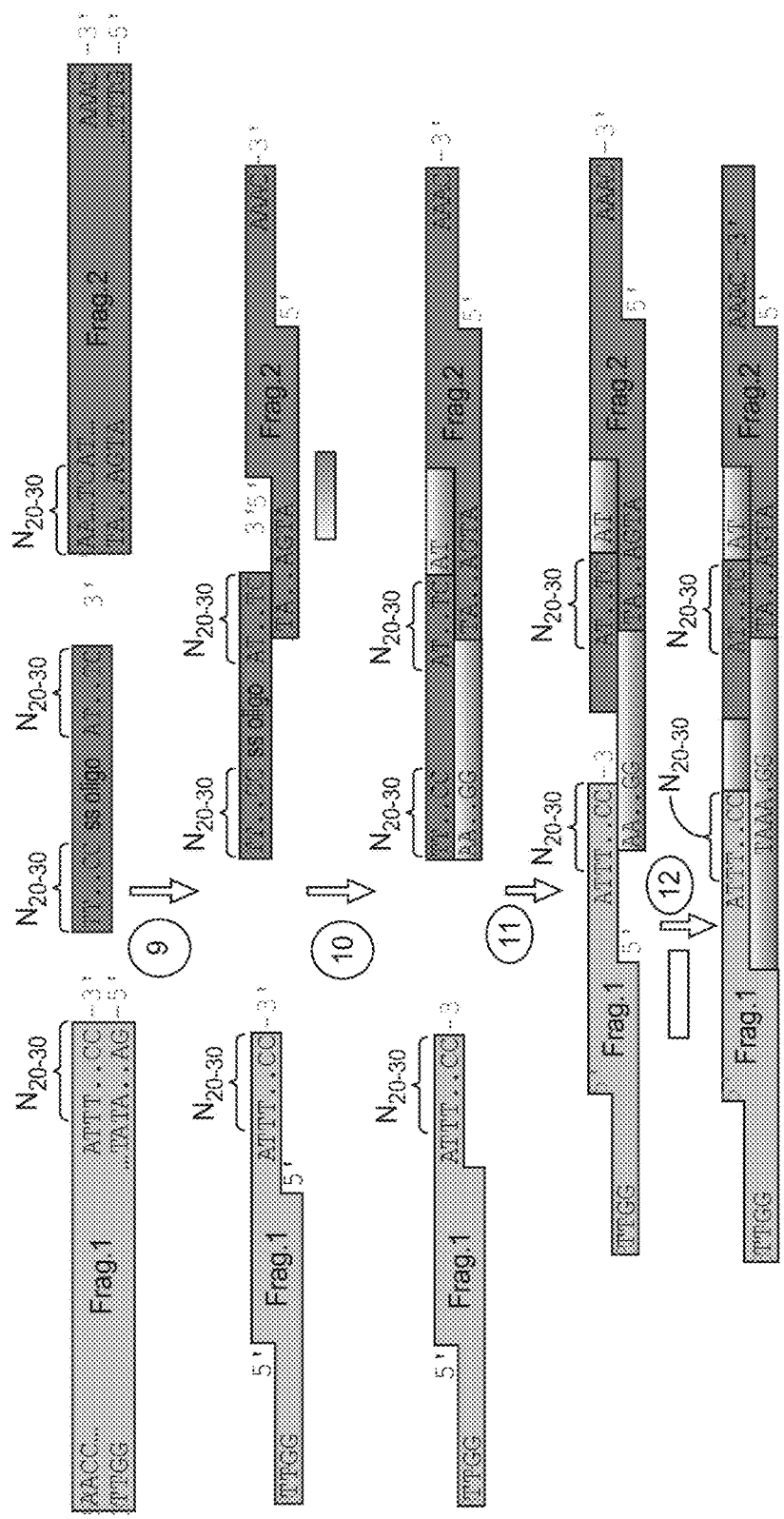
FIG. 7 shows a general diagram of DNA assembly between ss DNA oligonucleotides and ds DNA fragments. ss target DNA oligonucleotide is inserted into a DNA vector. The ss target DNA oligonucleotide has been synthesized so as to have an overlapping region of 20-30 nucleotides on each end with the 3' vector ends. However, the size of the oligonucleotide may have an overlapping region of less than 20 nucleotides for example less than 15 nucleotides or less than 10 nucleotides or alternatively more than 30 nucleotides, for example, at least 40 or 50 or 60 nucleotides or more. Beyond the overlapping regions, the oligonucleotide preferably has 1 or more nucleotides that are not overlapping positioned between the ends. The assembly master mix which contains a 5'-3' exonuclease, strand displacing polymerase, ligase and ss binding protein is added to the mixture of ss oligonucleotide and the vectors so as to permit the 5' end of the ds DNA vector to be chewed back so as to produce ss overhangs (9). The 3' end of the ss DNA is then able to anneal to a 5' end of the vector and the DNA polymerase then replicates the ss template to fill the gap and produce a blunt ended ds DNA. The nick is sealed by ligase (10). Again, the exonuclease (here T5 exonuclease) chews back the 5' end this time on the blunt end of the target DNA producing 3' ss regions so as to permit annealing of the complementary sequences and completion of the ds integration of target DNA into the DNA vector (11). Fragments can anneal with DNA polymerase filling the gap and ligase sealing the nick. (12) to produce a synthon.
Figure 10:
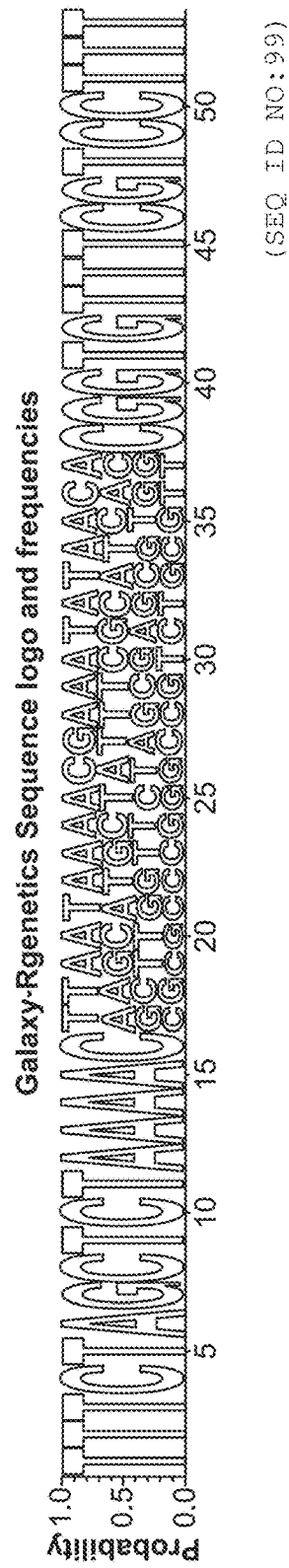
FIG. 10 presents the results of 187 colonies selected from a plate after the assembly reaction products were transformed into E. coli. Each colony was PCR amplified and sequenced to confirm the insertion of the ss DNA and the distribution of degenerate bases were analyzed. The results shown here confirmed that indeed different colonies contained different degenerate sequences. No bias was detected. Analysis was carried out by first converting the sequences into a fastq file and then using the fastx_quality_stats tool from the fastx toolkit on github. The sequence logo was created using weblogo from Berkeley.

The assembly process as described herein has been found to be very efficient. For example, 0.02 nM-100 nM of oligonucleotide (ss) or DNA fragment (ds) may be utilized to assemble a larger fragment where the concentration of ss oligonucleotides used in a reaction can be up to approximately 50 times more than the amount of ds DNA fragments used in a similar assembly reaction. Similarly, equal molarity of plasmid containing a single fragment and a selectable marker and a similar amount of the vector containing the assembled fragments with a different selectable marker may be used. These amounts are intended as guides but can be reduced whether the efficiency of the assembly is enhanced. For example, addition of the potassium salt, KCl can increase efficiency of productive assembly by 1.5 fold as determined by the number of colonies using the assembly of lacIZ as an indicator (see for example FIG. 5).

The assembly process for ss target oligonucleotides between two ds DNA molecules or into a linearized vector is also very efficient. An example is provided herein which is not intended to be limiting that uses specific/random sequences to identify guide RNAs for CRISPR-Cas gene editing protocols that can be introduced into cells to determine an altered phenotype. At the outset, it may not be known what sequence might be suitable for achieving this goal. The generation of a library containing degenerate sequences makes this type of analysis possible. CRISPR/Cas9-based gene editing is quickly growing in popularity in the field of genome editing. Due to the size of most commonly used Cas9-containing plasmids, construction of a sgRNA or sgRNA library into a Cas9/sgRNA expression vector can be cumbersome. This approach solves this problem, using ss DNA oligonucleotides.

In a separate embodiment, any DNA binding domain from Table 2 may be fused to a Bst polymerase, Bst large fragment or mutant thereof (see for example, U.S. Pat. No. 8,993,298 and US 2015/0152396 including all the Bst variants described and claimed therein).

Kits

Also provided by the present disclosure are kits for practicing the subject method as described above. In certain embodiments, a subject kit may contain: i. a 5'-3' exonuclease, ii. an optional a ligase, iii. a strand-displacing polymerase; and iv. a ss DNA binding protein. The components of the kit may be combined in one container, or each component may be in its own container. For example, the components of the kit may be combined in a single reaction tube or in one or more different reaction tubes. Further details of the components of this kit are described above. The kit may also contain other reagents described above and below that may be employed in the method, e.g., a mismatch repair enzyme such as mutHLS, cel-1 nuclease, T7 endo 1, uvrD, T4 EndoVII, E. coli EndoV, a buffer, dNTPs, plasmids into which to insert the synthon and/or competent cells to receive the plasmids, controls etc., depending on how the method is going to be implemented. In some embodiments, the kit does not contain a non-strand displacing polymerase and/or a crowding agent.

In certain embodiments, the kit may comprise a composition comprising a fusion protein, as described above, and a reaction buffer. The fusion protein itself may be in a storage buffer that contains a stabilizing agent, e.g., glycerol. The reaction buffer may be formulated to provide optimal conditions for the polymerase activity of the fusion protein, or a concentrated form thereof (e.g., at a 5× or 10× concentrate). In certain embodiments, the buffer may contain a buffering agent (e.g., Tris or the like), salt (e.g., NaCl$_2$ or the like), the salt of a divalent cation (MgCl or the like) and other necessary components.

In addition to above-mentioned components, the subject kit further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Compositions, kits and methods for assembling fragments and forming synthons as described herein result in a product that is a ds fully sealed DNA that can serve as a template for PCR, RCA or a variety of other molecular biology applications including direct transformation or transfection of a competent bacterial or eukaryotic host cell.

In order to further illustrate the present invention, the following specific examples are given with the understanding that they are being offered to illustrate the present invention and should not be construed in any way as limiting its scope.

All references cited herein including U.S. Ser. No. 14/837,820, filed on Aug. 27, 2015, US Provisional Ser. No.: 62/042,527, filed Aug. 27, 2014, 62/189,599, filed Jul. 7, 2015 plus 62/193,168, filed on Jul. 16, 2015, are incorporated by reference.

EXAMPLES

Example 1: Assay to Establish Strand Displacement Properties of a Polymerase

The data shown in FIGS. 3A, 3B, 4, 5, 6, 8C, 9C and 10), was produced using the polymerase of SEQ ID NO: 3.

Figure 1C:
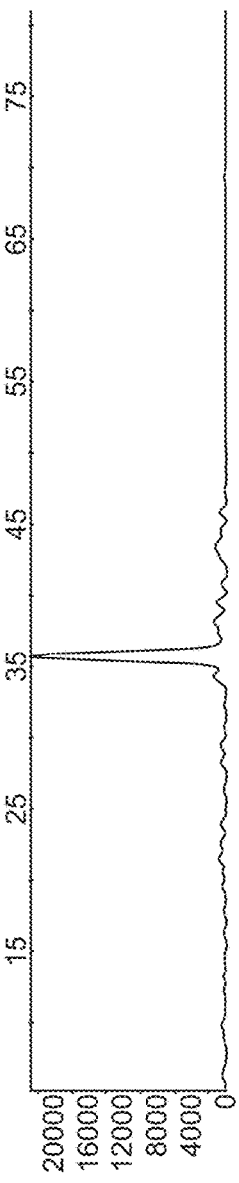
Figure 1D:
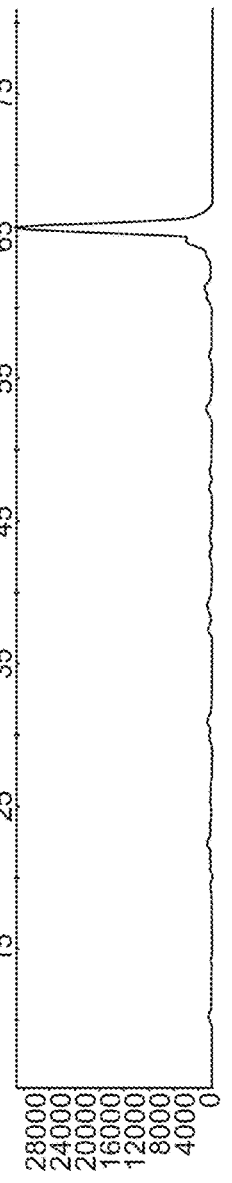
Figure 1E:
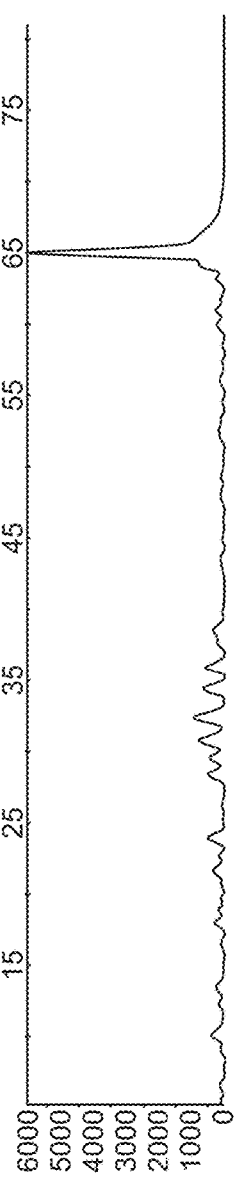
Figure 2A:
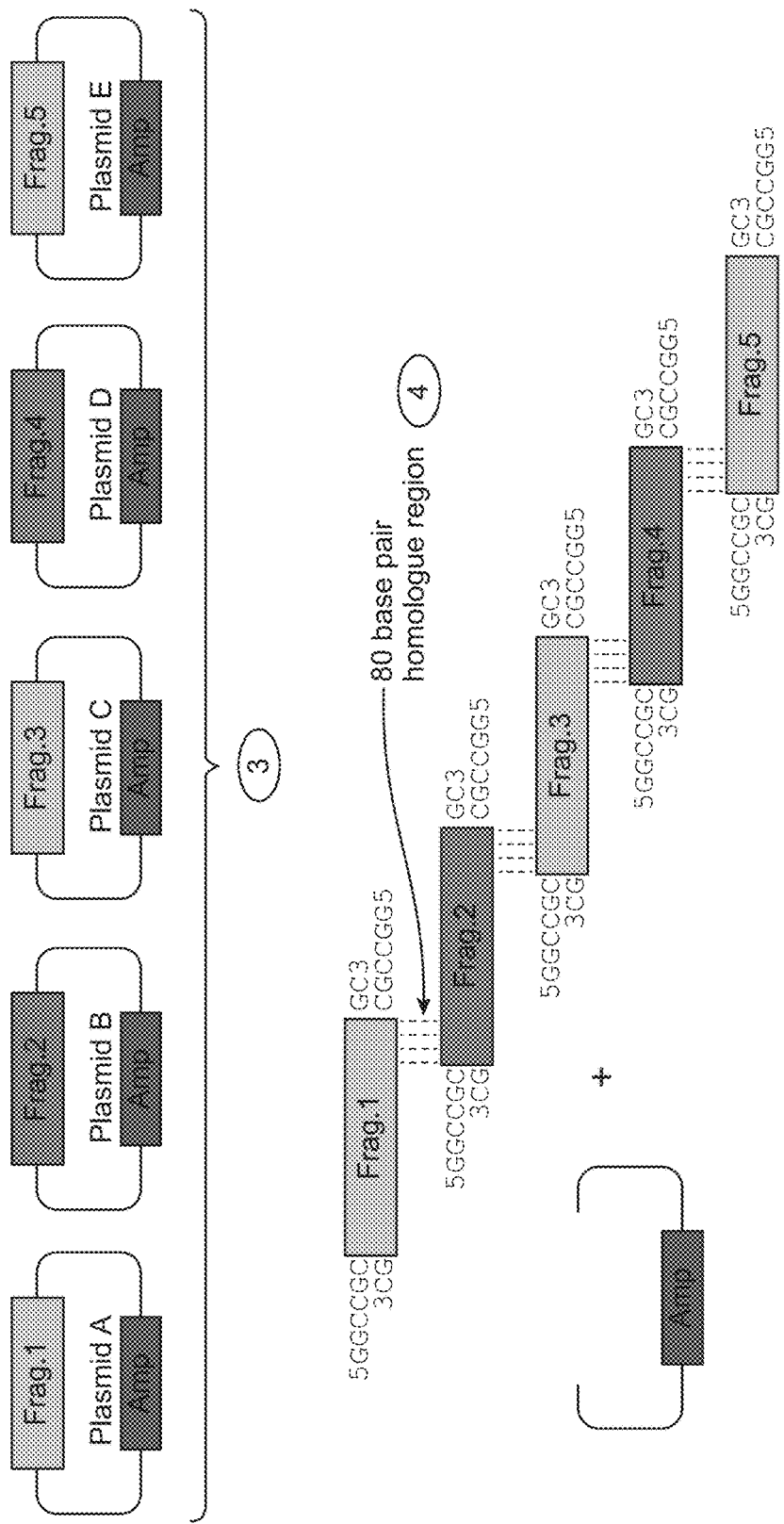
FIG. 2A-2C show the steps in a DNA assembly method.
Figure 2B:
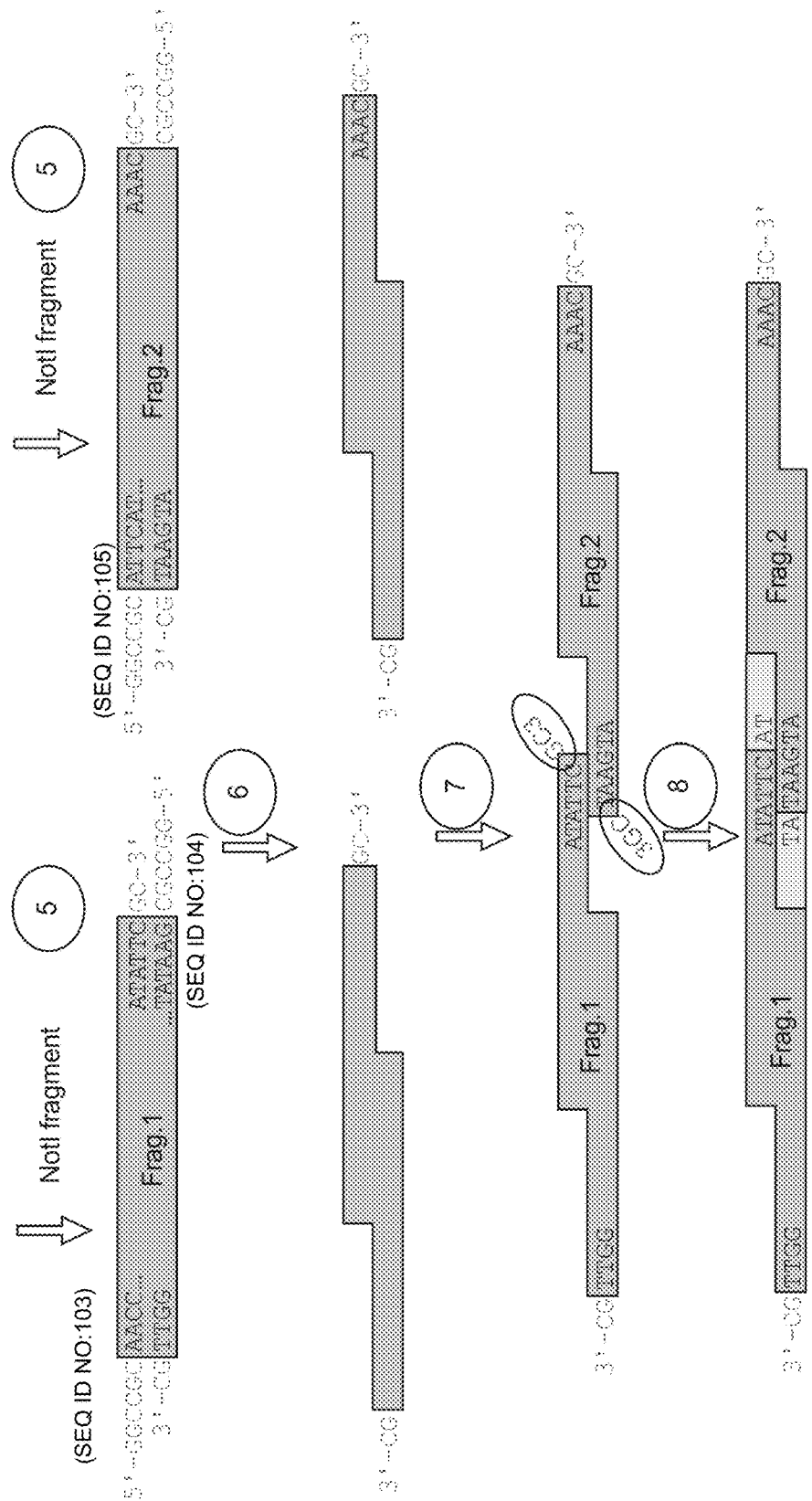
Figure 2C:
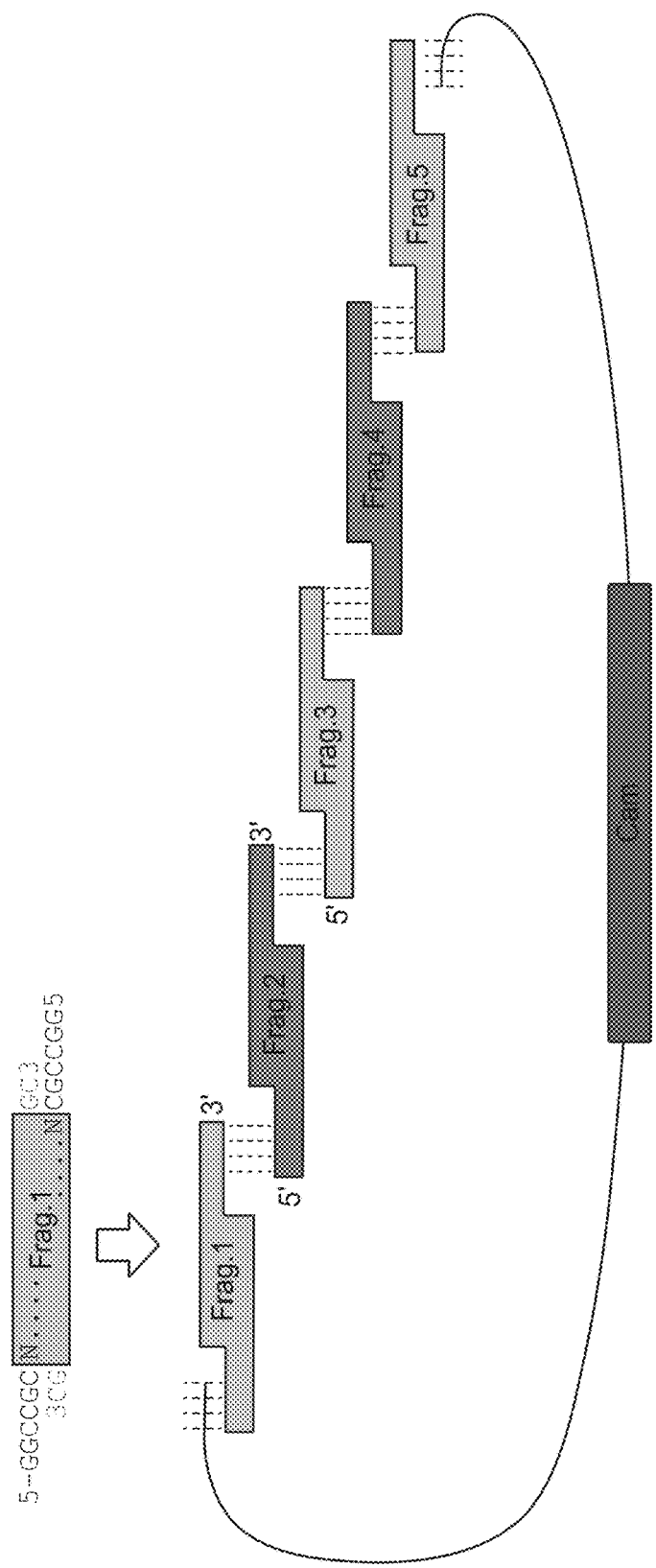
Figure 3A:
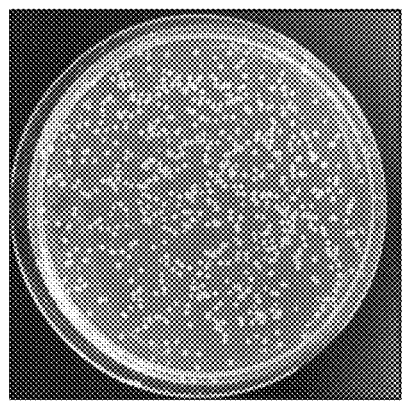
FIGS. 3A and 3B show chloramphenicol plates were used to select colonies for growth on plates and those colonies that contained the lacIZ gene generated blue colonies in the presence of IPTG and X-Gal. The assay provides a quantitative assessment of clones in which genes are assembled efficiently and in a functional form.
Figure 3B:
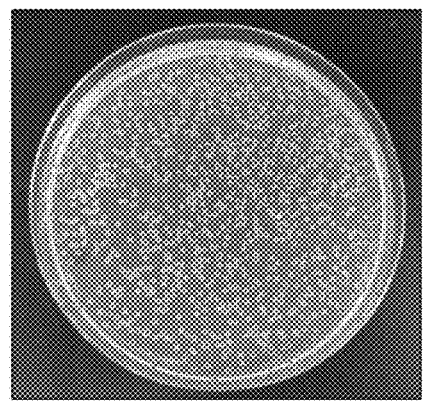
Figure 4:
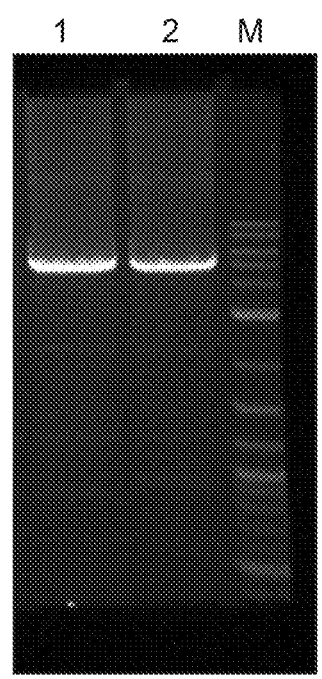
FIG. 4 shows that the plasmids did in fact contain the entire gene. Amplification by PCR of assembly product shown in FIG. 2B was performed to confirm all fragments were joined and ligated prior transformation. Lane 1 and 2 are duplicate PCR results. Lane M is 2-log DNA ladder from New England Biolabs, Ipswich, Mass.

An assay was developed to differentiate between strand-displacing and non-strand displacing polymerases-A 10 µl reaction containing 10 nM FAM-primer/Template/blocking oligonucleotide, 1× THERMOPOL® buffer (New England Biolabs, Ipswich, Mass.) (FIG. 1A) and 0.1 mM dNTP was prepared. FIG. 1B is the control which is the FAM labeled primer absent any polymerase. When a strand displacing DNA polymerase was added to the reaction, and incubated at 50° C. for 30 minutes with 1 µl of sample diluted 10 fold and analyzed by capillary electrophoresis, the FAM primer was extended through the blocking oligonucleotide which was displaced. The results are shown in FIG. 1D-1E. The position of the peak in FIG. 2D for Bst polymerase, an established strand displacing polymerase corresponds to the peak observed for a non-natural polymerase, SPB49F. The small size shift results from a blunt end generated by SPB49F resulting from 3'-5' exonuclease activity which is absent in Bst polymerase such that the product of Bst polymerase replication has a 3' dA. FIG. 1C shows the product of a non-strand displacing polymerase-T4DNA polymerase where synthesis is terminated at the blocking primer.

Example 2: Synthesis of a Large DNA Molecule from 6 Fragments Using a Strand Displacing Polymerase and Confirmation that Assembly was Efficient Using Strand Displacing Polymerases Plasmid A, B, C, D and E were constructed separately from PCR products (fragments (Frags) 1, 2, 3, 4, 5 that together cover the region of LacI- and LacZ gene) using NEB® PCR Cloning Kit (New England Biolabs, Ipswich, Mass.).

In this experiment, the 5 different fragments integrated into separate plasmids were used in the following concentrations—50 ng of each PCR (source of "fragments) and 25 ng of pMiniT™ vector (NEB # E1202) was the ampicillin containing plasmid. The 5 fragments for assembly were first amplified using PCR. Primers used in the preparation of LacI-lacZ DNA fragments assembly system as follows:

| | |
|---|---|
| 5PLacIZ-pACYC184VF1 | ttggtctggtgtcaaaaatgaATCGTCACGGCGATTTATG (SEQ ID NO: 4) |
| 5PLacIZ-pACYC184VR1 | gggtcattttcggcgaggacTGCATCAACGCATATAGCG (SEQ ID NO: 5) |
| Not-IZ F1 | GCGGCCGCgtcctcgccgaaaatgacccagag (SEQ ID NO: 6) |
| Not-IZ R1 | GCGGCCGCtggtgtcgatggtagaacgaagcg (SEQ ID NO: 7) |
| Not-IZ F2 | GCGGCCGCcccactgacgcgttgcgcgagaag (SEQ ID NO: 8) |
| Not-IZ R2 | GCGGCCGCggctgcgcaactgttgggaagggc (SEQ ID NO: 9) |
| Not-IZ F3 | GCGGCCGCtgcagcacatcccccttcgccag (SEQ ID NO: 10) |
| Not-IZ R3 | GCGGCCGCatgatgctcgtgacggttaacgcc (SEQ ID NO: 11) |
| Not-IZ F4 | GCGGCCGCaggtgcggattgaaaatggtctgc (SEQ ID NO: 12) |
| Not-IZ R4 | GCGGCCGCtcaccgcttgccagcggcttacca (SEQ ID NO: 13) |
| Not-IZ F5 | GCGGCCGCgaatacctgttccgtcatagcgat (SEQ ID NO: 14) |
| Not-IZ R5 | GCGGCCGCtcattttgacaccagaccaactgg (SEQ ID NO: 15) |

The amplified fragments were cloned and sequenced to confirm that no errors during amplification had been introduced.

Sequence of PCR amplified fragment 1
(SEQ ID NO: 16):
GCGGCCGCgtcctcgccgaaaatgacccagagcgctgccggcacctgtcc tacgagttgcatgataaagaagacagtcataagtgcggcgacgatagtca tgccccgcgcccaccggaaggagctgactgggttgaaggctctcaagggc atcggtcgagatcccggtgcctaatgagtgagctaacttacattaattgc gttgcgctcactgcccgctttccagtcgggaaacctgtcgtgccagctgc attaatgaatcggccaacgcgcggggagaggcggtttgcgtattgggcgc cagggtggtttttcttttcaccagtgagacgggcaacagctgattgccct tcaccgcctggccctgagagagttgcagcaagcggtccacgctggtttgc cccagcaggcgaaaatcctgtttgatggtggttaacggcgggatataacc aacgcgcagcccggactcggtaatatcccactaccgagatatccgcacca acgcgcagcccggactcggtaatggcgcgcattgcgcccagcgccatctg atcgttggcaaccagcatcgcagtgggaacgatgccctcattcagcattt gcatggtttgttgaaaaccggacatggcactccagtcgccttcccgttcc gctatcggctgaatttgattgcgagtgagatatttatgccagccagccag acgcagacgcgccgagacagaacttaatgggcccgctaacagcgcgattt gctggtgacccaatgcgaccagatgctccacgcccagtcgcgtaccgtct tcatggagaaaataatactgttgatgggtgtctggtcagagacatcaag aaataacgccggaacattagtgcaggcagcttccacagcaatggcatcct ggtcatccagcggatagttaatgatcagcccactgacgcgttgcgcgaga agattgtgcaccgccgctttacaggcttcgacgccgcttcgttctaccat cgacaccaGCGGCCGC Sequence of PCR amplified fragment 2
(SEQ ID NO: 17):
GCGGCCGCcccactgacgcgttgcgcgagaagattgtgcaccgccgcttt acaggcttcgacgccgcttcgttctaccatcgacaccaccacgctggcac ccagttgatcggcgcgagatttaatcgccgcgacaatttgcgacggcgcg tgcagggccagactggaggtggcaacgccaatcagcaacgactgtttgcc cgccagttgttgtgccacgcggttgggaatgtaattcagctccgccatcg ccgcttccacttttcccgcgttttcgcagaaacgtggctggcctggttc accacgcgggaaacggtctgataagagacaccggcatactctgcgacatc gtataacgttactggtttcacattcaccaccctgaattgactctcttccg ggcgctatcatgccataccgcgaaaggttttgcgccattcgatggtgtcc gggatctcgacgctctcccttatgcgactcctgcattaggaagcagccca gtagtaggttgaggccgttgagcaccgccgccgcaaggaatggtgcatgc aaggagatggcgcccaacagtccccggccacggggcctgccaccatacc cacgccgaaacaagcgctcatgagcccgaagtggcgagcccgatcttcc catcggtgatgtcggcgatataggcgccagcaaccgcacctgtggcgccg gtgatgccggccacgatgcgtccgcgtagaggatcgagatctcgatccc gcgaaattaatacgactcactataggggaattgtgagcggataacaattc ccctctagaaataattttgtttaactttaagaaggagatatacatatgac catgattacggattcactggccgtcgttttacaacgtcgtgactgggaaa accctggcgttacccaacttaatcgccttgcagcacatccccctttcgcc agctggcgtaatagcgaagaggcccgcaccgatcgcccttcccaacagtt gcgcagccGCGGCCGC Sequence of PCR fragment 3 (SEQ ID NO: 18):
GCGGCCGCtgcagcacatccccctttcgccagctggcgtaatagcgaaga ggcccgcaccgatcgcccttcccaacagttgcgcagcctgaatggcgaat ggcgctttgcctggtttccggcaccagaagcggtgccggaaagctggctg gagtgcgatcttcctgaggccgatactgtcgtcgtcccctcaaactggca gatgcacggttacgatgcgcccatctacaccaacgtgacctatcccatta cggtcaatccgccgtttgttcccacggagaatccgacgggttgttactcg ctcacatttaatgttgatgaaagctggctacaggaaggccagacgcgaat tattttgatgcgttaactcggcgtttcatctgtggtgcaacgggcgct gggtcggttacggccaggacagtcgtttgccgtctgaatttgacctgagc gcattttacgcgccggagaaaaccgcctcgcggtgatggtgctgcgctg gagtgacggcagttatctggaagatcaggatatgtggcggatgagcggca ttttccgtgacgtctcgttgctgcataaaccgactacacaaatcagcgat ttccatgttgccactcgctttaatgatgatttcagccgcgctgtactgga ggctgaagttcagatgtgcggcgagttgcgtgactacctacgggtaacag tttctttatggcagggtgaaacgcaggtcgccagcggcaccgcgcctttc ggcggtgaaattatcgatgagcgtggtggttatgccgatcgcgtcacact acgtctgaacgtcgaaaacccgaaactgtggagcgccgaaatcccgaatc tctatcgtgcggtggttgaactgcacaccgccgacggcacgctgattgaa gcagaagcctgcgatgtcggtttccgcgaggtgcggattgaaaatggtct gctgctgctgaacggcaagccgttgctgattcgaggcgttaaccgtcacg agcatcatGCGGCCGC Sequence of PCR fragment 4 (SEQ ID NO: 19):
GCGGCCGCaggtgcggattgaaaatggtctgctgctgctgaacggcaagc cgttgctgattcgaggcgttaaccgtcacgagcatcatcctctgcatggt caggtcatggatgagcagacgatggtgcaggatatcctgctgatgaagca gaacaactttaacgccgtgcgctgttcgcattatccgaaccatccgctgt ggtacacgctgtgcgaccgctacgcctgtatgtggtggatgaagccaat attgaaacccacggcatggtgccaatgaatcgtctgaccgatgatccgcg ctggctaccggcgatgagcgaacgcgtaacgcgaatggtgcagcgcgatc gtaatcacccgagtgtgatcatctggtcgctggggaatgaatcaggccac ggcgctaatcacgacgcgctgtatcgctggatcaaatctgtcgatccttc ccgcccggtgcagtatgaaggcggcggagccgacaccacggccaccgata ttatttgcccgatgtacgcgcgcgtggatgaagaccagcccttcccggct gtgccgaaatggtccatcaaaaaatggctttcgctacctggagagacgcg cccgctgatcctttgcgaatacgcccacgcgatgggtaacagtcttggcg gtttcgctaaatactggcaggcgtttcgtcagtatcccgtttacagggc ggcttcgtctgggactgggtggatcagtcgctgattaaatatgatgaaaa cggcaaccgtggtcggcttacggcggtgattttggcgatacgccgaacg atcgccagttctgtatgaacggtctggtctttgccgaccgcacgccgcat ccagcgctgacggaagcaaaacaccagcagcagttttccagttccgttt atccgggcaaaccatcgaagtgaccagcgaatacctgttccgtcatagcg ataacgagctcctgcactggatggtggcgctggatggtaagccgctggca agcggtgaGCGGCCGC Sequence of PCR fragment 5 (SEQ ID NO: 20):
GCGGCCGCgaatacctgttccgtcatagcgataacgagctcctgcactgg atggtggcgctggatggtaagccgctggcaagcggtgaagtgcctctgga tgtcgctccacaaggtaaacagttgattgaactgcctgaactaccgcagc cggagagcgccgggcaactctggctcacagtacgcgtagtgcaaccgaac gcgaccgcatggtcagaagccgggcacatcagcgcctggcagcagtggcg tctggcggaaaacctcagtgtgacgctccccgccgcgtcccacgccatcc cgcatctgaccaccagcgaaatggattttttgcatcgagctgggtaataag cgttggcaatttaaccgccagtcaggctttctttcacagatgtggattgg cgataaaaaacaactgctgacgccgctgcgcgatcagttcacccgtgcac cgctggataacgacattggcgtaagtgaagcgacccgcattgaccctaac gcctgggtcgaacgctggaaggcggcgggccattaccaggccgaagcagc gttgttgcagtgcacggcagatacacttgctgatgcggtgctgattacga ccgctcacgcgtggcagcatcaggggaaaaccttatttatcagccggaaa acctaccggattgatggtagtggtcaaatggcgattaccgttgatgttga agtggcgagcgatacaccgcatccggcgcggattggcctgaactgccagc tggcgcaggtagcagagcgggtaaactggctcggattagggccgcaagaa aactatcccgaccgccttactgccgcctgttttgaccgctgggatctgcc attgtcagacatgtataccccgtacgtcttcccgagcgaaaacggtctgc gctgcgggacgcgcgaattgaattatggcccacaccagtggcgcggcgac ttccagttcaacatcagccgctacagtcaacagcaactgatggaaaccag ccatcgccatctgctgcacgcggaagaaggcacatggctgaatatcgacg gtttccatatggggattggtggcgacgactcctggagcccgtcagtatcg gcggaattccagctgagcgccggtcgctaccattaccagttggtctggtg tcaaaaatgaGCGGCCGC The 5 fragments each had an overlapping region of 80 bp with an adjacent fragment in order of the final assembly by design (between fragment 1 and 2, 2 and 3, 3 and 4, 4 and 5). Fragment 1 and 5 also shared 20 bp overlap with the ends of vector. Any available vector may be used such as for example pACYC184 (New England Biolabs, Ipswich, Mass.). pACYC184 vector was prepared by the method of inverse PCR, which permitted assembly of fragments 1-5 in the presence of the assembly mix described above after treatment with NotI-HF® (New England Biolabs, Ipswich, Mass.) and heat-inactivation (see FIG. 2A-2C).

During assembly, the nucleotides extending from the shaded region were degraded by T5 exonuclease while nucleotides in grey were removed by the polymerase. After the fragments are assembled and transformed into *E. coli*, productive assembly determined by blue/white selection were recorded on a plate with IPTG and X-Gal.

T5 exonuclease, Taq ligase, a strand displacing DNA polymerase, and a ss binding domain (ET SSB) were combined in a reaction mixture in a buffer to form Mix 1. These enzymes were all obtained from New England Biolabs, Ipswich, Mass. Five of 150 ng of NotI-HF-digested plasmids (plasmid A, B, C, D and E) were mixed with 105 ng of vector and either with Mix 1 or GAMM in a total volume of 20 μl. The reactions were incubated at 50° C. for 60 minutes. 2 μl of the assembled products were used to transform into NEB 5-alpha (New England Biolabs, Ipswich, Mass.) competent cells. Cells were then spread on plates containing chloramphenicol. Positive assembly can be identified as a blue colony on a plate with chloramphenicol+IPTG+X-Gal and incubated at 37° C. overnight.

PCR of assembly product to confirm all fragments are joined and ligated prior transformation involved the following steps: 1 μl of assembled products were used in a PCR to ensured 5 fragments and vector are ligated together. Pairs of PCR primers that anneal on the vector were used to amplify the whole assembled LacIZ gene (5.3 kb). Lane 1 and 2 are duplicate PCR results. Lane M is 2-log DNA ladder from New England Biolabs, Ipswich, Mass. (see FIG. 4).

Sequencing results were obtained from 8 colonies that were picked and the plasmid DNA purified for the purpose of Sanger sequencing. 6 primers were used to sequence the 4.8 kb. The junction sequence between fragments as well as extension regions from the overlap region showed less than 2% sequence errors.

Primers used for sequencing the assembled DNA:

```
Seq Not-IZ-M0
                                  (SEQ ID NO: 21)
aaaaccaccctggcgcccaatacg Seq Not-IZ-M1
                                  (SEQ ID NO: 22)
cccggactcggtaatggcgcgcat Seq Not-IZ-M2
                                  (SEQ ID NO: 23)
ggaagcagcccagtagtaggttga Seq Not-IZ-M3
                                  (SEQ ID NO: 24)
ggtgctgcgctggagtgacggcag Seq Not-IZ-M4
                                  (SEQ ID NO: 25)
cggccaccgatattatttgcccga Seq Not-IZ-M5
                                  (SEQ ID NO: 26)
gattagggccgcaagaaaactatc
```

Example 3: Assembly of Single Strand Oligonucleotides into a Linearized Vector or Two Distinct Ds DNAs An oligonucleotide corresponding to sgRNA for targeting a gene from *H. sapiens* was designed as follows:

1. A PAM sequence was scanned for the desired target sequence. For example NGG in

```
                                  (SEQ ID NO: 27)
5'GCGAAGAACCTCTTCCCAAGANGG3'
```

2. A 71-base, ss DNA oligonucleotide, containing a 21 nucleotide target sequence flanked by a partial U6 promoter sequence and scaffold RNA sequence was designed.

See for example FIG. 8A-8C in which the ss oligonucleotide is defined as

```
                                  (SEQ ID NO: 28)
5'ATCTTGTGGAAAGGACGAAACACCGGCGAAGAACCTCTTCCCAAGAGT
TTTAGAGCTAGAAATAGCAAGTT3'
``` or FIG. 9A-9C where the ss oligonucleotide is designed to create a random library:

```
                                  (SEQ ID NO: 29)
5'ATCTTGTGGAAAGGACGAAACACCGN21GTTTTAGAGCTAGAAATAGCA
AGTT3'
```

3. The ss DNA oligonucleotide was prepared in 1× NEBuffer 2 (New England Biolabs, Ipswich, Mass.) to a final concentration of 0.2 μM.
4. A 10 μl reaction mix containing 5 μl of ss DNA oligonucleotide (0.2 μM), 30 ng of restriction enzyme-linearized vector and ddH$_2$O was formed.
5. A suitable vector for use in the above method is a ds vector from Life Technology (GeneArt® CRISPR Nuclease Vector with OFP Reporter Kit Catalog number: A21174). Other vectors are provided by Addgene plasmid #42230, pX330-U6-Chimeric_BB-CBh-hSpCas9. Alternatively, any plasmid containing an sgRNA scaffold under the control of a U6 promoter can be used.
6. 10 μl of a master mix containing an ss binding protein, a ligase, an exonuclease and a polymerase was added to the reaction mix, and the assembly reaction was incubated for 1 hour at 50° C.
7. NEB 10-beta Competent *E. coli* were transformed with 2 μl of the assembled product and the manufacturer's protocol followed (New England Biolabs).
8. 100 μl of transformed cells were spread on a plate with ampicillin antibiotic, and incubate overnight at 37° C.
9. 10 colonies were picked to grow, and the plasmid DNA was purified for sequencing.

Unlike traditional cloning methods, in which two oligonucleotides must be synthesized and re-annealed, this example offers a simple way to design an oligonucleotide and assemble it with the desired vector and represents a substantial improvement over traditional methods, specifically in time savings, ease-of-use and cost.

Example 4: Production and Screening of Fusion Proteins

Figure 12:
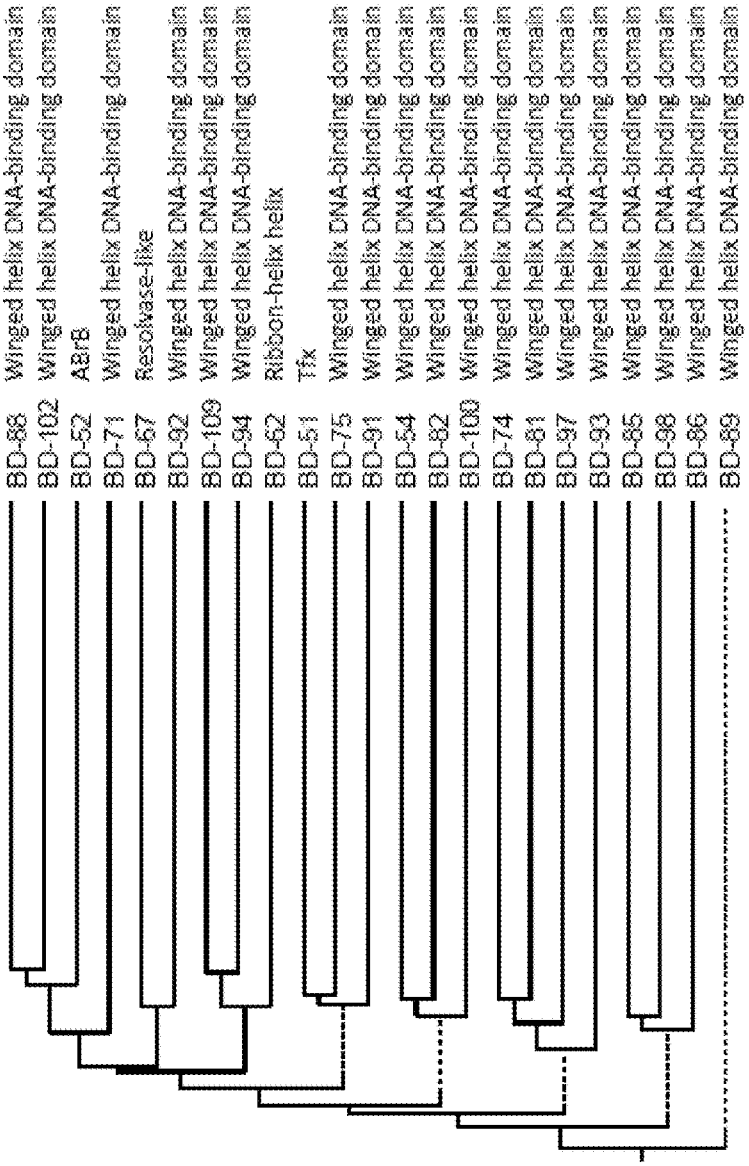
FIG. 12 shows a phylogenetic tree of the DNA binding domains shown in FIGS. 11A and 11B FIG. 44.
Figure 14:
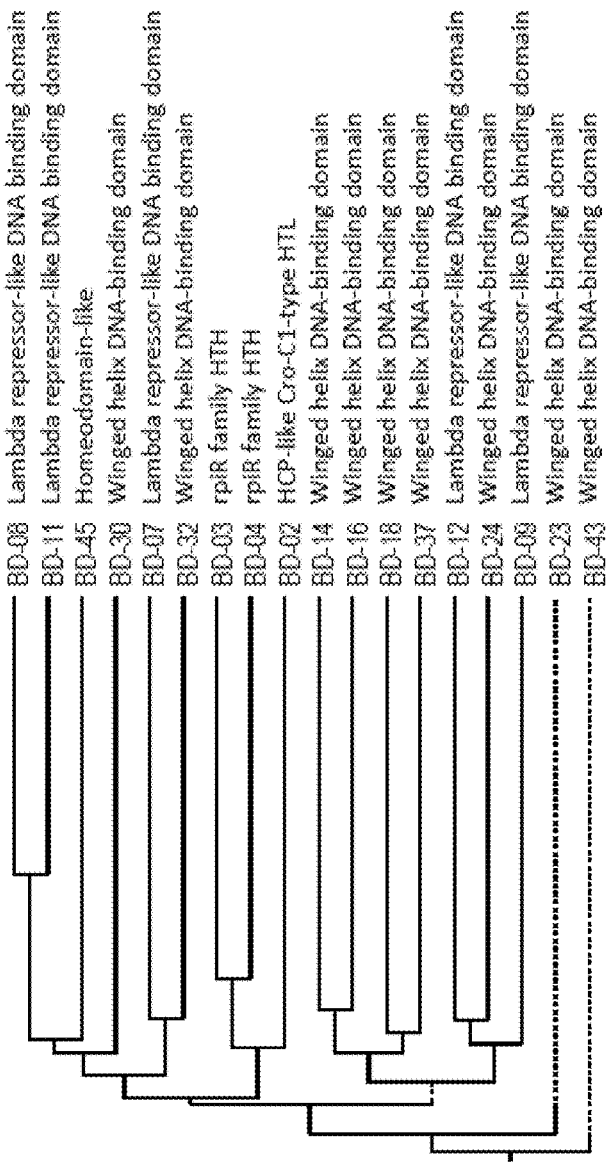
FIG. 14 shows a phylogenetic tree of the DNA binding domains shown in FIGS. 13A and 13B.

The sequences of several hundred DNA binding domains, most of which are expected to be sequence-specific based on their predicted structure (e.g., whether they have an HLH, LTH or WH structure, etc.) or similarity to known DNA binding proteins that are known to specifically bind DNA were identified by screening public and other databases using word searches and by sequence comparisons. Most, if not all, of the identified DNA binding domains were already annotated as being DNA binding domains and, on further analysis, could be identified as transcription factors. Further sequences were selected based on their annotation. Approximately a hundred DNA binding domains were selected for further analysis. The amino acid sequences of representative DNA binding domains from *Pyrococcus furiosus* and *Thermotoga maritima* are shown in FIGS. 11A, 11B, 13A and 13B, respectively. FIGS. 12 and 14 show that the selected DNA binding domains are diverse both in terms of sequence but also in their structure.

Figure 15:
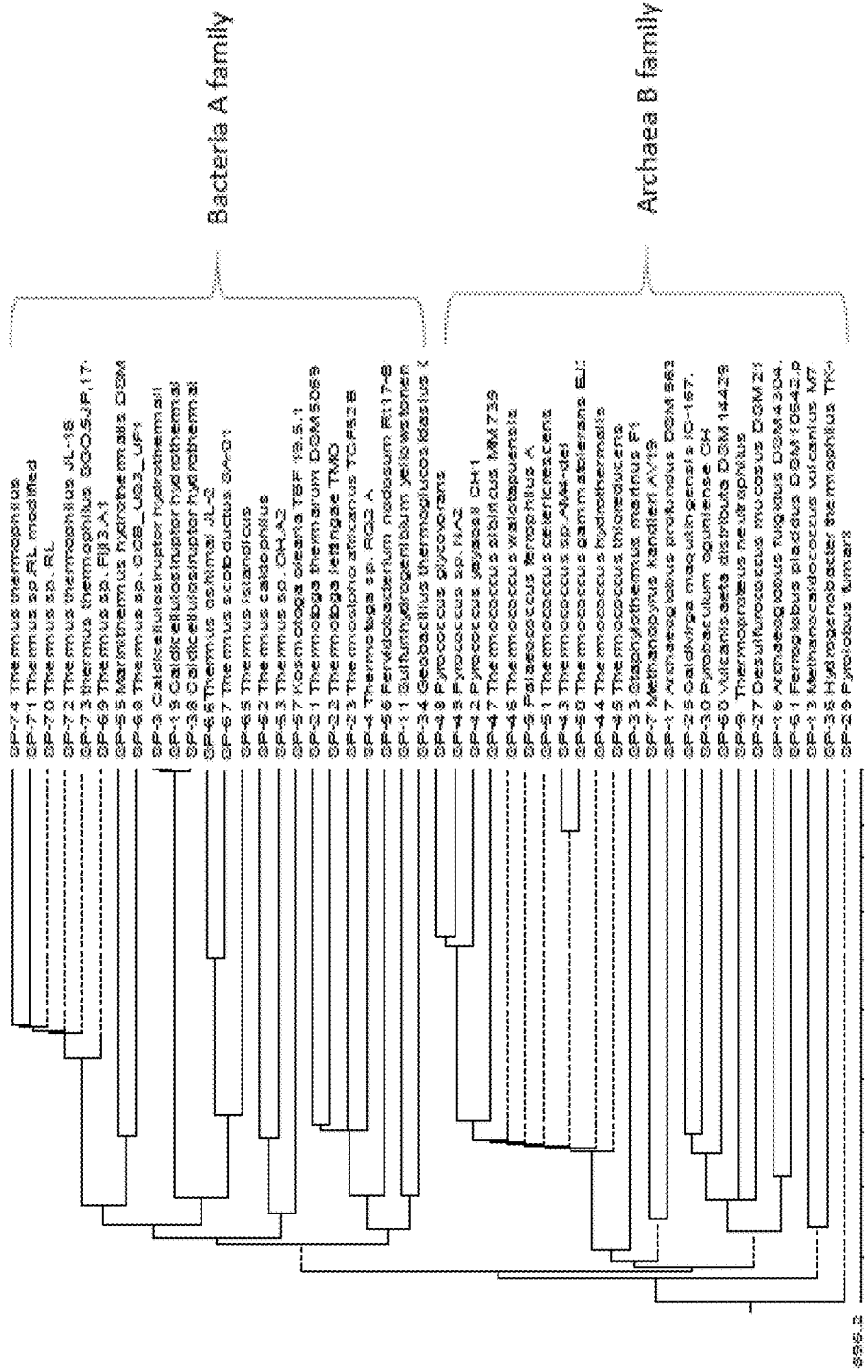
FIG. 15 shows a phylogenetic tree of various DNA polymerases used herein. As shown, the polymerases are derived from a variety of different bacterial and archaeal species.

In addition, several DNA polymerases from a diverse range of bacterial and archaeal species were identified by performing sequence comparisons on public and other databases. Most, if not all, of the identified polymerases were already annotated as being a polymerase. A phylogenetic tree of a representative number of polymerases is shown in FIG. 15. As shown, the polymerases are from family A as well as family B.

Approximately 300 fusion proteins were made and tested for an enhanced performance in a variety of PCR conditions. The selected polymerases were from family A and family B, and the DNA binding domains were diverse in sequence. The amino acid sequences of 18 exemplary polymerases are shown in FIGS. 16, 17, 18A, 18B, 19A and 19B. These sequences can be used to guide the construction of other fusion proteins.

The fusion proteins were compared to the polymerase portion of the fusion protein in a battery of PCR-related tests that included, but were not limited to, assays to determine the length of the fragments that can be amplified using a short extension cycle (e.g., 5 seconds to 30 seconds), the ability of the polymerase to tolerate different buffers (e.g., NEB Thermopol buffer, Phusion HF buffer, OneTaq Standard Reaction buffer), as well as the ability to amplify DNA template with higher GC content (>60% GC), ability to generated DNA template with better purity, ability to increase polymerase strand displacement activity. In general, these tests involved setting up a PCR reaction with genomic DNA as a template (e.g., human or bacterial genomic DNA, plasmid DNA), and then subjecting the reaction to the following thermocycling conditions: an initial denaturation step of 95° C., followed by 25-35 cycles of 15 seconds at 95° C., 20 seconds at 55° C. and 10 seconds −1 minute at 72° C.

Some polymerase fusions were inactive in the PCR assay. In these cases, many of the polymerases on their own (i.e., without the DNA binding domain) were also inactive. However, a significant portion of the polymerase fusions retained activity, some having increased activity and some having reduced activity, relative to the polymerase on its own (i.e., without the DNA binding domain). Collectively, more than 30% of the fusion proteins that either contained DNA polymerase SP-04 or the SP-17 DNA binding domain exhibited an enhanced performance relative to the polymerase domain of the fusion protein on its own, in at least one of the conditions tested. The data shown in FIGS. 20-23 shows data from the 18 fusion proteins shown in FIGS. 16, 17, 18A, 18B, 19A and 19B.

Figure 20:
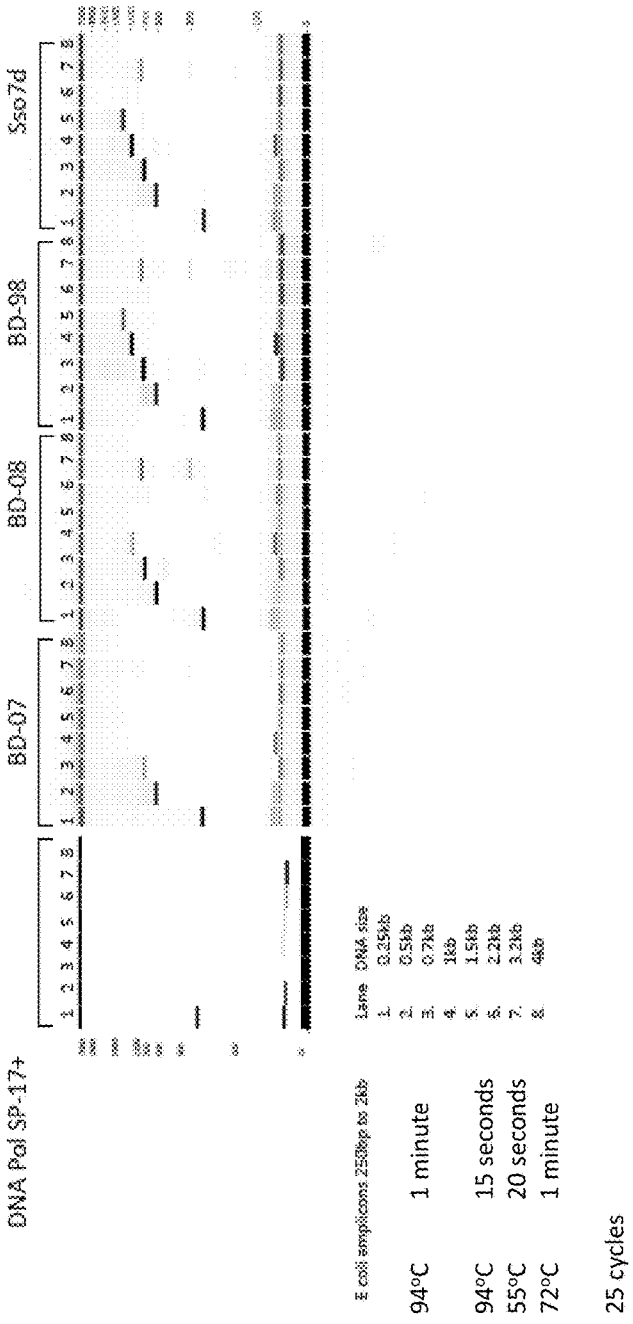
FIG. 20 shows data showing that DNA polymerase SP-17 (family B) has enhanced PCR activity after it is fused to various DNA binding domains. In this assay, enhanced PCR activity is the ability of the fusions to amplify longer DNA fragments. The data shown in lanes 1-8 on the left was produced using the SP-17 polymerase without a DNA binding domain. This polymerase was able to amplify longer fragments when it was fused to the BD-07, BD-08 and BD-98 DNA binding domains.

FIG. 20 show that BD-07 (a lambda repressor-like DNA binding domain from *T. maritima*), BD-08 (a lambda repressor-like DNA binding domain from *T. maritima*), and BD-98 (a winged helix domain from *P. furiosus*) enhance the ability of the SP-17 polymerase (an Archael family B polymerase from *Archaeoglobus profundus*) to amplify longer fragments.

Figure 21:
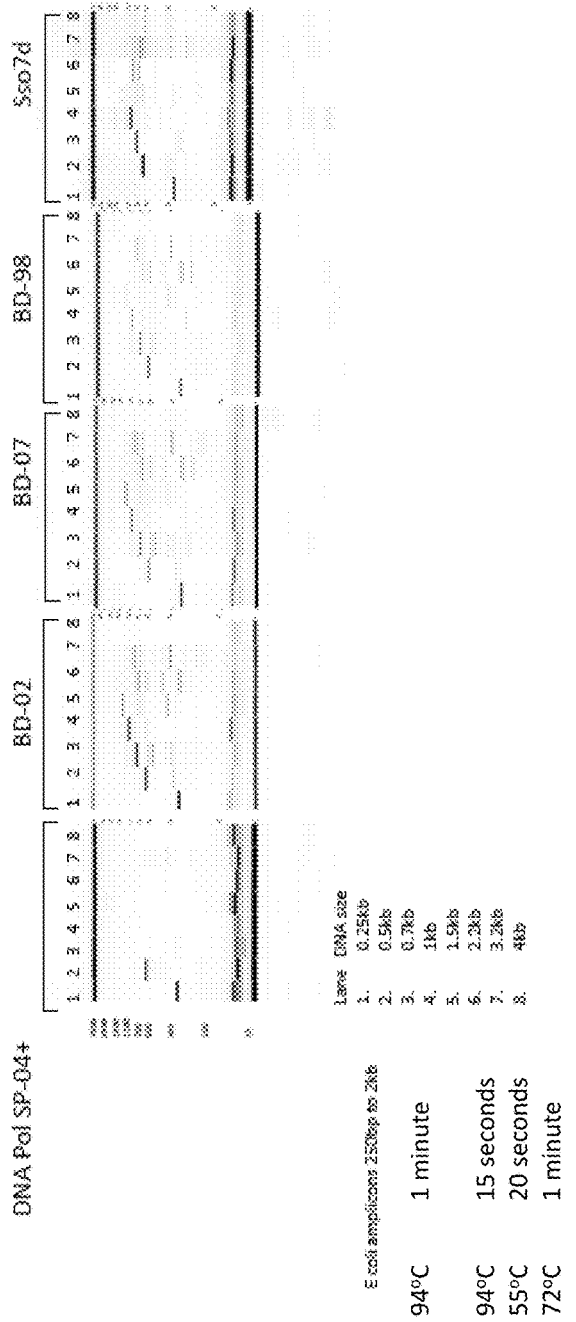
FIG. 21 shows data showing that DNA polymerase SP-04 (family A) has enhanced PCR activity after it is fused to various DNA binding domains. In this assay, enhanced PCR activity is the ability of the fusions to amplify longer DNA fragments. The data shown in lanes 1-8 on the left was produced using the SP-04 polymerase without a DNA binding domain. This polymerase was able to amplify longer fragments when it was fused to the BD-02, BD-07 and BD-98 DNA binding domains.

FIG. 21 show that BD-02 (an HCP-like CroI-C1-type HTL-type DNA binding domain from *T. maritima*), BD-07 (a lambda repressor-like DNA binding domain from *T. maritima*), and BD-98 (a winged helix domain from *P. furiosus*) enhance the ability of the SP-04 polymerase to amplify longer fragments.

Figure 22:
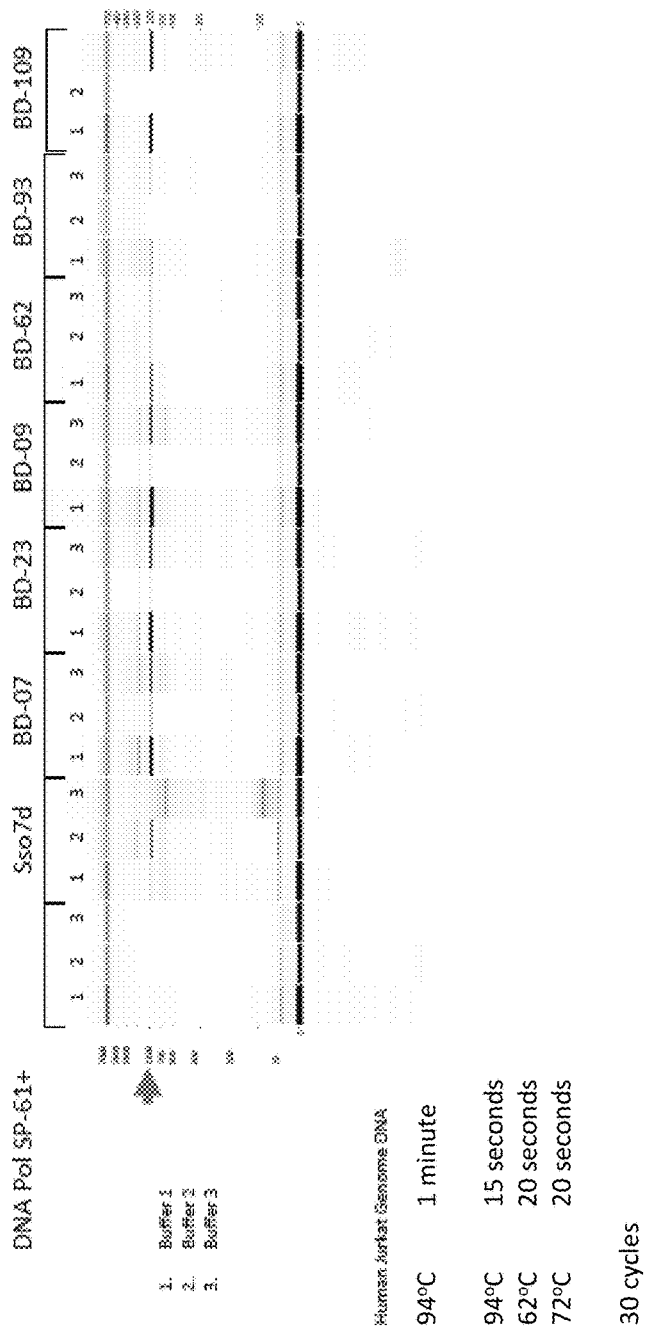
FIG. 22 shows data showing that DNA polymerase SP-61 (family B) has enhanced PCR activity after fused to DNA binding domains. In this assay, enhanced PCR activity is a higher tolerance to different buffers. The data shown in lanes 1-3 on the left was produced using the SP-61 polymerase without a DNA binding domain. This polymerase was able to amplify fragments in a wide variety of buffers when it was fused to the BD-07, BD-23, BD-09, BD-62, BD-93 and BD-109 DNA binding domains.

FIG. 22 show that BD-07 (a lambda repressor-like DNA binding domain from *T. maritima*), BD-23 (a winged helix domain from *T. maritima*), BD-09 (a lambda repressor-like DNA binding domain from *T. maritima*), BD-62 (a ribbon-helix helix DNA-binding domain from *P. furiosus*) and BD-93 (a winged helix DNA-binding domain from *P. furiosus*) and BD-109 (another winged helix DNA-binding domain from *P. furiosus*) enhance the ability of the SP-61 polymerase (an Archael family B polymerase from *Archaeoglobus profundus*) to tolerate different buffers.

Figure 23:
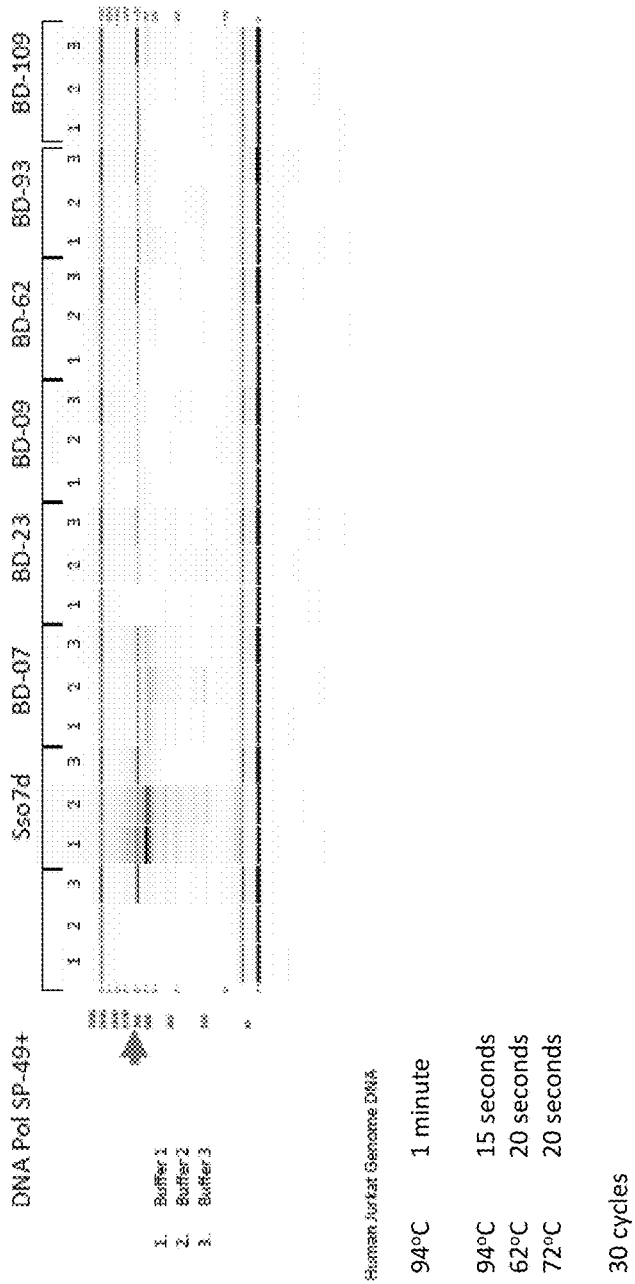
FIG. 23 shows data showing that DNA polymerase SP-49 (family B) has enhanced PCR activity after fused to DNA binding domains. In this assay, enhanced PCR activity is a higher tolerance to different buffers. The data shown in lanes 1-3 on the left was produced using the SP-49 polymerase without a DNA binding domain. This polymerase was able to amplify fragments in a wide variety of buffers when it was fused to the BD-07, BD-23, BD-09, BD-62, BD-93 and BD-109 DNA binding domains.

FIG. 23 show that BD-07 (a lambda repressor-like DNA binding domain from *T. maritima*), BD-23 (a winged helix domain from *T. maritima*), BD-09 (a lambda repressor-like DNA binding domain from *T. maritima*), BD-62 (a ribbon-helix helix DNA-binding domain from *P. furiosus*) and BD-93 (a winged helix DNA-binding domain from *P. furiosus*) and BD-109 (another winged helix DNA-binding domain from *P. furiosus*) enhance the ability of the SP-04 polymerase to tolerate different buffers.

The data shown in FIGS. 20-23 is representative only.

```
                                              SEQ ID NO: 1
MILDADYITEDGKPIIRLFKKENGRFKVEYDRNFRPYIYALLKDDSAIDD

VRKITSERHGKVVRVIDVEKVKKKFLGRPIEVWKLYFEHPQDVPAMRDKI

REHPAVIDIFEYDIPFAKRYLIDKGLIPMEGNEELTFLAVDIETLYHEGE

EFGKGPIIMISYADEEGAKVITWKKIDLPYVEVVANEREMIKRLIKVIRE

KDPDVIITYNGDNFDFPYLLKRAEKLGMKLPLGRDNSEPKMQRLGDSLAV

EIKGRIHFDLFPVIRRTINLPTYTLEAVYEAIFGKQKEKVYPHEIAEAWE

TGKGLERVAKYSMEDAKVTYELGKEFFPMEAQLARLVGQPLWDVSRSSTG

NLVEWYLLRKAYERNELAPNKPDEREYERRLRESYEGGYVKEPERGLWEG

IVSLDFRSLYPSIIITHNVSPDTLNKEGCGEYDEAPEVGHRFCKDFPGFI

PSLLGSLLEERQKIKKRMKESKDPVERKLLDYRQRAIKILANSFYGYYGY

AKARWYCKECAESVTAWGRQYIELVRRELEERGFKVLYIDTDGLYATIPG

EKNWEEIKRRALEFVNYINSKLPGILELEYEGFYTRGFFVTKKKYALIDE

EGKIVTRGLEIVRRDWSEIAKETQAKVLEAILKHGNVEEAVKIVKEVTEK

LSNYEIPVEKLVIYEQITRPLNEYKAIGPHVAVAKRLAAKGIKIKPGMVI

GYVVLRGDGPISKRAIAIEEFDGKKHKYDAEYYIENQVLPAVERILKAFG

YKREDLRWQKTKQVGLGAWLKVKKS

SEQ ID NO: 2
IINPQARLTPLELEILEIIKQKKSITITEIKEILSERRKSEYPLSLVSEY

ISRLERKGYVKKIAKGRKKFVEALI

SEQ ID NO: 3
MILDADYITEDGKPIIRLFKKENGRFKVEYDRNFRPYIYALLKDDSAIDD

VRKITSERHGKVVRVIDVEKVKKKFLGRPIEVWKLYFEHPQDVPAMRDKI

REHPAVIDIFEYDIPFAKRYLIDKGLIPMEGNEELTFLAVDIETLYHEGE

EFGKGPIIMISYADEEGAKVITWKKIDLPYVEVVANEREMIKRLIKVIRE

KDPDVIITYNGDNFDFPYLLKRAEKLGMKLPLGRDNSEPKMQRLGDSLAV

EIKGRIHFDLFPVIRRTINLPTYTLEAVYEAIFGKQKEKVYPHEIAEAWE
```

```
TGKGLERVAKYSMEDAKVTYELGKEFFPMEAQLARLVGQPLWDVSRSSTG

NLVEWYLLRKAYERNELAPNKPDEREYERRLRESYEGGYVKEPERGLWEG

IVSLDFRSLYPSIIITHNVSPDTLNKEGCGEYDEAPEVGHRFCKDFPGFI

PSLLGSLLEERQKIKKRMKESKDPVERKLLDYRQRAIKILANSFYGYYGY

AKARWYCKECAESVTAWGRQYIELVRRELEERGFKVLYIDTDGLYATIPG

EKNWEEIKRRALEFVNYINSKLPGILELEYEGFYTRGFFVTKKKYALIDE

EGKIVTRGLEIVRRDWSEIAKETQAKVLEAILKHGNVEEAVKIVKEVTEK

LSNYEIPVEKLVIYEQITRPLNEYKAIGPHVAVAKRLAAKGIKIKPGMVI

GYVVLRGDGPISKRAIAIEEFDGKKHKYDAEYYIENQVLPAVERILKAFG

YKREDLRWQKTKQVGLGAWLKVKKSGTGGGGIINPQARLTPLELEILEII

KQKKSITITEIKEILSERRKSEYPLSLVSEYISRLERKGYVKKIAKGRKK

FVEALI
```

SEQ ID NO: 33
```
MKEKAPKIDALIDCTYKTEDNRAVIYLYLLENILKDREFSPYFYVEMLKD

RIEKEDIDKIKEFLLKEDLLKFVENLEVVNKTILKKEKEIVKIIATHPQR

VPKLRKIKECDIVKEIYEHDIPFAKRYLIDSDIVPMTYWDFENRKQVSIE

IPKLKTVSFDMEVYNRDTEPDPEKDPILMASFWDDNGGKVITYKHFDHSN

IEVVNSEKDLIKKIVEMLRQYDVIFTYNGDNFDFPYLKARAKIYGIDIKL

GRDGEELKIKRGGMEFRSYIPGRVHIDLYPISRRLLKLTKYTLEDVVYNL

FGIEKLKIPHTKIVDYWANNDKILIEYSLQDAKYTHKIGKYFFPLEVMFS

RIVNQTPFEITRMSSGQMVEYLLMKNAFKENMIVPNKPDEKEYRKRLLTS

YEGGYVKEPEKGMFEDIISMDFRCHPRGTKVIVKNNGLTDIENVKVGDYV

LGIDGWQKVKRVWKYPYNGFLVNVNGLKSTPNHKIPVIKKENGKDRVIDV

SSIYLLNLKGCKILKIKNFESIGMFGKIFKKDTKIKKVKGLLEKIAYIDP

REGLVIKVKNEKEDIFKTVIPILKELNILYKQVDEKTIIIDSIDGLLKYI

VTIGFNDKNEEKIKEIIKEKSFLEFKELEDIKISIEEYEGYVYDLTEGR

PYYFANGILTHNSLYPSIIIAYNISPETLDCECCKDISEKILGHWFCKKR

EGLIPKTLRGLIERRINIKNKMKKMESEKEINEEYNLLDYEQRSLKILAN

SVYGYLAFPRARFYSRECAEVITYLGRKYILETIEEAEKFGFKVIYADSV

VKDAKVIIKEDGKIKEIKIEDLFKKVDYTIGDKEYCILNNVETLTIEDTK

LVWRKVPYIMRHRTNKKIYRVKVKDRYVDITEDHSIIGVKNNKLVELKPT

EIKDDETKLIILNKDLKSYNFASVEEINCIKYSDYVYDIEVENTHRFFAN

GILVHNTDGFYAVWKEKISKDDLIKKALEFVKYINSKLPGTMELEFEGYF

KRGIFITKKRYALIDENGRVIVKGLEFVRRDWSNLARITQRRVLEALLLE

GDINKAKKAIQDVIKDLREKKIKKEDLIIYTQLTKNPNEYKTTAPHVEIA

KKMMREGKKIKIGDVIGYIIVKGSKSISERAKLPEEVSIEEIDVNYYIDN

QILPPVLRIMEAVGVSKNELKKEGTQLTLDRFLK
```

SEQ ID NO: 34
```
MERVEGWLIDADYETIGGKAVVRLWCKDDQGIFVAYDYNFDPYFYVIGVD

EDILKNAATSTRREVIKLKSFEKAQLKTLGREVEGYIVYAHHPQHVPKLR

DYLSQFGDVREADIPFAYRYLIDKDLACMDGIAIEGEKQGGVIRSYKIEK
```

```
VERIPRMEFPELKMLVFDCEMLSSFGMPEPEKDPIIVISVKTNDDDEIIL

TGDERKIISDFVKLIKSYDPDIIVGYNQDAFDWPYLRKRAERWNIPLDVG

RDGSNVVFRGGRPKITGRLNVDLYDIAMRISDIKIKKLENVAEFLGTKIE

IADIEAKDIYRYWSRGEKEKVLNYARQDAINTYLIAKELLPMHYELSKMI

RLPVDDVTRMGRGKQVDWLLLSEAKKIGEIAPNPPEHAESYEGAFVLEPE

RGLHENVACLDFASMYPSIMIAFNISPDTYGCRDDCYEAPEVGHKFRKSP

DGFFKRILRMLIEKRRELKVELKNLSPESSEYKLLDIKQQTLKVLTNSFY

GYMGWNLARWYCHPCAEATTAWGRHFIRTSAKIAESMGFKVLYGDTDSIF

VTKAGMTKEDVDRLIDKLHEELPIQIEVDEYYSAIFFVEKKRYAGLTEDG

RLVVKGLEVRRGDWCELAKKVQREVIEVILKEKNPEKALSLVKDVILRIK

EGKVSLEEVVIYKGLTKKPSKYESMQAHVKAALKAREMGIIYPVSSKIGY

VIVKGSGNIGDRAYPIDLIEDFDGENLRIKTKSGIEIKKLDKDYYIDNQI

IPSVLRILERFGYTEASLKGSSQMSLDSFFS
```

SEQ ID NO: 35
```
MIKAWLLDVDYVTENDRAVIRLWCKDDKGVFVAYDRNFLPYFYVIGCKAE

DVMKVKVRTNEGIITPLKVEEIEAKSLGKPIKALKVYTRHPQHVPKLREE

IKKFAEVREADIPFAYRYLIDKDLACMDGIEIEPIAVKEGVLRAYEVRSV

RRVEKKGFPDLKILAFDCEMLAQFMPDPEKDPIIAIAVKCGDFEEVLHGD

ERDILRRFVSIIKEQDPDIIVGYNQDNFDWPYVKKRAEKFGIRLDIGRDR

SEISFRGGRPKIAGRLNVDLYDIALKIPDVKIKTLKKVAEFLGAKVEEED

IEGRDIYKCWMRGEKEKVFKHVLNDVLTTYRLALELLPMHYELSRMIRLP

LDDVARLGRGKQVDYFLLSEAKKINEIAPNPPEIEESYEGAFVLEPARGL

HENVACLDFASMYPSIMINFNISPDTLVKGECEDCYVAPEVGHKFRKSPD

GFFKRILKMLIEKRREMKRQMKELDPSEDYKLLDIKQQTLKVLTNSFYG

YTGWNLARWYCRECAEATTAWGRYFIKRAVKIAESMGFEVLYGDTDSLFI

KKNKLNLKDLEKECLKLIDVISKELPIQLEIDEFYKAIFFVEKKRYAGLT

DDDRIVVKGLEVRRGDWCELAKRVQREVIEIILRERNPDKALKFVKNVIE

EIKEGKFKLEDYVIYKGLTKKPDKYESKQAHVKAALRAMEMGIYYPIGTK

VGFVIVKGGGSISDRAYPIELIEEFDGENLKIRTPSGIMVKKIDKDYYID

HQIIPAVMRILERFGYTEASLKTTIQKTLFDFT
```

SEQ ID NO: 36
```
MKLVIFDGNSILYRAFFALPELTTSSNIPTNAIYGFINVILKYLEQEKPD

YIAVAFDKRGREARKSEYQEYKANRKPMPDNLQVQIPYVREILYALNIPI

VEFEGYEADDVIGSLVNKFKNTGLDIVIITGDRDTLQLLDKNVVVKIVST

KFDRTMEDLYTIENIKEKYGVWANQVPDYKALVGDQSDNIPGVKGIGEKS

AQKLLEEYSSLEEIYQNLDKIKGSIREKLEAGKDMAFLSKRLATIVCDLP

LNVNLEDLRTKEWNKERLYEILVQLEFKSIIKRLGLSENIQFEFVQQRTD

IPDVEQRELESISRIRSKEIPLMFVQDEKCFYLYDQESNTVFVTRDRHLV

EEILKSDTVKIVYDLKNIFHQLNEDTDNIKNCEDVMIASYVLDSTRSSY

ELETLFVSYLNTDIEAVKKDKKMVSVVLLKRLWDDLLRLIDLNSCQFLYE

NIERPLIPVLYEMEKTGFKVDRDALLQYTKEIENKILKLETQIYQIAGEW

FNINSPKQLSYILFEKLKLPVIKKTKTGYSTDAEVLEEFDKHEIVPLILD
```

-continued

YRMYTKILTTYCQGLLQAINPSSGRVHTTFIQTGTATGRLASSDPNLQNI

PVKYDEGKLIRKVFVPEEGHVLIDADYSQIELRILAHISEDERLINAFKN

NIDIHSQTAAEVFGVDIADVTPEMRSQAKAVNFGIVYGISDYGLARDIKI

SRKEAAEFINKYFERYPKVKEYLDNIVRFARENGYVLTLFNRKRYVKDIK

SANRNARSYAERIAMNSPIQGSAADIMKLAMIKVYQKLKENNLKSKIILQ

VHDELLIEAPYEEKDIVKRIVKREMENAVALKVPLVVEVKEGLNWYETK

SEQ ID NO: 37
MEKRVYLVDITYGLVGNSPEIRMFGVDENGEKVVILDRGFRPYFYVIPEE

GFEDQVARVIGKMQNVIKADVTERRLFGKPIKVVKVTVTVPDKVRELRDR

VKSIQHVKEVLEADIRFYIRYMIDNDIRPGWLMFSNLKPVDNKIGGVSNV

YLTETPPTSLDLGIMPRLNYMALDIEVYNPRGTPDPKRDPIIIIALANSN

GDVKLLTLDNYKHEREMLNDMMSVIKEWDPDVLFGYNSNKFDMPYLVNRA

DALNVKLQLSKYGTPPEQSVYGHWSIIGRAHIDLYNFIEDMTDVKRKSLD

YVAEYFGVMKRSERVNIPGHRIYQYWDDEGKRSQLIKYARDDVLSTLGLG

KILLPYAMQLASVSGLPLDQVGPASVGSRVEMMIMHEAYKMGELAPNRVE

RPYETYKGAIVLEPKPGIHYNIAVLDFSSMYPNIMLKYNISPDTLVLDSS

EGDYYTAPEVGYRFRKSPRGLYASLLQKLIEARREARDEMRNYPEGSFEW

VLLNERQRALKIMANAMYGYCGWLGARWYIREVAESVTAWGRYLLKTAMS

MAKERGLTVIYGDTDSLFVTYDKDKVADIISRINEMGFEVKIDKVYSKLI

FTESKKRYIGLTADGEVDIVGFEAVRGDWSELARNVQERVAELVLRESVD

EAVKYVKSVIDDLRNYRFTIDDVIIWKTLDKDINEYKAIQPHVVAARRLM

EKGYVVNKGDTVGFVIVKDSGDKLTQRAYPYVFINDVKEIDVDYYVEKQV

IPAALRILEVFGVNEAALLGKTGKSILDYFH

SEQ ID NO: 38
MTEVVFTVLDSSYEVVGKEPQVIIWGIAENGERVVLIDRSFRPYFYALLA

PGADPKQVAQRIRALSRPKSPIIGVEDDKRKYFGRPRRVLRIRTVLPEAV

REYRELVKNVDGVEDVLEADIRFAMRYLIDHDLFPFTWYRVEAEPLENKM

GFRVDKVYLVKSRPEPLYGEALAPTKLPDLRILAFDIEVYSKQGSPRPER

DPVIVIAVKTDDGDEVLFIAEGKDDRKPIREFVEYVKRYDPDIIVGYNNN

HFDWPYLLRRARILGIKLDVTRRVGAEPTTSVHGHVSVPGRLNVDLYDYA

EEMPEIKIKSLEEVAEYLGVMKKSERVIINWWEIPDYWDDPKKRPLLQY

ARDDVRATYGLAEKILPFAIQLSYVTGLPLDQVGAMSVGFRLEWYLIRAA

FKMKELVPNRVERPEETYRGAIVLEPLRGVHENIAVLDFSSMYPNIMIKY

NVGPDTLVRPGEECGECGCWEAPEVKHRFRRCPPGFFKTVLERLLELRKR

VRAEMKKYPPDSPEYRLLDERQKALKVLANASYGYMGWSGARWYCRECAE

AVTAWGRHLIRTAINIARKLGLKVIYGDTDSLFVTYDPEKVEKFIKIIEE

ELGFEIKLEKVYKRVFFTEAKKRYAGLLEDGRIDIVGFEAVRGDWCELAK

EVQTKVVEIVLKTSDVNKAVEYVRKIVKELEEGKVPIEKLVIWKTLSKRL

EEYTTEAPHVVAAKRMLSAGYRVSPGDKIGYVIVKGGGRISQRAWPYFMV

KDPSQIDVTYYVDHQIIPAALRILGYFGITEKKLKASATGQKTLFDFLAK

KSK

SEQ ID NO: 39
MEIRVWPLDVTYIVVGGVPEVRVFGIAEGGERVVLADRSFRPYFYVDCAG

CDPHAVKTHLGRTAPVEGVELVERRFLGRPRQFLKVVAKIPEDVRRLREA

ASTIPGVRGVYEADIRFYMRYVIDMGVVPCSWNVAEVEVADEKLGSLPVY

RVVKWGGAVEGFPPPLRVLAFDIEVYNERGTPDPARDPIVMIAVQSSDGR

LEVFEASGRDDRGVLRSFVEYVRSFDPDVVVGYNSNNFDWPYLAERAKAV

GVPLRVDRLGGAPQQSVYGHWSVLGRANVDLYNIVDEFPEIKLKTLDRVA

EYFGVMRRDERVLIPGHKIYEYWRDPSKRPLLRQYVIDDVRSTYGLAERL

LPFLIQLSSVSGLPLDQVAAASVGNRVEWMLLRYAYGLGEVAPNREEREY

EPYKGAIVLEPKPGLYSDVLVLDFSSMYPNVMMRYNLSPDTYLEPGEPDP

PEGVYVAPEVGHRFRKEPPGFIPQVLRRLVALRRAVREEMKKYQPDTPEY

RVLDERQKALKIMANAMYGYTGWVGARWYKKEVAESVTAFARAILKDVID

YARRLGIVVIYGDTDSLFVKKGGDLEKLARYVDEKYGIE1KVDKDYEKVL

FTEAKKRYAGLLRDGRIDIVGFEVVRGDWSELAKEVQLKVIELILKARDL

SEARQRVIKYVKDVIERLKSGKFDLDDLIIWKTLDKDLGEYKAYPPHVRA

ALILKKKGYKVGRGTTIGYVVVKGGEKVSERSLPYILVDDLAKIDVDYYI

EKQVIPAALRIAEVIGVKEGDLRAGRSEKSLLDFEE

SEQ ID NO: 40
MSEKINLEFYFLDNSYEVIGNEPHIIWGITRDGRRVLLRDRRFRPYFYA

ILKDKVNIEDLARKIRTYSDPKSPIIGVEPVEKKYFGRKVSALKIITMIP

EYVRKYREKIKSLPEVLEVVEADIRFSIRYIIDHDLRPCGWHVAEVVEVP

KKPIYRVDAEYEIIGDIKPLEQTLQPDLRIIAFDIEVYNKSGTPRPQTDP

IIIIGIMNNNGDIKQFLANKYDDKISVEEFVNYVKTFDPDIIVGYNTDGF

DWPYLIERSKYIGVKLDVTRRVGATPRTSTYGHISVPGRLNTDLYHFAEE

IPEVKVKSLENVAEYLGVMKKSERVIIEYIDIPKYWDDEKLRPKLLQYNI

DDVKSTYGLAEKFLPFAMQLSNITGLPLDQVGAASVGFRLEWYLMREAFR

YGELVPNRVERAAESYRGAVVLKPVKGVHENIAVLDFSSMYPNIMIKYNV

GPDTIVRNEKCNPDKHNIAPEVGHCFRKEPPGFFKRVLETLLRLRKQIKS

EMKKYPPTSYEYRLLDERQKAVKVLANATYGYMGWIHARWYCRECAEAVT

AWGRQTIKSAIELARKLGLKVIYGDTDSLFVTYDKDKVEKLIELIQTKLG

FEIKIDKIYKRVFFTEAKKRYAGLLEDGRIDIVGFEAVRGDWAEIAKEVQ

EKVTEILLKENSIDKAIEYVRQVIADLKAGKIPLDKLIIWKTLSKRIEEY

SVDAPHVVAAKKLIKAGIKVSTNDKIGYVILKGGGKISSRAEPYIFVKDP

KLIDTEYYVDHQIVPAALRILNYFGVTETQLKRAAASAGQKSLFDFFGGK

K

SEQ ID NO: 41
MILDADYITENGKPVVRIFKKENGEFKVEYDRSFRPYIYALLRDDSAIED

IKKITAERHGKVVRVVEAEKVRKKFLGRPIEVWKLYFEHPQDVPAIREKI

REHPAVIDIFEYDIPFAKRYLIDKGLIPMEGNEEELKLLAFDIETLYHEGD

EFGSGPIIMISYADEKGAKVITWKGVDLPYVEVVSSEREMIKRFLRVIRE

KDPDVIITYNGDNFDFPYLLKRAEKLGMKLPIGRDSEPKMQRMGDGFAV

EVKGRIHFDIYPVIRRTINLPTYTLEAVYEAVFGRPKEKVYPNEIARAWE

-continued

NCKGLERVAKYSMEDAKVTYELGREFFPMEAQLARLVGQPVWDVSRSSTG
NLVEWFLLRKAYERNELAPNRPDEREYERRLRESYEGGYVKEPEKGLWEG
IIYLDFRSLYPSIIITHNISPDTLNKEGCNSYDVAPKVGHRFCKDFPGFI
PSLLGQLLDERQKIKRKMKATIDPIERKLLDYRQRAIKILANSYYGYYGY
AKARWYCKECAESVTAWGREYIELVSRELEKRGFKVLYIDTDGLYATIPG
SREWDKIKERALEFVKYINARLPGLLELEYEGFYKRGFFVTKKKYALIDE
EGKIITRGLEIVRRDWSEIAKETQARVLEAILKEGNLEKAVKIVKEVTEK
LSKYEVPPEKLVIYEQITRDLKDYKAVGPHVAVAKRLAARGIKVRPGMVI
GYLVLRGDGPISRRAIPAEEFDPSRHKYDAEYYIENQVLPAVLRILEAFG
YRKEDLRYQKTRQAGLDAWLKRKASL

SEQ ID NO: 42
MILDTDYITENGKPVIRVFKKENGEFKIEYDRTFEPYFYALLKDDSAIED
VKKVTAKRHGTVVRVKKRAEKVQRKFLGRPIEVWKLYFTHPQDVPAIRDKI
RAHPAVIDIYEYDIPFAKRYLIDKGLIPMEGDEELTMLAFDIETLYHEGE
EFGTGPILMISYADGSEARVITWKKIDLPYVDVVSTEKEMIKRFLRIVKE
KDPDVLITYNGDNFDFAYLKKRCEKLGIKFTLGRDGSEPKIQRMGDRFAV
EVKGRIHFDLYPVIRRTINLPTYTLEAVYEAVFGKPKEKVYAEEIAQAWE
SGEGLERVARYSMEDAKVTYELGREFFPMEAQLSRLIGQSLWDVSRSSTG
NLVEWFLLRKAYERNELAPNKPDEKELARRRGGYAGGYVKEPERGLWDNI
VYLDFRSLYPSIIITHNVSPDTLNREGCKEYDVAPEVGHKFCKDFPGFIP
SLLGDLLEERQKIKRKMKATVDPLEKKLLDYRQRAIKILANSYYGYYGYA
KARWYCRECAESVTAWGREYIETTIREIEEKFGFKVLYADTDGFFATIPG
ADAETVKKKAKEFLKYINAKLPGLLELEYEGFYVRGFFVTKKKYAVIDEE
GKITTRGLEIVRRDWSEIAKETQARVLEAILKHGDVEEAVRIVKEVTEKL
SKYEVPPEKLVIHEQITRDLRDYKATGPHVAVAKRLAARGVKIRPGTVIS
YIVLKGSGRIGDRAIPFDEFDPTKHRYDAEYYIENQVLPAVERILKAFGY
RKEDLRYQKTKQVGLGAWLKVKK

SEQ ID NO: 43
MILDTDYITEDGKPVIRIFKKENGEFKIEYDREFEPYIYALLKDDSAIEE
VKKITAGRHGRVVKVKRAEKVKKKFLGRPIEVWKLYFTHPQDVPAIRDEI
RRHSAVVDIYEYDIPFAKRYLIDKGLIPMEGDEELKMMSFDIETLYHEGE
EFGTGPILMISYADEGEARVITWKKIDLPYVEVVSTEKEMIKRFLKVVKE
KDPDVLITYNGDNFDFAYLKKRCEKIGIKFTLRRDGSEPKIQRMGDRFAV
EVKGRIHFDLYPVIRRTINLPTYTLEAVYEAVFGTPKEKVYPEEITTAWE
TGEGLERVARYSMEDAKVTYELGREFFPMEAQLSRLIGQSLWDVSRSSTG
NLVEWFLLRKAYERNEIAPNKPDERELARRRGGYAGGYVKEPERGLWDNI
VYLDFMSLYPSIIITHNVSPDTFNREGCKEYDTAPQVGHKFCKDVQGFIP
SLLGALLDERQKIKKRMKASIDPLEKKLLDYRQKAIKILANSYYGYYGYA
RARWYCKECAESVTAWGRDYIETTIHEIEERFGFKVLYADTDGFFATIPG
ADAETVKKKAKEFLKYINAKLPGLLELEYEGFYVRGFFVTKKKYAVIDEE
GKITTRGLEIVRRDWSEIAKETQARVLEAILRHGDVEEAVRIVKDVTEKL
SKYEVPPEKLVIHEQITRELKDYKATGPHVAIAKRLAARGIKIRPGTVIS

YIVLKGSGRIGDRAIPFDEFDPTKHRYDAEYYIENQVLPAVERILKAFGY
KKEELRYQKTRQVGLGAWLKLKGKK

SEQ ID NO: 44
MILDADYITEDGKPVVRIFKKENGEFKIEYDREFEPYIYALLRDDSAIEE
IKKITADRHGKVVKVKRAEKVQKKFLGRPIEVWKLYFTHPQDVPAIRDEI
RKHPAVVDIYEYDIPFAKRYLIDKGLIPMEGDEEKLMLAFDIETLYHEGE
EFGTGPILMISYADEDGARVITWKKIDLPYVDVVSTEKEMIKRFLKVVKE
KDPDVLITYNGDNFDFAYLKKRCEKLGIKFTLGRDGSEPKIQRMGDRFAV
EVKGRIHFDLYPLIRRTINLPTYTLEAVYEAVFGKPKEKVYAEEIALAWE
SGEGLERVARYSMEDAKVTFELGREFFPMEAQLSRLIGQSLWDVSRSSTG
NLVEWFLLRKAYERNELAPNKPNERELARRRGGYAGGYVKEPERGLWDNI
VYLDFRSLYPSIIITHNVSPDTLNREGCKEYDRAPQVGHKFCKDVPGFIP
SLLGSLLDERQKIKRKMKATIDPIEKKLLDYRQRAIKILANSYYGYYGYA
RARWYCRECAESVTAWGREYIEMAIRELEEKFGFKVLYADTDGLHATIPG
ADAETVKKKAMEFLKYINPKLPGLLELEYEGFYARGFFVTKKKYAVIDEE
GKITTRGLEIVRRDWSEIAKETQARVLEAILRHGDVEEAVRIVKEVTEKL
SKYEVPPEKLVIHEQITRELKDYRATGPHVAIAKRLAKRGIKIRPGTVIS
YIVLKGSGRIGDRAIPFDEFDPTKHKYDAEYYIENQVLPAVERVLKAFGY
RKDDLRYQKTRQVGLGAWLKVKKR

SEQ ID NO: 45
MILDADYITEDGKPVIRVFKKEKGEFKINYDRDFEPYIYALLKDDSAIED
IKKITAERHGTTVRVTRAERVKKKFLGRPVEVWKLYFTHPQDVPAIRDKI
REHPAVVDIYEYDIPFAKRYLIDKGLIPMEGNEELRMLAFDIETLYHEGE
EFGEGPILMISYADEEGARVITWKNIDLPYVESVSTEKEMIKRFLKVIQE
KDPDVLITYNGDNFDFAYLKKRSETLGVKFILGRDGSEPKIQRMGDRFAV
EVKGRIHFDLYPVIRRTINLPTYTLETVYEAIFGQPKEKVYAEEIAQAWE
SGEGLERVARYSMEDAKATYELGKEFFPMEAQLSRLVGQSLWDVSRSSTG
NLVEWFLLRKAYERNELAPNKPDERELARRAESYAGGYVKEPEKGLWENI
VYLDYKSLYPSIIITHNVSPDTLNREGCREYDVAPQVGHRFCKDFPGFIP
SLLGDLLEERQKVKKKMKATVDPIERKLLDYRQRAIKILANSYYGYYGYA
NARWYCRECAESVTAWGRQYIETTMREIEEKFGFKVLYADTDGFFATIPG
ADAETVKKKTKEFLNYINPRLPGLLELEYEGFYRRGFFVTKKKYAVIDEE
DKITTRGLEIVRRDWSEIAKETQARVLEAILKHGDVEEAVRIVKEVTEKL
SRYEVPPEKLVIYEQITRNLRDYRATGPHVAVAKRLAARGIKIRPGTVIS
YIVLKGPGRVGDRAIPFDEFDPAKHRYDAEYYIENQVLPAVERILRAFGY
RKEDLRYQKTKQAGLGAWLKPKT

SEQ ID NO: 46
MILGADYITKDGKPIVRIFKKENGEFKIELDPHFQPYIYALLSEDSAIDE
IKQIKGERHGKTVRIVDAVKVEKKFLKKPVKVWKLILEHPQDVPAIRNKI
REHPAVQDIYEYDIPFAKRYLIDNGLIPMEGDEELKMLAFDIETFYHEGD
EFGKGEIIMISYADEEGARVITWKNIDLPYVDVVSNEREMIKRFIQIIKE
KDPDVIITYNGDNFDLPYLIKRAEKLGLRLILSRDNENPVPKIQRMGNSF

```
AVEIKGRIHFDLFPVVKRAVNLPTYTLEAVYETVLGKHKSKLGAEEIAAI
WETEEGLKKLAQYSMEDAKATYELGREFFPMEVELAKLIGQSVWDVSRSS
TGNLVEWYMLRVAYERNELAPNRPSDEEYKRRLRTTYLGGYVKEPERGLW
ENIIYLDFRSLYPSIIVTHNVSPDTLERKGCQNYDVAPIVGYKFCKDFSG
FIPSILEDLIETRQKIKKEMKSTIDPIKKKMLDYRQRAVKLLANSYYGYM
GYPKARWYSKECAESVTAWGRHYIEMTIREIEEKFGFKVLYADTDGFYAT
IPGADPETIKKKAKEFLNYINSKLPGLLELEYEGFYLRGFFVTKKRYAVI
DEEEKITTRGLEVVRRDWSEIAKETQARVLEAILREGSVEKAVEIVKEVV
EAITKYKVPLEKLIIHEQITRELRDYKAVGPHVAIAKRLAAKGIKIKPGT
IISYIVLRGSGKISDRVVLLTEYDPRKHKYDPDYYIENQVLPAVLRILEA
FGYRKEDLKYQSSKQTGLESWLKK
```

SEQ ID NO: 47
```
MILDADYITEDGKPIIRIFKKENGEFKVEYDRNFRPYIYALLKDDSQIDE
VKKITAERHGKIVRIVDVEKVKKKFLGRPIEVWKLYFEHPQDVPAIRDKI
REHPAVVDIFEYDIPFAKRYLIDKGLIPMEGDEELKLLAFDIETLYHEGE
EFAKGPIIMISYADEEGAKVITWKKVDLPYVEVVSSEREMIKRFLKVIRE
KDPDVIITYNGDSFDLPYLVKRAEKLGIKLPLGRDGSEPKMQRLGDMTAV
EIKGRIHFDLYHVIRRTINLPTYTLEAVYEAIFGKPKEKVYAHEIAEAWE
TGKGLERVAKYSMEDAKVTYELGREFFPMEAQLSRLVGQPLWDVSRSSTG
NLVEWYLLRKAYERNELAPNKPDEREYERRLRESYAGGYVKEPEKGLWEG
LVSLDFRSLYPSIIITHNVSPDTLNREGCMEYDVAPEVKHKFCKDFPGFI
PSLLKRLLDERQEIKRRMKASKDPIEKKMLDYRQRAIKILANSYYGYYGY
AKARWYCKECAESVTAWGREYIEFVRKELEEKFGFKVLYIDTDGLYATIP
GAKPEEIKRKALEFVEYINAKLPGLLELEYEGFYVRGFFVTKKKYALIDE
EGKIITRGLEIVRRDWSEIAKETQAKVLEAILKHGNVEEAVKIVKEVTEK
LSKYEIPPEKLVIYEQITRPLHEYKAIGPHVAVAKRLAARGVKVRPGMVI
GYIVLRGDGPISKRAILAEEFDPRKHKYDAEYYIENQVLPAVLRILEAFG
YRKEDLRWQKTKQTGLTAWLNVKKK
```

SEQ ID NO: 48
```
MILDADYITEDGKPIIRLFKKENGRFKVEYDRNFRPIYALLKDDSAIDD
VRKITSERHGKVVRVIDVEKVKKKFLGRPIEVWKLYFEHPQDVPAMRDKI
REHPAVIDIFEYDIPFAKRYLIDKGLIPMEGNEELTFLAVDIETLYHEGE
EFGKGPIIMISYADEEGAKVITWKKIDLPYVEVVANEREMIKRLIKVIRE
KDPDVIITYNGDNFDFPYLLKRAEKLGMKLPLGRDNSEPKMQRLGDSLAV
EIKGRIHFDLFPVIRRTINLPTYTLEAVYEAIFGKQKEKVYPHEIAEAWE
TGKGLERVAKYSMEDAKVTYELGKEFFPMEAQLARLVGQPLWDVSRSSTG
NLVEWYLLRKAYERNELAPNKPDEREYERRLRESYEGGYVKEPERGLWEG
IVSLDFRSLYPSIIITHNVSPDTLNKEGCGEYDEAPEVGHRFCKDFPGFI
PSLLGSLLEERQKIKKRMKESKDPVERKLLDYRQRAIKILANSFYGYYGY
AKARWYCKECAESVTAWGRQYIELVRRELEERGFKVLYIDTDGLYATIPG
EKNWEEIKRRALEFVNYINSKLPGILELEYEGFYTRGFFVTKKKYALIDE
EGKIVTRGLEIVRRDWSEIAKETQAKVLEAILKHGNVEEAVKIVKEVTEK
LSNYEIPVEKLVIYEQITRPLNEYKAIGPHVAVAKRLAAKGIKIKPGMVI
GYVVLRGDGPISKRAIAIEEFDGKKHKYDAEYYIENQVLPAVERILKAFG
YKREDLRWQKTKQVGLGAWLKVKKS
```

SEQ ID NO: 49
```
MEGWLLDADYITAEDGRAVVRLWCKDFDGNTFVVYDRNFQPYFYAFKNGL
SKEDIEKIVVKSREGVIKPFKVEEVRRKVFGKEVEVFKIYAYHPQHVPKL
REELKKITEVREADIPFAYRYLIDKDLACMDGIRVEGKVREERGLKVIDA
EHVERFEIPLPEPKVLAFDCEMLTELGMPDPEKDKIIIIGVKCGDFEEII
TGNEREILLRFVEIIKEQDPDVIVGYNQDNFDWPYIRKRAEKLSVKLNIG
RDGSEISFRGGRPKIAGRLNVDLYDIAMKLDVKVKTLENVAEFLGRKVEL
ADIEAKDIYKRWTSGDKESVLKYSKQDVLNTYFIAEELLPMHYELSRMIR
IPTDDVARIGRGKQVDWFLLSEAYKIGEIAPNPAEVEESYEGAFVLEPSR
GLHKNVVCLDFASMYPSIMIAYNISPDTYVFGKCDDCYVAPEVGHKFRKH
PDGFFKRILKMLIEKRREIKNQMKSLDRNSREYLLLNIKQQTLKILTNSF
YGYTGWSGARWYCRQCAEATTAWGRHLIKSAVEIAKKLGFEVLYGDTDSI
FVKKGNLSLEKIRGEVEKLIEEISEKFPVQIEVDEYYKTIFFVEKKRYAG
LTEDGILVVKGLEVRRGDWCELAKEVQKKVIEIILKEENPEKAAEYVRKV
INDIKSGKVKLEDVVIYKGLTKRPDKYESKQAHVKAALRAMELGIVYNVG
SKVGFVVVEGAGNVGDRAYPIDLIEEFDGENLVIRTRSGSIVKKLDKDYY
INHQIIPSVLRILERFGYNEASLKGATQKTLDAFW
```

SEQ ID NO: 50
```
MILDADYITENGKPVVRIFKKENGEFKVEYDRNFEPYIYALLKDDSAIEE
IKKITAERHGTVVRITKAEKVERKFLGRPVEVWKLYFTHPQDVPAIRDKI
RSHPAVVDIYEYDIPFAKRYLIDKGLVPMEGDEELKMLAFDIETLYHEGE
EFAEGPILMISYADESEARVITWKKVDLPYVDAVSTEKDMIKAFLRVVKE
KDPDVLITYNGDNFDFAYLKKRCEKLGVKFILGRDGSEPKIQRMGDRFAV
DVKGRIHFDLYPVIRRTINLPTYTLEAVYEAIFGRPKEKVYAEEIAQAWE
TNEGLERVARYSMEDAKVTYELGKEFFPMEAQLSRLIGQPLWDVSRSSTG
NLVEWFLLRKAYERNELAPNKPSGREYDERRGGYAGGYVKEPEKGLWENI
VYLDYKSLYPSIIITHNVSPDTLNREGCKEYDVAPQVGHRFCKDFPGFIP
SLLGDLLEERQKIKRKMKATIDPIERRLLDYRQRAIKILANSYYGYYYA
RARWYCKECAESVTAWGREYIEMSIREIEEKYGFKVLYADTDGFHATIPG
EDAETIKKKAMEFLKYINSKLPGALELEYEGFYRRGFFVTKKKYAVIDEE
GKITTRGLEIVRRDWSEIAKETQARVLEALLKDGNVEEAVSIVKEVTEKL
SKYEVPPEKLVIHEQITRELKDYKATGPHVAIAKRLAARGVKIRPGTVIS
YIVLKGSGRIGDRAIPFDEFDPAKHRYDAEYYIENQVLPAVERILKAFGY
RKEDLRYQKTRQVGLGAWLKPKGKK
```

SEQ ID NO: 51
```
MILDTDYITENGKPVIRVFKKENGEFKIEYDRTFEPYFYALLKDDSAIED
VKKVTAKRHGAVVKVKRAEKVQRKFLGRPIEVWKLYFTHPQDVPAIRDKI
RAHPAVVDIYEYDIPFAKRYLIDKGLIPMEGDEELRMLAFDIETLYHEGE
```

```
EFGTGPILMISYADENEARVITWKKIDLPYVDVVSTEKEMIKRFLRVVKE
KDPDVLITYNGDNFDFAYLKKRCEKLGIKFTLGRDGSEPKIQRMGDRFAV
EVKGRIHFDLYPVIRRTINLPTYTLEAVYEAVFGKPKEKVYAEEITEAWE
SGEGLERVARYSMEDAKVTYELGREFFPMEAQLSRLIGQSLWDVSRSSTG
NLVEWFLLRKAYERNELAPNKPDERELARRRESYAGGYVKEPERGLWDNI
VYLDFRSLYPSIIITHNVSPDTLNREGCKEYDVAPEVGHKFCKDFPGFIP
SLLGDLLEERQKIKRKMKATIDPLEKKLLDYRQRAIKILANSFYGYYYA
KARWYCKECAESVTAWGREYIETTIREIEEKFGFKVLYADTDGFFATIPG
ADAETVKKKAKEFLKYINAKLPGLLELEYEGFYVRGFFVTKKKYAVIDEE
GKITTRGLEIVRRDWSEIAKETQARVLEAILKHGDVEEAVRIVKEVTEKL
SKYEVPPEKLVIHEQITRDLRDYKATGPHVAVAKRLAAKGVKIRPGTVIS
YIVLKGSGRIGDRAIPADEFDPTKHRYDAEYYIENQVLPAVERILKAFGY
RKEDLRYQKTKQVGLGAWLKVKGKK
```

SEQ ID NO: 52
```
MILDTDYITEDGKPVIRIFKKDNGEFKIEYDRNFEPYIYALLRDDSAIED
VKKITAERHGRVVKVKRAEKVKKKFLGRPVEVWKLYFTRPQDVPAIRDRI
RAHPAVVDIYEYDIPFAKRYLIDKGIIPMEGDEELKMLAFDIETLYHEGE
EFAEGPILMISYADENEARVITWKKIDLPFVDVVSTEKEMIKRFLKVIKE
KDPDVLITYNGDNFDFAYLKKRCEKFGIKFTLGRDGSDPKIQRMGDRFAV
EVKGRIHFDLYPVILRTVNLPTYTLEAVYEAIFGTPKEKVYPEEITTAWE
TGEGLERVARYSMEDAKVTFELGREFFPMEAQLSRLVGQSFWDVSRSSTG
NLVEWFLLRKAYERNELAPNKPDERELVRRRNSYTGGYVKEPERGLWDNI
VYLDFRSLYPSIIITHNVSPDTLNREGCKEYDEAPQVGHKFCKDFPGFIP
SLLGNLLDERQKIKKRMKATIDPLEKKLLDYRQRAIKILANSYYGYYAYA
RARWYCKECAESVTAWGREYIEMSIREIEEKYGFKVLYADTDGFHATIPG
ADAETVKKKAMEFLKYINAKLPGALELEYEGFYKRGFFVTKKKYAVIDEE
GKITTRGLEIVRRDWSEIAKETQARVLEALLKDGNVEEAVSIVKEVTEKL
GKYEVPPEKLVIHEQITRELKDYKATGPHVAIAKRLAARGVKIRPGTVIS
YIVLKGSGRIGDRAIPFDEFDPTKHRYDAEYYIENQVLPAVERILKAFGY
RAEDLRYQKTRQVGLGVWLQPKGKK
```

SEQ ID NO: 53
```
MELAFWLLDITYGVIGNTPELRLFGITDDGKRVLVLDRSFRPYFYVIPSG
DVNAVFNNVKRKLEGKVLNVEVIKRKMFGNEVDAIRVTATIPEKVRELRE
LAAEVPGVEDVLEADIRFSQRYLLDMGVKPSNWIVVDQCEEVKGNYQVDL
VCLAKSRPRMIEEHKLPSFRVLAFDIEVYNPRGMPNPDRDPVIIISTMTK
EDGVKMFVVDDNKNDAKIIREFLDYFRKYDPDIVVGYNNNGFDWPYLVNR
SSRVGVRLALSRMGNPPEPSVYGHWSIIGRANVDLYNFIEEISEIKVKSL
DRAAEFFGIMKRSERVLIPGHRIHEYWDDKNKRDLLLKYARDDVVSTYGL
AEKLLPFAIQLSSISGLPLDQVGAASVGARVEWMIFYEAVKRGELAPNRE
ERPYETYKGAVVLEPRPGLHENIAVIDFSSMYPSIMMKYNVSPDTLVLGD
CGDCYVAPEVNYKFRRSPEGLYPGLLRILVESRRRVRDLMKKYPENSPEW
VLLNERQRALKVMANAMYGYCGWLGARWYRREVAEAVTAWGRNLLRTVIE
```

```
KARSLGLPIIYGDTDSLFVRNISDKVDALINYVNNELGFEVKVDKVYRRV
LFTEAKKRYVGLTVEGEVDIVGFEAVRGDWAEIAKDVQENVAEIVLTTGD
VGKAISYVKSVIDKVKAYQFDIDDVIIWKTLDKSLNEYKVLTPHVAAAKQ
LVEAGYKVGKGDMIGYVVVKGGGAKLAYKVKPYILIKDIREVDVDYYVEK
QIVPAAMRILEVLGVKESQLMEGKAGKSILDYFS
```

SEQ ID NO: 54
```
MLRTVWVDYARKGEPDVILVGRREDGNPAALVVKGFRPYFYAEVEDGFDP
SEVERLSGVVEVEEVLLEHPYGGDRVELLRIVATYPKVVPKLREQVKKLD
GVKEVYEADIPFVRRAAVDLNLPPASEVDVSDLDTGSWSGLPAYFADVED
ARELDHRPYPIEDLVVASFDLEVLAEPGTTIKGASGPIIAISFAYSTPDG
ERRNYVITWKGEDESFEVDGVETEVIVCRSEAAALRRFFDEFRRVDPDVV
FTYNGDEFDLPYLQHRAGKLGIDVSPLARPAGKRGIILKHGGGRYASDIF
GRAHVDLYHTARKNLKLERFTLEEAVKDVLGVEKEEMELADINEAWKRGN
LDELMRYSAEDAHYTLELGLELAQVELELSYLTRLPLPDATRFSFGQLAE
WRAIYKARQEDILVPNKPTRDEYKRRRRKAYKGAIVFEPEIGLHENVVCV
DFASLYPNVMVAHNISPDTFDCDCCPRVTVEEVDDPTDATVAPDVGHKFC
KRRKGFFPRLVEGLIERRRELKRRLRKLDTESHPHEAKILDVRQQAYKVL
ANSYYGYMGWANARWFCRECAESVTAWGRYYISEVRRIAEEKYGLKVVYG
DTDSLFVKLPDADLEETIERVKEFLKEVNGRLPVELELEDAYKRILFVTK
KKYAGYTEDGKIVTKGLEVVRRDWAPIARETQRRVLKRILADNDPEAALK
EIHEVLERLKSGDVDIDELAVTSQLTKKPSEYVQKGPHVRAALRLARHLG
VEPEPGTIVRYVIVRGPGSVSDKAYPVELVREEGKEPDVDYYIEHQILPA
VERIMRAIGYSRGQIVGETASQKTLDQFFG
```

SEQ ID NO: 55
```
MELKIWPLDVTYAVVGGYPEVRVFGLTEGGGRVVLVDRSFKPYFYVDCPT
CEVGVVKSSLSRVAPVDEVSAAERRFLGRPRRFLMVVARVPEDVRRLREA
AAQIPGVAGVYEADIRFYMRYMIDVGLLPCSWNRAEVEGGGKVGGLPQYT
VVQWLGPAGGFPPPLRVLAFDIEVYNERGTPDPARDPVVM1AVKTDDGRE
EVFEAEGRDDRGVLRSFVEFVKSYDPDVVVGYNSNGFDWPYLAGRARAIG
VPLRVDRLGGLPQQSVYGHWSIVGRANVDLYGIVEEFPEIKLKTLDRVAE
YFGVMRREERVLIPGHKIYEYWRDPGKRPLLRQYVLDDVRSTLGLADKLL
PFLIQLSSVSGLPLDQVAAASVGNRVEWMLLRYAYRLGEVAPNREEREYE
PYKGAIVLEPKPGMYEDVLVLDFSSMYPNIMMKYNLSPDTYLEPGEPDPP
EGVNAAPEVGHRFRRSPLGFVPQVLKSLVELRKAVREEAKRYPPDSPEFR
ILDERQRALKVMANAMYGYLGWVGARWYKREVAESVTAFARAILKDVIEQ
ARRLGIVVVYGDTDSLFVKKHVNVDKLIQYVEEKYGIEIKVDKDYAKVLF
TEAKKRYAGLLRDGRIDIVGFEVVRGDWSELAKEVQLKVVEIILNSRDVA
EARRRVTQYVREIIERLREYKFNVDDLIIWKTLDKELGEYKAYPPHVHAA
LILKRHGYKVGKGNMVGYVVVKGGGKISEKALPYILLDDVKKIDVEYYIE
RQIIPAALRIAEVIGVKEADLKTGKSERSLLDFF
```

SEQ ID NO: 56
MKTFLTEQQIKVLMLRAKGYKQSEIAKILGTSRANVSILEKRAMEKIEKA
RNTLLLWEQINSKVIVEIKAGEDIFSIPEKFFKKADKVGVKVPYSTAEII
TFLVEHAPVEDRLAKRDFVLFLDSKNKLRIGDCLVIEEIKED

SEQ ID NO: 57
MPITKVTRNYQITIPAEIRKALGIKEGELLEVRLENGKIIIERLKKERKT
LKLGKKLTLEEIEKAIEEGMKQCMQ

SEQ ID NO: 58
TKIEILRLLKEREMYAYEIWSLLGKPLKYQAVHQHIKELLELGLVEQAYR
KGKRVYYKITEKGLRILQNFEDLENI

SEQ ID NO: 59
MNTGAQGVSEMSRMKIISVQLPQSLIHGLDALVKRGIYPNRSEAIRVAIR
ELLKKELYKEEIQEEIPEYVVK

SEQ ID NO: 60
VIIPRPIDPRDIRRIRKELGITQEELARKAGVTQAYIAKLEAGKVDPRLS
TFNKILRALIECQKAKI

SEQ ID NO: 61
NNCECMVVKEKLYTVKQASEILGVHPKTIQKWDREGKIKTVRTPGGRRRI
PESEIKRLLGISEEK

SEQ ID NO: 62
MLKDSAPKRKILEELRKGETVSGDYLASKLGVSRVAIWKHIRELKELGYG
IIADKKGYKLVYEPKKPYPWE

SEQ ID NO: 63
MIDERDKIILEILEKDARTPFTEIAKKLGISETAVRKRVKALEEKGIIEG
YTIKINPKKLGYSLVTITGVDTKPEKLFEVAEKLKE

SEQ ID NO: 64
MEIDDLDRKILSLLIEDSRLSYREIAKKLNVAVGTIYNRIKKLEDMGVIQ
GFTVKLNYEKLGYELTAIIGIKAQGKK

SEQ ID NO: 65
EMLWMYILKLLKDRPMYAYEIRNELKKRFGFEPATVSSYVVLYRLEEGGY
VSSEWHESEAGRPSRKYYRLTEKGEKLLEKGIETIEDVLNMLKS

SEQ ID NO: 66
MKVSKATASKVLRSLENKGIVERERRGKTYLVRLTNKGLELLEEISKAGK
ELDEKIFAEMSVDERIVL

SEQ ID NO: 67
SEDYMLQNRRKVLAKVLELLNYNPKALNISELARMFGVSRDTIYNDIQQI
IKNVEV

SEQ ID NO: 68
SKEISRFLKVISNPIRYGILKMLNDRWMCVCLISEALEIDQTLVSHHIRI
LKELDLLEERKEGKLRFYRTNKEKLREYLEKVLEDFNHGTSKGS

SEQ ID NO: 69
MCRKDVMIISDPKQIKALSDPTRVKILELLRYHPMTVSEISRVIGKDKST
IYRHIKALEEAGLVEEVEKIGNETVYGR

SEQ ID NO: 70
MEPVEFKLNQKGIKSILPTMEAEIMEYMWEIKEATAGEVYEYMKTKYPEI
RRSTVSILMNRLCERGLLKRRMEKGKGGIRYVYSITTTREEFERKVVEKI
IESLMMNFREATFAYLSKINKK

SEQ ID NO: 71
MKKSNLDLLILLAKAGGIEKEILTTSRELSKMLNVSPQTIVRWLEDLEKD
GLIKKSESRKGTLVTITEEGVKFLEKLHEELSDALYR

SEQ ID NO: 72
MEIPPEISHALSEIGFTKYEILTYWTLLVYGPSTAKEISTKSGIPYNRVY
DTISSLKLRGFVTEIEGTPKVYAAYSPRIAFFRFKKELEDIMKKLEIELN
NVKK

SEQ ID NO: 73
IINPQARLTPLELEILEIIKQKKSITITEIKEILSERRKSEYPLSLVSEY
ISRLERKGYVKKIAKGRKKFVEALI

SEQ ID NO: 74
GIDVVIPEIKHDPIARDIVKILFDLRRANVSQIARELKGRRGKASRNTVR
KKLKELEKLGVVKEVPGERGSVYTLSREVVKKWLDLIGIPINLL

SEQ ID NO: 75
MTKRVKVITDPEVIKVMLEDTRRKILQLLRNREMTISQLSEILGKMPQTI
YHHIEKLKEAGLVEVKR

SEQ ID NO: 76
MEEIKEIMKSHTLGNPVRLGIMIYLFPRRRAPFSHIQKALDLTPGNLDSH
IKVLEKHGFVRTYKVIADRPRTMVEITDYGMEETRKFLSHLKTVIDAIHF

SEQ ID NO: 77
MGEELNRLLDVLGNETRRRILFLLTKRPYFVSELSRELGVGQKAVLEHLR
ILEEAGLIESRVEKIPRGRPRKYYMIKKGLRLEILLTPTLFGSEMYEAK

SEQ ID NO: 78
MRRMDKVDLQLIKILSQNSRLTYRELAEMLGTTRQRVARKVDKLKKLGII
RKFTIIPNLEK

SEQ ID NO: 79
GRKVRTQQNEILNLLNEKEKAVLRAILEHGGEIKQEDLPELVGYSRPTIS
KVIQELENKGLIKREKSGKTFVVKIERKIKLD

SEQ ID NO: 80
KSLQRFLRRNTTSIKHLSEITGVARNRLSDILNGKTQKIRGETLRKIAKA
FEKSNILSF

SEQ ID NO: 81
DVIQRIKEKYDEFTNAEKKIADTILSDPKGIIESSISDLSEKAGVKSEAS
VVKFYKKLGLNSFQQFKVLLAQSISRAPLEIVYEDVSSEDDTKTITEKIF
KATVRAI

SEQ ID NO: 82
KIRDKILNVYTQFSPAERKVADYVLERPDDVIHYSITEFAKIVGVSETTI
HRMIKKLDFEGYQAFKIALARELSGLEETIERRDFIDEEIDILRRLKDTL
D

SEQ ID NO: 83
KRRPTINDVAKLAGVSISTVSRYLKDPSQVSEKLGERIREAIKKLGYKPN
KIAQGLRTGD

SEQ ID NO: 84
MASIKDVAKLAGVSIATVSRVINGYNNVSEETRKKVIDAIRKLNYHPVYA
VKGAVLKR

SEQ ID NO: 85
MKKKYVTIRDIAEKAGVSINTVSRALNNKPDISEETRRKILKIAQELGYV
KNATASSLRSK

SEQ ID NO: 86
MPTIEDVAKLAGVSIATVSRVINGSGYVSEKTRYKVWKAIEELGYKPEIS
AKLLASKG

SEQ ID NO: 87
MRIGEKLRKLRLSRGLTQEELAERTDLSRSFISQLESDKTSPSIDTLERI
LEALGTDLKHF

SEQ ID NO: 88
MHMKTVRQERLKSIVRILERSKEPVSGAQLAEELSVSRQVIVQDIAYLRS
LGYNIVATPRGYVLAGG

SEQ ID NO: 89
MNTLKKAFEILDFIVKNPGDVSVSEIAEKFNMSVSNAYKYMVVLEEKGFV
LRKKDKRYVPGYKLIEYGSFVLRRF

SEQ ID NO: 90
MKISKKRRQELIRKIIHEKKISNQFQIVEELKKYGIKAVQPTVARDLKEI
GAVKIMDESGNYVYKLLDETPVIDPWKELKR

SEQ ID NO: 91
MHKKLNPKSMKRENKKMVLRYLIESGPHSRVEIARKTGLAQSAIWRIIEE
LVNEGLVEEKGTATGRRRKAVTYGPTRSFITS

SEQ ID NO: 92
MPSPLLRRENKIKILRYILKNGKTTRNQLASNLNLAHSTLSYIIDELLDE
GFLVFEEIKKKRGRPYQILSVNPEKFTAI

SEQ ID NO: 93
MKEERLKEILDIVDRNGFISMKDLQEQLGVSMITVRRDVAELVKRNLVKK
VHGGIRKVNYFEKETDFMKRLSINREAKE

SEQ ID NO: 94
MFTMRSEYALRLMIVMAKEYGNYLSMTEILEKAKQSVPREFAEKILYTLK
KAGLVKTRRGKSGGYMLSRPPKEIKVSEIVFLLDRKSKVFFDMPGCPDEL
DCVIRALWKRVENEIEKILSGVTLEDLVREQEEKMKQ

SEQ ID NO: 95
MRDTKGHLKFLVLHIISQQPSHGYYIMKKISQIIGAEPPSPGALYPILSS
LRKQKYIETYNEGKRKVYRLTDKGRKYLEEHKEEIKKALDFAERF

SEQ ID NO: 96
MRHRGGRGFRGWWLASTILLLVAEKPSHGYELAERLAEFGIEIPGIHMG
NIYRVLADLEESGFLSTEWDTTVSPPRKIYRITPQGKLYLREILRSLEDM
KRRIETLEERIKRVLQEE

SEQ ID NO: 97
MLSKRDAILKAAVEVFGKKGYDRATTDEIAEKAGVAKGLIFHYFKNKEEL
YYQAYMSVTEKLQKEFENFL

SEQ ID NO: 98
MSKSWGKFIEEEEAEMASRRNLMIVDGTNLGFRFKHNNSKKPFASSYVST
IQSLAKSYSARTTIVLGDKGKSVFRLEHLPEYKGNRDEKYAQRTEEEKAL
DEQFFEYLKDAFELCKTTFPTFTIRGVEADDMAAYIVKLIGHLYDHVWLI
STDGDWDTLLTDKVSRFSFTTRREYHLRDMYEHHNVDDVEQFISLKAIMG
DLGDNIRGVEGIGAKRGYNIIREFGNVLDIIDQLPLPGKQKYIQNLNASE
ELLFRNLILVDLPTYCVDAIAAVGQDVLDKFTKDILEIAEQ

SEQ ID NO: 100
MEEKVGNLKPNMESVNVTVRVLEASEARQIQTKNGVRTISEAIVGDETGR
VKLTLWGKHAGSIKEGQVVKIENAWTTAFKGQVQLNAGSKTKIAEASEDG
FPESSQIPENTPTAPQQMRGGGRGFRGGGRRYGRRGGRRQENEEGEEE

SEQ ID NO: 101
MTLEEARKRVNELRDLIRYHNYRYYVLADPISDAEYDRLLRELKELEERF
PELKSPDSPTLQVGARPLEATFRPVRHPTRMYSLDNAFNLDELKAFEERI
ERALGRKGPFAYTVEHKVDGLSVNLYYEEGVLVYGATRGDGEVGEEVTQN
LLTIPTIPRRLKGVPERLEVRGEMPIEAFLRLNEELEERGERIFKNPRNA
AAGSLRQKDPRITAKRGLRATFYALGLGLEEVEREGVATQFALLHWLKEK
GFPVEHGYARAVGAEGVEAVYQDWLKKRRALPFEADGVVVKLDELALWRE
LGYTARAPRFAIAYKFPAEEKETRLLDVVFQVGRTGRVTPVGILEPVFLE
GSEVSRVTLHNESYIEELDIRIGDWVLVHKAGGVIPEVLRVLKERRTGEE
RPIRWPETCPECGHRLLKEGKVHRCPNPLCPAKRFEAIRHFASRKAMDIQ
GLGEKLIERLLEKGLVKDVADLYRLRKEDLVGLERMGEKSAQNLLRQIEE
SKKRGLERLLYALGLPGVGEVLARNLAARFGNMDRLLEASLEELLEVEEV
GELTARAILETLKDPAFRDLVRRLKEAGVEMEAKEKGGEALKGLTFVITG
ELSRPREEVKALLRR

SEQ ID NO: 102
MILDADYITEDGKPIIRIFKKENGEFKVEYDRNFRPYIYALLKDDSAIDD
VKKITAERHGKVVRVVDVEKVKKKFLGRPIEVWKLYFEHPQDVPAIRDKI
REHPAVIDIFEYDIPFAKRYLIDKGLIPMEGNEELKLLAFDIETLYHEGE
EFGKGPIIMISYADEEGAKVITWKKVDLPYVEVVSSEREMIKRFLKVIRE
KDPDVIITYNGDNFDFPYLLKRAEKLGMKLPLGRDGSEPKMQRLGDSLAV
EIKGRIHFDLYPVIRRTINLPTYTLEAVYEAIFGKPKEKVYPHEIAEAWE
TGKGLERVAKYSMEDAKVTYELGREFFPMEAQLARLVGQPLWDVSRSSTG
NLVEWYLLRKAYERNELAPNKPDEREYERRLRESYEGGYVKEPEKGLWEG
IVSLDFRSLYPSIIITHNVSPDTLNKEGCGEYDVAPEVGHRFCKDFPGFI
PSLLGSLLDERQKIKRRMKASKDPIERKLLDYRQRAIKILANSYYGYYGY
AKARWYCKECAESVTAWGREYIELVRRELEERGFKVLYIDTDGLYATIPG
EKNWEEIKRRALEFVNYINAKLPGLLELEYEGFYTRGFFVTKKKYALIDE
EGKIITRGLEIVRRDWSEIAKETQAKVLEAILKHGNVEEAVKIVKEVTEK
LSKYEIPPEKLVIYEQITRPLNEYKAIGPHVAVAKRLAARGIKVRPGMVI
GYVVLRGDGPISKRAIAAEEFDPKKHKYDAEYYIENQVLPAVLRILEAFG
YRKEDLRWQKTKQVGLGAWLKVKKSLGAKVTDSVSRKTSYLVVGENPGSK
LEKARALGVPTLTEEELYRLLEARTGKKAEELV

What is claimed is:

1. A composition comprising:
   (a) a fusion protein comprising a DNA polymerase and a sequence-specific DNA binding domain;
   (b) an exonuclease; and
   (c) a ligase;
   wherein the composition optionally comprises dNTPs.

2. The composition of claim 1, wherein the fusion protein comprises:
   (i) an amino acid sequence that has at least 90% sequence identity to SEQ ID NO:3,
   (ii) an amino acid sequence that has at least 90% sequence identity to SEQ ID NO:1; and
   (iii) an amino acid sequence that has at least 90% sequence identity to SEQ ID NO:2.

3. The composition of claim 1, wherein the fusion protein comprises:
   (i) an amino acid sequence that has at least 95% sequence identity to SEQ ID NO:3,
   (ii) an amino acid sequence that has at least 95% sequence identity to SEQ ID NO:1; and
   (iii) an amino acid sequence that has at least 95% sequence identity to SEQ ID NO:2.

4. The composition of claim 1, wherein the fusion protein comprises the amino acid sequence of SEQ ID NO:3.

5. The composition of claim 1, wherein the exonuclease is a 5'-3' exonuclease.

6. The composition of claim 5, wherein the exonuclease is exonuclease T5.

7. The composition of claim 1, wherein the ligase is thermostable.

8. The composition of claim 1, wherein the ligase is NAD+ dependent and the composition further comprises NAD+.

9. The composition of claim 8, wherein the ligase is Taq ligase.

10. The composition of claim 1, wherein the ligase is ATP dependent and the composition further comprises ATP.

11. The composition of claim 1, further comprising a single-stranded DNA binding protein.

12. The composition of claim 11, wherein the single-stranded DNA binding protein is ET SSB (Extreme Thermostable Single-Stranded DNA Binding Protein), E. coli recA, T7 gene 2.5 product, phage lambda RedB or Rac prophage RecT.

13. The composition of claim 1, wherein the composition does not comprise a crowding agent.

14. The composition of claim 1, wherein the composition does not comprise a non strand-displacing polymerase.

15. The composition of claim 1, wherein the composition comprises a potassium salt.

16. The composition of claim 15, wherein the potassium salt is potassium chloride and the potassium chloride is at a concentration in the range of 7 mM to 150 mM.

17. The composition of claim 1, wherein the composition comprises dNTPs.

18. The composition of claim 1, wherein the composition comprises a non-naturally occurring buffering agent.

19. The composition of claim 1, wherein the composition further comprises a set of overlapping polynucleotides.

20. The composition of claim 19, wherein at least two of the oligonucleotides in the set have an overlap of at least 15 nucleotides.

21. The composition of claim 19, wherein the set of overlapping polynucleotides has at least two members.

22. The composition of claim 19, wherein the set of overlapping polynucleotides has at least five members.

23. The composition of claim 19, wherein the set of overlapping polynucleotides comprises:
double-stranded polynucleotides;
at least one double strand polynucleotide and at least one single strand oligonucleotide;
single stranded oligonucleotides; and/or
a subpopulation of polynucleotides that are otherwise identical to one another except for a sequence that varies between the members of the sub-population.

24. The composition of claim 1, wherein the fusion protein exhibits increased processivity relative to the polymerase of (a) in the absence of the DNA binding domain of (a).

25. The composition of claim 1, wherein the sequence-specific DNA binding domain is N-terminal of the polymerase.

26. The composition of claim 1, wherein the DNA polymerase is a type A polymerase.

27. The composition of claim 1, wherein the DNA polymerase is a type B polymerase.

28. The composition of claim 1, wherein the sequence-specific DNA binding domain has a helix-loop-helix, ribbon-helix-helix, helix-turn-helix, winged helix, or homeodomain structure.

29. The composition of claim 1, wherein the sequence-specific DNA binding domain is from a transcriptional activator.

30. The composition of claim 1, wherein the polymerase has proofreading activity.

31. The composition of claim 1, wherein the amino acid sequence of the sequence-specific DNA binding domain is at least 90% identical to a DNA binding domain of SEQ ID NOS 56-97.

32. The composition of claim 1, wherein the amino acid sequence of the polymerase is at least 90% identical to the amino acid sequence of any of SEQ ID NOS. 33-55.

33. The composition of claim 1, wherein the polymerase is bacterial or archaebacterial.

34. The composition of claim 1, wherein the amino acid sequence of the polymerase is at least 90% identical to the amino acid sequence of a wild type Pyrococcal polymerase of any of SEQ ID NOS. 41, 47, or 48 or the amino acid sequence of a wild type Thermococcal polymerase of any of SEQ ID NOS. 42-46, 51 or 52.

35. The composition of claim 1, wherein the polymerase is thermostable.

36. The composition of claim 1, wherein the sequence-specific DNA binding domain is thermostable.

* * * * *

SEQUENCE LISTING

<160> NUMBER OF SEQ ID NOS: 130

<210> SEQ ID NO 1
<211> LENGTH: 775
<212> TYPE: PRT
<213> ORGANISM: Artificial Sequence
<220> FEATURE:
<223> OTHER INFORMATION: Synthetic construct

<400> SEQUENCE: 1

Met Ile Leu Asp Ala Asp Tyr Ile Thr Glu Asp Gly Lys Pro Ile Ile
1               5                   10                  15

Arg Leu Phe Lys Lys Glu Asn Gly Arg Phe Lys Val Glu Tyr Asp Arg
                20                  25                  30

Asn Phe Arg Pro Tyr Ile Tyr Ala Leu Leu Lys Asp Asp Ser Ala Ile
            35                  40                  45

Asp Asp Val Arg Lys Ile Thr Ser Glu Arg His Gly Lys Val Val Arg
    50                  55                  60

Val Ile Asp Val Glu Lys Val Lys Lys Phe Leu Gly Arg Pro Ile
65                  70                  75                  80

Glu Val Trp Lys Leu Tyr Phe Glu His Pro Gln Asp Val Pro Ala Met
                85                  90                  95

Arg Asp Lys Ile Arg Glu His Pro Ala Val Ile Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ala Asn Glu Arg Glu Met Ile Lys
            180                 185                 190

Arg Leu Ile Lys Val Ile Arg Glu Lys Asp Pro Asp Val Ile Ile Thr
    195                 200                 205

Tyr Asn Gly Asp Asn Phe Asp Phe Pro Tyr Leu Leu Lys Arg Ala Glu
210                 215                 220

Lys Leu Gly Met Lys Leu Pro Leu Gly Arg Asp Asn Ser Glu Pro Lys
225                 230                 235                 240

Met Gln Arg Leu Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Gln Lys Glu
    275                 280                 285

Lys Val Tyr Pro His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Phe Pro Met Glu Ala Gln Leu Ala Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala 355                 360                 365
Pro Asn Lys Pro Asp Glu Arg Glu Tyr Glu Arg Arg Leu Arg Glu Ser
    370                 375                 380
Tyr Glu Gly Gly Tyr Val Lys Glu Pro Glu Arg Gly Leu Trp Glu Gly
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Lys Glu Gly Cys Gly Glu Tyr
            420                 425                 430
Asp Glu Ala Pro Glu Val Gly His Arg Phe Cys Lys Asp Phe Pro Gly
            435                 440                 445
Phe Ile Pro Ser Leu Leu Gly Ser Leu Leu Glu Glu Arg Gln Lys Ile
        450                 455                 460
Lys Lys Arg Met Lys Glu Ser Lys Asp Pro Val Glu Arg Lys Leu Leu
465                 470                 475                 480
Asp Tyr Arg Gln Arg Ala Ile Lys Ile Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Gln Tyr Ile Glu Leu Val Arg Arg Glu
            515                 520                 525
Leu Glu Glu Arg Gly Phe Lys Val Leu Tyr Ile Asp Thr Asp Gly Leu
    530                 535                 540
Tyr Ala Thr Ile Pro Gly Glu Lys Asn Trp Glu Glu Ile Lys Arg Arg
545                 550                 555                 560
Ala Leu Glu Phe Val Asn Tyr Ile Asn Ser Lys Leu Pro Gly Ile Leu
                565                 570                 575
Glu Leu Glu Tyr Glu Gly Phe Tyr Thr Arg Gly Phe Phe Val Thr Lys
            580                 585                 590
Lys Lys Tyr Ala Leu Ile Asp Glu Glu Gly Lys Ile Val Thr Arg Gly
            595                 600                 605
Leu Glu Ile Val Arg Arg Asp Trp Ser Glu Ile Ala Lys Glu Thr Gln
    610                 615                 620
Ala Lys Val Leu Glu Ala Ile Leu Lys His Gly Asn Val Glu Glu Ala
625                 630                 635                 640
Val Lys Ile Val Lys Glu Val Thr Glu Lys Leu Ser Asn Tyr Glu Ile
                645                 650                 655
Pro Val Glu Lys Leu Val Ile Tyr Glu Gln Ile Thr Arg Pro Leu Asn
            660                 665                 670
Glu Tyr Lys Ala Ile Gly Pro His Val Ala Val Ala Lys Arg Leu Ala
        675                 680                 685
Ala Lys Gly Ile Lys Ile Lys Pro Gly Met Val Ile Gly Tyr Val Val
    690                 695                 700
Leu Arg Gly Asp Gly Pro Ile Ser Lys Arg Ala Ile Ala Ile Glu Glu
705                 710                 715                 720
Phe Asp Gly Lys Lys His Lys Tyr Asp Ala Glu Tyr Tyr Ile Glu Asn
                725                 730                 735
Gln Val Leu Pro Ala Val Glu Arg Ile Leu Lys Ala Phe Gly Tyr Lys
            740                 745                 750
Arg Glu Asp Leu Arg Trp Gln Lys Thr Lys Gln Val Gly Leu Gly Ala
            755                 760                 765
Trp Leu Lys Val Lys Lys Ser
    770                 775

<210> SEQ ID NO 2
<211> LENGTH: 75
<212> TYPE: PRT
<213> ORGANISM: Pyrococcus furiosus

<400> SEQUENCE: 2

```
Ile Ile Asn Pro Gln Ala Arg Leu Thr Pro Leu Glu Leu Glu Ile Leu
1               5                   10                  15
Glu Ile Ile Lys Gln Lys Lys Ser Ile Thr Ile Thr Glu Ile Lys Glu
            20                  25                  30
Ile Leu Ser Glu Arg Arg Lys Ser Glu Tyr Pro Leu Ser Leu Val Ser
        35                  40                  45
Glu Tyr Ile Ser Arg Leu Glu Arg Lys Gly Tyr Val Lys Lys Ile Ala
    50                  55                  60
Lys Gly Arg Lys Lys Phe Val Glu Ala Leu Ile
65                  70                  75
```

<210> SEQ ID NO 3
<211> LENGTH: 856
<212> TYPE: PRT
<213> ORGANISM: Artificial Sequence
<220> FEATURE:
<223> OTHER INFORMATION: Synthetic construct

<400> SEQUENCE: 3

```
Met Ile Leu Asp Ala Asp Tyr Ile Thr Glu Asp Gly Lys Pro Ile Ile
1               5                   10                  15
Arg Leu Phe Lys Lys Glu Asn Gly Arg Phe Lys Val Glu Tyr Asp Arg
            20                  25                  30
Asn Phe Arg Pro Tyr Ile Tyr Ala Leu Leu Lys Asp Asp Ser Ala Ile
        35                  40                  45
Asp Asp Val Arg Lys Ile Thr Ser Glu Arg His Gly Lys Val Val Arg
    50                  55                  60
Val Ile Asp Val Glu Lys Val Lys Lys Phe Leu Gly Arg Pro Ile
65                  70                  75                  80
Glu Val Trp Lys Leu Tyr Phe Glu His Pro Gln Asp Val Pro Ala Met
            85                  90                  95
Arg Asp Lys Ile Arg Glu His Pro Ala Val Ile Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asn Glu Glu Leu Thr Phe Leu Ala Val Asp Ile Glu Thr
    130                 135                 140
Leu Tyr His Glu Gly Glu Glu Phe Gly Lys Gly Pro Ile Ile Met Ile
145                 150                 155                 160
Ser Tyr Ala Asp Glu Glu Gly Ala Lys Val Ile Thr Trp Lys Lys Ile
            165                 170                 175
Asp Leu Pro Tyr Val Glu Val Val Ala Asn Glu Arg Glu Met Ile Lys
        180                 185                 190
Arg Leu Ile Lys Val Ile Arg Glu Lys Asp Pro Asp Val Ile Ile Thr
    195                 200                 205
Tyr Asn Gly Asp Asn Phe Asp Phe Pro Tyr Leu Leu Lys Arg Ala Glu
    210                 215                 220
Lys Leu Gly Met Lys Leu Pro Leu Gly Arg Asp Asn Ser Glu Pro Lys
225                 230                 235                 240
```

```
Met Gln Arg Leu Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Gln Lys Glu
        275                 280                 285

Lys Val Tyr Pro His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Phe Pro Met Glu Ala Gln Leu Ala Arg Leu
                325                 330                 335

Val Gly Gln Pro Leu Trp Asp Val Ser Arg Ser Thr Gly Asn Leu
            340                 345                 350

Val Glu Trp Tyr Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Arg Gly Leu Trp Glu Gly
385                 390                 395                 400

Ile Val Ser Leu Asp Phe Arg Ser Leu Tyr Pro Ser Ile Ile Thr
                405                 410                 415

His Asn Val Ser Pro Asp Thr Leu Asn Lys Glu Gly Cys Gly Glu Tyr
            420                 425                 430

Asp Glu Ala Pro Glu Val Gly His Arg Phe Cys Lys Asp Phe Pro Gly
        435                 440                 445

Phe Ile Pro Ser Leu Leu Gly Ser Leu Leu Glu Glu Arg Gln Lys Ile
    450                 455                 460

Lys Lys Arg Met Lys Glu Ser Lys Asp Pro Val Glu Arg Lys Leu Leu
465                 470                 475                 480

Asp Tyr Arg Gln Arg Ala Ile Lys Ile Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Glu Leu Val Arg Arg Glu
        515                 520                 525

Leu Glu Glu Arg Gly Phe Lys Val Leu Tyr Ile Asp Thr Asp Gly Leu
    530                 535                 540

Tyr Ala Thr Ile Pro Gly Glu Lys Asn Trp Glu Glu Ile Lys Arg Arg
545                 550                 555                 560

Ala Leu Glu Phe Val Asn Tyr Ile Asn Ser Lys Leu Pro Gly Ile Leu
                565                 570                 575

Glu Leu Glu Tyr Glu Gly Phe Tyr Thr Arg Gly Phe Phe Val Thr Lys
            580                 585                 590

Lys Lys Tyr Ala Leu Ile Asp Glu Glu Gly Lys Ile Val Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Asn Tyr Glu Ile
                645                 650                 655

Pro Val Glu Lys Leu Val Ile Tyr Glu Gln Ile Thr Arg Pro Leu Asn
```

```
                        660                 665                 670
Glu Tyr Lys Ala Ile Gly Pro His Val Ala Val Ala Lys Arg Leu Ala
            675                 680                 685
Ala Lys Gly Ile Lys Ile Lys Pro Gly Met Val Ile Gly Tyr Val Val
        690                 695                 700
Leu Arg Gly Asp Gly Pro Ile Ser Lys Arg Ala Ile Ala Ile Glu Glu
705                 710                 715                 720
Phe Asp Gly Lys Lys His Lys Tyr Asp Ala Glu Tyr Tyr Ile Glu Asn
                725                 730                 735
Gln Val Leu Pro Ala Val Glu Arg Ile Leu Lys Ala Phe Gly Tyr Lys
            740                 745                 750
Arg Glu Asp Leu Arg Trp Gln Lys Thr Lys Gln Val Gly Leu Gly Ala
        755                 760                 765
Trp Leu Lys Val Lys Lys Ser Gly Thr Gly Gly Gly Ile Ile Asn
        770                 775                 780
Pro Gln Ala Arg Leu Thr Pro Leu Glu Leu Glu Ile Leu Glu Ile Ile
785                 790                 795                 800
Lys Gln Lys Lys Ser Ile Thr Ile Thr Glu Ile Lys Glu Ile Leu Ser
                805                 810                 815
Glu Arg Arg Lys Ser Glu Tyr Pro Leu Ser Leu Val Ser Glu Tyr Ile
            820                 825                 830
Ser Arg Leu Glu Arg Lys Gly Tyr Val Lys Lys Ile Ala Lys Gly Arg
        835                 840                 845
Lys Lys Phe Val Glu Ala Leu Ile
    850                 855

<210> SEQ ID NO 4
<211> LENGTH: 40
<212> TYPE: DNA
<213> ORGANISM: Artificial Sequence
<220> FEATURE:
<223> OTHER INFORMATION: Synthetic construct

<400> SEQUENCE: 4
ttggtctggt gtcaaaaatg aatcgtcacg gcgatttatg                    40

<210> SEQ ID NO 5
<211> LENGTH: 39
<212> TYPE: DNA
<213> ORGANISM: Artificial Sequence
<220> FEATURE:
<223> OTHER INFORMATION: Synthetic construct

<400> SEQUENCE: 5
gggtcatttt cggcgaggac tgcatcaacg catatagcg                     39

<210> SEQ ID NO 6
<211> LENGTH: 32
<212> TYPE: DNA
<213> ORGANISM: Artificial Sequence
<220> FEATURE:
<223> OTHER INFORMATION: Synthetic construct

<400> SEQUENCE: 6
gcggccgcgt cctcgccgaa aatgacccag ag                            32

<210> SEQ ID NO 7
<211> LENGTH: 32
<212> TYPE: DNA
<213> ORGANISM: Artificial Sequence
```

-continued

```
<220> FEATURE:
<223> OTHER INFORMATION: Synthetic construct

<400> SEQUENCE: 7
gcggccgctg gtgtcgatgg tagaacgaag cg                                32

<210> SEQ ID NO 8
<211> LENGTH: 32
<212> TYPE: DNA
<213> ORGANISM: Artificial Sequence
<220> FEATURE:
<223> OTHER INFORMATION: Synthetic construct

<400> SEQUENCE: 8
gcggccgccc cactgacgcg ttgcgcgaga ag                                32

<210> SEQ ID NO 9
<211> LENGTH: 32
<212> TYPE: DNA
<213> ORGANISM: Artificial Sequence
<220> FEATURE:
<223> OTHER INFORMATION: Synthetic construct

<400> SEQUENCE: 9
gcggccgcgg ctgcgcaact gttgggaagg gc                                32

<210> SEQ ID NO 10
<211> LENGTH: 32
<212> TYPE: DNA
<213> ORGANISM: Artificial Sequence
<220> FEATURE:
<223> OTHER INFORMATION: Synthetic construct

<400> SEQUENCE: 10
gcggccgctg cagcacatcc ccctttcgcc ag                                32

<210> SEQ ID NO 11
<211> LENGTH: 32
<212> TYPE: DNA
<213> ORGANISM: Artificial Sequence
<220> FEATURE:
<223> OTHER INFORMATION: Synthetic construct

<400> SEQUENCE: 11
gcggccgcat gatgctcgtg acggttaacg cc                                32

<210> SEQ ID NO 12
<211> LENGTH: 32
<212> TYPE: DNA
<213> ORGANISM: Artificial Sequence
<220> FEATURE:
<223> OTHER INFORMATION: Synthetic construct

<400> SEQUENCE: 12
gcggccgcag gtgcggattg aaaatggtct gc                                32

<210> SEQ ID NO 13
<211> LENGTH: 32
<212> TYPE: DNA
<213> ORGANISM: Artificial Sequence
<220> FEATURE:
<223> OTHER INFORMATION: Synthetic construct

<400> SEQUENCE: 13
gcggccgctc accgcttgcc agcggcttac ca                                32
```

<210> SEQ ID NO 14
<211> LENGTH: 32
<212> TYPE: DNA
<213> ORGANISM: Artificial Sequence
<220> FEATURE:
<223> OTHER INFORMATION: Synthetic construct

<400> SEQUENCE: 14
gcggccgcga atacctgttc cgtcatagcg at                                32

<210> SEQ ID NO 15
<211> LENGTH: 33
<212> TYPE: DNA
<213> ORGANISM: Artificial Sequence
<220> FEATURE:
<223> OTHER INFORMATION: Synthetic construct

<400> SEQUENCE: 15
gcggccgctc atttttgaca ccagaccaac tgg                               33

<210> SEQ ID NO 16
<211> LENGTH: 1016
<212> TYPE: DNA
<213> ORGANISM: Artificial Sequence
<220> FEATURE:
<223> OTHER INFORMATION: Synthetic construct

<400> SEQUENCE: 16
gcggccgcgt cctcgccgaa aatgacccag agcgctgccg gcacctgtcc tacgagttgc    60
atgataaaga agacagtcat aagtgcggcg acgatagtca tgccccgcgc ccaccggaag   120
gagctgactg ggttgaaggc tctcaagggc atcggtcgag atcccggtgc taatgagtg    180 agctaactta cattaattgc gttgcgctca ctgcccgctt ccagtcggg aaacctgtcg    240 tgccagctgc attaatgaat cggccaacgc gcggggagag gcggtttgcg tattgggcgc   300
cagggtggtt tttcttttca ccagtgagac gggcaacagc tgattgccct tcaccgcctg   360
gccctgagag agttgcagca agcggtccac gctggtttgc cccagcaggc gaaaatcctg   420
tttgatggtg gttaacggcg ggatataacc aacgcgcagc ccggactcgg taatatccca   480
ctaccgagat atccgcacca acgcgcagcc cggactcggt aatggcgcgc attgcgccca   540
gcgccatctg atcgttggca accagcatcg cagtgggaac gatgccctca ttcagcattt    600
gcatggtttg ttgaaaaccg gacatggcac tccagtcgcc ttcccgttcc gctatcggct   660
gaatttgatt gcgagtgaga tatttatgcc agccagccag acgcagacgc gccgagacag   720
aacttaatgg gcccgctaac agcgcgattt gctggtgacc caatgcgacc agatgctcca   780
cgcccagtcg cgtaccgtct tcatgggaga aataatact gttgatgggt gtctggtcag    840
agacatcaag aaataacgcc ggaacattag tgcaggcagc ttccacagca atggcatcct    900
ggtcatccag cggatagtta atgatcagcc cactgacgcg ttgcgcgaga agattgtgca    960
ccgccgcttt acaggcttcg acgccgcttc gttctaccat cgacaccagc ggccgc      1016

<210> SEQ ID NO 17
<211> LENGTH: 1016
<212> TYPE: DNA
<213> ORGANISM: Artificial Sequence
<220> FEATURE:
<223> OTHER INFORMATION: Synthetic construct

<400> SEQUENCE: 17
gcggccgccc cactgacgcg ttgcgcgaga agattgtgca ccgccgcttt acaggcttcg    60

```
acgccgcttc gttctaccat cgacaccacc acgctggcac ccagttgatc ggcgcgagat      120
ttaatcgccg cgacaatttg cgacggcgcg tgcagggcca gactggaggt ggcaacgcca      180
atcagcaacg actgtttgcc cgccagttgt tgtgccacgc ggttgggaat gtaattcagc      240
tccgccatcg ccgcttccac ttttccccgc gttttcgcag aaacgtggct ggcctggttc      300
accacgcggg aaacggtctg ataagagaca ccggcatact ctgcgacatc gtataacgtt      360
actggtttca cattcaccac cctgaattga ctctcttccg ggcgctatca tgccataccg      420
cgaaaggttt tgcgccattc gatggtgtcc gggatctcga cgctctccct tatgcgactc      480
ctgcattagg aagcagccca gtagtaggtt gaggccgttg agcaccgccg ccgcaaggaa      540
tggtgcatgc aaggagatgg cgcccaacag tcccccggcc acgggcctg ccaccatacc       600 cacgccgaaa caagcgctca tgagcccgaa gtggcgagcc cgatcttccc catcggtgat      660
gtcggcgata taggcgccag caaccgcacc tgtggcgccg gtgatgccgg ccacgatgcg      720
tccggcgtag aggatcgaga tctcgatccc gcgaaattaa tacgactcac tatagggga      780 ttgtgagcgg ataacaattc ccctctagaa ataattttgt ttaactttaa gaaggagata      840
tacatatgac catgattacg gattcactgg ccgtcgtttt acaacgtcgt gactgggaaa      900
accctggcgt tacccaactt aatcgccttg cagcacatcc ccctttcgcc agctggcgta      960
atagcgaaga ggcccgcacc gatcgccctt cccaacagtt gcgcagccgc ggccgc         1016

<210> SEQ ID NO 18
<211> LENGTH: 1016
<212> TYPE: DNA
<213> ORGANISM: Artificial Sequence
<220> FEATURE:
<223> OTHER INFORMATION: Synthetic construct

<400> SEQUENCE: 18
gcggccgctg cagcacatcc cccctttcgcc agctggcgta atagcgaaga ggcccgcacc      60
gatcgccctt cccaacagtt gcgcagcctg aatggcgaat ggcgctttgc ctggtttccg     120
gcaccagaag cggtgccgga aagctggctg gagtgcgatc ttcctgaggc cgatactgtc     180
gtcgtcccct caaactggca gatgcacggt tacgatgcgc ccatctacac caacgtgacc     240
tatcccatta cggtcaatcc gccgtttgtt cccacggaga atccgacggg ttgttactcg     300
ctcacattta atgttgatga agctggctac caggaaggcc agacgcgaat tatttttgat     360
ggcgttaact cggcgtttca tctgtggtgc aacgggcgct gggtcggtta cggccaggac     420
agtcgtttgc cgtctgaatt tgacctgagc gcatttttac gcgccggaga aaaccgcctc     480
gcggtgatgg tgctgcgctg gagtgacggc agttatctgg aagatcagga tatgtggcgg     540
atgagcggca ttttccgtga cgtctcgttg ctgcataaac cgactacaca aatcagcgat     600
ttccatgttg ccactcgctt taatgatgat ttcagccgcg ctgtactgga ggctgaagtt     660
cagatgtgcg gcgagttgcg tgactaccta cgggtaacag tttctttatg caggtgaa      720 acgcaggtcg ccagcggcac cgcgcctttc ggcggtgaaa ttatcgatga cgtggtggt     780 tatgccgatc gcgtcacact acgtctgaac gtcgaaaacc gaaactgtg agcgccgaa     840 atcccgaatc tctatcgtgc ggtggttgaa ctgcacaccg ccgacggcac gctgattgaa     900
gcagaagcct gcgatgtcgg tttccgcgag gtgcggattg aaaatggtct gctgctgctg     960
aacggcaagc cgttgctgat tcgaggcgtt aaccgtcacg agcatcatgc ggccgc         1016

<210> SEQ ID NO 19
```

```
<211> LENGTH: 1016
<212> TYPE: DNA
<213> ORGANISM: Artificial Sequence
<220> FEATURE:
<223> OTHER INFORMATION: Synthetic construct

<400> SEQUENCE: 19
gcggccgcag gtgcggattg aaaatggtct gctgctgctg aacggcaagc cgttgctgat      60
tcgaggcgtt aaccgtcacg agcatcatcc tctgcatggt caggtcatgg atgagcagac     120
gatggtgcag gatatcctgc tgatgaagca gaacaacttt aacgccgtgc gctgttcgca     180
ttatccgaac catccgctgt ggtacacgct gtgcgaccgc tacggcctgt atgtggtgga     240
tgaagccaat attgaaaccc acggcatggt gccaatgaat cgtctgaccg atgatccgcg     300
ctggctaccg gcgatgagcg aacgcgtaac gcgaatggtg cagcgcgatc gtaatcaccc     360
gagtgtgatc atctggtcgc tggggaatga atcaggccac ggcgctaatc acgacgcgct     420
gtatcgctgg atcaaatctg tcgatccttc ccgcccggtg cagtatgaag cggcggagc     480
cgacaccacg gccaccgata ttatttgccc gatgtacgcg cgcgtggatg aagaccagcc     540
cttcccggct gtgccgaaat ggtccatcaa aaaatggctt tcgctacctg gagagacgcg     600
cccgctgatc ctttgcgaat acgcccacgc gatgggtaac agtcttggcg gtttcgctaa     660
atactggcag gcgtttcgtc agtatccccg tttacagggc ggcttcgtct gggactgggt     720
ggatcagtcg ctgattaaat atgatgaaaa cggcaacccg tggtcggctt acggcggtga     780
ttttggcgat acgccgaacg atcgccagtt ctgtatgaac ggtctggtct ttgccgaccg     840
cacgccgcat ccagcgctga cggaagcaaa acaccagcag cagttttttcc agttccgttt     900
atccgggcaa accatcgaag tgaccagcga ataccgtttc cgtcatagcg ataacgagct     960
cctgcactgg atggtggcgc tggatggtaa gccgctggca agcggtgagc ggccgc        1016

<210> SEQ ID NO 20
<211> LENGTH: 1168
<212> TYPE: DNA
<213> ORGANISM: Artificial Sequence
<220> FEATURE:
<223> OTHER INFORMATION: Synthetic construct

<400> SEQUENCE: 20
gcggccgcga atacctgttc cgtcatagcg ataacgagct cctgcactgg atggtggcgc      60
tggatggtaa gccgctggca agcggtgaag tgcctctgga tgtcgctcca caaggtaaac     120
agttgattga actgcctgaa ctaccgcagc cggagagcgc cgggcaactc tggctcacag     180
tacgcgtagt gcaaccgaac gcgaccgcat ggtcagaagc cgggcacatc agcgcctggc     240
agcagtggcg tctggcggaa aacctcagtg tgacgctccc cgccgcgtcc cacgccatcc     300
cgcatctgac caccagcgaa atggattttt gcatcgagct gggtaataag cgttggcaat     360
taaccgccca gtcaggcttt ctttcacaga tgtggattgg cgataaaaaa caactgctga     420
cgccgctgcg cgatcagttc acccgtgcac cgctggataa cgacattggc gtaagtgaag     480
cgacccgcat tgaccctaac gcctgggtcg aacgctggaa ggcggcgggc cattaccagg     540
ccgaagcagc gttgttgcag tgcacggcag atacacttgc tgatgcggtg ctgattacga     600
ccgctcacgc gtggcagcat caggggaaaa ccttatttat cagccggaaa acctaccgga     660
ttgatggtag tggtcaaatg gcgattaccg ttgatgttga agtggcgagc gatacaccgc     720
atccggcgcg gattggcctg aactgccagc tggcgcaggt agcagagcgg gtaaactggc     780
tcggattagg gccgcaagaa aactatcccg accgccttac tgccgcctgt tttgaccgct     840
```

```
gggatctgcc attgtcagac atgtatacccc cgtacgtctt cccgagcgaa aacggtctgc    900
gctgcgggac gcgcgaattg aattatggcc cacaccagtg gcgcggcgac ttccagttca    960
acatcagccg ctacagtcaa cagcaactga tggaaaccag ccatcgccat ctgctgcacg   1020
cggaagaagg cacatggctg aatatcgacg gtttccatat ggggattggt ggcgacgact   1080
cctggagccc gtcagtatcg gcggaattcc agctgagcgc cggtcgctac cattaccagt   1140
tggtctggtg tcaaaaatga gcggccgc                                      1168
```

<210> SEQ ID NO 21  
<211> LENGTH: 24  
<212> TYPE: DNA  
<213> ORGANISM: Artificial Sequence  
<220> FEATURE:  
<223> OTHER INFORMATION: Synthetic construct

<400> SEQUENCE: 21

```
aaaaccaccc tggcgcccaa tacg                                            24
```

<210> SEQ ID NO 22  
<211> LENGTH: 24  
<212> TYPE: DNA  
<213> ORGANISM: Artificial Sequence  
<220> FEATURE:  
<223> OTHER INFORMATION: Synthetic construct

<400> SEQUENCE: 22

```
cccggactcg gtaatggcgc gcat                                            24
```

<210> SEQ ID NO 23  
<211> LENGTH: 24  
<212> TYPE: DNA  
<213> ORGANISM: Artificial Sequence  
<220> FEATURE:  
<223> OTHER INFORMATION: Synthetic construct

<400> SEQUENCE: 23

```
ggaagcagcc cagtagtagg ttga                                            24
```

<210> SEQ ID NO 24  
<211> LENGTH: 24  
<212> TYPE: DNA  
<213> ORGANISM: Artificial Sequence  
<220> FEATURE:  
<223> OTHER INFORMATION: Synthetic construct

<400> SEQUENCE: 24

```
ggtgctgcgc tggagtgacg gcag                                            24
```

<210> SEQ ID NO 25  
<211> LENGTH: 24  
<212> TYPE: DNA  
<213> ORGANISM: Artificial Sequence  
<220> FEATURE:  
<223> OTHER INFORMATION: Synthetic construct

<400> SEQUENCE: 25

```
cggccaccga tattatttgc ccga                                            24
```

<210> SEQ ID NO 26  
<211> LENGTH: 24  
<212> TYPE: DNA  
<213> ORGANISM: Artificial Sequence  
<220> FEATURE:

<223> OTHER INFORMATION: Synthetic construct

<400> SEQUENCE: 26
gattagggcc gcaagaaaac tatc                                           24

<210> SEQ ID NO 27
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is a, c, g, or t

<400> SEQUENCE: 27
gcgaagaacc tcttcccaag angg                                           24

<210> SEQ ID NO 28
<211> LENGTH: 71
<212> TYPE: DNA
<213> ORGANISM: Artificial Sequence
<220> FEATURE:
<223> OTHER INFORMATION: Synthetic construct

<400> SEQUENCE: 28
atcttgtgga aaggacgaaa caccggcgaa gaacctcttc ccaagagttt tagagctaga    60
aatagcaagt t                                                         71

<210> SEQ ID NO 29
<211> LENGTH: 71
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (26)..(46)
<223> OTHER INFORMATION: n is a, c, g, or t

<400> SEQUENCE: 29
atcttgtgga aaggacgaaa caccgnnnnn nnnnnnnnnn nnnnnngttt tagagctaga    60
aatagcaagt t                                                         71

<210> SEQ ID NO 30
<211> LENGTH: 24
<212> TYPE: DNA
<213> ORGANISM: Artificial Sequence
<220> FEATURE:
<223> OTHER INFORMATION: Synthetic construct

<400> SEQUENCE: 30
cgccagggtt ttcccagtca cgac                                           24

<210> SEQ ID NO 31
<211> LENGTH: 27
<212> TYPE: DNA
<213> ORGANISM: Artificial Sequence
<220> FEATURE:
<223> OTHER INFORMATION: Synthetic construct

<400> SEQUENCE: 31
gccaagcttg catgcctgca ggtcgac                                        27

<210> SEQ ID NO 32
<211> LENGTH: 71
<212> TYPE: DNA
<213> ORGANISM: Artificial Sequence
<220> FEATURE:
<223> OTHER INFORMATION: Synthetic construct

<400> SEQUENCE: 32

```
gtcgacctgc aggcatgcaa gcttggcact ggccgtcgtt ttacaacgtc gtgactggga    60
aaaccctggc g                                                         71
```

<210> SEQ ID NO 33
<211> LENGTH: 1184
<212> TYPE: PRT
<213> ORGANISM: Methanocaldococcus vulcanius

<400> SEQUENCE: 33

```
Met Lys Glu Lys Ala Pro Lys Ile Asp Ala Leu Ile Asp Cys Thr Tyr
1               5                   10                  15

Lys Thr Glu Asp Asn Arg Ala Val Ile Tyr Leu Tyr Leu Leu Glu Asn
            20                  25                  30

Ile Leu Lys Asp Arg Glu Phe Ser Pro Tyr Phe Tyr Val Glu Met Leu
        35                  40                  45

Lys Asp Arg Ile Glu Lys Glu Asp Ile Asp Lys Ile Lys Glu Phe Leu
    50                  55                  60

Leu Lys Glu Asp Leu Leu Lys Phe Val Glu Asn Leu Glu Val Val Asn
65                  70                  75                  80

Lys Thr Ile Leu Lys Lys Glu Lys Glu Ile Val Lys Ile Ile Ala Thr
                85                  90                  95

His Pro Gln Arg Val Pro Lys Leu Arg Lys Ile Lys Glu Cys Asp Ile
            100                 105                 110

Val Lys Glu Ile Tyr Glu His Asp Ile Pro Phe Ala Lys Arg Tyr Leu
        115                 120                 125

Ile Asp Ser Asp Ile Val Pro Met Thr Tyr Trp Asp Phe Glu Asn Arg
    130                 135                 140

Lys Gln Val Ser Ile Glu Ile Pro Lys Leu Lys Thr Val Ser Phe Asp
145                 150                 155                 160

Met Glu Val Tyr Asn Arg Asp Thr Glu Pro Asp Pro Glu Lys Asp Pro
                165                 170                 175

Ile Leu Met Ala Ser Phe Trp Asp Asp Asn Gly Gly Lys Val Ile Thr
            180                 185                 190

Tyr Lys His Phe Asp His Ser Asn Ile Glu Val Val Asn Ser Glu Lys
        195                 200                 205

Asp Leu Ile Lys Lys Ile Val Glu Met Leu Arg Gln Tyr Asp Val Ile
    210                 215                 220

Phe Thr Tyr Asn Gly Asp Asn Phe Asp Phe Pro Tyr Leu Lys Ala Arg
225                 230                 235                 240

Ala Lys Ile Tyr Gly Ile Asp Ile Lys Leu Gly Arg Asp Gly Glu Glu
                245                 250                 255

Leu Lys Ile Lys Arg Gly Gly Met Glu Phe Arg Ser Tyr Ile Pro Gly
            260                 265                 270

Arg Val His Ile Asp Leu Tyr Pro Ile Ser Arg Arg Leu Leu Lys Leu
        275                 280                 285

Thr Lys Tyr Thr Leu Glu Asp Val Val Tyr Asn Leu Phe Gly Ile Glu
    290                 295                 300

Lys Leu Lys Ile Pro His Thr Lys Ile Val Asp Tyr Trp Ala Asn Asn
```

-continued

```
        305                 310                 315                 320
Asp Lys Ile Leu Ile Glu Tyr Ser Leu Gln Asp Ala Lys Tyr Thr His
                    325                 330                 335

Lys Ile Gly Lys Tyr Phe Phe Pro Leu Glu Val Met Phe Ser Arg Ile
                340                 345                 350

Val Asn Gln Thr Pro Phe Glu Ile Thr Arg Met Ser Ser Gly Gln Met
                355                 360                 365

Val Glu Tyr Leu Leu Met Lys Asn Ala Phe Lys Glu Asn Met Ile Val
            370                 375                 380

Pro Asn Lys Pro Asp Glu Lys Glu Tyr Arg Lys Arg Leu Leu Thr Ser
385                 390                 395                 400

Tyr Glu Gly Gly Tyr Val Lys Glu Pro Glu Lys Gly Met Phe Glu Asp
                405                 410                 415

Ile Ile Ser Met Asp Phe Arg Cys His Pro Arg Gly Thr Lys Val Ile
                420                 425                 430

Val Lys Asn Asn Gly Leu Thr Asp Ile Glu Asn Val Lys Val Gly Asp
            435                 440                 445

Tyr Val Leu Gly Ile Asp Gly Trp Gln Lys Val Lys Arg Val Trp Lys
            450                 455                 460

Tyr Pro Tyr Asn Gly Phe Leu Val Asn Val Asn Gly Leu Lys Ser Thr
465                 470                 475                 480

Pro Asn His Lys Ile Pro Val Ile Lys Lys Glu Asn Gly Lys Asp Arg
                485                 490                 495

Val Ile Asp Val Ser Ser Ile Tyr Leu Leu Asn Leu Lys Gly Cys Lys
                500                 505                 510

Ile Leu Lys Ile Lys Asn Phe Glu Ser Ile Gly Met Phe Gly Lys Ile
                515                 520                 525

Phe Lys Lys Asp Thr Lys Ile Lys Lys Val Lys Gly Leu Leu Glu Lys
            530                 535                 540

Ile Ala Tyr Ile Asp Pro Arg Glu Gly Leu Val Ile Lys Val Lys Asn
545                 550                 555                 560

Glu Lys Glu Asp Ile Phe Lys Thr Val Ile Pro Ile Leu Lys Glu Leu
                565                 570                 575

Asn Ile Leu Tyr Lys Gln Val Asp Glu Lys Thr Ile Ile Asp Ser
                580                 585                 590

Ile Asp Gly Leu Leu Lys Tyr Ile Val Thr Ile Gly Phe Asn Asp Lys
            595                 600                 605

Asn Glu Glu Lys Ile Lys Glu Ile Ile Lys Glu Lys Ser Phe Leu Glu
            610                 615                 620

Phe Lys Glu Leu Glu Asp Ile Lys Ile Ser Ile Glu Glu Tyr Glu Gly
625                 630                 635                 640

Tyr Val Tyr Asp Leu Thr Leu Glu Gly Arg Pro Tyr Tyr Phe Ala Asn
                645                 650                 655

Gly Ile Leu Thr His Asn Ser Leu Tyr Pro Ser Ile Ile Ile Ala Tyr
                660                 665                 670

Asn Ile Ser Pro Glu Thr Leu Asp Cys Glu Cys Cys Lys Asp Ile Ser
                675                 680                 685

Glu Lys Ile Leu Gly His Trp Phe Cys Lys Lys Arg Glu Gly Leu Ile
            690                 695                 700

Pro Lys Thr Leu Arg Gly Leu Ile Glu Arg Arg Ile Asn Ile Lys Asn
705                 710                 715                 720

Lys Met Lys Lys Met Glu Ser Glu Lys Glu Ile Asn Glu Glu Tyr Asn
                725                 730                 735
```

-continued

```
Leu Leu Asp Tyr Glu Gln Arg Ser Leu Lys Ile Leu Ala Asn Ser Val
            740                 745                 750

Tyr Gly Tyr Leu Ala Phe Pro Arg Ala Arg Phe Tyr Ser Arg Glu Cys
            755                 760                 765

Ala Glu Val Ile Thr Tyr Leu Gly Arg Lys Tyr Ile Leu Glu Thr Ile
770                 775                 780

Glu Glu Ala Glu Lys Phe Gly Phe Lys Val Ile Tyr Ala Asp Ser Val
785                 790                 795                 800

Val Lys Asp Ala Lys Val Ile Ile Lys Glu Asp Gly Lys Ile Lys Glu
                805                 810                 815

Ile Lys Ile Glu Asp Leu Phe Lys Lys Val Asp Tyr Thr Ile Gly Asp
            820                 825                 830

Lys Glu Tyr Cys Ile Leu Asn Asn Val Glu Thr Leu Thr Ile Glu Asp
            835                 840                 845

Thr Lys Leu Val Trp Arg Lys Val Pro Tyr Ile Met Arg His Arg Thr
850                 855                 860

Asn Lys Lys Ile Tyr Arg Val Lys Val Lys Asp Arg Tyr Val Asp Ile
865                 870                 875                 880

Thr Glu Asp His Ser Ile Ile Gly Val Lys Asn Asn Lys Leu Val Glu
                885                 890                 895

Leu Lys Pro Thr Glu Ile Lys Asp Asp Glu Thr Lys Leu Ile Ile Leu
            900                 905                 910

Asn Lys Asp Leu Lys Ser Tyr Asn Phe Ala Ser Val Glu Glu Ile Asn
            915                 920                 925

Cys Ile Lys Tyr Ser Asp Tyr Val Tyr Asp Ile Glu Val Glu Asn Thr
930                 935                 940

His Arg Phe Phe Ala Asn Gly Ile Leu Val His Asn Thr Asp Gly Phe
945                 950                 955                 960

Tyr Ala Val Trp Lys Glu Lys Ile Ser Lys Asp Asp Leu Ile Lys Lys
                965                 970                 975

Ala Leu Glu Phe Val Lys Tyr Ile Asn Ser Lys Leu Pro Gly Thr Met
            980                 985                 990

Glu Leu Glu Phe Glu Gly Tyr Phe  Lys Arg Gly Ile Phe  Ile Thr Lys
            995                 1000                1005

Lys Arg  Tyr Ala Leu Ile Asp  Glu Asn Gly Arg Val  Ile Val Lys
    1010                1015                1020

Gly Leu  Glu Phe Val Arg Arg  Asp Trp Ser Asn Leu  Ala Arg Ile
    1025                1030                1035

Thr Gln  Arg Arg Val Leu Glu  Ala Leu Leu Leu Glu  Gly Asp Ile
    1040                1045                1050

Asn Lys  Ala Lys Lys Ala Ile  Gln Asp Val Ile Lys  Asp Leu Arg
    1055                1060                1065

Glu Lys  Lys Ile Lys Lys Glu  Asp Leu Ile Ile Tyr  Thr Gln Leu
    1070                1075                1080

Thr Lys  Asn Pro Asn Glu Tyr  Lys Thr Thr Ala Pro  His Val Glu
    1085                1090                1095

Ile Ala  Lys Lys Met Met Arg  Glu Gly Lys Lys Ile  Lys Ile Gly
    1100                1105                1110

Asp Val  Ile Gly Tyr Ile Ile  Val Lys Gly Ser Lys  Ser Ile Ser
    1115                1120                1125

Glu Arg  Ala Lys Leu Pro Glu  Glu Val Ser Ile Glu  Glu Ile Asp
    1130                1135                1140
```

Val Asn Tyr Tyr Ile Asp Asn Gln Ile Leu Pro Pro Val Leu Arg
1145                1150                1155

Ile Met Glu Ala Val Gly Val Ser Lys Asn Glu Leu Lys Lys Glu
1160                1165                1170

Gly Thr Gln Leu Thr Leu Asp Arg Phe Leu Lys
1175                1180

<210> SEQ ID NO 34
<211> LENGTH: 781
<212> TYPE: PRT
<213> ORGANISM: Archaeoglobus fulgidus

<400> SEQUENCE: 34

Met Glu Arg Val Glu Gly Trp Leu Ile Asp Ala Asp Tyr Glu Thr Ile
1               5                   10                  15

Gly Gly Lys Ala Val Val Arg Leu Trp Cys Lys Asp Asp Gln Gly Ile
                20                  25                  30

Phe Val Ala Tyr Asp Tyr Asn Phe Asp Pro Tyr Phe Tyr Val Ile Gly
            35                  40                  45

Val Asp Glu Asp Ile Leu Lys Asn Ala Ala Thr Ser Thr Arg Arg Glu
        50                  55                  60

Val Ile Lys Leu Lys Ser Phe Glu Lys Ala Gln Leu Lys Thr Leu Gly
65                  70                  75                  80

Arg Glu Val Glu Gly Tyr Ile Val Tyr Ala His His Pro Gln His Val
                85                  90                  95

Pro Lys Leu Arg Asp Tyr Leu Ser Gln Phe Gly Asp Val Arg Glu Ala
            100                 105                 110

Asp Ile Pro Phe Ala Tyr Arg Tyr Leu Ile Asp Lys Asp Leu Ala Cys
        115                 120                 125

Met Asp Gly Ile Ala Ile Glu Gly Glu Lys Gln Gly Gly Val Ile Arg
    130                 135                 140

Ser Tyr Lys Ile Glu Lys Val Glu Arg Ile Pro Arg Met Glu Phe Pro
145                 150                 155                 160

Glu Leu Lys Met Leu Val Phe Asp Cys Glu Met Leu Ser Ser Phe Gly
                165                 170                 175

Met Pro Glu Pro Glu Lys Asp Pro Ile Ile Val Ile Ser Val Lys Thr
            180                 185                 190

Asn Asp Asp Asp Glu Ile Ile Leu Thr Gly Asp Glu Arg Lys Ile Ile
        195                 200                 205

Ser Asp Phe Val Lys Leu Ile Lys Ser Tyr Asp Pro Asp Ile Ile Val
    210                 215                 220

Gly Tyr Asn Gln Asp Ala Phe Asp Trp Pro Tyr Leu Arg Lys Arg Ala
225                 230                 235                 240

Glu Arg Trp Asn Ile Pro Leu Asp Val Gly Arg Asp Gly Ser Asn Val
                245                 250                 255

Val Phe Arg Gly Gly Arg Pro Lys Ile Thr Gly Arg Leu Asn Val Asp
            260                 265                 270

Leu Tyr Asp Ile Ala Met Arg Ile Ser Asp Ile Lys Ile Lys Lys Leu
        275                 280                 285

Glu Asn Val Ala Glu Phe Leu Gly Thr Lys Ile Glu Ile Ala Asp Ile
    290                 295                 300

Glu Ala Lys Asp Ile Tyr Arg Tyr Trp Ser Arg Gly Glu Lys Glu Lys
305                 310                 315                 320

Val Leu Asn Tyr Ala Arg Gln Asp Ala Ile Asn Thr Tyr Leu Ile Ala
                325                 330                 335

```
Lys Glu Leu Leu Pro Met His Tyr Glu Leu Ser Lys Met Ile Arg Leu
                340                 345                 350

Pro Val Asp Asp Val Thr Arg Met Gly Arg Gly Lys Gln Val Asp Trp
                355                 360                 365

Leu Leu Leu Ser Glu Ala Lys Lys Ile Gly Glu Ile Ala Pro Asn Pro
            370                 375                 380

Pro Glu His Ala Glu Ser Tyr Glu Gly Ala Phe Val Leu Glu Pro Glu
385                 390                 395                 400

Arg Gly Leu His Glu Asn Val Ala Cys Leu Asp Phe Ala Ser Met Tyr
                405                 410                 415

Pro Ser Ile Met Ile Ala Phe Asn Ile Ser Pro Asp Thr Tyr Gly Cys
            420                 425                 430

Arg Asp Asp Cys Tyr Glu Ala Pro Glu Val Gly His Lys Phe Arg Lys
            435                 440                 445

Ser Pro Asp Gly Phe Phe Lys Arg Ile Leu Arg Met Leu Ile Glu Lys
        450                 455                 460

Arg Arg Glu Leu Lys Val Glu Leu Lys Asn Leu Ser Pro Glu Ser Ser
465                 470                 475                 480

Glu Tyr Lys Leu Leu Asp Ile Lys Gln Gln Thr Leu Lys Val Leu Thr
                485                 490                 495

Asn Ser Phe Tyr Gly Tyr Met Gly Trp Asn Leu Ala Arg Trp Tyr Cys
            500                 505                 510

His Pro Cys Ala Glu Ala Thr Thr Ala Trp Gly Arg His Phe Ile Arg
        515                 520                 525

Thr Ser Ala Lys Ile Ala Glu Ser Met Gly Phe Lys Val Leu Tyr Gly
        530                 535                 540

Asp Thr Asp Ser Ile Phe Val Thr Lys Ala Gly Met Thr Lys Glu Asp
545                 550                 555                 560

Val Asp Arg Leu Ile Asp Lys Leu His Glu Glu Leu Pro Ile Gln Ile
                565                 570                 575

Glu Val Asp Glu Tyr Tyr Ser Ala Ile Phe Phe Val Glu Lys Lys Arg
            580                 585                 590

Tyr Ala Gly Leu Thr Glu Asp Gly Arg Leu Val Val Lys Gly Leu Glu
            595                 600                 605

Val Arg Arg Gly Asp Trp Cys Glu Leu Ala Lys Lys Val Gln Arg Glu
        610                 615                 620

Val Ile Glu Val Ile Leu Lys Glu Lys Asn Pro Glu Lys Ala Leu Ser
625                 630                 635                 640

Leu Val Lys Asp Val Ile Leu Arg Ile Lys Glu Gly Lys Val Ser Leu
                645                 650                 655

Glu Glu Val Val Ile Tyr Lys Gly Leu Thr Lys Lys Pro Ser Lys Tyr
            660                 665                 670

Glu Ser Met Gln Ala His Val Lys Ala Ala Leu Lys Ala Arg Glu Met
        675                 680                 685

Gly Ile Ile Tyr Pro Val Ser Ser Lys Ile Gly Tyr Val Ile Val Lys
        690                 695                 700

Gly Ser Gly Asn Ile Gly Asp Arg Ala Tyr Pro Ile Asp Leu Ile Glu
705                 710                 715                 720

Asp Phe Asp Gly Glu Asn Leu Arg Ile Lys Thr Lys Ser Gly Ile Glu
                725                 730                 735

Ile Lys Lys Leu Asp Lys Asp Tyr Tyr Ile Asp Asn Gln Ile Ile Pro
            740                 745                 750
```

```
Ser Val Leu Arg Ile Leu Glu Arg Phe Gly Tyr Thr Glu Ala Ser Leu
            755                 760                 765

Lys Gly Ser Ser Gln Met Ser Leu Asp Ser Phe Phe Ser
        770                 775                 780

<210> SEQ ID NO 35
<211> LENGTH: 783
<212> TYPE: PRT
<213> ORGANISM: Archaeoglobus profundus

<400> SEQUENCE: 35

Met Ile Lys Ala Trp Leu Leu Asp Val Asp Tyr Val Thr Glu Asn Asp
1               5                   10                  15

Arg Ala Val Ile Arg Leu Trp Cys Lys Asp Asp Lys Gly Val Phe Val
            20                  25                  30

Ala Tyr Asp Arg Asn Phe Leu Pro Tyr Phe Tyr Val Ile Gly Cys Lys
        35                  40                  45

Ala Glu Asp Val Met Lys Val Lys Val Arg Thr Asn Glu Gly Ile Ile
    50                  55                  60

Thr Pro Leu Lys Val Glu Glu Ile Glu Ala Lys Ser Leu Gly Lys Pro
65                  70                  75                  80

Ile Lys Ala Leu Lys Val Tyr Thr Arg His Pro Gln His Val Pro Lys
                85                  90                  95

Leu Arg Glu Glu Ile Lys Lys Phe Ala Glu Val Arg Glu Ala Asp Ile
            100                 105                 110

Pro Phe Ala Tyr Arg Tyr Leu Ile Asp Lys Asp Leu Ala Cys Met Asp
        115                 120                 125

Gly Ile Glu Ile Glu Pro Ile Ala Val Lys Glu Gly Val Leu Arg Ala
    130                 135                 140

Tyr Glu Val Arg Ser Val Arg Val Glu Lys Lys Gly Phe Pro Asp
145                 150                 155                 160

Leu Lys Ile Leu Ala Phe Asp Cys Glu Met Leu Ala Gln Phe Met Pro
                165                 170                 175

Asp Pro Glu Lys Asp Pro Ile Ile Ala Ile Ala Val Lys Cys Gly Asp
            180                 185                 190

Phe Glu Glu Val Leu His Gly Asp Glu Arg Asp Ile Leu Arg Arg Phe
        195                 200                 205

Val Ser Ile Ile Lys Glu Gln Asp Pro Asp Ile Ile Val Gly Tyr Asn
    210                 215                 220

Gln Asp Asn Phe Asp Trp Pro Tyr Val Lys Lys Arg Ala Glu Lys Phe
225                 230                 235                 240

Gly Ile Arg Leu Asp Ile Gly Arg Asp Arg Ser Glu Ile Ser Phe Arg
                245                 250                 255

Gly Gly Arg Pro Lys Ile Ala Gly Arg Leu Asn Val Asp Leu Tyr Asp
            260                 265                 270

Ile Ala Leu Lys Ile Pro Asp Val Lys Ile Lys Thr Leu Lys Lys Val
        275                 280                 285

Ala Glu Phe Leu Gly Ala Lys Val Glu Glu Glu Asp Ile Glu Gly Arg
    290                 295                 300

Asp Ile Tyr Lys Cys Trp Met Arg Gly Glu Lys Glu Lys Val Phe Lys
305                 310                 315                 320

His Val Leu Asn Asp Val Leu Thr Thr Tyr Arg Leu Ala Leu Glu Leu
                325                 330                 335

Leu Pro Met His Tyr Glu Leu Ser Arg Met Ile Arg Leu Pro Leu Asp
            340                 345                 350
```

```
Asp Val Ala Arg Leu Gly Arg Gly Lys Gln Val Asp Tyr Phe Leu Leu
        355                 360                 365

Ser Glu Ala Lys Lys Ile Asn Glu Ile Ala Pro Asn Pro Pro Glu Ile
370                 375                 380

Glu Glu Ser Tyr Glu Gly Ala Phe Val Leu Glu Pro Ala Arg Gly Leu
385                 390                 395                 400

His Glu Asn Val Ala Cys Leu Asp Phe Ala Ser Met Tyr Pro Ser Ile
                405                 410                 415

Met Ile Asn Phe Asn Ile Ser Pro Asp Thr Leu Val Lys Gly Glu Cys
            420                 425                 430

Glu Asp Cys Tyr Val Ala Pro Glu Val Gly His Lys Phe Arg Lys Ser
        435                 440                 445

Pro Asp Gly Phe Phe Lys Arg Ile Leu Lys Met Leu Ile Glu Lys Arg
    450                 455                 460

Arg Glu Met Lys Arg Gln Met Lys Glu Leu Asp Pro Asp Ser Glu Asp
465                 470                 475                 480

Tyr Lys Leu Leu Asp Ile Lys Gln Gln Thr Leu Lys Val Leu Thr Asn
                485                 490                 495

Ser Phe Tyr Gly Tyr Thr Gly Trp Asn Leu Ala Arg Trp Tyr Cys Arg
            500                 505                 510

Glu Cys Ala Glu Ala Thr Thr Ala Trp Gly Arg Tyr Phe Ile Lys Arg
        515                 520                 525

Ala Val Lys Ile Ala Glu Ser Met Gly Phe Glu Val Leu Tyr Gly Asp
    530                 535                 540

Thr Asp Ser Leu Phe Ile Lys Lys Asn Lys Leu Asn Leu Lys Asp Leu
545                 550                 555                 560

Glu Lys Glu Cys Leu Lys Leu Ile Asp Val Ile Ser Lys Glu Leu Pro
                565                 570                 575

Ile Gln Leu Glu Ile Asp Glu Phe Tyr Lys Ala Ile Phe Phe Val Glu
            580                 585                 590

Lys Lys Arg Tyr Ala Gly Leu Thr Asp Asp Asp Arg Ile Val Val Lys
        595                 600                 605

Gly Leu Glu Val Arg Arg Gly Asp Trp Cys Glu Leu Ala Lys Arg Val
    610                 615                 620

Gln Arg Glu Val Ile Glu Ile Ile Leu Arg Glu Arg Asn Pro Asp Lys
625                 630                 635                 640

Ala Leu Lys Phe Val Lys Asn Val Ile Glu Glu Ile Lys Glu Gly Lys
                645                 650                 655

Phe Lys Leu Glu Asp Tyr Val Ile Tyr Lys Gly Leu Thr Lys Lys Pro
            660                 665                 670

Asp Lys Tyr Glu Ser Lys Gln Ala His Val Lys Ala Ala Leu Arg Ala
        675                 680                 685

Met Glu Met Gly Ile Tyr Tyr Pro Ile Gly Thr Lys Val Gly Phe Val
    690                 695                 700

Ile Val Lys Gly Gly Ser Ile Ser Asp Arg Ala Tyr Pro Ile Glu
705                 710                 715                 720

Leu Ile Glu Glu Phe Asp Gly Glu Asn Leu Lys Ile Arg Thr Pro Ser
                725                 730                 735

Gly Ile Met Val Lys Lys Ile Asp Lys Asp Tyr Tyr Ile Asp His Gln
            740                 745                 750

Ile Ile Pro Ala Val Met Arg Ile Leu Glu Arg Phe Gly Tyr Thr Glu
        755                 760                 765
```

```
Ala Ser Leu Lys Thr Thr Ile Gln Lys Thr Leu Phe Asp Phe Thr
    770                 775                 780
```

<210> SEQ ID NO 36
<211> LENGTH: 849
<212> TYPE: PRT
<213> ORGANISM: Caldicellulosiruptor hydrothermalis

<400> SEQUENCE: 36

```
Met Lys Leu Val Ile Phe Asp Gly Asn Ser Ile Leu Tyr Arg Ala Phe
 1               5                  10                  15

Phe Ala Leu Pro Glu Leu Thr Thr Ser Ser Asn Ile Pro Thr Asn Ala
            20                  25                  30

Ile Tyr Gly Phe Ile Asn Val Ile Leu Lys Tyr Leu Glu Gln Glu Lys
        35                  40                  45

Pro Asp Tyr Ile Ala Val Ala Phe Asp Lys Arg Gly Arg Glu Ala Arg
    50                  55                  60

Lys Ser Glu Tyr Gln Glu Tyr Lys Ala Asn Arg Lys Pro Met Pro Asp
65                  70                  75                  80

Asn Leu Gln Val Gln Ile Pro Tyr Val Arg Glu Ile Leu Tyr Ala Leu
                85                  90                  95

Asn Ile Pro Ile Val Glu Phe Glu Gly Tyr Glu Ala Asp Asp Val Ile
            100                 105                 110

Gly Ser Leu Val Asn Lys Phe Lys Asn Thr Gly Leu Asp Ile Val Ile
        115                 120                 125

Ile Thr Gly Asp Arg Asp Thr Leu Gln Leu Leu Asp Lys Asn Val Val
    130                 135                 140

Val Lys Ile Val Ser Thr Lys Phe Asp Arg Thr Met Glu Asp Leu Tyr
145                 150                 155                 160

Thr Ile Glu Asn Ile Lys Glu Lys Tyr Gly Val Trp Ala Asn Gln Val
                165                 170                 175

Pro Asp Tyr Lys Ala Leu Val Gly Asp Gln Ser Asp Asn Ile Pro Gly
            180                 185                 190

Val Lys Gly Ile Gly Glu Lys Ser Ala Gln Lys Leu Leu Glu Glu Tyr
        195                 200                 205

Ser Ser Leu Glu Glu Ile Tyr Gln Asn Leu Asp Lys Ile Lys Gly Ser
    210                 215                 220

Ile Arg Glu Lys Leu Glu Ala Gly Lys Asp Met Ala Phe Leu Ser Lys
225                 230                 235                 240

Arg Leu Ala Thr Ile Val Cys Asp Leu Pro Leu Asn Val Asn Leu Glu
                245                 250                 255

Asp Leu Arg Thr Lys Glu Trp Asn Lys Glu Arg Leu Tyr Glu Ile Leu
            260                 265                 270

Val Gln Leu Glu Phe Lys Ser Ile Ile Lys Arg Leu Gly Leu Ser Glu
        275                 280                 285

Asn Ile Gln Phe Glu Phe Val Gln Gln Arg Thr Asp Ile Pro Asp Val
    290                 295                 300

Glu Gln Arg Glu Leu Glu Ser Ile Ser Arg Ile Arg Ser Lys Glu Ile
305                 310                 315                 320

Pro Leu Met Phe Val Gln Asp Glu Lys Cys Phe Tyr Leu Tyr Asp Gln
                325                 330                 335

Glu Ser Asn Thr Val Phe Val Thr Arg Asp Arg His Leu Val Glu Glu
            340                 345                 350

Ile Leu Lys Ser Asp Thr Val Lys Ile Val Tyr Asp Leu Lys Asn Ile
        355                 360                 365
```

Phe His Gln Leu Asn Leu Glu Asp Thr Asp Asn Ile Lys Asn Cys Glu
    370                 375                 380

Asp Val Met Ile Ala Ser Tyr Val Leu Asp Ser Thr Arg Ser Ser Tyr
385                 390                 395                 400

Glu Leu Glu Thr Leu Phe Val Ser Tyr Leu Asn Thr Asp Ile Glu Ala
            405                 410                 415

Val Lys Lys Asp Lys Lys Met Val Ser Val Val Leu Leu Lys Arg Leu
                420                 425                 430

Trp Asp Asp Leu Leu Arg Leu Ile Asp Leu Asn Ser Cys Gln Phe Leu
            435                 440                 445

Tyr Glu Asn Ile Glu Arg Pro Leu Ile Pro Val Leu Tyr Glu Met Glu
    450                 455                 460

Lys Thr Gly Phe Lys Val Asp Arg Asp Ala Leu Leu Gln Tyr Thr Lys
465                 470                 475                 480

Glu Ile Glu Asn Lys Ile Leu Lys Leu Glu Thr Gln Ile Tyr Gln Ile
                485                 490                 495

Ala Gly Glu Trp Phe Asn Ile Asn Ser Pro Lys Gln Leu Ser Tyr Ile
            500                 505                 510

Leu Phe Glu Lys Leu Lys Leu Pro Val Ile Lys Thr Lys Thr Gly
    515                 520                 525

Tyr Ser Thr Asp Ala Glu Val Leu Glu Glu Phe Asp Lys His Glu Ile
530                 535                 540

Val Pro Leu Ile Leu Asp Tyr Arg Met Tyr Thr Lys Ile Leu Thr Thr
545                 550                 555                 560

Tyr Cys Gln Gly Leu Leu Gln Ala Ile Asn Pro Ser Ser Gly Arg Val
            565                 570                 575

His Thr Thr Phe Ile Gln Thr Gly Thr Ala Thr Gly Arg Leu Ala Ser
            580                 585                 590

Ser Asp Pro Asn Leu Gln Asn Ile Pro Val Lys Tyr Asp Glu Gly Lys
        595                 600                 605

Leu Ile Arg Lys Val Phe Val Pro Glu Glu Gly His Val Leu Ile Asp
    610                 615                 620

Ala Asp Tyr Ser Gln Ile Glu Leu Arg Ile Leu Ala His Ile Ser Glu
625                 630                 635                 640

Asp Glu Arg Leu Ile Asn Ala Phe Lys Asn Asn Ile Asp Ile His Ser
            645                 650                 655

Gln Thr Ala Ala Glu Val Phe Gly Val Asp Ile Ala Asp Val Thr Pro
            660                 665                 670

Glu Met Arg Ser Gln Ala Lys Ala Val Asn Phe Gly Ile Val Tyr Gly
    675                 680                 685

Ile Ser Asp Tyr Gly Leu Ala Arg Asp Ile Lys Ile Ser Arg Lys Glu
    690                 695                 700

Ala Ala Glu Phe Ile Asn Lys Tyr Phe Glu Arg Tyr Pro Lys Val Lys
705                 710                 715                 720

Glu Tyr Leu Asp Asn Ile Val Arg Phe Ala Arg Glu Asn Gly Tyr Val
            725                 730                 735

Leu Thr Leu Phe Asn Arg Lys Arg Tyr Val Lys Asp Ile Lys Ser Ala
            740                 745                 750

Asn Arg Asn Ala Arg Ser Tyr Ala Glu Arg Ile Ala Met Asn Ser Pro
        755                 760                 765

Ile Gln Gly Ser Ala Ala Asp Ile Met Lys Leu Ala Met Ile Lys Val
    770                 775                 780

-continued

Tyr Gln Lys Leu Lys Glu Asn Asn Leu Lys Ser Lys Ile Ile Leu Gln
785                 790                 795                 800

Val His Asp Glu Leu Leu Ile Glu Ala Pro Tyr Glu Glu Lys Asp Ile
            805                 810                 815

Val Lys Arg Ile Val Lys Arg Glu Met Glu Asn Ala Val Ala Leu Lys
            820                 825                 830

Val Pro Leu Val Val Glu Val Lys Glu Gly Leu Asn Trp Tyr Glu Thr
            835                 840                 845

Lys

<210> SEQ ID NO 37
<211> LENGTH: 781
<212> TYPE: PRT
<213> ORGANISM: Desulfurococcus mucosus

<400> SEQUENCE: 37

Met Glu Lys Arg Val Tyr Leu Val Asp Ile Thr Tyr Gly Leu Val Gly
1               5                   10                  15

Asn Ser Pro Glu Ile Arg Met Phe Gly Val Asp Glu Asn Gly Glu Lys
            20                  25                  30

Val Val Ile Leu Asp Arg Gly Phe Arg Pro Tyr Phe Tyr Val Ile Pro
        35                  40                  45

Glu Glu Gly Phe Glu Asp Gln Val Ala Arg Val Ile Gly Lys Met Gln
50                  55                  60

Asn Val Ile Lys Ala Asp Val Thr Glu Arg Arg Leu Phe Gly Lys Pro
65                  70                  75                  80

Ile Lys Val Val Lys Val Thr Val Thr Val Pro Asp Lys Val Arg Glu
                85                  90                  95

Leu Arg Asp Arg Val Lys Ser Ile Gln His Val Lys Glu Val Leu Glu
            100                 105                 110

Ala Asp Ile Arg Phe Tyr Ile Arg Tyr Met Ile Asp Asn Asp Ile Arg
        115                 120                 125

Pro Gly Trp Leu Met Phe Ser Asn Leu Lys Pro Val Asp Asn Lys Ile
130                 135                 140

Gly Gly Val Ser Asn Val Tyr Leu Thr Glu Thr Pro Pro Thr Ser Leu
145                 150                 155                 160

Asp Leu Gly Ile Met Pro Arg Leu Asn Tyr Met Ala Leu Asp Ile Glu
                165                 170                 175

Val Tyr Asn Pro Arg Gly Thr Pro Asp Pro Lys Arg Asp Pro Ile Ile
            180                 185                 190

Ile Ile Ala Leu Ala Asn Ser Asn Gly Asp Val Lys Leu Leu Thr Leu
        195                 200                 205

Asp Asn Tyr Lys His Glu Arg Glu Met Leu Asn Asp Met Met Ser Val
210                 215                 220

Ile Lys Glu Trp Asp Pro Asp Val Leu Phe Gly Tyr Asn Ser Asn Lys
225                 230                 235                 240

Phe Asp Met Pro Tyr Leu Val Asn Arg Ala Asp Ala Leu Asn Val Lys
                245                 250                 255

Leu Gln Leu Ser Lys Tyr Gly Thr Pro Pro Glu Gln Ser Val Tyr Gly
            260                 265                 270

His Trp Ser Ile Ile Gly Arg Ala His Ile Asp Leu Tyr Asn Phe Ile
        275                 280                 285

Glu Asp Met Thr Asp Val Lys Arg Lys Ser Leu Asp Tyr Val Ala Glu
290                 295                 300

```
Tyr Phe Gly Val Met Lys Arg Ser Glu Arg Val Asn Ile Pro Gly His
305                 310                 315                 320

Arg Ile Tyr Gln Tyr Trp Asp Asp Glu Gly Lys Arg Ser Gln Leu Ile
            325                 330                 335

Lys Tyr Ala Arg Asp Asp Val Leu Ser Thr Leu Gly Leu Gly Lys Ile
            340                 345                 350

Leu Leu Pro Tyr Ala Met Gln Leu Ala Ser Val Ser Gly Leu Pro Leu
            355                 360                 365

Asp Gln Val Gly Pro Ala Ser Val Gly Ser Arg Val Glu Met Met Ile
370                 375                 380

Met His Glu Ala Tyr Lys Met Gly Glu Leu Ala Pro Asn Arg Val Glu
385                 390                 395                 400

Arg Pro Tyr Glu Thr Tyr Lys Gly Ala Ile Val Leu Glu Pro Lys Pro
            405                 410                 415

Gly Ile His Tyr Asn Ile Ala Val Leu Asp Phe Ser Ser Met Tyr Pro
            420                 425                 430

Asn Ile Met Leu Lys Tyr Asn Ile Ser Pro Asp Thr Leu Val Leu Asp
            435                 440                 445

Ser Ser Glu Gly Asp Tyr Tyr Thr Ala Pro Glu Val Gly Tyr Arg Phe
450                 455                 460

Arg Lys Ser Pro Arg Gly Leu Tyr Ala Ser Leu Leu Gln Lys Leu Ile
465                 470                 475                 480

Glu Ala Arg Arg Glu Ala Arg Asp Glu Met Arg Asn Tyr Pro Glu Gly
                485                 490                 495

Ser Phe Glu Trp Val Leu Leu Asn Glu Arg Gln Arg Ala Leu Lys Ile
            500                 505                 510

Met Ala Asn Ala Met Tyr Gly Tyr Cys Gly Trp Leu Gly Ala Arg Trp
            515                 520                 525

Tyr Ile Arg Glu Val Ala Glu Ser Val Thr Ala Trp Gly Arg Tyr Leu
530                 535                 540

Leu Lys Thr Ala Met Ser Met Ala Lys Glu Arg Gly Leu Thr Val Ile
545                 550                 555                 560

Tyr Gly Asp Thr Asp Ser Leu Phe Val Thr Tyr Asp Lys Asp Lys Val
            565                 570                 575

Ala Asp Ile Ile Ser Arg Ile Asn Glu Met Gly Phe Glu Val Lys Ile
            580                 585                 590

Asp Lys Val Tyr Ser Lys Leu Ile Phe Thr Glu Ser Lys Lys Arg Tyr
            595                 600                 605

Ile Gly Leu Thr Ala Asp Gly Glu Val Asp Ile Val Gly Phe Glu Ala
            610                 615                 620

Val Arg Gly Asp Trp Ser Glu Leu Ala Arg Asn Val Gln Glu Arg Val
625                 630                 635                 640

Ala Glu Leu Val Leu Arg Glu Ser Val Asp Glu Ala Val Lys Tyr Val
            645                 650                 655

Lys Ser Val Ile Asp Asp Leu Arg Asn Tyr Arg Phe Thr Ile Asp Asp
            660                 665                 670

Val Ile Ile Trp Lys Thr Leu Asp Lys Asp Ile Asn Glu Tyr Lys Ala
            675                 680                 685

Ile Gln Pro His Val Val Ala Ala Arg Arg Leu Met Glu Lys Gly Tyr
            690                 695                 700

Val Val Asn Lys Gly Asp Thr Val Gly Phe Val Ile Val Lys Asp Ser
705                 710                 715                 720

Gly Asp Lys Leu Thr Gln Arg Ala Tyr Pro Tyr Val Phe Ile Asn Asp
```

```
                        725                 730                 735
Val Lys Glu Ile Asp Val Asp Tyr Tyr Val Glu Lys Gln Val Ile Pro
                740                 745                 750

Ala Ala Leu Arg Ile Leu Glu Val Phe Gly Val Asn Glu Ala Ala Leu
            755                 760                 765

Leu Gly Lys Thr Gly Lys Ser Ile Leu Asp Tyr Phe His
        770                 775                 780

<210> SEQ ID NO 38
<211> LENGTH: 803
<212> TYPE: PRT
<213> ORGANISM: Pyrolobus fumarii

<400> SEQUENCE: 38

Met Thr Glu Val Val Phe Thr Val Leu Asp Ser Ser Tyr Glu Val Val
1               5                   10                  15

Gly Lys Glu Pro Gln Val Ile Ile Trp Gly Ile Ala Glu Asn Gly Glu
            20                  25                  30

Arg Val Val Leu Ile Asp Arg Ser Phe Arg Pro Tyr Phe Tyr Ala Leu
        35                  40                  45

Leu Ala Pro Gly Ala Asp Pro Lys Gln Val Ala Gln Arg Ile Arg Ala
    50                  55                  60

Leu Ser Arg Pro Lys Ser Pro Ile Ile Gly Val Glu Asp Asp Lys Arg
65                  70                  75                  80

Lys Tyr Phe Gly Arg Pro Arg Arg Val Leu Arg Ile Arg Thr Val Leu
                85                  90                  95

Pro Glu Ala Val Arg Glu Tyr Arg Glu Leu Val Lys Asn Val Asp Gly
            100                 105                 110

Val Glu Asp Val Leu Glu Ala Asp Ile Arg Phe Ala Met Arg Tyr Leu
        115                 120                 125

Ile Asp His Asp Leu Phe Pro Phe Thr Trp Tyr Arg Val Glu Ala Glu
    130                 135                 140

Pro Leu Glu Asn Lys Met Gly Phe Arg Val Asp Lys Val Tyr Leu Val
145                 150                 155                 160

Lys Ser Arg Pro Glu Pro Leu Tyr Gly Glu Ala Leu Ala Pro Thr Lys
                165                 170                 175

Leu Pro Asp Leu Arg Ile Leu Ala Phe Asp Ile Glu Val Tyr Ser Lys
            180                 185                 190

Gln Gly Ser Pro Arg Pro Glu Arg Asp Pro Val Ile Val Ile Ala Val
        195                 200                 205

Lys Thr Asp Asp Gly Asp Glu Val Leu Phe Ile Ala Glu Gly Lys Asp
    210                 215                 220

Asp Arg Lys Pro Ile Arg Glu Phe Val Glu Tyr Val Lys Arg Tyr Asp
225                 230                 235                 240

Pro Asp Ile Ile Val Gly Tyr Asn Asn Asn His Phe Asp Trp Pro Tyr
                245                 250                 255

Leu Leu Arg Arg Ala Arg Ile Leu Gly Ile Lys Leu Asp Val Thr Arg
            260                 265                 270

Arg Val Gly Ala Glu Pro Thr Thr Ser Val His Gly His Val Ser Val
        275                 280                 285

Pro Gly Arg Leu Asn Val Asp Leu Tyr Asp Tyr Ala Glu Glu Met Pro
    290                 295                 300

Glu Ile Lys Ile Lys Ser Leu Glu Glu Val Ala Glu Tyr Leu Gly Val
305                 310                 315                 320
```

```
Met Lys Lys Ser Glu Arg Val Ile Ile Asn Trp Trp Glu Ile Pro Asp
                325                 330                 335
Tyr Trp Asp Asp Pro Lys Lys Arg Pro Leu Leu Leu Gln Tyr Ala Arg
            340                 345                 350
Asp Asp Val Arg Ala Thr Tyr Gly Leu Ala Glu Lys Ile Leu Pro Phe
        355                 360                 365
Ala Ile Gln Leu Ser Tyr Val Thr Gly Leu Pro Leu Asp Gln Val Gly
    370                 375                 380
Ala Met Ser Val Gly Phe Arg Leu Glu Trp Tyr Leu Ile Arg Ala Ala
385                 390                 395                 400
Phe Lys Met Lys Glu Leu Val Pro Asn Arg Val Glu Arg Pro Glu Glu
                405                 410                 415
Thr Tyr Arg Gly Ala Ile Val Leu Glu Pro Leu Arg Gly Val His Glu
            420                 425                 430
Asn Ile Ala Val Leu Asp Phe Ser Ser Met Tyr Pro Asn Ile Met Ile
        435                 440                 445
Lys Tyr Asn Val Gly Pro Asp Thr Leu Val Arg Pro Gly Glu Glu Cys
    450                 455                 460
Gly Glu Cys Gly Cys Trp Glu Ala Pro Glu Val Lys His Arg Phe Arg
465                 470                 475                 480
Arg Cys Pro Pro Gly Phe Phe Lys Thr Val Leu Glu Arg Leu Leu Glu
                485                 490                 495
Leu Arg Lys Arg Val Arg Ala Glu Met Lys Lys Tyr Pro Pro Asp Ser
            500                 505                 510
Pro Glu Tyr Arg Leu Leu Asp Glu Arg Gln Lys Ala Leu Lys Val Leu
        515                 520                 525
Ala Asn Ala Ser Tyr Gly Tyr Met Gly Trp Ser Gly Ala Arg Trp Tyr
    530                 535                 540
Cys Arg Glu Cys Ala Glu Ala Val Thr Ala Trp Gly Arg His Leu Ile
545                 550                 555                 560
Arg Thr Ala Ile Asn Ile Ala Arg Lys Leu Gly Leu Lys Val Ile Tyr
                565                 570                 575
Gly Asp Thr Asp Ser Leu Phe Val Thr Tyr Asp Pro Glu Lys Val Glu
            580                 585                 590
Lys Phe Ile Lys Ile Ile Glu Glu Leu Gly Phe Glu Ile Lys Leu
        595                 600                 605
Glu Lys Val Tyr Lys Arg Val Phe Phe Thr Glu Ala Lys Lys Arg Tyr
    610                 615                 620
Ala Gly Leu Leu Glu Asp Gly Arg Ile Asp Ile Val Gly Phe Glu Ala
625                 630                 635                 640
Val Arg Gly Asp Trp Cys Glu Leu Ala Lys Glu Val Gln Thr Lys Val
                645                 650                 655
Val Glu Ile Val Leu Lys Thr Ser Asp Val Asn Lys Ala Val Glu Tyr
            660                 665                 670
Val Arg Lys Ile Val Lys Glu Leu Glu Glu Gly Lys Val Pro Ile Glu
        675                 680                 685
Lys Leu Val Ile Trp Lys Thr Leu Ser Lys Arg Leu Glu Glu Tyr Thr
    690                 695                 700
Thr Glu Ala Pro His Val Ala Ala Lys Met Leu Ser Ala Gly
705                 710                 715                 720
Tyr Arg Val Ser Pro Gly Asp Lys Ile Gly Tyr Val Ile Val Lys Gly
                725                 730                 735
Gly Gly Arg Ile Ser Gln Arg Ala Trp Pro Tyr Phe Met Val Lys Asp
```

-continued

```
                740                 745                 750
Pro Ser Gln Ile Asp Val Thr Tyr Tyr Val Asp His Gln Ile Ile Pro
            755                 760                 765

Ala Ala Leu Arg Ile Leu Gly Tyr Phe Gly Ile Thr Glu Lys Lys Leu
            770                 775                 780

Lys Ala Ser Ala Thr Gly Gln Lys Thr Leu Phe Asp Phe Leu Ala Lys
785                 790                 795                 800

Lys Ser Lys

<210> SEQ ID NO 39
<211> LENGTH: 786
<212> TYPE: PRT
<213> ORGANISM: Pyrobaculum oguniense

<400> SEQUENCE: 39

Met Glu Ile Arg Val Trp Pro Leu Asp Val Thr Tyr Ile Val Val Gly
1               5                   10                  15

Gly Val Pro Glu Val Arg Val Phe Gly Ile Ala Glu Gly Gly Glu Arg
            20                  25                  30

Val Val Leu Ala Asp Arg Ser Phe Arg Pro Tyr Phe Tyr Val Asp Cys
        35                  40                  45

Ala Gly Cys Asp Pro His Ala Val Lys Thr His Leu Gly Arg Thr Ala
    50                  55                  60

Pro Val Glu Gly Val Glu Leu Val Glu Arg Arg Phe Leu Gly Arg Pro
65                  70                  75                  80

Arg Gln Phe Leu Lys Val Val Ala Lys Ile Pro Glu Asp Val Arg Arg
                85                  90                  95

Leu Arg Glu Ala Ala Ser Thr Ile Pro Gly Val Arg Gly Val Tyr Glu
            100                 105                 110

Ala Asp Ile Arg Phe Tyr Met Arg Tyr Val Ile Asp Met Gly Val Val
        115                 120                 125

Pro Cys Ser Trp Asn Val Ala Glu Val Glu Val Ala Asp Glu Lys Leu
    130                 135                 140

Gly Ser Leu Pro Val Tyr Arg Val Val Lys Trp Gly Gly Ala Val Glu
145                 150                 155                 160

Gly Phe Pro Pro Leu Arg Val Leu Ala Phe Asp Ile Glu Val Tyr
                165                 170                 175

Asn Glu Arg Gly Thr Pro Asp Pro Ala Arg Asp Pro Ile Val Met Ile
            180                 185                 190

Ala Val Gln Ser Ser Asp Gly Arg Leu Glu Val Phe Glu Ala Ser Gly
        195                 200                 205

Arg Asp Asp Arg Gly Val Leu Arg Ser Phe Val Glu Tyr Val Arg Ser
    210                 215                 220

Phe Asp Pro Asp Val Val Val Gly Tyr Asn Ser Asn Phe Asp Trp
225                 230                 235                 240

Pro Tyr Leu Ala Glu Arg Ala Lys Ala Val Gly Val Pro Leu Arg Val
                245                 250                 255

Asp Arg Leu Gly Gly Ala Pro Gln Gln Ser Val Tyr Gly His Trp Ser
            260                 265                 270

Val Leu Gly Arg Ala Asn Val Asp Leu Tyr Asn Ile Val Asp Glu Phe
        275                 280                 285

Pro Glu Ile Lys Leu Lys Thr Leu Asp Arg Val Ala Glu Tyr Phe Gly
    290                 295                 300

Val Met Arg Arg Asp Glu Arg Val Leu Ile Pro Gly His Lys Ile Tyr
```

-continued

```
            305                 310                 315                 320
        Glu Tyr Trp Arg Asp Pro Ser Lys Arg Pro Leu Leu Arg Gln Tyr Val
                        325                 330                 335
        Ile Asp Asp Val Arg Ser Thr Tyr Gly Leu Ala Glu Arg Leu Leu Pro
                        340                 345                 350
        Phe Leu Ile Gln Leu Ser Ser Val Ser Gly Leu Pro Leu Asp Gln Val
                        355                 360                 365
        Ala Ala Ala Ser Val Gly Asn Arg Val Glu Trp Met Leu Leu Arg Tyr
                        370                 375                 380
        Ala Tyr Gly Leu Gly Glu Val Ala Pro Asn Arg Glu Glu Arg Glu Tyr
        385                 390                 395                 400
        Glu Pro Tyr Lys Gly Ala Ile Val Leu Glu Pro Lys Pro Gly Leu Tyr
                        405                 410                 415
        Ser Asp Val Leu Val Leu Asp Phe Ser Ser Met Tyr Pro Asn Val Met
                        420                 425                 430
        Met Arg Tyr Asn Leu Ser Pro Asp Thr Tyr Leu Glu Pro Gly Glu Pro
                        435                 440                 445
        Asp Pro Pro Glu Gly Val Tyr Val Ala Pro Glu Val Gly His Arg Phe
        450                 455                 460
        Arg Lys Glu Pro Pro Gly Phe Ile Pro Gln Val Leu Arg Arg Leu Val
        465                 470                 475                 480
        Ala Leu Arg Arg Ala Val Arg Glu Glu Met Lys Lys Tyr Gln Pro Asp
                        485                 490                 495
        Thr Pro Glu Tyr Arg Val Leu Asp Glu Arg Gln Lys Ala Leu Lys Ile
                        500                 505                 510
        Met Ala Asn Ala Met Tyr Gly Tyr Thr Gly Trp Val Gly Ala Arg Trp
                        515                 520                 525
        Tyr Lys Lys Glu Val Ala Glu Ser Val Thr Ala Phe Ala Arg Ala Ile
                        530                 535                 540
        Leu Lys Asp Val Ile Asp Tyr Ala Arg Arg Leu Gly Ile Val Val Ile
        545                 550                 555                 560
        Tyr Gly Asp Thr Asp Ser Leu Phe Val Lys Lys Gly Gly Asp Leu Glu
                        565                 570                 575
        Lys Leu Ala Arg Tyr Val Asp Glu Lys Tyr Gly Ile Glu Ile Lys Val
                        580                 585                 590
        Asp Lys Asp Tyr Glu Lys Val Leu Phe Thr Glu Ala Lys Lys Arg Tyr
                        595                 600                 605
        Ala Gly Leu Leu Arg Asp Gly Arg Ile Asp Ile Val Gly Phe Glu Val
                        610                 615                 620
        Val Arg Gly Asp Trp Ser Glu Leu Ala Lys Glu Val Gln Leu Lys Val
        625                 630                 635                 640
        Ile Glu Leu Ile Leu Lys Ala Arg Asp Leu Ser Glu Ala Arg Gln Arg
                        645                 650                 655
        Val Ile Lys Tyr Val Lys Asp Val Ile Glu Arg Leu Lys Ser Gly Lys
                        660                 665                 670
        Phe Asp Leu Asp Asp Leu Ile Ile Trp Lys Thr Leu Asp Lys Asp Leu
                        675                 680                 685
        Gly Glu Tyr Lys Ala Tyr Pro Pro His Val Arg Ala Ala Leu Ile Leu
                        690                 695                 700
        Lys Lys Lys Gly Tyr Lys Val Gly Arg Gly Thr Thr Ile Gly Tyr Val
        705                 710                 715                 720
        Val Val Lys Gly Gly Glu Lys Val Ser Glu Arg Ser Leu Pro Tyr Ile
                        725                 730                 735
```

```
Leu Val Asp Asp Leu Ala Lys Ile Asp Val Asp Tyr Tyr Ile Glu Lys
                740                 745                 750

Gln Val Ile Pro Ala Ala Leu Arg Ile Ala Glu Val Ile Gly Val Lys
                755                 760                 765

Glu Gly Asp Leu Arg Ala Gly Arg Ser Glu Lys Ser Leu Leu Asp Phe
                770                 775                 780

Phe Glu
785

<210> SEQ ID NO 40
<211> LENGTH: 801
<212> TYPE: PRT
<213> ORGANISM: Staphylothermus marinus

<400> SEQUENCE: 40

Met Ser Glu Lys Ile Asn Leu Glu Phe Tyr Phe Leu Asp Asn Ser Tyr
1               5                   10                  15

Glu Val Ile Gly Asn Glu Pro His Ile Ile Trp Gly Ile Thr Arg
                20                  25                  30

Asp Gly Arg Arg Val Leu Leu Arg Asp Arg Arg Phe Arg Pro Tyr Phe
            35                  40                  45

Tyr Ala Ile Leu Lys Asp Lys Val Asn Ile Glu Asp Leu Ala Arg Lys
        50                  55                  60

Ile Arg Thr Tyr Ser Asp Pro Lys Ser Pro Ile Ile Gly Val Glu Pro
65                  70                  75                  80

Val Glu Lys Lys Tyr Phe Gly Arg Lys Val Ser Ala Leu Lys Ile Ile
                85                  90                  95

Thr Met Ile Pro Glu Tyr Val Arg Lys Tyr Arg Glu Lys Ile Lys Ser
                100                 105                 110

Leu Pro Glu Val Leu Glu Val Glu Ala Asp Ile Arg Phe Ser Ile
            115                 120                 125

Arg Tyr Ile Ile Asp His Asp Leu Arg Pro Cys Gly Trp His Val Ala
        130                 135                 140

Glu Val Glu Val Pro Lys Lys Pro Ile Tyr Arg Val Asp Ala Glu
145                 150                 155                 160

Tyr Glu Ile Ile Gly Asp Ile Lys Pro Leu Glu Gln Thr Leu Gln Pro
                165                 170                 175

Asp Leu Arg Ile Ile Ala Phe Asp Ile Glu Val Tyr Asn Lys Ser Gly
            180                 185                 190

Thr Pro Arg Pro Gln Thr Asp Pro Ile Ile Ile Gly Ile Met Asn
        195                 200                 205

Asn Asn Gly Asp Ile Lys Gln Phe Leu Ala Asn Lys Tyr Asp Asp Lys
210                 215                 220

Ile Ser Val Glu Glu Phe Val Asn Tyr Val Lys Thr Phe Asp Pro Asp
225                 230                 235                 240

Ile Ile Val Gly Tyr Asn Thr Asp Gly Phe Asp Trp Pro Tyr Leu Ile
                245                 250                 255

Glu Arg Ser Lys Tyr Ile Gly Val Lys Leu Asp Val Thr Arg Arg Val
            260                 265                 270

Gly Ala Thr Pro Arg Thr Ser Thr Tyr Gly His Ile Ser Val Pro Gly
        275                 280                 285

Arg Leu Asn Thr Asp Leu Tyr His Phe Ala Glu Glu Ile Pro Glu Val
        290                 295                 300

Lys Val Lys Ser Leu Glu Asn Val Ala Glu Tyr Leu Gly Val Met Lys
```

```
            305                 310                 315                 320

Lys Ser Glu Arg Val Ile Ile Glu Tyr Ile Asp Ile Pro Lys Tyr Trp
                    325                 330                 335

Asp Asp Glu Lys Leu Arg Pro Lys Leu Leu Gln Tyr Asn Ile Asp Asp
                    340                 345                 350

Val Lys Ser Thr Tyr Gly Leu Ala Glu Lys Phe Leu Pro Phe Ala Met
                    355                 360                 365

Gln Leu Ser Asn Ile Thr Gly Leu Pro Leu Asp Gln Val Gly Ala Ala
            370                 375                 380

Ser Val Gly Phe Arg Leu Glu Trp Tyr Leu Met Arg Glu Ala Phe Arg
385                 390                 395                 400

Tyr Gly Glu Leu Val Pro Asn Arg Val Glu Arg Ala Ala Glu Ser Tyr
                    405                 410                 415

Arg Gly Ala Val Val Leu Lys Pro Val Lys Gly Val His Glu Asn Ile
                    420                 425                 430

Ala Val Leu Asp Phe Ser Ser Met Tyr Pro Asn Ile Met Ile Lys Tyr
            435                 440                 445

Asn Val Gly Pro Asp Thr Ile Val Arg Asn Glu Lys Cys Asn Pro Asp
450                 455                 460

Lys His Asn Ile Ala Pro Glu Val Gly His Cys Phe Arg Lys Glu Pro
465                 470                 475                 480

Pro Gly Phe Phe Lys Arg Val Leu Glu Thr Leu Leu Arg Leu Arg Lys
                    485                 490                 495

Gln Ile Lys Ser Glu Met Lys Lys Tyr Pro Pro Thr Ser Tyr Glu Tyr
                    500                 505                 510

Arg Leu Leu Asp Glu Arg Gln Lys Ala Val Lys Val Leu Ala Asn Ala
            515                 520                 525

Thr Tyr Gly Tyr Met Gly Trp Ile His Ala Arg Trp Tyr Cys Arg Glu
            530                 535                 540

Cys Ala Glu Ala Val Thr Ala Trp Gly Arg Gln Thr Ile Lys Ser Ala
545                 550                 555                 560

Ile Glu Leu Ala Arg Lys Leu Gly Leu Lys Val Ile Tyr Gly Asp Thr
                    565                 570                 575

Asp Ser Leu Phe Val Thr Tyr Asp Lys Asp Lys Val Glu Lys Leu Ile
                    580                 585                 590

Glu Leu Ile Gln Thr Lys Leu Gly Phe Glu Ile Lys Ile Asp Lys Ile
            595                 600                 605

Tyr Lys Arg Val Phe Phe Thr Glu Ala Lys Lys Arg Tyr Ala Gly Leu
            610                 615                 620

Leu Glu Asp Gly Arg Ile Asp Ile Val Gly Phe Glu Ala Val Arg Gly
625                 630                 635                 640

Asp Trp Ala Glu Ile Ala Lys Glu Val Gln Glu Lys Val Thr Glu Ile
                    645                 650                 655

Leu Leu Lys Glu Asn Ser Ile Asp Lys Ala Ile Glu Tyr Val Arg Gln
                    660                 665                 670

Val Ile Ala Asp Leu Lys Ala Gly Lys Ile Pro Leu Asp Lys Leu Ile
            675                 680                 685

Ile Trp Lys Thr Leu Ser Lys Arg Ile Glu Glu Tyr Ser Val Asp Ala
            690                 695                 700

Pro His Val Val Ala Ala Lys Lys Leu Ile Lys Ala Gly Ile Lys Val
705                 710                 715                 720

Ser Thr Asn Asp Lys Ile Gly Tyr Val Ile Leu Lys Gly Gly Gly Lys
                    725                 730                 735
```

```
Ile Ser Ser Arg Ala Glu Pro Tyr Ile Phe Val Lys Asp Pro Lys Leu
            740                 745                 750

Ile Asp Thr Glu Tyr Tyr Val Asp His Gln Ile Val Pro Ala Ala Leu
            755                 760                 765

Arg Ile Leu Asn Tyr Phe Gly Val Thr Glu Thr Gln Leu Lys Arg Ala
            770                 775                 780

Ala Ala Ser Ala Gly Gln Lys Ser Leu Phe Asp Phe Gly Gly Lys
785                 790                 795                 800

Lys

<210> SEQ ID NO 41
<211> LENGTH: 776
<212> TYPE: PRT
<213> ORGANISM: Pyrococcus yayaosii

<400> SEQUENCE: 41

Met Ile Leu Asp Ala Asp Tyr Ile Thr Glu Asn Gly Lys Pro Val Val
1               5                   10                  15

Arg Ile Phe Lys Lys Glu Asn Gly Glu Phe Lys Val Glu Tyr Asp Arg
            20                  25                  30

Ser Phe Arg Pro Tyr Ile Tyr Ala Leu Leu Arg Asp Asp Ser Ala Ile
            35                  40                  45

Glu Asp Ile Lys Lys Ile Thr Ala Glu Arg His Gly Lys Val Val Arg
50                  55                  60

Val Val Glu Ala Glu Lys Val Arg Lys Phe Leu Gly Arg Pro Ile
65                  70                  75                  80

Glu Val Trp Lys Leu Tyr Phe Glu His Pro Gln Asp Val Pro Ala Ile
            85                  90                  95

Arg Glu Lys Ile Arg Glu His Pro Ala Val Ile Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asn Glu Glu Leu Lys Leu Leu Ala Phe Asp Ile Glu Thr
            130                 135                 140

Leu Tyr His Glu Gly Asp Glu Phe Gly Ser Gly Pro Ile Ile Met Ile
145                 150                 155                 160

Ser Tyr Ala Asp Glu Lys Gly Ala Lys Val Ile Thr Trp Lys Gly Val
            165                 170                 175

Asp Leu Pro Tyr Val Glu Val Val Ser Ser Glu Arg Glu Met Ile Lys
            180                 185                 190

Arg Phe Leu Arg Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
            210                 215                 220

Lys Leu Gly Met Lys Leu Pro Ile Gly Arg Asp Gly Ser Glu Pro Lys
225                 230                 235                 240

Met Gln Arg Met Gly Asp Gly Phe Ala Val Glu Val Lys Gly Arg Ile
            245                 250                 255

His Phe Asp Ile Tyr Pro Val Ile Arg Arg Thr Ile Asn Leu Pro Thr
            260                 265                 270

Tyr Thr Leu Glu Ala Val Tyr Glu Ala Val Phe Gly Arg Pro Lys Glu
            275                 280                 285

Lys Val Tyr Pro Asn Glu Ile Ala Arg Ala Trp Glu Asn Cys Lys Gly
            290                 295                 300
```

```
Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ala Arg Leu
            325                 330                 335

Val Gly Gln Pro Val Trp Asp Val Ser Arg Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Arg Pro Asp Glu Arg Glu Tyr Glu Arg Arg Leu Arg Glu Ser
            370                 375                 380

Tyr Glu Gly Gly Tyr Val Lys Glu Pro Glu Lys Gly Leu Trp Glu Gly
385                 390                 395                 400

Ile Ile Tyr Leu Asp Phe Arg Ser Leu Tyr Pro Ser Ile Ile Ile Thr
                405                 410                 415

His Asn Ile Ser Pro Asp Thr Leu Asn Lys Glu Gly Cys Asn Ser Tyr
                420                 425                 430

Asp Val Ala Pro Lys Val Gly His Arg Phe Cys Lys Asp Phe Pro Gly
            435                 440                 445

Phe Ile Pro Ser Leu Leu Gly Gln Leu Leu Asp Glu Arg Gln Lys Ile
450                 455                 460

Lys Arg Lys Met Lys Ala Thr Ile Asp Pro Ile Glu Arg Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Leu Val Ser Arg Glu
                515                 520                 525

Leu Glu Lys Arg Gly Phe Lys Val Leu Tyr Ile Asp Thr Asp Gly Leu
            530                 535                 540

Tyr Ala Thr Ile Pro Gly Ser Arg Glu Trp Asp Lys Ile Lys Glu Arg
545                 550                 555                 560

Ala Leu Glu Phe Val Lys Tyr Ile Asn Ala Arg Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Ala Ile Leu Lys Glu Gly Asn Leu Glu Lys Ala
625                 630                 635                 640

Val Lys Ile Val Lys Glu Val Thr Glu Lys Leu Ser Lys Tyr Glu Val
            645                 650                 655

Pro Pro Glu Lys Leu Val Ile Tyr Glu Gln Ile Thr Arg Asp Leu Lys
            660                 665                 670

Asp Tyr Lys Ala Val Gly Pro His Val Ala Val Ala Lys Arg Leu Ala
            675                 680                 685

Ala Arg Gly Ile Lys Val Arg Pro Gly Met Val Ile Gly Tyr Leu Val
            690                 695                 700

Leu Arg Gly Asp Gly Pro Ile Ser Arg Arg Ala Ile Pro Ala Glu Glu
705                 710                 715                 720
```

-continued

```
Phe Asp Pro Ser Arg His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Tyr Gln Lys Thr Arg Gln Ala Gly Leu Asp Ala
        755                 760                 765

Trp Leu Lys Arg Lys Ala Ser Leu
770                 775
```

<210> SEQ ID NO 42
<211> LENGTH: 773
<212> TYPE: PRT
<213> ORGANISM: Thermococcus sp.AM4-del

<400> SEQUENCE: 42

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Arg
    50                  55                  60

Val Lys Arg Ala Glu Lys Val Gln Arg Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Arg Ala His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Ile Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320
```

```
Glu Leu Gly Arg Glu Phe Pro Met Glu Ala Gln Leu Ser Arg Leu
            325                 330                 335

Ile Gly Gln Ser Leu Trp Asp Val Ser Arg Ser Thr Gly Asn Leu
        340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Lys Ala Arg Trp Tyr Cys Arg Glu Cys Ala Glu Ser
            500                 505                 510

Val Thr Ala Trp Gly Arg Glu Tyr Ile Glu Thr Thr Ile Arg Glu Ile
        515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Ala
545                 550                 555                 560

Lys Glu Phe Leu Lys Tyr Ile Asn Ala Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Thr Lys His Arg Tyr Asp Ala Glu Tyr Tyr Ile Glu Asn Gln
                725                 730                 735
```

```
Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Lys
    770

<210> SEQ ID NO 43
<211> LENGTH: 775
<212> TYPE: PRT
<213> ORGANISM: Thermococcus hydrothermalis

<400> SEQUENCE: 43

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Glu Phe Glu Pro Tyr Ile Tyr Ala Leu Leu Lys Asp Asp Ser Ala Ile
        35                  40                  45

Glu Glu Val Lys Lys Ile Thr Ala Gly Arg His Gly Arg Val Val Lys
    50                  55                  60

Val Lys Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Glu Ile Arg Arg His Ser Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Gly Glu Ala Arg Val Ile Thr Trp Lys Lys Ile
                165                 170                 175

Asp Leu Pro Tyr Val Glu Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Ile Gly Ile Lys Phe Thr Leu Arg Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Thr Pro Lys Glu
        275                 280                 285

Lys Val Tyr Pro Glu Glu Ile Thr Thr Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335
```

```
Ile Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Ile Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Met Ser Leu Tyr Pro Ser Ile Ile Ile Thr His
                    405                 410                 415

Asn Val Ser Pro Asp Thr Phe Asn Arg Glu Gly Cys Lys Glu Tyr Asp
            420                 425                 430

Thr Ala Pro Gln Val Gly His Lys Phe Cys Lys Asp Val Gln Gly Phe
            435                 440                 445

Ile Pro Ser Leu Leu Gly Ala Leu Leu Asp Glu Arg Gln Lys Ile Lys
            450                 455                 460

Lys Arg Met Lys Ala Ser Ile Asp Pro Leu Glu Lys Lys Leu Leu Asp
465                 470                 475                 480

Tyr Arg Gln Lys Ala Ile Lys Ile Leu Ala Asn Ser Tyr Tyr Gly Tyr
                    485                 490                 495

Tyr Gly Tyr Ala Arg Ala Arg Trp Tyr Cys Lys Glu Cys Ala Glu Ser
            500                 505                 510

Val Thr Ala Trp Gly Arg Asp Tyr Ile Glu Thr Thr Ile His Glu Ile
            515                 520                 525

Glu Glu Arg Phe Gly Phe Lys Val Leu Tyr Ala Asp Thr Asp Gly Phe
            530                 535                 540

Phe Ala Thr Ile Pro Gly Ala Asp Ala Glu Thr Val Lys Lys Lys Ala
545                 550                 555                 560

Lys Glu Phe Leu Lys Tyr Ile Asn Ala Lys Leu Pro Gly Leu Leu Glu
                    565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Arg His Gly Asp Val Glu Glu Ala Val
625                 630                 635                 640

Arg Ile Val Lys Asp Val Thr Glu Lys Leu Ser Lys Tyr Glu Val Pro
                    645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
            675                 680                 685

Arg Gly Ile Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Arg Tyr Asp Ala Glu Tyr Tyr Ile Glu Asn Gln
                    725                 730                 735

Val Leu Pro Ala Val Glu Arg Ile Leu Lys Ala Phe Gly Tyr Lys Lys
            740                 745                 750
```

Glu Glu Leu Arg Tyr Gln Lys Thr Arg Gln Val Gly Gly Ala Trp
                755                 760                 765

Leu Lys Leu Lys Gly Lys Lys
    770             775

<210> SEQ ID NO 44
<211> LENGTH: 774
<212> TYPE: PRT
<213> ORGANISM: Thermococcus thioreducens

<400> SEQUENCE: 44

Met Ile Leu Asp Ala Asp Tyr Ile Thr Glu Asp Gly Lys Pro Val Val
1               5                   10                  15

Arg Ile Phe Lys Lys Glu Asn Gly Glu Phe Lys Ile Glu Tyr Asp Arg
                20                  25                  30

Glu Phe Glu Pro Tyr Ile Tyr Ala Leu Leu Arg Asp Asp Ser Ala Ile
            35                  40                  45

Glu Glu Ile Lys Lys Ile Thr Ala Asp Arg His Gly Lys Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Glu Ile Arg Lys His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Glu Asp Gly Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Leu Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Leu Ala Trp Glu Ser Gly Glu Gly
    290                 295                 300

Leu Glu Arg Val Ala Arg Tyr Ser Met Glu Asp Ala Lys Val Thr Phe
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asn Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Arg Ala Pro Gln Val Gly His Lys Phe Cys Lys Asp Val Pro Gly Phe
            435                 440                 445

Ile Pro Ser Leu Leu Gly Ser Leu Leu Asp Glu Arg Gln Lys Ile Lys
            450                 455                 460

Arg Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Ala Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Met Glu Phe Leu Lys Tyr Ile Asn Pro Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
                660                 665                 670

Tyr Arg Ala Thr Gly Pro His Val Ala Ile Ala Lys Arg Leu Ala Lys
            675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Val Leu Lys Ala Phe Gly Tyr Arg Lys
            740                 745                 750

Asp Asp Leu Arg Tyr Gln Lys Thr Arg Gln Val Gly Leu Gly Ala Trp
            755                 760                 765

Leu Lys Val Lys Lys Arg
    770

<210> SEQ ID NO 45
<211> LENGTH: 773
<212> TYPE: PRT
<213> ORGANISM: Thermococcus waiotapuensis

<400> SEQUENCE: 45

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Arg Met Leu Ala Phe Asp Ile Glu Thr
130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

```
Pro Asn Lys Pro Asp Glu Arg Glu Leu Ala Arg Arg Ala Glu Ser Tyr
    370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Ile Thr His
                405                 410                 415
Asn Val Ser Pro Asp Thr Leu Asn Arg Glu Gly Cys Arg Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Val Lys
    450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Asn Ala Arg Trp Tyr Cys Arg Glu Cys Ala Glu Ser
            500                 505                 510
Val Thr Ala Trp Gly Arg Gln Tyr Ile Glu Thr Thr Met Arg Glu Ile
        515                 520                 525
Glu Glu Lys Phe Gly Phe Lys Val Leu Tyr Ala Asp Thr Asp Gly Phe
    530                 535                 540
Phe Ala Thr Ile Pro Gly Ala Asp Ala Glu Thr Val Lys Lys Lys Thr
545                 550                 555                 560
Lys Glu Phe Leu Asn Tyr Ile Asn Pro Arg Leu Pro Gly Leu Leu Glu
                565                 570                 575
Leu Glu Tyr Glu Gly Phe Tyr Arg Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Arg Tyr Glu Val Pro
                645                 650                 655
Pro Glu Lys Leu Val Ile Tyr Glu Gln Ile Thr Arg Asn Leu Arg Asp
            660                 665                 670
Tyr Arg Ala Thr Gly Pro His Val Ala Val Ala Lys Arg Leu Ala Ala
        675                 680                 685
Arg Gly Ile Lys Ile Arg Pro Gly Thr Val Ile Ser Tyr Ile Val Leu
    690                 695                 700
Lys Gly Pro Gly Arg Val Gly Asp Arg Ala Ile Pro Phe Asp Glu Phe
705                 710                 715                 720
Asp Pro Ala Lys His Arg Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Lys Gln Ala Gly Leu Gly Ala Trp
        755                 760                 765
Leu Lys Pro Lys Thr
    770
```

<210> SEQ ID NO 46
<211> LENGTH: 774
<212> TYPE: PRT
<213> ORGANISM: Thermococcus sibiricus

<400> SEQUENCE: 46

```
Met Ile Leu Gly Ala Asp Tyr Ile Thr Lys Asp Gly Lys Pro Ile Val
1               5                   10                  15
Arg Ile Phe Lys Lys Glu Asn Gly Glu Phe Lys Ile Glu Leu Asp Pro
            20                  25                  30
His Phe Gln Pro Tyr Ile Tyr Ala Leu Leu Ser Glu Asp Ser Ala Ile
        35                  40                  45
Asp Glu Ile Lys Gln Ile Lys Gly Glu Arg His Gly Lys Thr Val Arg
    50                  55                  60
Ile Val Asp Ala Val Lys Val Glu Lys Lys Phe Leu Lys Lys Pro Val
65                  70                  75                  80
Lys Val Trp Lys Leu Ile Leu Glu His Pro Gln Asp Val Pro Ala Ile
                85                  90                  95
Arg Asn Lys Ile Arg Glu His Pro Ala Val Gln Asp Ile Tyr Glu Tyr
            100                 105                 110
Asp Ile Pro Phe Ala Lys Arg Tyr Leu Ile Asp Asn Gly Leu Ile Pro
        115                 120                 125
Met Glu Gly Asp Glu Glu Leu Lys Met Leu Ala Phe Asp Ile Glu Thr
    130                 135                 140
Phe Tyr His Glu Gly Asp Glu Phe Gly Lys Gly Glu Ile Ile Met Ile
145                 150                 155                 160
Ser Tyr Ala Asp Glu Glu Gly Ala Arg Val Ile Thr Trp Lys Asn Ile
                165                 170                 175
Asp Leu Pro Tyr Val Asp Val Val Ser Asn Glu Arg Glu Met Ile Lys
            180                 185                 190
Arg Phe Ile Gln Ile Ile Lys Glu Lys Asp Pro Asp Val Ile Ile Thr
        195                 200                 205
Tyr Asn Gly Asp Asn Phe Asp Leu Pro Tyr Leu Ile Lys Arg Ala Glu
    210                 215                 220
Lys Leu Gly Leu Arg Leu Ile Leu Ser Arg Asp Asn Glu Asn Pro Val
225                 230                 235                 240
Pro Lys Ile Gln Arg Met Gly Asn Ser Phe Ala Val Glu Ile Lys Gly
                245                 250                 255
Arg Ile His Phe Asp Leu Phe Pro Val Val Lys Arg Ala Val Asn Leu
            260                 265                 270
Pro Thr Tyr Thr Leu Glu Ala Val Tyr Glu Thr Val Leu Gly Lys His
        275                 280                 285
Lys Ser Lys Leu Gly Ala Glu Ile Ala Ala Ile Trp Glu Thr Glu
    290                 295                 300
Glu Gly Leu Lys Lys Leu Ala Gln Tyr Ser Met Glu Asp Ala Lys Ala
305                 310                 315                 320
Thr Tyr Glu Leu Gly Arg Glu Phe Phe Pro Met Glu Val Glu Leu Ala
                325                 330                 335
Lys Leu Ile Gly Gln Ser Val Trp Asp Val Ser Arg Ser Ser Thr Gly
            340                 345                 350
Asn Leu Val Glu Trp Tyr Met Leu Arg Val Ala Tyr Glu Arg Asn Glu
        355                 360                 365
Leu Ala Pro Asn Arg Pro Ser Asp Glu Glu Tyr Lys Arg Arg Leu Arg
    370                 375                 380
```

Thr Thr Tyr Leu Gly Gly Tyr Val Lys Glu Pro Glu Arg Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Arg Lys Gly Cys Gln
            420                 425                 430

Asn Tyr Asp Val Ala Pro Ile Val Gly Tyr Lys Phe Cys Lys Asp Phe
        435                 440                 445

Ser Gly Phe Ile Pro Ser Ile Leu Glu Asp Leu Ile Glu Thr Arg Gln
    450                 455                 460

Lys Ile Lys Lys Glu Met Lys Ser Thr Ile Asp Pro Ile Lys Lys Lys
465                 470                 475                 480

Met Leu Asp Tyr Arg Gln Arg Ala Val Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Ala Asp Pro Glu Thr Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Lys Ile Thr Thr
        595                 600                 605

Arg Gly Leu Glu Val Val Arg Arg Asp Trp Ser Glu Ile Ala Lys Glu
    610                 615                 620

Thr Gln Ala Arg Val Leu Glu Ala Ile Leu Arg Glu Gly Ser Val Glu
625                 630                 635                 640

Lys Ala Val Glu Ile Val Lys Glu Val Val Glu Ala Ile Thr Lys Tyr
                645                 650                 655

Lys Val Pro Leu Glu Lys Leu Ile Ile His Glu Gln Ile Thr Arg Glu
            660                 665                 670

Leu Arg Asp Tyr Lys Ala Val Gly Pro His Val Ala Ile Ala Lys Arg
        675                 680                 685

Leu Ala Ala Lys Gly Ile Lys Ile Lys Pro Gly Thr Ile Ile Ser Tyr
    690                 695                 700

Ile Val Leu Arg Gly Ser Gly Lys Ile Ser Asp Arg Val Val Leu Leu
705                 710                 715                 720

Thr Glu Tyr Asp Pro Arg Lys His Lys Tyr Asp Pro Asp Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Lys Tyr Gln Ser Ser Lys Gln Thr Gly Leu
        755                 760                 765

Glu Ser Trp Leu Lys Lys
    770

<210> SEQ ID NO 47
<211> LENGTH: 775

<212> TYPE: PRT
<213> ORGANISM: Pyrococcus glycovorans

<400> SEQUENCE: 47

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Lys Lys Ile Thr Ala Glu Arg His Gly Lys Ile Val Arg
        50                  55                  60

Ile Val Asp Val Glu Lys Val Lys Lys Phe Leu Gly Arg Pro Ile
65                  70                  75                  80

Glu Val Trp Lys Leu Tyr Phe Glu His Pro Gln Asp Val Pro Ala Ile
                85                  90                  95

Arg Asp Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Gly Ala Lys Val Ile Thr Trp Lys Lys Val
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Leu Arg Glu Ser
370                 375                 380

Tyr Ala Gly Gly Tyr Val Lys Glu Pro Glu Lys Gly Leu Trp Glu Gly
385                 390                 395                 400
```

```
Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Met Glu Tyr
            420                 425                 430

Asp Val Ala Pro Glu Val Lys His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Arg Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Arg Lys
545                 550                 555                 560

Ala Leu Glu Phe Val Glu Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Pro Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Val Lys Lys Lys
    770                 775

<210> SEQ ID NO 48
<211> LENGTH: 775
<212> TYPE: PRT
<213> ORGANISM: Pyrococcus sp. NA2
```

```
<400> SEQUENCE: 48

Met Ile Leu Asp Ala Asp Tyr Ile Thr Glu Asp Gly Lys Pro Ile Ile
1               5                   10                  15

Arg Leu Phe Lys Lys Glu Asn Gly Arg Phe Lys Val Glu Tyr Asp Arg
            20                  25                  30

Asn Phe Arg Pro Tyr Ile Tyr Ala Leu Leu Lys Asp Asp Ser Ala Ile
        35                  40                  45

Asp Asp Val Arg Lys Ile Thr Ser Glu Arg His Gly Lys Val Val Arg
50                  55                  60

Val Ile Asp Val Glu Lys Val Lys Lys Phe Leu Gly Arg Pro Ile
65                  70                  75                  80

Glu Val Trp Lys Leu Tyr Phe Glu His Pro Gln Asp Val Pro Ala Met
                85                  90                  95

Arg Asp Lys Ile Arg Glu His Pro Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ala Asn Glu Arg Glu Met Ile Lys
            180                 185                 190

Arg Leu Ile Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
210                 215                 220

Lys Leu Gly Met Lys Leu Pro Leu Gly Arg Asp Asn Ser Glu Pro Lys
225                 230                 235                 240

Met Gln Arg Leu Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Gln Lys Glu
        275                 280                 285

Lys Val Tyr Pro His Glu Ile Ala Glu Ala Trp Glu Thr Gly Lys Gly
290                 295                 300

Leu Glu Arg Val Ala Lys Tyr Ser Met Glu Asp Ala Lys Val Thr Tyr
305                 310                 315                 320

Glu Leu Gly Lys Glu Phe Phe Pro Met Glu Ala Gln Leu Ala Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Leu Arg Glu Ser
370                 375                 380

Tyr Glu Gly Gly Tyr Val Lys Glu Pro Glu Arg Gly Leu Trp Glu Gly
385                 390                 395                 400

Ile Val Ser Leu Asp Phe Arg Ser Leu Tyr Pro Ser Ile Ile Ile Thr
                405                 410                 415
```

His Asn Val Ser Pro Asp Thr Leu Asn Lys Glu Gly Cys Gly Glu Tyr
            420                 425                 430

Asp Glu Ala Pro Glu Val Gly His Arg Phe Cys Lys Asp Phe Pro Gly
            435                 440                 445

Phe Ile Pro Ser Leu Leu Gly Ser Leu Leu Glu Arg Gln Lys Ile
450                 455                 460

Lys Lys Arg Met Lys Glu Ser Lys Asp Pro Val Glu Arg Lys Leu Leu
465                 470                 475                 480

Asp Tyr Arg Gln Arg Ala Ile Lys Ile Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Glu Leu Val Arg Arg Glu
            515                 520                 525

Leu Glu Glu Arg Gly Phe Lys Val Leu Tyr Ile Asp Thr Asp Gly Leu
            530                 535                 540

Tyr Ala Thr Ile Pro Gly Glu Lys Asn Trp Glu Glu Ile Lys Arg Arg
545                 550                 555                 560

Ala Leu Glu Phe Val Asn Tyr Ile Asn Ser Lys Leu Pro Gly Ile Leu
                565                 570                 575

Glu Leu Glu Tyr Glu Gly Phe Tyr Thr Arg Gly Phe Phe Val Thr Lys
            580                 585                 590

Lys Lys Tyr Ala Leu Ile Asp Glu Glu Gly Lys Ile Val Thr Arg Gly
            595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Asn Tyr Glu Ile
                645                 650                 655

Pro Val Glu Lys Leu Val Ile Tyr Glu Gln Ile Thr Arg Pro Leu Asn
            660                 665                 670

Glu Tyr Lys Ala Ile Gly Pro His Val Ala Val Ala Lys Arg Leu Ala
            675                 680                 685

Ala Lys Gly Ile Lys Ile Lys Pro Gly Met Val Ile Gly Tyr Val Val
            690                 695                 700

Leu Arg Gly Asp Gly Pro Ile Ser Lys Arg Ala Ile Ala Ile Glu Glu
705                 710                 715                 720

Phe Asp Gly Lys Lys His Lys Tyr Asp Ala Glu Tyr Tyr Ile Glu Asn
                725                 730                 735

Gln Val Leu Pro Ala Val Glu Arg Ile Leu Lys Ala Phe Gly Tyr Lys
            740                 745                 750

Arg Glu Asp Leu Arg Trp Gln Lys Thr Lys Gln Val Gly Leu Gly Ala
            755                 760                 765

Trp Leu Lys Val Lys Lys Ser
770                 775

<210> SEQ ID NO 49
<211> LENGTH: 785
<212> TYPE: PRT
<213> ORGANISM: Ferroglobus placidus

<400> SEQUENCE: 49

Met Glu Gly Trp Leu Leu Asp Ala Asp Tyr Ile Thr Ala Glu Asp Gly

-continued

```
1               5                   10                  15
Arg Ala Val Val Arg Leu Trp Cys Lys Asp Phe Asp Gly Asn Thr Phe
            20                  25                  30
Val Val Tyr Asp Arg Asn Phe Gln Pro Tyr Phe Tyr Ala Phe Lys Asn
            35                  40                  45
Gly Leu Ser Lys Glu Asp Ile Glu Lys Ile Val Val Lys Ser Arg Glu
            50                  55                  60
Gly Val Ile Lys Pro Phe Lys Val Glu Val Arg Arg Lys Val Phe
65                  70                  75                  80
Gly Lys Glu Val Glu Val Phe Lys Ile Tyr Ala Tyr His Pro Gln His
                    85                  90                  95
Val Pro Lys Leu Arg Glu Glu Leu Lys Lys Ile Thr Glu Val Arg Glu
                    100                 105                 110
Ala Asp Ile Pro Phe Ala Tyr Arg Tyr Leu Ile Asp Lys Asp Leu Ala
                    115                 120                 125
Cys Met Asp Gly Ile Arg Val Glu Gly Lys Val Arg Glu Glu Arg Gly
        130                 135                 140
Leu Lys Val Ile Asp Ala Glu His Val Glu Arg Phe Glu Ile Pro Leu
145                 150                 155                 160
Pro Glu Pro Lys Val Leu Ala Phe Asp Cys Glu Met Leu Thr Glu Leu
                    165                 170                 175
Gly Met Pro Asp Pro Glu Lys Asp Lys Ile Ile Ile Gly Val Lys
                    180                 185                 190
Cys Gly Asp Phe Glu Glu Ile Ile Thr Gly Asn Glu Arg Glu Ile Leu
        195                 200                 205
Leu Arg Phe Val Glu Ile Ile Lys Glu Gln Asp Pro Asp Val Ile Val
210                 215                 220
Gly Tyr Asn Gln Asp Asn Phe Asp Trp Pro Tyr Ile Arg Lys Arg Ala
225                 230                 235                 240
Glu Lys Leu Ser Val Lys Leu Asn Ile Gly Arg Asp Gly Ser Glu Ile
                    245                 250                 255
Ser Phe Arg Gly Gly Arg Pro Lys Ile Ala Gly Arg Leu Asn Val Asp
            260                 265                 270
Leu Tyr Asp Ile Ala Met Lys Leu Asp Val Lys Val Lys Thr Leu Glu
            275                 280                 285
Asn Val Ala Glu Phe Leu Gly Arg Lys Val Glu Leu Ala Asp Ile Glu
            290                 295                 300
Ala Lys Asp Ile Tyr Lys Arg Trp Thr Ser Gly Asp Lys Glu Ser Val
305                 310                 315                 320
Leu Lys Tyr Ser Lys Gln Asp Val Leu Asn Thr Tyr Phe Ile Ala Glu
                    325                 330                 335
Glu Leu Leu Pro Met His Tyr Glu Leu Ser Arg Met Ile Arg Ile Pro
            340                 345                 350
Thr Asp Asp Val Ala Arg Ile Gly Arg Gly Lys Gln Val Asp Trp Phe
            355                 360                 365
Leu Leu Ser Glu Ala Tyr Lys Ile Gly Glu Ile Ala Pro Asn Pro Ala
            370                 375                 380
Glu Val Glu Glu Ser Tyr Glu Gly Ala Phe Val Leu Glu Pro Ser Arg
385                 390                 395                 400
Gly Leu His Lys Asn Val Val Cys Leu Asp Phe Ala Ser Met Tyr Pro
                    405                 410                 415
Ser Ile Met Ile Ala Tyr Asn Ile Ser Pro Asp Thr Tyr Val Phe Gly
            420                 425                 430
```

```
Lys Cys Asp Asp Cys Tyr Val Ala Pro Glu Val Gly His Lys Phe Arg
        435                 440                 445
Lys His Pro Asp Gly Phe Phe Lys Arg Ile Leu Lys Met Leu Ile Glu
    450                 455                 460
Lys Arg Arg Glu Ile Lys Asn Gln Met Lys Ser Leu Asp Arg Asn Ser
465                 470                 475                 480
Arg Glu Tyr Leu Leu Leu Asn Ile Lys Gln Gln Thr Leu Lys Ile Leu
                485                 490                 495
Thr Asn Ser Phe Tyr Gly Tyr Thr Gly Trp Ser Gly Ala Arg Trp Tyr
            500                 505                 510
Cys Arg Gln Cys Ala Glu Ala Thr Thr Ala Trp Gly Arg His Leu Ile
        515                 520                 525
Lys Ser Ala Val Glu Ile Ala Lys Lys Leu Gly Phe Glu Val Leu Tyr
    530                 535                 540
Gly Asp Thr Asp Ser Ile Phe Val Lys Gly Asn Leu Ser Leu Glu
545                 550                 555                 560
Lys Ile Arg Gly Glu Val Lys Leu Ile Glu Ile Ser Glu Lys
                565                 570                 575
Phe Pro Val Gln Ile Glu Val Asp Glu Tyr Tyr Lys Thr Ile Phe Phe
            580                 585                 590
Val Glu Lys Lys Arg Tyr Ala Gly Leu Thr Glu Asp Gly Ile Leu Val
        595                 600                 605
Val Lys Gly Leu Glu Val Arg Arg Gly Asp Trp Cys Glu Leu Ala Lys
    610                 615                 620
Glu Val Gln Lys Lys Val Ile Glu Ile Leu Lys Glu Asn Pro
625                 630                 635                 640
Glu Lys Ala Ala Glu Tyr Val Arg Lys Val Ile Asn Asp Ile Lys Ser
                645                 650                 655
Gly Lys Val Lys Leu Glu Asp Val Val Ile Tyr Lys Gly Leu Thr Lys
            660                 665                 670
Arg Pro Asp Lys Tyr Glu Ser Lys Gln Ala His Val Lys Ala Ala Leu
        675                 680                 685
Arg Ala Met Glu Leu Gly Ile Val Tyr Asn Val Gly Ser Lys Val Gly
    690                 695                 700
Phe Val Val Glu Gly Ala Gly Asn Val Gly Asp Arg Ala Tyr Pro
705                 710                 715                 720
Ile Asp Leu Ile Glu Glu Phe Asp Gly Glu Asn Leu Val Ile Arg Thr
                725                 730                 735
Arg Ser Gly Ser Ile Val Lys Lys Leu Asp Lys Asp Tyr Tyr Ile Asn
            740                 745                 750
His Gln Ile Ile Pro Ser Val Leu Arg Ile Leu Glu Arg Phe Gly Tyr
        755                 760                 765
Asn Glu Ala Ser Leu Lys Gly Ala Thr Gln Lys Thr Leu Asp Ala Phe
    770                 775                 780
Trp
785

<210> SEQ ID NO 50
<211> LENGTH: 775
<212> TYPE: PRT
<213> ORGANISM: Palaeococcus ferrophilus

<400> SEQUENCE: 50

Met Ile Leu Asp Ala Asp Tyr Ile Thr Glu Asn Gly Lys Pro Val Val
```

```
1               5                   10                  15
Arg Ile Phe Lys Lys Glu Asn Gly Glu Phe Lys Val Glu Tyr Asp Arg
                20                  25                  30

Asn Phe Glu Pro Tyr Ile Tyr Ala Leu Leu Lys Asp Asp Ser Ala Ile
                35                  40                  45

Glu Glu Ile Lys Lys Ile Thr Ala Glu Arg His Gly Thr Val Val Arg
                50                  55                  60

Ile Thr Lys Ala Glu Lys Val Glu Arg Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Ser His Pro Ala Val Val Asp Ile Tyr Glu Tyr
                100                 105                 110

Asp Ile Pro Phe Ala Lys Arg Tyr Leu Ile Asp Lys Gly Leu Val Pro
                115                 120                 125

Met Glu Gly Asp Glu Glu Leu Lys Met Leu Ala Phe Asp Ile Glu Thr
                130                 135                 140

Leu Tyr His Glu Gly Glu Glu Phe Ala Glu Gly Pro Ile Leu Met Ile
145                 150                 155                 160

Ser Tyr Ala Asp Glu Ser Glu Ala Arg Val Ile Thr Trp Lys Lys Val
                165                 170                 175

Asp Leu Pro Tyr Val Asp Ala Val Ser Thr Glu Lys Asp Met Ile Lys
                180                 185                 190

Ala Phe Leu Arg Val Val Lys Glu Lys Asp Pro Asp Val Leu Ile Thr
                195                 200                 205

Tyr Asn Gly Asp Asn Phe Asp Phe Ala Tyr Leu Lys Lys Arg Cys Glu
                210                 215                 220

Lys Leu Gly Val Lys Phe Ile Leu Gly Arg Asp Gly Ser Glu Pro Lys
225                 230                 235                 240

Ile Gln Arg Met Gly Asp Arg Phe Ala Val Asp Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Arg Pro Lys Glu
                275                 280                 285

Lys Val Tyr Ala Glu Glu Ile Ala Gln Ala Trp Glu Thr Asn Glu Gly
                290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Ile Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Ser Gly Arg Glu Tyr Asp Glu Arg Arg Gly Gly Tyr
                370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430
```

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Ile Asp Pro Ile Glu Arg Arg Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
        500                 505                 510

Val Thr Ala Trp Gly Arg Glu Tyr Ile Glu Met Ser Ile Arg Glu Ile
        515                 520                 525

Glu Glu Lys Tyr Gly Phe Lys Val Leu Tyr Ala Asp Thr Asp Gly Phe
        530                 535                 540

His Ala Thr Ile Pro Gly Glu Asp Ala Glu Thr Ile Lys Lys Lys Ala
545                 550                 555                 560

Met Glu Phe Leu Lys Tyr Ile Asn Ser Lys Leu Pro Gly Ala Leu Glu
                565                 570                 575

Leu Glu Tyr Glu Gly Phe Tyr Arg Arg Gly Phe Phe Val Thr Lys Lys
        580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Leu Leu Lys Asp Gly Asn Val Glu Glu Ala Val
625                 630                 635                 640

Ser Ile Val Lys Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
        660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Arg Gln Val Gly Leu Gly Ala Trp
        755                 760                 765

Leu Lys Pro Lys Gly Lys Lys
770                 775

<210> SEQ ID NO 51
<211> LENGTH: 775
<212> TYPE: PRT
<213> ORGANISM: Thermococcus gammatolerans

<400> SEQUENCE: 51

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg

```
            20                  25                  30
Thr Phe Glu Pro Tyr Phe Tyr Ala Leu Leu Lys Asp Asp Ser Ala Ile
        35                  40                  45
Glu Asp Val Lys Lys Val Thr Ala Lys Arg His Gly Ala Val Val Lys
    50                  55                  60
Val Lys Arg Ala Glu Lys Val Gln Arg Lys Phe Leu Gly Arg Pro Ile
65                  70                  75                  80
Glu Val Trp Lys Leu Tyr Phe Thr His Pro Gln Asp Val Pro Ala Ile
                85                  90                  95
Arg Asp Lys Ile Arg Ala His Pro Ala Val Val Asp Ile Tyr Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Leu Arg Met Leu Ala Phe Asp Ile Glu Thr
    130                 135                 140
Leu Tyr His Glu Gly Glu Glu Phe Gly Thr Gly Pro Ile Leu Met Ile
145                 150                 155                 160
Ser Tyr Ala Asp Glu Asn Glu Ala Arg Val Ile Thr Trp Lys Lys Ile
                165                 170                 175
Asp Leu Pro Tyr Val Asp Val Val Ser Thr Glu Lys Glu Met Ile Lys
            180                 185                 190
Arg Phe Leu Arg Val Val Lys Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Lys Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Lys Pro Lys Glu
        275                 280                 285
Lys Val Tyr Ala Glu Glu Ile Thr Glu Ala Trp Glu Ser Gly Glu Gly
    290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Leu Ala Arg Arg Glu Ser Tyr
    370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
        435                 440                 445
```

```
Ile Pro Ser Leu Leu Gly Asp Leu Glu Glu Arg Gln Lys Ile Lys
    450                 455                 460

Arg Lys Met Lys Ala Thr Ile Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Lys Tyr Ile Asn Ala Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Lys Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 52
<211> LENGTH: 775
<212> TYPE: PRT
<213> ORGANISM: Thermococcus celericrescens

<400> SEQUENCE: 52

Met Ile Leu Asp Thr Asp Tyr Ile Thr Glu Asp Gly Lys Pro Val Ile
1               5                   10                  15

Arg Ile Phe Lys Lys Asp Asn Gly Glu Phe Lys Ile Glu Tyr Asp Arg
                20                  25                  30

Asn Phe Glu Pro Tyr Ile Tyr Ala Leu Leu Arg Asp Asp Ser Ala Ile
```

```
            35                  40                  45
Glu Asp Val Lys Lys Ile Thr Ala Glu Arg His Gly Arg Val Val Lys
 50                  55                  60

Val Lys Arg Ala Glu Lys Val Lys Lys Phe Leu Gly Arg Pro Val
 65                  70                  75                  80

Glu Val Trp Lys Leu Tyr Phe Thr Arg Pro Gln Asp Val Pro Ala Ile
                 85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Ile Ile Pro
                115                 120                 125

Met Glu Gly Asp Glu Glu Leu Lys Met Leu Ala Phe Asp Ile Glu Thr
                130                 135                 140

Leu Tyr His Glu Gly Glu Glu Phe Ala Glu Gly Pro Ile Leu Met Ile
145                 150                 155                 160

Ser Tyr Ala Asp Glu Asn Glu Ala Arg Val Ile Thr Trp Lys Lys Ile
                165                 170                 175

Asp Leu Pro Phe Val Asp Val Val Ser Thr Glu Lys Glu Met Ile Lys
                180                 185                 190

Arg Phe Leu Lys Val Ile Lys Glu Lys Asp Pro Asp Val Leu Ile Thr
                195                 200                 205

Tyr Asn Gly Asp Asn Phe Asp Phe Ala Tyr Leu Lys Lys Arg Cys Glu
                210                 215                 220

Lys Phe Gly Ile Lys Phe Thr Leu Gly Arg Asp Gly Ser Asp Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Leu Arg Thr Val Asn Leu Pro Thr
                260                 265                 270

Tyr Thr Leu Glu Ala Val Tyr Glu Ala Ile Phe Gly Thr Pro Lys Glu
                275                 280                 285

Lys Val Tyr Pro Glu Glu Ile Thr Thr Ala Trp Glu Thr Gly Glu Gly
                290                 295                 300

Leu Glu Arg Val Ala Arg Tyr Ser Met Glu Asp Ala Lys Val Thr Phe
305                 310                 315                 320

Glu Leu Gly Arg Glu Phe Phe Pro Met Glu Ala Gln Leu Ser Arg Leu
                325                 330                 335

Val Gly Gln Ser Phe Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Leu Val Arg Arg Asn Ser Tyr
                370                 375                 380

Thr Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Glu Ala Pro Gln Val Gly His Lys Phe Cys Lys Asp Phe Pro Gly Phe
                435                 440                 445

Ile Pro Ser Leu Leu Gly Asn Leu Leu Asp Glu Arg Gln Lys Ile Lys
450                 455                 460
```

```
Lys Arg Met Lys Ala Thr Ile Asp Pro Leu Glu Lys Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Ala Tyr Ala Arg Ala Arg Trp Tyr Cys Lys Glu Cys Ala Glu Ser
            500                 505                 510

Val Thr Ala Trp Gly Arg Glu Tyr Ile Glu Met Ser Ile Arg Glu Ile
        515                 520                 525

Glu Glu Lys Tyr Gly Phe Lys Val Leu Tyr Ala Asp Thr Asp Gly Phe
    530                 535                 540

His Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asn Val Glu Glu Ala Val
625                 630                 635                 640

Ser Ile Val Lys Glu Val Thr Glu Lys Leu Gly Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Ala
            740                 745                 750

Glu Asp Leu Arg Tyr Gln Lys Thr Arg Gln Val Gly Leu Gly Val Trp
        755                 760                 765

Leu Gln Pro Lys Gly Lys Lys
770                 775

<210> SEQ ID NO 53
<211> LENGTH: 784
<212> TYPE: PRT
<213> ORGANISM: Vulcanisaeta distributa

<400> SEQUENCE: 53

Met Glu Leu Ala Phe Trp Leu Leu Asp Ile Thr Tyr Gly Val Ile Gly
1               5                   10                  15

Asn Thr Pro Glu Leu Arg Leu Phe Gly Ile Thr Asp Asp Gly Lys Arg
                20                  25                  30

Val Leu Val Leu Asp Arg Ser Phe Arg Pro Tyr Phe Tyr Val Ile Pro
            35                  40                  45

Ser Gly Asp Val Asn Ala Val Phe Asn Asn Val Lys Arg Lys Leu Glu
```

```
                50                  55                  60
Gly Lys Val Leu Asn Val Glu Val Ile Lys Arg Lys Met Phe Gly Asn
 65                  70                  75                  80

Glu Val Asp Ala Ile Arg Val Thr Ala Thr Ile Pro Glu Lys Val Arg
                 85                  90                  95

Glu Leu Arg Glu Leu Ala Ala Glu Val Pro Gly Val Glu Asp Val Leu
            100                 105                 110

Glu Ala Asp Ile Arg Phe Ser Gln Arg Tyr Leu Leu Asp Met Gly Val
            115                 120                 125

Lys Pro Ser Asn Trp Ile Val Val Asp Gln Cys Glu Glu Val Lys Gly
        130                 135                 140

Asn Tyr Gln Val Asp Leu Val Cys Leu Ala Lys Ser Arg Pro Arg Met
145                 150                 155                 160

Ile Glu Glu His Lys Leu Pro Ser Phe Arg Val Leu Ala Phe Asp Ile
                165                 170                 175

Glu Val Tyr Asn Pro Arg Gly Met Pro Asn Pro Asp Arg Asp Pro Val
            180                 185                 190

Ile Ile Ile Ser Thr Met Thr Lys Glu Asp Gly Val Lys Met Phe Val
        195                 200                 205

Val Asp Asp Asn Lys Asn Asp Ala Lys Ile Ile Arg Glu Phe Leu Asp
210                 215                 220

Tyr Phe Arg Lys Tyr Asp Pro Asp Ile Val Val Gly Tyr Asn Asn Asn
225                 230                 235                 240

Gly Phe Asp Trp Pro Tyr Leu Val Asn Arg Ser Ser Arg Val Gly Val
                245                 250                 255

Arg Leu Ala Leu Ser Arg Met Gly Asn Pro Pro Glu Pro Ser Val Tyr
            260                 265                 270

Gly His Trp Ser Ile Ile Gly Arg Ala Asn Val Asp Leu Tyr Asn Phe
        275                 280                 285

Ile Glu Glu Ile Ser Glu Ile Lys Val Lys Ser Leu Asp Arg Ala Ala
        290                 295                 300

Glu Phe Phe Gly Ile Met Lys Arg Ser Glu Arg Val Leu Ile Pro Gly
305                 310                 315                 320

His Arg Ile His Glu Tyr Trp Asp Ala Lys Asn Lys Arg Asp Leu Leu
                325                 330                 335

Leu Lys Tyr Ala Arg Asp Asp Val Ser Thr Tyr Gly Leu Ala Glu
            340                 345                 350

Lys Leu Leu Pro Phe Ala Ile Gln Leu Ser Ser Ile Ser Gly Leu Pro
            355                 360                 365

Leu Asp Gln Val Gly Ala Ala Ser Val Gly Ala Arg Val Glu Trp Met
        370                 375                 380

Ile Phe Tyr Glu Ala Val Lys Arg Gly Glu Leu Ala Pro Asn Arg Glu
385                 390                 395                 400

Glu Arg Pro Tyr Glu Thr Tyr Lys Gly Ala Val Val Leu Glu Pro Arg
                405                 410                 415

Pro Gly Leu His Glu Asn Ile Ala Val Ile Asp Phe Ser Ser Met Tyr
            420                 425                 430

Pro Ser Ile Met Met Lys Tyr Asn Val Ser Pro Asp Thr Leu Val Leu
        435                 440                 445

Gly Asp Cys Gly Asp Cys Tyr Val Ala Pro Glu Val Asn Tyr Lys Phe
    450                 455                 460

Arg Arg Ser Pro Glu Gly Leu Tyr Pro Gly Leu Leu Arg Ile Leu Val
465                 470                 475                 480
```

```
Glu Ser Arg Arg Arg Val Arg Asp Leu Met Lys Lys Tyr Pro Glu Asn
                485                 490                 495

Ser Pro Glu Trp Val Leu Leu Asn Glu Arg Gln Arg Ala Leu Lys Val
            500                 505                 510

Met Ala Asn Ala Met Tyr Gly Tyr Cys Gly Trp Leu Gly Ala Arg Trp
        515                 520                 525

Tyr Arg Arg Glu Val Ala Glu Ala Val Thr Ala Trp Gly Arg Asn Leu
    530                 535                 540

Leu Arg Thr Val Ile Glu Lys Ala Arg Ser Leu Gly Leu Pro Ile Ile
545                 550                 555                 560

Tyr Gly Asp Thr Asp Ser Leu Phe Val Arg Asn Ile Ser Asp Lys Val
                565                 570                 575

Asp Ala Leu Ile Asn Tyr Val Asn Asn Glu Leu Gly Phe Glu Val Lys
            580                 585                 590

Val Asp Lys Val Tyr Arg Arg Val Leu Phe Thr Glu Ala Lys Lys Arg
        595                 600                 605

Tyr Val Gly Leu Thr Val Glu Gly Glu Val Asp Ile Val Gly Phe Glu
    610                 615                 620

Ala Val Arg Gly Asp Trp Ala Glu Ile Ala Lys Asp Val Gln Glu Asn
625                 630                 635                 640

Val Ala Glu Ile Val Leu Thr Thr Gly Asp Val Gly Lys Ala Ile Ser
                645                 650                 655

Tyr Val Lys Ser Val Ile Asp Lys Val Lys Ala Tyr Gln Phe Asp Ile
            660                 665                 670

Asp Asp Val Ile Ile Trp Lys Thr Leu Asp Lys Ser Leu Asn Glu Tyr
        675                 680                 685

Lys Val Leu Thr Pro His Val Ala Ala Lys Gln Leu Val Glu Ala
    690                 695                 700

Gly Tyr Lys Val Gly Lys Gly Asp Met Ile Gly Tyr Val Val Lys
705                 710                 715                 720

Gly Gly Gly Ala Lys Leu Ala Tyr Lys Val Lys Pro Tyr Ile Leu Ile
                725                 730                 735

Lys Asp Ile Arg Glu Val Asp Val Asp Tyr Tyr Val Glu Lys Gln Ile
            740                 745                 750

Val Pro Ala Ala Met Arg Ile Leu Glu Val Leu Gly Val Lys Glu Ser
        755                 760                 765

Gln Leu Met Glu Gly Lys Ala Gly Lys Ser Ile Leu Asp Tyr Phe Ser
    770                 775                 780

<210> SEQ ID NO 54
<211> LENGTH: 830
<212> TYPE: PRT
<213> ORGANISM: Methanopyrus kandleri

<400> SEQUENCE: 54

Met Leu Arg Thr Val Trp Val Asp Tyr Ala Arg Lys Gly Glu Pro Asp
1               5                   10                  15

Val Ile Leu Val Gly Arg Arg Glu Asp Gly Asn Pro Ala Ala Leu Val
            20                  25                  30

Val Lys Gly Phe Arg Pro Tyr Phe Tyr Ala Glu Val Glu Asp Gly Phe
        35                  40                  45

Asp Pro Ser Glu Val Glu Arg Leu Ser Gly Val Glu Val Glu Glu
    50                  55                  60

Val Leu Leu Glu His Pro Tyr Gly Gly Asp Arg Val Glu Leu Leu Arg
```

-continued

```
            65                  70                  75                  80
Ile Val Ala Thr Tyr Pro Lys Val Val Pro Lys Leu Arg Glu Gln Val
                    85                  90                  95
Lys Lys Leu Asp Gly Val Lys Glu Val Tyr Glu Ala Asp Ile Pro Phe
                    100                 105                 110
Val Arg Arg Ala Ala Val Asp Leu Asn Leu Pro Pro Ala Ser Glu Val
                    115                 120                 125
Asp Val Ser Asp Leu Asp Thr Gly Ser Trp Ser Gly Leu Pro Ala Tyr
                    130                 135                 140
Phe Ala Asp Val Glu Asp Ala Arg Glu Leu Asp His Arg Pro Tyr Pro
145                 150                 155                 160
Ile Glu Asp Leu Val Val Ala Ser Phe Asp Leu Glu Val Leu Ala Glu
                    165                 170                 175
Pro Gly Thr Thr Ile Lys Gly Ala Ser Gly Pro Ile Ile Ala Ile Ser
                    180                 185                 190
Phe Ala Tyr Ser Thr Pro Asp Gly Glu Arg Arg Asn Tyr Val Ile Thr
                    195                 200                 205
Trp Lys Gly Glu Asp Glu Ser Phe Glu Val Asp Gly Val Glu Thr Glu
                    210                 215                 220
Val Ile Val Cys Arg Ser Glu Ala Ala Ala Leu Arg Arg Phe Phe Asp
225                 230                 235                 240
Glu Phe Arg Arg Val Asp Pro Asp Val Val Phe Thr Tyr Asn Gly Asp
                    245                 250                 255
Glu Phe Asp Leu Pro Tyr Leu Gln His Arg Ala Gly Lys Leu Gly Ile
                    260                 265                 270
Asp Val Ser Pro Leu Ala Arg Pro Ala Gly Lys Arg Gly Ile Ile Leu
                    275                 280                 285
Lys His Gly Gly Arg Tyr Ala Ser Asp Ile Phe Gly Arg Ala His
                    290                 295                 300
Val Asp Leu Tyr His Thr Ala Arg Lys Asn Leu Lys Leu Glu Arg Phe
305                 310                 315                 320
Thr Leu Glu Glu Ala Val Lys Asp Val Leu Gly Val Glu Lys Glu Glu
                    325                 330                 335
Met Glu Leu Ala Asp Ile Asn Glu Ala Trp Lys Arg Gly Asn Leu Asp
                    340                 345                 350
Glu Leu Met Arg Tyr Ser Ala Glu Asp Ala His Tyr Thr Leu Glu Leu
                    355                 360                 365
Gly Leu Glu Leu Ala Gln Val Glu Leu Glu Leu Ser Tyr Leu Thr Arg
                    370                 375                 380
Leu Pro Leu Pro Asp Ala Thr Arg Phe Ser Phe Gly Gln Leu Ala Glu
385                 390                 395                 400
Trp Arg Ala Ile Tyr Lys Ala Arg Gln Glu Asp Ile Leu Val Pro Asn
                    405                 410                 415
Lys Pro Thr Arg Asp Glu Tyr Lys Arg Arg Arg Lys Ala Tyr Lys
                    420                 425                 430
Gly Ala Ile Val Phe Glu Pro Glu Ile Gly Leu His Glu Asn Val Val
                    435                 440                 445
Cys Val Asp Phe Ala Ser Leu Tyr Pro Asn Val Met Val Ala His Asn
                    450                 455                 460
Ile Ser Pro Asp Thr Phe Asp Cys Asp Cys Cys Pro Arg Val Thr Val
465                 470                 475                 480
Glu Glu Val Asp Asp Pro Thr Asp Ala Thr Val Ala Pro Asp Val Gly
                    485                 490                 495
```

-continued

His Lys Phe Cys Lys Arg Arg Lys Gly Phe Pro Arg Leu Val Glu
                500                 505                 510

Gly Leu Ile Glu Arg Arg Glu Leu Lys Arg Arg Leu Arg Lys Leu
        515                 520                 525

Asp Thr Glu Ser His Pro His Glu Ala Lys Ile Leu Asp Val Arg Gln
530                 535                 540

Gln Ala Tyr Lys Val Leu Ala Asn Ser Tyr Tyr Gly Tyr Met Gly Trp
545                 550                 555                 560

Ala Asn Ala Arg Trp Phe Cys Arg Glu Cys Ala Glu Ser Val Thr Ala
                565                 570                 575

Trp Gly Arg Tyr Tyr Ile Ser Glu Val Arg Arg Ile Ala Glu Glu Lys
        580                 585                 590

Tyr Gly Leu Lys Val Val Tyr Gly Asp Thr Asp Ser Leu Phe Val Lys
        595                 600                 605

Leu Pro Asp Ala Asp Leu Glu Glu Thr Ile Glu Arg Val Lys Glu Phe
        610                 615                 620

Leu Lys Glu Val Asn Gly Arg Leu Pro Val Glu Leu Glu Leu Glu Asp
625                 630                 635                 640

Ala Tyr Lys Arg Ile Leu Phe Val Thr Lys Lys Tyr Ala Gly Tyr
                645                 650                 655

Thr Glu Asp Gly Lys Ile Val Thr Lys Gly Leu Glu Val Val Arg Arg
                660                 665                 670

Asp Trp Ala Pro Ile Ala Arg Glu Thr Gln Arg Arg Val Leu Lys Arg
        675                 680                 685

Ile Leu Ala Asp Asn Asp Pro Glu Ala Ala Leu Lys Glu Ile His Glu
        690                 695                 700

Val Leu Glu Arg Leu Lys Ser Gly Asp Val Asp Ile Asp Glu Leu Ala
705                 710                 715                 720

Val Thr Ser Gln Leu Thr Lys Lys Pro Ser Glu Tyr Val Gln Lys Gly
                725                 730                 735

Pro His Val Arg Ala Ala Leu Arg Leu Ala Arg His Leu Gly Val Glu
                740                 745                 750

Pro Glu Pro Gly Thr Ile Val Arg Tyr Val Ile Val Arg Gly Pro Gly
        755                 760                 765

Ser Val Ser Asp Lys Ala Tyr Pro Val Glu Leu Val Arg Glu Glu Gly
770                 775                 780

Lys Glu Pro Asp Val Asp Tyr Tyr Ile Glu His Gln Ile Leu Pro Ala
785                 790                 795                 800

Val Glu Arg Ile Met Arg Ala Ile Gly Tyr Ser Arg Gly Gln Ile Val
                805                 810                 815

Gly Glu Thr Ala Ser Gln Lys Thr Leu Asp Gln Phe Phe Gly
                820                 825                 830

<210> SEQ ID NO 55
<211> LENGTH: 784
<212> TYPE: PRT
<213> ORGANISM: Thermoproteus neutrophilus

<400> SEQUENCE: 55

Met Glu Leu Lys Ile Trp Pro Leu Asp Val Thr Tyr Ala Val Val Gly
1               5                   10                  15

Gly Tyr Pro Glu Val Arg Val Phe Gly Leu Thr Glu Gly Gly Gly Arg
                20                  25                  30

Val Val Leu Val Asp Arg Ser Phe Lys Pro Tyr Phe Tyr Val Asp Cys

-continued

```
                35                  40                  45
Pro Thr Cys Glu Val Gly Val Val Lys Ser Ser Leu Ser Arg Val Ala
    50                  55                  60
Pro Val Asp Glu Val Ser Ala Ala Glu Arg Arg Phe Leu Gly Arg Pro
65                  70                  75                  80
Arg Arg Phe Leu Met Val Val Ala Arg Val Pro Glu Asp Val Arg Arg
                85                  90                  95
Leu Arg Glu Ala Ala Gln Ile Pro Gly Val Ala Gly Val Tyr Glu
            100                 105                 110
Ala Asp Ile Arg Phe Tyr Met Arg Tyr Met Ile Asp Val Gly Leu Leu
            115                 120                 125
Pro Cys Ser Trp Asn Arg Ala Glu Val Glu Gly Gly Lys Val Gly
    130                 135                 140
Gly Leu Pro Gln Tyr Thr Val Val Gln Trp Leu Gly Pro Ala Gly Gly
145                 150                 155                 160
Phe Pro Pro Pro Leu Arg Val Leu Ala Phe Asp Ile Glu Val Tyr Asn
                165                 170                 175
Glu Arg Gly Thr Pro Asp Pro Ala Arg Asp Pro Val Val Met Ile Ala
            180                 185                 190
Val Lys Thr Asp Asp Gly Arg Glu Glu Val Phe Glu Ala Glu Gly Arg
        195                 200                 205
Asp Asp Arg Gly Val Leu Arg Ser Phe Val Glu Phe Val Lys Ser Tyr
210                 215                 220
Asp Pro Asp Val Val Gly Tyr Asn Ser Asn Gly Phe Asp Trp Pro
225                 230                 235                 240
Tyr Leu Ala Gly Arg Ala Arg Ala Ile Gly Val Pro Leu Arg Val Asp
                245                 250                 255
Arg Leu Gly Gly Leu Pro Gln Gln Ser Val Tyr Gly His Trp Ser Ile
            260                 265                 270
Val Gly Arg Ala Asn Val Asp Leu Tyr Gly Ile Val Glu Glu Phe Pro
        275                 280                 285
Glu Ile Lys Leu Lys Thr Leu Asp Arg Val Ala Glu Tyr Phe Gly Val
290                 295                 300
Met Arg Arg Glu Glu Arg Val Leu Ile Pro Gly His Lys Ile Tyr Glu
305                 310                 315                 320
Tyr Trp Arg Asp Pro Gly Lys Arg Pro Leu Leu Arg Gln Tyr Val Leu
                325                 330                 335
Asp Asp Val Arg Ser Thr Leu Gly Leu Ala Asp Lys Leu Leu Pro Phe
            340                 345                 350
Leu Ile Gln Leu Ser Ser Val Ser Gly Leu Pro Leu Asp Gln Val Ala
        355                 360                 365
Ala Ala Ser Val Gly Asn Arg Val Glu Trp Met Leu Leu Arg Tyr Ala
    370                 375                 380
Tyr Arg Leu Gly Glu Val Ala Pro Asn Arg Glu Glu Arg Glu Tyr Glu
385                 390                 395                 400
Pro Tyr Lys Gly Ala Ile Val Leu Glu Pro Lys Pro Gly Met Tyr Glu
                405                 410                 415
Asp Val Leu Val Leu Asp Phe Ser Ser Met Tyr Pro Asn Ile Met Met
            420                 425                 430
Lys Tyr Asn Leu Ser Pro Asp Thr Tyr Leu Glu Pro Gly Glu Pro Asp
        435                 440                 445
Pro Pro Glu Gly Val Asn Ala Ala Pro Glu Val Gly His Arg Phe Arg
    450                 455                 460
```

-continued

Arg Ser Pro Leu Gly Phe Val Pro Gln Val Leu Lys Ser Leu Val Glu
465                 470                 475                 480

Leu Arg Lys Ala Val Arg Glu Glu Ala Lys Arg Tyr Pro Pro Asp Ser
            485                 490                 495

Pro Glu Phe Arg Ile Leu Asp Glu Arg Gln Arg Ala Leu Lys Val Met
        500                 505                 510

Ala Asn Ala Met Tyr Gly Tyr Leu Gly Trp Val Gly Ala Arg Trp Tyr
    515                 520                 525

Lys Arg Glu Val Ala Glu Ser Val Thr Ala Phe Ala Arg Ala Ile Leu
530                 535                 540

Lys Asp Val Ile Glu Gln Ala Arg Arg Leu Gly Ile Val Val Val Tyr
545                 550                 555                 560

Gly Asp Thr Asp Ser Leu Phe Val Lys Lys His Val Asn Val Asp Lys
                565                 570                 575

Leu Ile Gln Tyr Val Glu Glu Lys Tyr Gly Ile Glu Ile Lys Val Asp
            580                 585                 590

Lys Asp Tyr Ala Lys Val Leu Phe Thr Glu Ala Lys Lys Arg Tyr Ala
    595                 600                 605

Gly Leu Leu Arg Asp Gly Arg Ile Asp Ile Val Gly Phe Glu Val Val
610                 615                 620

Arg Gly Asp Trp Ser Glu Leu Ala Lys Glu Val Gln Leu Lys Val Val
625                 630                 635                 640

Glu Ile Ile Leu Asn Ser Arg Asp Val Ala Glu Ala Arg Arg Arg Val
                645                 650                 655

Thr Gln Tyr Val Arg Glu Ile Ile Glu Arg Leu Arg Glu Tyr Lys Phe
            660                 665                 670

Asn Val Asp Asp Leu Ile Ile Trp Lys Thr Leu Asp Lys Glu Leu Gly
    675                 680                 685

Glu Tyr Lys Ala Tyr Pro Pro His Val His Ala Ala Leu Ile Leu Lys
690                 695                 700

Arg His Gly Tyr Lys Val Gly Lys Gly Asn Met Val Gly Tyr Val Val
705                 710                 715                 720

Val Lys Gly Gly Gly Lys Ile Ser Glu Lys Ala Leu Pro Tyr Ile Leu
                725                 730                 735

Leu Asp Asp Val Lys Lys Ile Asp Val Glu Tyr Tyr Ile Glu Arg Gln
            740                 745                 750

Ile Ile Pro Ala Ala Leu Arg Ile Ala Glu Val Ile Gly Val Lys Glu
    755                 760                 765

Ala Asp Leu Lys Thr Gly Lys Ser Glu Arg Ser Leu Leu Asp Phe Phe
770                 775                 780

<210> SEQ ID NO 56
<211> LENGTH: 142
<212> TYPE: PRT
<213> ORGANISM: Pyrococcus furiosus

<400> SEQUENCE: 56

Met Lys Thr Phe Leu Thr Glu Gln Gln Ile Lys Val Leu Met Leu Arg
1               5                   10                  15

Ala Lys Gly Tyr Lys Gln Ser Glu Ile Ala Lys Ile Leu Gly Thr Ser
            20                  25                  30

Arg Ala Asn Val Ser Ile Leu Glu Lys Arg Ala Met Glu Lys Ile Glu
        35                  40                  45

Lys Ala Arg Asn Thr Leu Leu Leu Trp Glu Gln Ile Asn Ser Lys Val

```
                50                  55                  60
Ile Val Glu Ile Lys Ala Gly Glu Asp Ile Phe Ser Ile Pro Glu Lys
 65                  70                  75                  80

Phe Phe Lys Lys Ala Asp Lys Val Gly Val Lys Val Pro Tyr Ser Thr
                 85                  90                  95

Ala Glu Ile Ile Thr Phe Leu Val Glu His Ala Pro Val Glu Asp Arg
                100                 105                 110

Leu Ala Lys Arg Asp Phe Val Leu Phe Leu Asp Ser Lys Asn Lys Leu
            115                 120                 125

Arg Ile Gly Asp Cys Leu Val Ile Glu Glu Ile Lys Glu Asp
        130                 135                 140

<210> SEQ ID NO 57
<211> LENGTH: 75
<212> TYPE: PRT
<213> ORGANISM: Pyrococcus furiosus

<400> SEQUENCE: 57

Met Pro Ile Thr Lys Val Thr Arg Asn Tyr Gln Ile Thr Ile Pro Ala
  1               5                  10                  15

Glu Ile Arg Lys Ala Leu Gly Ile Lys Glu Gly Glu Leu Leu Glu Val
                 20                  25                  30

Arg Leu Glu Asn Gly Lys Ile Ile Glu Arg Leu Lys Lys Glu Arg
             35                  40                  45

Lys Thr Leu Lys Leu Gly Lys Lys Leu Thr Leu Glu Glu Ile Glu Lys
 50                  55                  60

Ala Ile Glu Glu Gly Met Lys Gln Cys Met Gln
 65                  70                  75

<210> SEQ ID NO 58
<211> LENGTH: 76
<212> TYPE: PRT
<213> ORGANISM: Pyrococcus furiosus

<400> SEQUENCE: 58

Thr Lys Ile Glu Ile Leu Arg Leu Leu Lys Glu Arg Glu Met Tyr Ala
  1               5                  10                  15

Tyr Glu Ile Trp Ser Leu Leu Gly Lys Pro Leu Lys Tyr Gln Ala Val
                 20                  25                  30

His Gln His Ile Lys Glu Leu Leu Glu Leu Gly Leu Val Glu Gln Ala
             35                  40                  45

Tyr Arg Lys Gly Lys Arg Val Tyr Tyr Lys Ile Thr Glu Lys Gly Leu
 50                  55                  60

Arg Ile Leu Gln Asn Phe Glu Asp Leu Glu Asn Ile
 65                  70                  75

<210> SEQ ID NO 59
<211> LENGTH: 72
<212> TYPE: PRT
<213> ORGANISM: Pyrococcus furiosus

<400> SEQUENCE: 59

Met Asn Thr Gly Ala Gln Gly Val Ser Glu Met Ser Arg Met Lys Ile
  1               5                  10                  15

Ile Ser Val Gln Leu Pro Gln Ser Leu Ile His Gly Leu Asp Ala Leu
                 20                  25                  30

Val Lys Arg Gly Ile Tyr Pro Asn Arg Ser Glu Ala Ile Arg Val Ala
             35                  40                  45
```

```
Ile Arg Glu Leu Leu Lys Lys Glu Leu Tyr Lys Glu Ile Gln Glu
         50                  55                  60

Glu Ile Pro Glu Tyr Val Val Lys
 65                  70
```

<210> SEQ ID NO 60
<211> LENGTH: 67
<212> TYPE: PRT
<213> ORGANISM: Pyrococcus furiosus

<400> SEQUENCE: 60

```
Val Ile Ile Pro Arg Pro Ile Asp Pro Arg Asp Ile Arg Arg Ile Arg
 1               5                  10                  15

Lys Glu Leu Gly Ile Thr Gln Glu Leu Ala Arg Lys Ala Gly Val
             20                  25                  30

Thr Gln Ala Tyr Ile Ala Lys Leu Glu Ala Gly Lys Val Asp Pro Arg
             35                  40                  45

Leu Ser Thr Phe Asn Lys Ile Leu Arg Ala Leu Ile Glu Cys Gln Lys
         50                  55                  60

Ala Lys Ile
 65
```

<210> SEQ ID NO 61
<211> LENGTH: 65
<212> TYPE: PRT
<213> ORGANISM: Pyrococcus furiosus

<400> SEQUENCE: 61

```
Asn Asn Cys Glu Cys Met Val Val Lys Glu Lys Leu Tyr Thr Val Lys
 1               5                  10                  15

Gln Ala Ser Glu Ile Leu Gly Val His Pro Lys Thr Ile Gln Lys Trp
             20                  25                  30

Asp Arg Glu Gly Lys Ile Lys Thr Val Arg Thr Pro Gly Gly Arg Arg
             35                  40                  45

Arg Ile Pro Glu Ser Glu Ile Lys Arg Leu Leu Gly Ile Ser Glu Glu
         50                  55                  60

Lys
 65
```

<210> SEQ ID NO 62
<211> LENGTH: 71
<212> TYPE: PRT
<213> ORGANISM: Pyrococcus furiosus

<400> SEQUENCE: 62

```
Met Leu Lys Asp Ser Ala Pro Lys Arg Lys Ile Leu Glu Glu Leu Arg
 1               5                  10                  15

Lys Gly Glu Thr Val Ser Gly Asp Tyr Leu Ala Ser Lys Leu Gly Val
             20                  25                  30

Ser Arg Val Ala Ile Trp Lys His Ile Arg Glu Leu Lys Glu Leu Gly
             35                  40                  45

Tyr Gly Ile Ile Ala Asp Lys Lys Gly Tyr Lys Leu Val Tyr Glu Pro
         50                  55                  60

Lys Lys Pro Tyr Pro Trp Glu
 65                  70
```

<210> SEQ ID NO 63
<211> LENGTH: 86

<212> TYPE: PRT
<213> ORGANISM: Pyrococcus furiosus

<400> SEQUENCE: 63

Met Ile Asp Glu Arg Asp Lys Ile Ile Leu Glu Ile Leu Glu Lys Asp
1               5                   10                  15

Ala Arg Thr Pro Phe Thr Glu Ile Ala Lys Lys Leu Gly Ile Ser Glu
            20                  25                  30

Thr Ala Val Arg Lys Arg Val Lys Ala Leu Glu Glu Lys Gly Ile Ile
        35                  40                  45

Glu Gly Tyr Thr Ile Lys Ile Asn Pro Lys Lys Leu Gly Tyr Ser Leu
    50                  55                  60

Val Thr Ile Thr Gly Val Asp Thr Lys Pro Glu Lys Leu Phe Glu Val
65                  70                  75                  80

Ala Glu Lys Leu Lys Glu
            85

<210> SEQ ID NO 64
<211> LENGTH: 77
<212> TYPE: PRT
<213> ORGANISM: Pyrococcus furiosus

<400> SEQUENCE: 64

Met Glu Ile Asp Asp Leu Asp Arg Lys Ile Leu Ser Leu Leu Ile Glu
1               5                   10                  15

Asp Ser Arg Leu Ser Tyr Arg Glu Ile Ala Lys Lys Leu Asn Val Ala
            20                  25                  30

Val Gly Thr Ile Tyr Asn Arg Ile Lys Lys Leu Glu Asp Met Gly Val
        35                  40                  45

Ile Gln Gly Phe Thr Val Lys Leu Asn Tyr Glu Lys Leu Gly Tyr Glu
    50                  55                  60

Leu Thr Ala Ile Ile Gly Ile Lys Ala Gln Gly Lys Lys
65                  70                  75

<210> SEQ ID NO 65
<211> LENGTH: 94
<212> TYPE: PRT
<213> ORGANISM: Pyrococcus furiosus

<400> SEQUENCE: 65

Glu Met Leu Trp Met Tyr Ile Leu Lys Leu Leu Lys Asp Arg Pro Met
1               5                   10                  15

Tyr Ala Tyr Glu Ile Arg Asn Glu Leu Lys Lys Arg Phe Gly Phe Glu
            20                  25                  30

Pro Ala Thr Val Ser Ser Tyr Val Val Leu Tyr Arg Leu Glu Glu Gly
        35                  40                  45

Gly Tyr Val Ser Ser Glu Trp His Glu Ser Glu Ala Gly Arg Pro Ser
    50                  55                  60

Arg Lys Tyr Tyr Arg Leu Thr Glu Lys Gly Glu Lys Leu Leu Glu Lys
65                  70                  75                  80

Gly Ile Glu Thr Ile Glu Asp Val Leu Asn Met Leu Lys Ser
            85                  90

<210> SEQ ID NO 66
<211> LENGTH: 68
<212> TYPE: PRT
<213> ORGANISM: Pyrococcus furiosus

<400> SEQUENCE: 66

```
Met Lys Val Ser Lys Ala Thr Ala Ser Lys Val Leu Arg Ser Leu Glu
1               5                   10                  15

Asn Lys Gly Ile Val Glu Arg Glu Arg Gly Lys Thr Tyr Leu Val
            20                  25                  30

Arg Leu Thr Asn Lys Gly Leu Glu Leu Leu Glu Ile Ser Lys Ala
            35                  40                  45

Gly Lys Glu Leu Asp Lys Ile Phe Ala Glu Met Ser Val Asp Glu
        50                  55                  60

Arg Ile Val Leu
65
```

<210> SEQ ID NO 67
<211> LENGTH: 56
<212> TYPE: PRT
<213> ORGANISM: Pyrococcus furiosus

<400> SEQUENCE: 67

```
Ser Glu Asp Tyr Met Leu Gln Asn Arg Arg Lys Val Leu Ala Lys Val
1               5                   10                  15

Leu Glu Leu Leu Asn Tyr Asn Pro Lys Ala Leu Asn Ile Ser Glu Leu
            20                  25                  30

Ala Arg Met Phe Gly Val Ser Arg Asp Thr Ile Tyr Asn Asp Ile Gln
            35                  40                  45

Gln Ile Ile Lys Asn Val Glu Val
        50                  55
```

<210> SEQ ID NO 68
<211> LENGTH: 94
<212> TYPE: PRT
<213> ORGANISM: Pyrococcus furiosus

<400> SEQUENCE: 68

```
Ser Lys Glu Ile Ser Arg Phe Leu Lys Val Ile Ser Asn Pro Ile Arg
1               5                   10                  15

Tyr Gly Ile Leu Lys Met Leu Asn Asp Arg Trp Met Cys Val Cys Leu
            20                  25                  30

Ile Ser Glu Ala Leu Glu Ile Asp Gln Thr Leu Val Ser His His Ile
            35                  40                  45

Arg Ile Leu Lys Glu Leu Asp Leu Leu Glu Arg Lys Glu Gly Lys
        50                  55                  60

Leu Arg Phe Tyr Arg Thr Asn Lys Glu Lys Leu Arg Glu Tyr Leu Glu
65                  70                  75                  80

Lys Val Leu Glu Asp Phe Asn His Gly Thr Ser Lys Gly Ser
                85                  90
```

<210> SEQ ID NO 69
<211> LENGTH: 78
<212> TYPE: PRT
<213> ORGANISM: Pyrococcus furiosus

<400> SEQUENCE: 69

```
Met Cys Arg Lys Asp Val Met Ile Ile Ser Asp Pro Lys Gln Ile Lys
1               5                   10                  15

Ala Leu Ser Asp Pro Thr Arg Val Lys Ile Leu Glu Leu Leu Arg Tyr
            20                  25                  30

His Pro Met Thr Val Ser Glu Ile Ser Arg Val Ile Gly Lys Asp Lys
            35                  40                  45
```

Ser Thr Ile Tyr Arg His Ile Lys Ala Leu Glu Glu Ala Gly Leu Val
    50                  55                  60

Glu Glu Val Glu Lys Ile Gly Asn Glu Thr Val Tyr Gly Arg
65                  70                  75

<210> SEQ ID NO 70
<211> LENGTH: 122
<212> TYPE: PRT
<213> ORGANISM: Pyrococcus furiosus

<400> SEQUENCE: 70

Met Glu Pro Val Glu Phe Lys Leu Asn Gln Lys Gly Ile Lys Ser Ile
1               5                   10                  15

Leu Pro Thr Met Glu Ala Glu Ile Met Glu Tyr Met Trp Glu Ile Lys
            20                  25                  30

Glu Ala Thr Ala Gly Glu Val Tyr Glu Tyr Met Lys Thr Lys Tyr Pro
        35                  40                  45

Glu Ile Arg Arg Ser Thr Val Ser Ile Leu Met Asn Arg Leu Cys Glu
    50                  55                  60

Arg Gly Leu Leu Lys Arg Arg Met Glu Lys Gly Lys Gly Ile Arg
65                  70                  75                  80

Tyr Val Tyr Ser Ile Thr Thr Thr Arg Glu Glu Phe Glu Arg Lys Val
                85                  90                  95

Val Glu Lys Ile Ile Glu Ser Leu Met Met Asn Phe Arg Glu Ala Thr
            100                 105                 110

Phe Ala Tyr Leu Ser Lys Ile Asn Lys Lys
        115                 120

<210> SEQ ID NO 71
<211> LENGTH: 87
<212> TYPE: PRT
<213> ORGANISM: Pyrococcus furiosus

<400> SEQUENCE: 71

Met Lys Lys Ser Asn Leu Asp Leu Leu Ile Leu Leu Ala Lys Ala Gly
1               5                   10                  15

Gly Ile Glu Lys Glu Ile Leu Thr Thr Ser Arg Glu Leu Ser Lys Met
            20                  25                  30

Leu Asn Val Ser Pro Gln Thr Ile Val Arg Trp Leu Glu Asp Leu Glu
        35                  40                  45

Lys Asp Gly Leu Ile Lys Lys Ser Glu Ser Arg Lys Gly Thr Leu Val
    50                  55                  60

Thr Ile Thr Glu Glu Gly Val Lys Phe Leu Glu Lys Leu His Glu Glu
65                  70                  75                  80

Leu Ser Asp Ala Leu Tyr Arg
            85

<210> SEQ ID NO 72
<211> LENGTH: 104
<212> TYPE: PRT
<213> ORGANISM: Thermococcaceae

<400> SEQUENCE: 72

Met Glu Ile Pro Pro Glu Ile Ser His Ala Leu Ser Glu Ile Gly Phe
1               5                   10                  15

Thr Lys Tyr Glu Ile Leu Thr Tyr Trp Thr Leu Leu Val Tyr Gly Pro
            20                  25                  30

Ser Thr Ala Lys Glu Ile Ser Thr Lys Ser Gly Ile Pro Tyr Asn Arg

```
              35                  40                  45
Val Tyr Asp Thr Ile Ser Ser Leu Lys Leu Arg Gly Phe Val Thr Glu
 50                  55                  60

Ile Glu Gly Thr Pro Lys Val Tyr Ala Ala Tyr Ser Pro Arg Ile Ala
65                  70                  75                  80

Phe Phe Arg Phe Lys Glu Leu Glu Asp Ile Met Lys Lys Leu Glu
                 85                  90                  95

Ile Glu Leu Asn Asn Val Lys Lys
            100
```

<210> SEQ ID NO 73
<211> LENGTH: 75
<212> TYPE: PRT
<213> ORGANISM: Pyrococcus furiosus

<400> SEQUENCE: 73

```
Ile Ile Asn Pro Gln Ala Arg Leu Thr Pro Leu Glu Leu Glu Ile Leu
1               5                   10                  15

Glu Ile Ile Lys Gln Lys Lys Ser Ile Thr Ile Thr Glu Ile Lys Glu
                20                  25                  30

Ile Leu Ser Glu Arg Arg Lys Ser Glu Tyr Pro Leu Ser Leu Val Ser
            35                  40                  45

Glu Tyr Ile Ser Arg Leu Glu Arg Lys Gly Tyr Val Lys Lys Ile Ala
 50                  55                  60

Lys Gly Arg Lys Lys Phe Val Glu Ala Leu Ile
65                  70                  75
```

<210> SEQ ID NO 74
<211> LENGTH: 94
<212> TYPE: PRT
<213> ORGANISM: Pyrococcus furiosus

<400> SEQUENCE: 74

```
Gly Ile Asp Val Val Ile Pro Glu Ile Lys His Asp Pro Ile Ala Arg
1               5                   10                  15

Asp Ile Val Lys Ile Leu Phe Asp Leu Arg Arg Ala Asn Val Ser Gln
                20                  25                  30

Ile Ala Arg Glu Leu Lys Gly Arg Gly Lys Ala Ser Arg Asn Thr
            35                  40                  45

Val Arg Lys Lys Leu Lys Glu Leu Lys Leu Gly Val Val Lys Glu
 50                  55                  60

Val Pro Gly Glu Arg Gly Ser Val Tyr Thr Leu Ser Arg Glu Val Val
65                  70                  75                  80

Lys Lys Trp Leu Asp Leu Ile Gly Ile Pro Ile Asn Leu Leu
                85                  90
```

<210> SEQ ID NO 75
<211> LENGTH: 67
<212> TYPE: PRT
<213> ORGANISM: Pyrococcus furiosus

<400> SEQUENCE: 75

```
Met Thr Lys Arg Val Lys Val Ile Thr Asp Pro Glu Val Ile Lys Val
1               5                   10                  15

Met Leu Glu Asp Thr Arg Arg Lys Ile Leu Gln Leu Leu Arg Asn Arg
                20                  25                  30

Glu Met Thr Ile Ser Gln Leu Ser Glu Ile Leu Gly Lys Met Pro Gln
            35                  40                  45
```

```
Thr Ile Tyr His His Ile Glu Lys Leu Lys Glu Ala Gly Leu Val Glu
        50                  55                  60

Val Lys Arg
 65
```

```
<210> SEQ ID NO 76
<211> LENGTH: 100
<212> TYPE: PRT
<213> ORGANISM: Pyrococcus furiosus

<400> SEQUENCE: 76

Met Glu Glu Ile Lys Glu Ile Met Lys Ser His Thr Leu Gly Asn Pro
 1               5                  10                  15

Val Arg Leu Gly Ile Met Ile Tyr Leu Phe Pro Arg Arg Arg Ala Pro
                20                  25                  30

Phe Ser His Ile Gln Lys Ala Leu Asp Leu Thr Pro Gly Asn Leu Asp
            35                  40                  45

Ser His Ile Lys Val Leu Glu Lys His Gly Phe Val Arg Thr Tyr Lys
        50                  55                  60

Val Ile Ala Asp Arg Pro Arg Thr Met Val Glu Ile Thr Asp Tyr Gly
 65                  70                  75                  80

Met Glu Glu Thr Arg Lys Phe Leu Ser His Leu Lys Thr Val Ile Asp
                85                  90                  95

Ala Ile His Phe
            100
```

```
<210> SEQ ID NO 77
<211> LENGTH: 99
<212> TYPE: PRT
<213> ORGANISM: Pyrococcus furiosus

<400> SEQUENCE: 77

Met Gly Glu Glu Leu Asn Arg Leu Leu Asp Val Leu Gly Asn Glu Thr
 1               5                  10                  15

Arg Arg Arg Ile Leu Phe Leu Leu Thr Lys Arg Pro Tyr Phe Val Ser
                20                  25                  30

Glu Leu Ser Arg Glu Leu Gly Val Gly Gln Lys Ala Val Leu Glu His
            35                  40                  45

Leu Arg Ile Leu Glu Glu Ala Gly Leu Ile Glu Ser Arg Val Glu Lys
        50                  55                  60

Ile Pro Arg Gly Arg Pro Arg Lys Tyr Tyr Met Ile Lys Lys Gly Leu
 65                  70                  75                  80

Arg Leu Glu Ile Leu Leu Thr Pro Thr Leu Phe Gly Ser Glu Met Tyr
                85                  90                  95

Glu Ala Lys
```

```
<210> SEQ ID NO 78
<211> LENGTH: 61
<212> TYPE: PRT
<213> ORGANISM: Pyrococcus furiosus

<400> SEQUENCE: 78

Met Arg Arg Met Asp Lys Val Asp Leu Gln Leu Ile Lys Ile Leu Ser
 1               5                  10                  15

Gln Asn Ser Arg Leu Thr Tyr Arg Glu Leu Ala Glu Met Leu Gly Thr
                20                  25                  30

Thr Arg Gln Arg Val Ala Arg Lys Val Asp Lys Leu Lys Lys Leu Gly
```

35                  40                  45

Ile Ile Arg Lys Phe Thr Ile Ile Pro Asn Leu Glu Lys
    50                  55                  60

<210> SEQ ID NO 79
<211> LENGTH: 82
<212> TYPE: PRT
<213> ORGANISM: Pyrococcus furiosus

<400> SEQUENCE: 79

Gly Arg Lys Val Arg Thr Gln Gln Asn Glu Ile Leu Asn Leu Leu Asn
1               5                   10                  15

Glu Lys Glu Lys Ala Val Leu Arg Ala Ile Leu Glu His Gly Gly Glu
                20                  25                  30

Ile Lys Gln Glu Asp Leu Pro Glu Leu Val Gly Tyr Ser Arg Pro Thr
            35                  40                  45

Ile Ser Lys Val Ile Gln Glu Leu Glu Asn Lys Gly Leu Ile Lys Arg
    50                  55                  60

Glu Lys Ser Gly Lys Thr Phe Val Val Lys Ile Glu Arg Lys Ile Lys
65                  70                  75                  80

Leu Asp

<210> SEQ ID NO 80
<211> LENGTH: 59
<212> TYPE: PRT
<213> ORGANISM: Thermotoga maritima

<400> SEQUENCE: 80

Lys Ser Leu Gln Arg Phe Leu Arg Arg Asn Thr Thr Ser Ile Lys His
1               5                   10                  15

Leu Ser Glu Ile Thr Gly Val Ala Arg Asn Arg Leu Ser Asp Ile Leu
                20                  25                  30

Asn Gly Lys Thr Gln Lys Ile Arg Gly Glu Thr Leu Arg Lys Ile Ala
            35                  40                  45

Lys Ala Phe Glu Lys Ser Asn Ile Leu Ser Phe
    50                  55

<210> SEQ ID NO 81
<211> LENGTH: 107
<212> TYPE: PRT
<213> ORGANISM: Thermotoga

<400> SEQUENCE: 81

Asp Val Ile Gln Arg Ile Lys Glu Lys Tyr Asp Glu Phe Thr Asn Ala
1               5                   10                  15

Glu Lys Lys Ile Ala Asp Thr Ile Leu Ser Asp Pro Lys Gly Ile Ile
                20                  25                  30

Glu Ser Ser Ile Ser Asp Leu Ser Glu Lys Ala Gly Val Lys Ser Glu
            35                  40                  45

Ala Ser Val Val Lys Phe Tyr Lys Lys Leu Gly Leu Asn Ser Phe Gln
    50                  55                  60

Gln Phe Lys Val Leu Leu Ala Gln Ser Ile Ser Arg Ala Pro Leu Glu
65                  70                  75                  80

Ile Val Tyr Glu Asp Val Ser Ser Glu Asp Asp Thr Lys Thr Ile Thr
                85                  90                  95

Glu Lys Ile Phe Lys Ala Thr Val Arg Ala Ile
            100                 105

<210> SEQ ID NO 82
<211> LENGTH: 101
<212> TYPE: PRT
<213> ORGANISM: Thermotoga maritima

<400> SEQUENCE: 82

Lys Ile Arg Asp Lys Ile Leu Asn Val Tyr Thr Gln Phe Ser Pro Ala
1               5                   10                  15

Glu Arg Lys Val Ala Asp Tyr Val Leu Glu Arg Pro Asp Asp Val Ile
            20                  25                  30

His Tyr Ser Ile Thr Glu Phe Ala Lys Ile Val Gly Val Ser Glu Thr
        35                  40                  45

Thr Ile His Arg Met Ile Lys Lys Leu Asp Phe Glu Gly Tyr Gln Ala
    50                  55                  60

Phe Lys Ile Ala Leu Ala Arg Glu Leu Ser Gly Leu Glu Glu Thr Ile
65                  70                  75                  80

Glu Arg Arg Asp Phe Ile Asp Glu Ile Asp Ile Leu Arg Arg Leu
                85                  90                  95

Lys Asp Thr Leu Asp
            100

<210> SEQ ID NO 83
<211> LENGTH: 60
<212> TYPE: PRT
<213> ORGANISM: Thermotoga maritima

<400> SEQUENCE: 83

Lys Arg Arg Pro Thr Ile Asn Asp Val Ala Lys Leu Ala Gly Val Ser
1               5                   10                  15

Ile Ser Thr Val Ser Arg Tyr Leu Lys Asp Pro Ser Gln Val Ser Glu
            20                  25                  30

Lys Leu Gly Glu Arg Ile Arg Glu Ala Ile Lys Leu Gly Tyr Lys
        35                  40                  45

Pro Asn Lys Ile Ala Gln Gly Leu Arg Thr Gly Asp
    50                  55                  60

<210> SEQ ID NO 84
<211> LENGTH: 58
<212> TYPE: PRT
<213> ORGANISM: Thermotoga maritima

<400> SEQUENCE: 84

Met Ala Ser Ile Lys Asp Val Ala Lys Leu Ala Gly Val Ser Ile Ala
1               5                   10                  15

Thr Val Ser Arg Val Ile Asn Gly Tyr Asn Asn Val Ser Glu Glu Thr
            20                  25                  30

Arg Lys Lys Val Ile Asp Ala Ile Arg Lys Leu Asn Tyr His Pro Val
        35                  40                  45

Tyr Ala Val Lys Gly Ala Val Leu Lys Arg
    50                  55

<210> SEQ ID NO 85
<211> LENGTH: 61
<212> TYPE: PRT
<213> ORGANISM: Thermotoga maritima

<400> SEQUENCE: 85

Met Lys Lys Lys Tyr Val Thr Ile Arg Asp Ile Ala Glu Lys Ala Gly
1               5                   10                  15

Val Ser Ile Asn Thr Val Ser Arg Ala Leu Asn Asn Lys Pro Asp Ile
            20                  25                  30

Ser Glu Glu Thr Arg Arg Lys Ile Leu Lys Ile Ala Gln Glu Leu Gly
        35                  40                  45

Tyr Val Lys Asn Ala Thr Ala Ser Ser Leu Arg Ser Lys
50                  55                  60

<210> SEQ ID NO 86
<211> LENGTH: 58
<212> TYPE: PRT
<213> ORGANISM: Thermotoga

<400> SEQUENCE: 86

Met Pro Thr Ile Glu Asp Val Ala Lys Leu Ala Gly Val Ser Ile Ala
1               5                   10                  15

Thr Val Ser Arg Val Ile Asn Gly Ser Gly Tyr Val Ser Glu Lys Thr
            20                  25                  30

Arg Tyr Lys Val Trp Lys Ala Ile Glu Glu Leu Gly Tyr Lys Pro Glu
        35                  40                  45

Ile Ser Ala Lys Leu Leu Ala Ser Lys Gly
50                  55

<210> SEQ ID NO 87
<211> LENGTH: 61
<212> TYPE: PRT
<213> ORGANISM: Thermotoga maritima

<400> SEQUENCE: 87

Met Arg Ile Gly Glu Lys Leu Arg Lys Leu Arg Leu Ser Arg Gly Leu
1               5                   10                  15

Thr Gln Glu Glu Leu Ala Glu Arg Thr Asp Leu Ser Arg Ser Phe Ile
            20                  25                  30

Ser Gln Leu Glu Ser Asp Lys Thr Ser Pro Ser Ile Asp Thr Leu Glu
        35                  40                  45

Arg Ile Leu Glu Ala Leu Gly Thr Asp Leu Lys His Phe
50                  55                  60

<210> SEQ ID NO 88
<211> LENGTH: 67
<212> TYPE: PRT
<213> ORGANISM: Thermotoga maritima

<400> SEQUENCE: 88

Met His Met Lys Thr Val Arg Gln Glu Arg Leu Lys Ser Ile Val Arg
1               5                   10                  15

Ile Leu Glu Arg Ser Lys Glu Pro Val Ser Gly Ala Gln Leu Ala Glu
            20                  25                  30

Glu Leu Ser Val Ser Arg Gln Val Ile Val Gln Asp Ile Ala Tyr Leu
        35                  40                  45

Arg Ser Leu Gly Tyr Asn Ile Val Ala Thr Pro Arg Gly Tyr Val Leu
50                  55                  60

Ala Gly Gly
65

<210> SEQ ID NO 89
<211> LENGTH: 75
<212> TYPE: PRT
<213> ORGANISM: Thermotoga maritima

```
<400> SEQUENCE: 89

Met Asn Thr Leu Lys Lys Ala Phe Glu Ile Leu Asp Phe Ile Val Lys
1               5                   10                  15

Asn Pro Gly Asp Val Ser Val Ser Glu Ile Ala Glu Lys Phe Asn Met
            20                  25                  30

Ser Val Ser Asn Ala Tyr Lys Tyr Met Val Val Leu Glu Glu Lys Gly
            35                  40                  45

Phe Val Leu Arg Lys Lys Asp Lys Arg Tyr Val Pro Gly Tyr Lys Leu
    50                  55                  60

Ile Glu Tyr Gly Ser Phe Val Leu Arg Arg Phe
65                  70                  75

<210> SEQ ID NO 90
<211> LENGTH: 81
<212> TYPE: PRT
<213> ORGANISM: Thermotoga maritima

<400> SEQUENCE: 90

Met Lys Ile Ser Lys Lys Arg Arg Gln Glu Leu Ile Arg Lys Ile Ile
1               5                   10                  15

His Glu Lys Lys Ile Ser Asn Gln Phe Gln Ile Val Glu Glu Leu Lys
            20                  25                  30

Lys Tyr Gly Ile Lys Ala Val Gln Pro Thr Val Ala Arg Asp Leu Lys
            35                  40                  45

Glu Ile Gly Ala Val Lys Ile Met Asp Glu Ser Gly Asn Tyr Val Tyr
    50                  55                  60

Lys Leu Leu Asp Glu Thr Pro Val Ile Asp Pro Trp Lys Glu Leu Lys
65                  70                  75                  80

Arg

<210> SEQ ID NO 91
<211> LENGTH: 82
<212> TYPE: PRT
<213> ORGANISM: Thermotoga maritima

<400> SEQUENCE: 91

Met His Lys Lys Leu Asn Pro Lys Ser Met Lys Arg Glu Asn Lys Lys
1               5                   10                  15

Met Val Leu Arg Tyr Leu Ile Glu Ser Gly Pro His Ser Arg Val Glu
            20                  25                  30

Ile Ala Arg Lys Thr Gly Leu Ala Gln Ser Ala Ile Trp Arg Ile Ile
            35                  40                  45

Glu Glu Leu Val Asn Glu Gly Leu Val Glu Glu Lys Gly Thr Ala Thr
    50                  55                  60

Gly Arg Arg Arg Lys Ala Val Thr Tyr Gly Pro Thr Arg Ser Phe Ile
65                  70                  75                  80

Thr Ser

<210> SEQ ID NO 92
<211> LENGTH: 79
<212> TYPE: PRT
<213> ORGANISM: Thermotoga maritima

<400> SEQUENCE: 92

Met Pro Ser Pro Leu Leu Arg Arg Glu Asn Lys Ile Lys Ile Leu Arg
1               5                   10                  15

Tyr Ile Leu Lys Asn Gly Lys Thr Thr Arg Asn Gln Leu Ala Ser Asn
```

```
                    20                  25                  30
Leu Asn Leu Ala His Ser Thr Leu Ser Tyr Ile Ile Asp Glu Leu Leu
            35                  40                  45

Asp Glu Gly Phe Leu Val Phe Glu Glu Ile Lys Lys Arg Gly Arg
        50                  55                  60

Pro Tyr Gln Ile Leu Ser Val Asn Pro Glu Lys Phe Thr Ala Ile
65                  70                  75
```

<210> SEQ ID NO 93
<211> LENGTH: 79
<212> TYPE: PRT
<213> ORGANISM: Thermotoga maritima

<400> SEQUENCE: 93

```
Met Lys Glu Glu Arg Leu Lys Glu Ile Leu Asp Ile Val Asp Arg Asn
1               5                   10                  15

Gly Phe Ile Ser Met Lys Asp Leu Gln Glu Gln Leu Gly Val Ser Met
            20                  25                  30

Ile Thr Val Arg Arg Asp Val Ala Glu Leu Val Lys Arg Asn Leu Val
            35                  40                  45

Lys Lys Val His Gly Gly Ile Arg Lys Val Asn Tyr Phe Glu Lys Glu
        50                  55                  60

Thr Asp Phe Met Lys Arg Leu Ser Ile Asn Arg Glu Ala Lys Glu
65                  70                  75
```

<210> SEQ ID NO 94
<211> LENGTH: 137
<212> TYPE: PRT
<213> ORGANISM: Thermotoga maritima

<400> SEQUENCE: 94

```
Met Phe Thr Met Arg Ser Glu Tyr Ala Leu Arg Leu Met Ile Val Met
1               5                   10                  15

Ala Lys Glu Tyr Gly Asn Tyr Leu Ser Met Thr Glu Ile Leu Glu Lys
            20                  25                  30

Ala Lys Gln Ser Val Pro Arg Glu Phe Ala Glu Lys Ile Leu Tyr Thr
            35                  40                  45

Leu Lys Lys Ala Gly Leu Val Lys Thr Arg Arg Gly Lys Ser Gly Gly
        50                  55                  60

Tyr Met Leu Ser Arg Pro Pro Lys Glu Ile Lys Val Ser Glu Ile Val
65                  70                  75                  80

Phe Leu Leu Asp Arg Lys Ser Leu Val Phe Phe Asp Met Pro Gly Cys
            85                  90                  95

Pro Asp Glu Leu Asp Cys Val Ile Arg Ala Leu Trp Lys Arg Val Glu
            100                 105                 110

Asn Glu Ile Glu Lys Ile Leu Ser Gly Val Thr Leu Glu Asp Leu Val
        115                 120                 125

Arg Glu Gln Glu Glu Lys Met Lys Gln
    130                 135
```

<210> SEQ ID NO 95
<211> LENGTH: 95
<212> TYPE: PRT
<213> ORGANISM: Thermotoga naphthophila

<400> SEQUENCE: 95

```
Met Arg Asp Thr Lys Gly His Leu Lys Phe Leu Val Leu His Ile Ile
1               5                   10                  15
```

```
Ser Gln Gln Pro Ser His Gly Tyr Tyr Ile Met Lys Lys Ile Ser Gln
            20                  25                  30

Ile Ile Gly Ala Glu Pro Pro Ser Pro Gly Ala Leu Tyr Pro Ile Leu
        35                  40                  45

Ser Ser Leu Arg Lys Gln Lys Tyr Ile Glu Thr Tyr Asn Glu Gly Lys
50                  55                  60

Arg Lys Val Tyr Arg Leu Thr Asp Lys Gly Arg Lys Tyr Leu Glu Glu
65                  70                  75                  80

His Lys Glu Glu Ile Lys Lys Ala Leu Asp Phe Ala Glu Arg Phe
                85                  90                  95

<210> SEQ ID NO 96
<211> LENGTH: 118
<212> TYPE: PRT
<213> ORGANISM: Thermotoga maritima

<400> SEQUENCE: 96

Met Arg His Arg Gly Gly Arg Gly Phe Arg Gly Trp Trp Leu Ala Ser
1               5                   10                  15

Thr Ile Leu Leu Leu Val Ala Glu Lys Pro Ser His Gly Tyr Glu Leu
            20                  25                  30

Ala Glu Arg Leu Ala Glu Phe Gly Ile Glu Ile Pro Gly Ile Gly His
        35                  40                  45

Met Gly Asn Ile Tyr Arg Val Leu Ala Asp Leu Glu Glu Ser Gly Phe
    50                  55                  60

Leu Ser Thr Glu Trp Asp Thr Thr Val Ser Pro Pro Arg Lys Ile Tyr
65                  70                  75                  80

Arg Ile Thr Pro Gln Gly Lys Leu Tyr Leu Arg Glu Ile Leu Arg Ser
                85                  90                  95

Leu Glu Asp Met Lys Arg Arg Ile Glu Thr Leu Glu Glu Arg Ile Lys
                100                 105                 110

Arg Val Leu Gln Glu Glu
        115

<210> SEQ ID NO 97
<211> LENGTH: 70
<212> TYPE: PRT
<213> ORGANISM: Thermotoga maritima

<400> SEQUENCE: 97

Met Leu Ser Lys Arg Asp Ala Ile Leu Lys Ala Ala Val Glu Val Phe
1               5                   10                  15

Gly Lys Lys Gly Tyr Asp Arg Ala Thr Thr Asp Glu Ile Ala Glu Lys
            20                  25                  30

Ala Gly Val Ala Lys Gly Leu Ile Phe His Tyr Phe Lys Asn Lys Glu
        35                  40                  45

Glu Leu Tyr Tyr Gln Ala Tyr Met Ser Val Thr Glu Lys Leu Gln Lys
    50                  55                  60

Glu Phe Glu Asn Phe Leu
65                  70

<210> SEQ ID NO 98
<211> LENGTH: 291
<212> TYPE: PRT
<213> ORGANISM: Artificial Sequence
<220> FEATURE:
<223> OTHER INFORMATION: Synthetic construct
```

<400> SEQUENCE: 98

Met Ser Lys Ser Trp Gly Lys Phe Ile Glu Glu Glu Ala Glu Met
1               5                   10                  15

Ala Ser Arg Arg Asn Leu Met Ile Val Asp Gly Thr Asn Leu Gly Phe
            20                  25                  30

Arg Phe Lys His Asn Asn Ser Lys Pro Phe Ala Ser Ser Tyr Val
        35                  40                  45

Ser Thr Ile Gln Ser Leu Ala Lys Ser Tyr Ser Ala Arg Thr Thr Ile
    50                  55                  60

Val Leu Gly Asp Lys Gly Lys Ser Val Phe Arg Leu Glu His Leu Pro
65                  70                  75                  80

Glu Tyr Lys Gly Asn Arg Asp Glu Lys Tyr Ala Gln Arg Thr Glu Glu
                85                  90                  95

Glu Lys Ala Leu Asp Glu Gln Phe Phe Glu Tyr Leu Lys Asp Ala Phe
            100                 105                 110

Glu Leu Cys Lys Thr Thr Phe Pro Thr Phe Thr Ile Arg Gly Val Glu
        115                 120                 125

Ala Asp Asp Met Ala Ala Tyr Ile Val Lys Leu Ile Gly His Leu Tyr
    130                 135                 140

Asp His Val Trp Leu Ile Ser Thr Asp Gly Asp Trp Asp Thr Leu Leu
145                 150                 155                 160

Thr Asp Lys Val Ser Arg Phe Ser Phe Thr Thr Arg Arg Glu Tyr His
                165                 170                 175

Leu Arg Asp Met Tyr Glu His His Asn Val Asp Asp Val Glu Gln Phe
            180                 185                 190

Ile Ser Leu Lys Ala Ile Met Gly Asp Leu Gly Asp Asn Ile Arg Gly
        195                 200                 205

Val Glu Gly Ile Gly Ala Lys Arg Gly Tyr Asn Ile Ile Arg Glu Phe
    210                 215                 220

Gly Asn Val Leu Asp Ile Ile Asp Gln Leu Pro Leu Pro Gly Lys Gln
225                 230                 235                 240

Lys Tyr Ile Gln Asn Leu Asn Ala Ser Glu Glu Leu Leu Phe Arg Asn
                245                 250                 255

Leu Ile Leu Val Asp Leu Pro Thr Tyr Cys Val Asp Ala Ile Ala Ala
            260                 265                 270

Val Gly Gln Asp Val Leu Asp Lys Phe Thr Lys Asp Ile Leu Glu Ile
        275                 280                 285

Ala Glu Gln
        290

<210> SEQ ID NO 99
<211> LENGTH: 53
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (17)..(37)
<223> OTHER INFORMATION: n is a, c, g, or t

<400> SEQUENCE: 99
tttctagctc taaaacnnnn nnnnnnnnnn nnnnnnncgg tgtttcgtcc ttt        53

<210> SEQ ID NO 100
<211> LENGTH: 148
<212> TYPE: PRT

<213> ORGANISM: Sulfolobus solfataricus

<400> SEQUENCE: 100

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Gly Arg Gly Phe Arg Gly Gly
        115                 120                 125

Gly Arg Arg Tyr Gly Arg Arg Gly Gly Arg Arg Gln Glu Asn Glu Glu
    130                 135                 140

Gly Glu Glu Glu
145

<210> SEQ ID NO 101
<211> LENGTH: 673
<212> TYPE: PRT
<213> ORGANISM: Thermus thermophilus

<400> SEQUENCE: 101

Met Thr Leu Glu Glu Ala Arg Lys Arg Val Asn Glu Leu Arg Asp Leu
1               5                   10                  15

Ile Arg Tyr His Asn Tyr Arg Tyr Tyr Val Leu Ala Asp Pro Ile Ser
            20                  25                  30

Asp Ala Glu Tyr Asp Arg Leu Leu Arg Glu Leu Lys Glu Leu Glu Glu
        35                  40                  45

Arg Phe Pro Glu Leu Lys Ser Pro Asp Ser Pro Thr Leu Gln Val Gly
    50                  55                  60

Ala Arg Pro Leu Glu Ala Thr Phe Arg Pro Val Arg His Pro Thr Arg
65                  70                  75                  80

Met Tyr Ser Leu Asp Asn Ala Phe Asn Leu Asp Glu Leu Lys Ala Phe
                85                  90                  95

Glu Glu Arg Ile Glu Arg Ala Leu Gly Arg Lys Gly Pro Phe Ala Tyr
            100                 105                 110

Thr Val Glu His Lys Val Asp Gly Leu Ser Val Asn Leu Tyr Tyr Glu
        115                 120                 125

Glu Gly Val Leu Val Tyr Gly Ala Thr Arg Gly Asp Gly Glu Val Gly
    130                 135                 140

Glu Glu Val Thr Gln Asn Leu Leu Thr Ile Pro Thr Ile Pro Arg Arg
145                 150                 155                 160

Leu Lys Gly Val Pro Glu Arg Leu Glu Val Arg Gly Glu Met Pro Ile
                165                 170                 175

Glu Ala Phe Leu Arg Leu Asn Glu Glu Leu Glu Glu Arg Gly Glu Arg
            180                 185                 190

Ile Phe Lys Asn Pro Arg Asn Ala Ala Ala Gly Ser Leu Arg Gln Lys

```
              195                 200                 205
Asp Pro Arg Ile Thr Ala Lys Arg Gly Leu Arg Ala Thr Phe Tyr Ala
210                 215                 220

Leu Gly Leu Gly Leu Glu Glu Val Glu Arg Glu Gly Val Ala Thr Gln
225                 230                 235                 240

Phe Ala Leu Leu His Trp Leu Lys Glu Lys Gly Phe Pro Val Glu His
                245                 250                 255

Gly Tyr Ala Arg Ala Val Gly Ala Glu Gly Val Glu Ala Val Tyr Gln
                260                 265                 270

Asp Trp Leu Lys Lys Arg Arg Ala Leu Pro Phe Glu Ala Asp Gly Val
                275                 280                 285

Val Val Lys Leu Asp Glu Leu Ala Leu Trp Arg Glu Leu Gly Tyr Thr
290                 295                 300

Ala Arg Ala Pro Arg Phe Ala Ile Ala Tyr Lys Phe Pro Ala Glu Glu
305                 310                 315                 320

Lys Glu Thr Arg Leu Leu Asp Val Val Phe Gln Val Gly Arg Thr Gly
                325                 330                 335

Arg Val Thr Pro Val Gly Ile Leu Glu Pro Val Phe Leu Glu Gly Ser
                340                 345                 350

Glu Val Ser Arg Val Thr Leu His Asn Glu Ser Tyr Ile Glu Glu Leu
                355                 360                 365

Asp Ile Arg Ile Gly Asp Trp Val Leu Val His Lys Ala Gly Gly Val
370                 375                 380

Ile Pro Glu Val Leu Arg Val Leu Lys Glu Arg Arg Thr Gly Glu Glu
385                 390                 395                 400

Arg Pro Ile Arg Trp Pro Glu Thr Cys Pro Glu Cys Gly His Arg Leu
                405                 410                 415

Leu Lys Glu Gly Lys Val His Arg Cys Pro Asn Pro Leu Cys Pro Ala
                420                 425                 430

Lys Arg Phe Glu Ala Ile Arg His Phe Ala Ser Arg Lys Ala Met Asp
                435                 440                 445

Ile Gln Gly Leu Gly Glu Lys Leu Ile Glu Arg Leu Leu Glu Lys Gly
450                 455                 460

Leu Val Lys Asp Val Ala Asp Leu Tyr Arg Leu Arg Lys Glu Asp Leu
465                 470                 475                 480

Val Gly Leu Glu Arg Met Gly Glu Lys Ser Ala Gln Asn Leu Leu Arg
                485                 490                 495

Gln Ile Glu Glu Ser Lys Lys Arg Gly Leu Glu Arg Leu Leu Tyr Ala
                500                 505                 510

Leu Gly Leu Pro Gly Val Gly Glu Val Leu Ala Arg Asn Leu Ala Ala
                515                 520                 525

Arg Phe Gly Asn Met Asp Arg Leu Leu Glu Ala Ser Leu Glu Glu Leu
                530                 535                 540

Leu Glu Val Glu Glu Val Gly Glu Leu Thr Ala Arg Ala Ile Leu Glu
545                 550                 555                 560

Thr Leu Lys Asp Pro Ala Phe Arg Asp Leu Val Arg Arg Leu Lys Glu
                565                 570                 575

Ala Gly Val Glu Met Glu Ala Lys Glu Lys Gly Gly Glu Ala Leu Lys
                580                 585                 590

Gly Leu Thr Phe Val Ile Thr Gly Glu Leu Ser Arg Pro Arg Glu Glu
                595                 600                 605

Val Lys Ala Leu Leu Arg Arg Leu Gly Ala Lys Val Thr Asp Ser Val
610                 615                 620
```

```
Ser Arg Lys Thr Ser Tyr Leu Val Val Gly Glu Asn Pro Gly Ser Lys
625                 630                 635                 640

Leu Glu Lys Ala Arg Ala Leu Gly Val Pro Thr Leu Thr Glu Glu Glu
                645                 650                 655

Leu Tyr Arg Leu Leu Glu Ala Arg Thr Gly Lys Lys Ala Glu Glu Leu
            660                 665                 670

Val

<210> SEQ ID NO 102
<211> LENGTH: 775
<212> TYPE: PRT
<213> ORGANISM: Artificial Sequence
<220> FEATURE:
<223> OTHER INFORMATION: Synthetic construct

<400> SEQUENCE: 102

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Ala Ile
            35                  40                  45

Asp Asp Val Lys Lys Ile Thr Ala Glu Arg His Gly Lys Val Val Arg
50                  55                  60

Val Val Asp Val Glu Lys Val Lys Lys Phe Leu Gly Arg Pro Ile
65                  70                  75                  80

Glu Val Trp Lys Leu Tyr Phe Glu His Pro Gln Asp Val Pro Ala Ile
                85                  90                  95

Arg Asp Lys Ile Arg Glu His Pro Ala Val Ile Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asn Glu Glu Leu Lys Leu Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Lys Val
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
210                 215                 220

Lys Leu Gly Met Lys Leu Pro Leu Gly Arg Asp Gly Ser Glu Pro Lys
225                 230                 235                 240

Met Gln Arg Leu Gly Asp Ser Leu Ala Val Glu Ile Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Pro His Glu Ile Ala Glu Ala Trp Glu Thr Gly Lys Gly
        290                 295                 300
```

-continued

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ala Arg Leu
            325                 330                 335

Val Gly Gln Pro Leu Trp Asp Val Ser Arg Ser Ser Thr Gly Asn Leu
        340                 345                 350

Val Glu Trp Tyr Leu Leu Arg Lys Ala Tyr Glu Arg Asn Glu Leu Ala
    355                 360                 365

Pro Asn Lys Pro Asp Glu Arg Glu Tyr Glu Arg Leu Arg Glu Ser
370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Thr
            405                 410                 415

His Asn Val Ser Pro Asp Thr Leu Asn Lys Glu Gly Cys Gly Glu Tyr
                420                 425                 430

Asp Val Ala Pro Glu Val Gly His Arg Phe Cys Lys Asp Phe Pro Gly
            435                 440                 445

Phe Ile Pro Ser Leu Leu Gly Ser Leu Leu Asp Glu Arg Gln Lys Ile
    450                 455                 460

Lys Arg Arg Met Lys Ala Ser Lys Asp Pro Ile Glu Arg Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Leu Val Arg Arg Glu
            515                 520                 525

Leu Glu Glu Arg Gly Phe Lys Val Leu Tyr Ile Asp Thr Asp Gly Leu
530                 535                 540

Tyr Ala Thr Ile Pro Gly Glu Lys Asn Trp Glu Ile Lys Arg Arg
545                 550                 555                 560

Ala Leu Glu Phe Val Asn Tyr Ile Asn Ala Lys Leu Pro Gly Leu Leu
            565                 570                 575

Glu Leu Glu Tyr Glu Gly Phe Tyr Thr Arg Gly Phe Phe Val Thr Lys
        580                 585                 590

Lys Lys Tyr Ala Leu Ile Asp Glu Glu Gly Lys Ile Ile Thr Arg Gly
    595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
            645                 650                 655

Pro Pro Glu Lys Leu Val Ile Tyr Glu Gln Ile Thr Arg Pro Leu Asn
        660                 665                 670

Glu Tyr Lys Ala Ile Gly Pro His Val Ala Val Ala Lys Arg Leu Ala
    675                 680                 685

Ala Arg Gly Ile Lys Val Arg Pro Gly Met Val Ile Gly Tyr Val Val
        690                 695                 700

Leu Arg Gly Asp Gly Pro Ile Ser Lys Arg Ala Ile Ala Ala Glu Glu
705                 710                 715                 720

Phe Asp Pro Lys Lys His Lys Tyr Asp Ala Glu Tyr Tyr Ile Glu Asn

```
            725                 730                 735
Gln Val Leu Pro Ala Val Leu Arg Ile Leu Glu Ala Phe Gly Tyr Arg
        740                 745                 750
Lys Glu Asp Leu Arg Trp Gln Lys Thr Lys Gln Val Gly Leu Gly Ala
    755                 760                 765
Trp Leu Lys Val Lys Lys Ser
    770                 775
```

<210> SEQ ID NO 103
<211> LENGTH: 10
<212> TYPE: DNA
<213> ORGANISM: Artificial Sequence
<220> FEATURE:
<223> OTHER INFORMATION: Synthetic construct

<400> SEQUENCE: 103
ggccgcaacc                                                            10

<210> SEQ ID NO 104
<211> LENGTH: 12
<212> TYPE: DNA
<213> ORGANISM: Artificial Sequence
<220> FEATURE:
<223> OTHER INFORMATION: Synthetic construct

<400> SEQUENCE: 104
ggccgcgaat at                                                         12

<210> SEQ ID NO 105
<211> LENGTH: 12
<212> TYPE: DNA
<213> ORGANISM: Artificial Sequence
<220> FEATURE:
<223> OTHER INFORMATION: Synthetic construct

<400> SEQUENCE: 105
ggccgcattc at                                                         12

<210> SEQ ID NO 106
<211> LENGTH: 148
<212> TYPE: DNA
<213> ORGANISM: Artificial Sequence
<220> FEATURE:
<223> OTHER INFORMATION: Synthetic construct

<400> SEQUENCE: 106
cgtaacttga aagtatttcg atttcttggc tttatatatc ttgtggaaag gacgaaacac      60
cggcgaagaa cctcttccca agagttttag agctagaaat agcaagttaa aataaggcta    120
gtccgttatc aacttgaaaa agtggcac                                       148

<210> SEQ ID NO 107
<211> LENGTH: 73
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (27)..(47)
<223> OTHER INFORMATION: n is a, c, g, or t

<400> SEQUENCE: 107
taacttgcta tttctagctc taaaacnnnn nnnnnnnnnn nnnnnnncgg tgtttcgtcc      60
tttccacaag ata                                                      73

<210> SEQ ID NO 108
<211> LENGTH: 104
<212> TYPE: PRT
<213> ORGANISM: Pyrococcus furiosus

<400> SEQUENCE: 108

Met Gly Arg Asp Lys Lys Asn Thr Ala Leu Leu Asp Ile Ala Arg Asp
1               5                   10                  15

Ile Gly Gly Asp Glu Ala Val Glu Val Val Lys Ala Leu Glu Lys Lys
            20                  25                  30

Gly Glu Ala Thr Asp Glu Glu Leu Ala Glu Leu Thr Gly Val Arg Val
        35                  40                  45

Asn Thr Val Arg Lys Ile Leu Tyr Ala Leu Tyr Asp Ala Lys Leu Ala
    50                  55                  60

Thr Phe Arg Arg Val Arg Asp Asp Glu Thr Gly Trp Tyr Tyr Tyr Tyr
65                  70                  75                  80

Trp Arg Ile Asp Thr Lys Arg Leu Pro Glu Val Ile Arg Thr Arg Lys
                85                  90                  95

Leu Gln Glu Leu Glu Lys Leu Lys
            100

<210> SEQ ID NO 109
<211> LENGTH: 66
<212> TYPE: PRT
<213> ORGANISM: Thermotoga maritima

<400> SEQUENCE: 109

Met Arg Gly Thr Val Lys Trp Phe Asp Ser Lys Lys Gly Tyr Gly Phe
1               5                   10                  15

Ile Thr Met Glu Asn Gly Glu Asp Ile Phe Val His Trp Ser Ala Ile
            20                  25                  30

Gln Met Asp Gly Phe Lys Thr Leu Arg Glu Asn Glu Thr Val Glu Phe
        35                  40                  45

Glu Val Gln Lys Gly Thr Lys Gly Pro Gln Ala Val Asn Val Arg Pro
    50                  55                  60

Val Arg
65

<210> SEQ ID NO 110
<211> LENGTH: 97
<212> TYPE: PRT
<213> ORGANISM: Thermotoga maritima

<400> SEQUENCE: 110

Met Arg Arg Leu Asn Arg Lys Asn Asn Glu Ala Leu Lys Lys Leu Asn
1               5                   10                  15

Asp Arg Gln Arg Lys Val Leu Tyr Cys Ile Val Arg Glu Tyr Ile Glu
            20                  25                  30

Asn Lys Lys Pro Val Ser Ser Gln Arg Val Leu Glu Val Ser Asn Ile
        35                  40                  45

Glu Phe Ser Ser Ala Thr Ile Arg Asn Asp Met Lys Lys Leu Glu Tyr
    50                  55                  60

Leu Gly Tyr Ile Tyr Gln Pro His Thr Ser Ala Gly Arg Ile Pro Thr
65                  70                  75                  80

Asp Lys Gly Leu Arg Phe Tyr Tyr Glu Glu Met Leu Lys Ile Ser Lys
                85                  90                  95

Glu

<210> SEQ ID NO 111
<211> LENGTH: 68
<212> TYPE: PRT
<213> ORGANISM: Thermotoga Maritima

<400> SEQUENCE: 111

Met Pro Lys Ser Val Arg Ala Glu Asn Ile Ser Arg Ile Leu Lys Arg
1               5                   10                  15

Ile Met Lys Ser Pro Val Ser Arg Val Glu Leu Ala Glu Leu Gly
            20                  25                  30

Leu Thr Lys Thr Thr Val Gly Glu Ile Ala Lys Ile Phe Leu Glu Lys
        35                  40                  45

Gly Ile Val Val Glu Glu Lys Asp Ser Pro Lys Gly Val Gly Arg Pro
    50                  55                  60

Thr Lys Ser Leu
65

<210> SEQ ID NO 112
<211> LENGTH: 109
<212> TYPE: PRT
<213> ORGANISM: Thermotoga maritima

<400> SEQUENCE: 112

Ile Thr Ala Leu Asn Tyr Leu Lys Glu His Phe Asn Glu Ser Val Asn
1               5                   10                  15

Met Lys Arg Leu Ala Glu Met Val Gly Met Ser Val Ser Thr Phe Tyr
            20                  25                  30

Gln Asn Phe Lys Ile Leu Thr Gly Met Thr Pro Leu Gln Tyr Gln Lys
        35                  40                  45

Lys Leu Arg Leu Cys Glu Ala Arg Lys Leu Leu Met Ala Gly Ser Asp
    50                  55                  60

Val Thr Thr Ala Ala Tyr Gln Val Gly Tyr Glu Ser Leu Ser Gln Phe
65                  70                  75                  80

Ser Arg Glu Tyr Lys Arg Phe Phe Gly Val Ser Pro Ser Gln Asp Ala
            85                  90                  95

Lys Lys Leu Lys Glu Glu Pro Tyr Thr Arg Ile Leu Tyr
        100                 105

<210> SEQ ID NO 113
<211> LENGTH: 849
<212> TYPE: PRT
<213> ORGANISM: Artificial Sequence
<220> FEATURE:
<223> OTHER INFORMATION: Synthetic construct

<400> SEQUENCE: 113

Met Ile Lys Ala Trp Leu Leu Asp Val Asp Tyr Val Thr Glu Asn Asp
1               5                   10                  15

Arg Ala Val Ile Arg Leu Trp Cys Lys Asp Asp Lys Gly Val Phe Val
            20                  25                  30

Ala Tyr Asp Arg Asn Phe Leu Pro Tyr Phe Tyr Val Ile Gly Cys Lys
        35                  40                  45

Ala Glu Asp Val Met Lys Val Lys Val Arg Thr Asn Glu Gly Ile Ile
    50                  55                  60

Thr Pro Leu Lys Val Glu Glu Ile Glu Ala Lys Ser Leu Gly Lys Pro
65                  70                  75                  80

```
Ile Lys Ala Leu Lys Val Tyr Thr Arg His Pro Gln His Val Pro Lys
                85                  90                  95

Leu Arg Glu Glu Ile Lys Lys Phe Ala Glu Val Arg Glu Ala Asp Ile
            100                 105                 110

Pro Phe Ala Tyr Arg Tyr Leu Ile Asp Lys Asp Leu Ala Cys Met Asp
        115                 120                 125

Gly Ile Glu Ile Glu Pro Ile Ala Val Lys Glu Gly Val Leu Arg Ala
    130                 135                 140

Tyr Glu Val Arg Ser Val Arg Arg Val Glu Lys Lys Gly Phe Pro Asp
145                 150                 155                 160

Leu Lys Ile Leu Ala Phe Asp Cys Glu Met Leu Ala Gln Phe Met Pro
                165                 170                 175

Asp Pro Glu Lys Asp Pro Ile Ile Ala Ile Ala Val Lys Cys Gly Asp
            180                 185                 190

Phe Glu Glu Val Leu His Gly Asp Glu Arg Asp Ile Leu Arg Arg Phe
        195                 200                 205

Val Ser Ile Ile Lys Glu Gln Asp Pro Asp Ile Ile Val Gly Tyr Asn
    210                 215                 220

Gln Asp Asn Phe Asp Trp Pro Tyr Val Lys Lys Arg Ala Glu Lys Phe
225                 230                 235                 240

Gly Ile Arg Leu Asp Ile Gly Arg Asp Arg Ser Glu Ile Ser Phe Arg
                245                 250                 255

Gly Gly Arg Pro Lys Ile Ala Gly Arg Leu Asn Val Asp Leu Tyr Asp
            260                 265                 270

Ile Ala Leu Lys Ile Pro Asp Val Lys Ile Lys Thr Leu Lys Lys Val
        275                 280                 285

Ala Glu Phe Leu Gly Ala Lys Val Glu Glu Asp Ile Glu Gly Arg
    290                 295                 300

Asp Ile Tyr Lys Cys Trp Met Arg Gly Glu Lys Glu Lys Val Phe Lys
305                 310                 315                 320

His Val Leu Asn Asp Val Leu Thr Thr Tyr Arg Leu Ala Leu Glu Leu
                325                 330                 335

Leu Pro Met His Tyr Glu Leu Ser Arg Met Ile Arg Leu Pro Leu Asp
            340                 345                 350

Asp Val Ala Arg Leu Gly Arg Gly Lys Gln Val Asp Tyr Phe Leu Leu
        355                 360                 365

Ser Glu Ala Lys Lys Ile Asn Glu Ile Ala Pro Asn Pro Glu Ile
    370                 375                 380

Glu Glu Ser Tyr Glu Gly Ala Phe Val Leu Glu Pro Ala Arg Gly Leu
385                 390                 395                 400

His Glu Asn Val Ala Cys Leu Asp Phe Ala Ser Met Tyr Pro Ser Ile
                405                 410                 415

Met Ile Asn Phe Asn Ile Ser Pro Asp Thr Leu Val Lys Gly Glu Cys
            420                 425                 430

Glu Asp Cys Tyr Val Ala Pro Glu Val Gly His Lys Phe Arg Lys Ser
        435                 440                 445

Pro Asp Gly Phe Phe Lys Arg Ile Leu Lys Met Leu Ile Glu Lys Arg
    450                 455                 460

Arg Glu Met Lys Arg Gln Met Lys Glu Leu Asp Pro Asp Ser Glu Asp
465                 470                 475                 480

Tyr Lys Leu Leu Asp Ile Lys Gln Gln Thr Leu Lys Val Leu Thr Asn
                485                 490                 495
```

Ser Phe Tyr Gly Tyr Thr Gly Trp Asn Leu Ala Arg Trp Tyr Cys Arg
                500                 505                 510

Glu Cys Ala Glu Ala Thr Thr Ala Trp Gly Arg Tyr Phe Ile Lys Arg
            515                 520                 525

Ala Val Lys Ile Ala Glu Ser Met Gly Phe Glu Val Leu Tyr Gly Asp
        530                 535                 540

Thr Asp Ser Leu Phe Ile Lys Lys Asn Lys Leu Asn Leu Lys Asp Leu
545                 550                 555                 560

Glu Lys Glu Cys Leu Lys Leu Ile Asp Val Ile Ser Lys Glu Leu Pro
                565                 570                 575

Ile Gln Leu Glu Ile Asp Glu Phe Tyr Lys Ala Ile Phe Phe Val Glu
            580                 585                 590

Lys Lys Arg Tyr Ala Gly Leu Thr Asp Asp Arg Ile Val Val Lys
        595                 600                 605

Gly Leu Glu Val Arg Arg Gly Asp Trp Cys Glu Leu Ala Lys Arg Val
    610                 615                 620

Gln Arg Glu Val Ile Glu Ile Leu Arg Glu Arg Asn Pro Asp Lys
625                 630                 635                 640

Ala Leu Lys Phe Val Lys Asn Val Ile Glu Glu Ile Lys Glu Gly Lys
                645                 650                 655

Phe Lys Leu Glu Asp Tyr Val Ile Tyr Lys Gly Leu Thr Lys Lys Pro
            660                 665                 670

Asp Lys Tyr Glu Ser Lys Gln Ala His Val Lys Ala Ala Leu Arg Ala
        675                 680                 685

Met Glu Met Gly Ile Tyr Tyr Pro Ile Gly Thr Lys Val Gly Phe Val
    690                 695                 700

Ile Val Lys Gly Gly Ser Ile Ser Asp Arg Ala Tyr Pro Ile Glu
705                 710                 715                 720

Leu Ile Glu Glu Phe Asp Gly Glu Asn Leu Lys Ile Arg Thr Pro Ser
                725                 730                 735

Gly Ile Met Val Lys Lys Ile Asp Lys Asp Tyr Tyr Ile Asp His Gln
            740                 745                 750

Ile Ile Pro Ala Val Met Arg Ile Leu Glu Arg Phe Gly Tyr Thr Glu
        755                 760                 765

Ala Ser Leu Lys Thr Thr Ile Gln Lys Thr Leu Phe Asp Phe Thr Gly
    770                 775                 780

Thr Gly Gly Gly Gly Lys Arg Arg Pro Thr Ile Asn Asp Val Ala Lys
785                 790                 795                 800

Leu Ala Gly Val Ser Ile Ser Thr Val Ser Arg Tyr Leu Lys Asp Pro
                805                 810                 815

Ser Gln Val Ser Glu Lys Leu Gly Glu Arg Ile Arg Glu Ala Ile Lys
            820                 825                 830

Lys Leu Gly Tyr Lys Pro Asn Lys Ile Ala Gln Gly Leu Arg Thr Gly
        835                 840                 845

Asp

<210> SEQ ID NO 114
<211> LENGTH: 846
<212> TYPE: PRT
<213> ORGANISM: Artificial Sequence
<220> FEATURE:
<223> OTHER INFORMATION: Synthetic construct

<400> SEQUENCE: 114

Met Ile Lys Ala Trp Leu Leu Asp Val Asp Tyr Val Thr Glu Asn Asp

-continued

```
1               5                   10                  15
Arg Ala Val Ile Arg Leu Trp Cys Lys Asp Asp Lys Gly Val Phe Val
                20                  25                  30
Ala Tyr Asp Arg Asn Phe Leu Pro Tyr Phe Tyr Val Ile Gly Cys Lys
                35                  40                  45
Ala Glu Asp Val Met Lys Val Lys Val Arg Thr Asn Glu Gly Ile Ile
                50                  55                  60
Thr Pro Leu Lys Val Glu Glu Ile Glu Ala Lys Ser Leu Gly Lys Pro
65                  70                  75                  80
Ile Lys Ala Leu Lys Val Tyr Thr Arg His Pro Gln His Val Pro Lys
                85                  90                  95
Leu Arg Glu Glu Ile Lys Lys Phe Ala Glu Val Arg Glu Ala Asp Ile
                100                 105                 110
Pro Phe Ala Tyr Arg Tyr Leu Ile Asp Lys Asp Leu Ala Cys Met Asp
                115                 120                 125
Gly Ile Glu Ile Glu Pro Ile Ala Val Lys Glu Gly Val Leu Arg Ala
                130                 135                 140
Tyr Glu Val Arg Ser Val Arg Arg Val Glu Lys Lys Gly Phe Pro Asp
145                 150                 155                 160
Leu Lys Ile Leu Ala Phe Asp Cys Glu Met Leu Ala Gln Phe Met Pro
                165                 170                 175
Asp Pro Glu Lys Asp Pro Ile Ile Ala Ile Ala Val Lys Cys Gly Asp
                180                 185                 190
Phe Glu Glu Val Leu His Gly Asp Glu Arg Asp Ile Leu Arg Arg Phe
                195                 200                 205
Val Ser Ile Ile Lys Glu Gln Asp Pro Asp Ile Ile Val Gly Tyr Asn
210                 215                 220
Gln Asp Asn Phe Asp Trp Pro Tyr Val Lys Lys Arg Ala Glu Lys Phe
225                 230                 235                 240
Gly Ile Arg Leu Asp Ile Gly Arg Asp Arg Ser Glu Ile Ser Phe Arg
                245                 250                 255
Gly Gly Arg Pro Lys Ile Ala Gly Arg Leu Asn Val Asp Leu Tyr Asp
                260                 265                 270
Ile Ala Leu Lys Ile Pro Asp Val Lys Ile Lys Thr Leu Lys Lys Val
                275                 280                 285
Ala Glu Phe Leu Gly Ala Lys Val Glu Glu Asp Ile Glu Gly Arg
                290                 295                 300
Asp Ile Tyr Lys Cys Trp Met Arg Gly Glu Lys Glu Lys Val Phe Lys
305                 310                 315                 320
His Val Leu Asn Asp Val Leu Thr Thr Tyr Arg Leu Ala Leu Glu Leu
                325                 330                 335
Leu Pro Met His Tyr Glu Leu Ser Arg Met Ile Arg Leu Pro Leu Asp
                340                 345                 350
Asp Val Ala Arg Leu Gly Arg Gly Lys Gln Val Asp Tyr Phe Leu Leu
                355                 360                 365
Ser Glu Ala Lys Lys Ile Asn Glu Ile Ala Pro Asn Pro Glu Ile
                370                 375                 380
Glu Glu Ser Tyr Glu Gly Ala Phe Val Leu Glu Pro Ala Arg Gly Leu
385                 390                 395                 400
His Glu Asn Val Ala Cys Leu Asp Phe Ala Ser Met Tyr Pro Ser Ile
                405                 410                 415
Met Ile Asn Phe Asn Ile Ser Pro Asp Thr Leu Val Lys Gly Glu Cys
                420                 425                 430
```

```
Glu Asp Cys Tyr Val Ala Pro Glu Val Gly His Lys Phe Arg Lys Ser
        435                 440                 445

Pro Asp Gly Phe Phe Lys Arg Ile Leu Lys Met Leu Ile Glu Lys Arg
    450                 455                 460

Arg Glu Met Lys Arg Gln Met Lys Glu Leu Asp Pro Asp Ser Glu Asp
465                 470                 475                 480

Tyr Lys Leu Leu Asp Ile Lys Gln Gln Thr Leu Lys Val Leu Thr Asn
                485                 490                 495

Ser Phe Tyr Gly Tyr Thr Gly Trp Asn Leu Ala Arg Trp Tyr Cys Arg
                500                 505                 510

Glu Cys Ala Glu Ala Thr Thr Ala Trp Gly Arg Tyr Phe Ile Lys Arg
            515                 520                 525

Ala Val Lys Ile Ala Glu Ser Met Gly Phe Glu Val Leu Tyr Gly Asp
            530                 535                 540

Thr Asp Ser Leu Phe Ile Lys Lys Asn Lys Leu Asn Leu Lys Asp Leu
545                 550                 555                 560

Glu Lys Glu Cys Leu Lys Leu Ile Asp Val Ile Ser Lys Glu Leu Pro
                565                 570                 575

Ile Gln Leu Glu Ile Asp Glu Phe Tyr Lys Ala Ile Phe Phe Val Glu
                580                 585                 590

Lys Lys Arg Tyr Ala Gly Leu Thr Asp Asp Arg Ile Val Val Lys
            595                 600                 605

Gly Leu Glu Val Arg Arg Gly Asp Trp Cys Glu Leu Ala Lys Arg Val
    610                 615                 620

Gln Arg Glu Val Ile Glu Ile Leu Arg Glu Arg Asn Pro Asp Lys
625                 630                 635                 640

Ala Leu Lys Phe Val Lys Asn Val Ile Glu Glu Ile Lys Glu Gly Lys
                645                 650                 655

Phe Lys Leu Glu Asp Tyr Val Ile Tyr Lys Gly Leu Thr Lys Lys Pro
                660                 665                 670

Asp Lys Tyr Glu Ser Lys Gln Ala His Val Lys Ala Ala Leu Arg Ala
            675                 680                 685

Met Glu Met Gly Ile Tyr Tyr Pro Ile Gly Thr Lys Val Gly Phe Val
    690                 695                 700

Ile Val Lys Gly Gly Ser Ile Ser Asp Arg Ala Tyr Pro Ile Glu
705                 710                 715                 720

Leu Ile Glu Glu Phe Asp Gly Glu Asn Leu Lys Ile Arg Thr Pro Ser
                725                 730                 735

Gly Ile Met Val Lys Lys Ile Asp Lys Asp Tyr Tyr Ile Asp His Gln
            740                 745                 750

Ile Ile Pro Ala Val Met Arg Ile Leu Glu Arg Phe Gly Tyr Thr Glu
            755                 760                 765

Ala Ser Leu Lys Thr Thr Ile Gln Lys Thr Leu Phe Asp Phe Thr Gly
    770                 775                 780

Thr Gly Gly Gly Gly Ala Ser Ile Lys Asp Val Ala Lys Leu Ala Gly
785                 790                 795                 800

Val Ser Ile Ala Thr Val Ser Arg Val Ile Asn Gly Tyr Asn Asn Val
                805                 810                 815

Ser Glu Glu Thr Arg Lys Lys Val Ile Asp Ala Ile Arg Lys Leu Asn
            820                 825                 830

Tyr His Pro Val Tyr Ala Val Lys Gly Ala Val Leu Lys Arg
    835                 840                 845
```

<210> SEQ ID NO 115
<211> LENGTH: 888
<212> TYPE: PRT
<213> ORGANISM: Artificial Sequence
<220> FEATURE:
<223> OTHER INFORMATION: Synthetic construct

<400> SEQUENCE: 115

```
Met Ile Lys Ala Trp Leu Leu Asp Val Asp Tyr Val Thr Glu Asn Asp
1               5                   10                  15

Arg Ala Val Ile Arg Leu Trp Cys Lys Asp Lys Gly Val Phe Val
            20                  25                  30

Ala Tyr Asp Arg Asn Phe Leu Pro Tyr Phe Tyr Val Ile Gly Cys Lys
        35                  40                  45

Ala Glu Asp Val Met Lys Val Lys Val Arg Thr Asn Glu Gly Ile Ile
    50                  55                      60

Thr Pro Leu Lys Val Glu Glu Ile Glu Ala Lys Ser Leu Gly Lys Pro
65                  70                  75                  80

Ile Lys Ala Leu Lys Val Tyr Thr Arg His Pro Gln His Val Pro Lys
                85                  90                  95

Leu Arg Glu Glu Ile Lys Lys Phe Ala Glu Val Arg Glu Ala Asp Ile
            100                 105                 110

Pro Phe Ala Tyr Arg Tyr Leu Ile Asp Lys Asp Leu Ala Cys Met Asp
        115                 120                 125

Gly Ile Glu Ile Glu Pro Ile Ala Val Lys Glu Gly Val Leu Arg Ala
    130                 135                 140

Tyr Glu Val Arg Ser Val Arg Arg Val Glu Lys Lys Gly Phe Pro Asp
145                 150                 155                 160

Leu Lys Ile Leu Ala Phe Asp Cys Glu Met Leu Ala Gln Phe Met Pro
                165                 170                 175

Asp Pro Glu Lys Asp Pro Ile Ile Ala Ile Ala Val Lys Cys Gly Asp
            180                 185                 190

Phe Glu Glu Val Leu His Gly Asp Glu Arg Asp Ile Leu Arg Arg Phe
        195                 200                 205

Val Ser Ile Ile Lys Glu Gln Asp Pro Asp Ile Ile Val Gly Tyr Asn
    210                 215                     220

Gln Asp Asn Phe Asp Trp Pro Tyr Val Lys Lys Arg Ala Glu Lys Phe
225                 230                 235                 240

Gly Ile Arg Leu Asp Ile Gly Arg Asp Arg Ser Glu Ile Ser Phe Arg
                245                 250                 255

Gly Gly Arg Pro Lys Ile Ala Gly Arg Leu Asn Val Asp Leu Tyr Asp
            260                 265                 270

Ile Ala Leu Lys Ile Pro Asp Val Lys Ile Lys Thr Leu Lys Lys Val
        275                 280                 285

Ala Glu Phe Leu Gly Ala Lys Val Glu Glu Glu Asp Ile Glu Gly Arg
    290                 295                 300

Asp Ile Tyr Lys Cys Trp Met Arg Gly Glu Lys Glu Lys Val Phe Lys
305                 310                 315                 320

His Val Leu Asn Asp Val Leu Thr Thr Tyr Arg Leu Ala Leu Glu Leu
                325                 330                 335

Leu Pro Met His Tyr Glu Leu Ser Arg Met Ile Arg Leu Pro Leu Asp
            340                 345                 350

Asp Val Ala Arg Leu Gly Arg Gly Lys Gln Val Asp Tyr Phe Leu Leu
        355                 360                 365
```

```
Ser Glu Ala Lys Lys Ile Asn Glu Ile Ala Pro Asn Pro Pro Glu Ile
    370                 375                 380

Glu Glu Ser Tyr Glu Gly Ala Phe Val Leu Glu Pro Ala Arg Gly Leu
385                 390                 395                 400

His Glu Asn Val Ala Cys Leu Asp Phe Ala Ser Met Tyr Pro Ser Ile
                405                 410                 415

Met Ile Asn Phe Asn Ile Ser Pro Asp Thr Leu Val Lys Gly Glu Cys
            420                 425                 430

Glu Asp Cys Tyr Val Ala Pro Glu Val Gly His Lys Phe Arg Lys Ser
        435                 440                 445

Pro Asp Gly Phe Phe Lys Arg Ile Leu Lys Met Leu Ile Glu Lys Arg
    450                 455                 460

Arg Glu Met Lys Arg Gln Met Lys Glu Leu Asp Pro Asp Ser Glu Asp
465                 470                 475                 480

Tyr Lys Leu Leu Asp Ile Lys Gln Gln Thr Leu Lys Val Leu Thr Asn
                485                 490                 495

Ser Phe Tyr Gly Tyr Thr Gly Trp Asn Leu Ala Arg Trp Tyr Cys Arg
            500                 505                 510

Glu Cys Ala Glu Ala Thr Thr Ala Trp Gly Arg Tyr Phe Ile Lys Arg
        515                 520                 525

Ala Val Lys Ile Ala Glu Ser Met Gly Phe Glu Val Leu Tyr Gly Asp
    530                 535                 540

Thr Asp Ser Leu Phe Ile Lys Lys Asn Lys Leu Asn Leu Lys Asp Leu
545                 550                 555                 560

Glu Lys Glu Cys Leu Lys Leu Ile Asp Val Ile Ser Lys Glu Leu Pro
                565                 570                 575

Ile Gln Leu Glu Ile Asp Glu Phe Tyr Lys Ala Ile Phe Phe Val Glu
            580                 585                 590

Lys Lys Arg Tyr Ala Gly Leu Thr Asp Asp Asp Arg Ile Val Val Lys
        595                 600                 605

Gly Leu Glu Val Arg Arg Gly Asp Trp Cys Glu Leu Ala Lys Arg Val
    610                 615                 620

Gln Arg Glu Val Ile Glu Ile Ile Leu Arg Glu Arg Asn Pro Asp Lys
625                 630                 635                 640

Ala Leu Lys Phe Val Lys Asn Val Ile Glu Glu Ile Lys Glu Gly Lys
                645                 650                 655

Phe Lys Leu Glu Asp Tyr Val Ile Tyr Lys Gly Leu Thr Lys Lys Pro
            660                 665                 670

Asp Lys Tyr Glu Ser Lys Gln Ala His Val Lys Ala Ala Leu Arg Ala
        675                 680                 685

Met Glu Met Gly Ile Tyr Tyr Pro Ile Gly Thr Lys Val Gly Phe Val
    690                 695                 700

Ile Val Lys Gly Gly Gly Ser Ile Ser Asp Arg Ala Tyr Pro Ile Glu
705                 710                 715                 720

Leu Ile Glu Glu Phe Asp Gly Glu Asn Leu Lys Ile Arg Thr Pro Ser
                725                 730                 735

Gly Ile Met Val Lys Lys Ile Asp Lys Asp Tyr Tyr Ile Asp His Gln
            740                 745                 750

Ile Ile Pro Ala Val Met Arg Ile Leu Glu Arg Phe Gly Tyr Thr Glu
        755                 760                 765

Ala Ser Leu Lys Thr Thr Ile Gln Lys Thr Leu Phe Asp Phe Thr Gly
    770                 775                 780

Thr Gly Gly Gly Gly Glu Glu Ile Lys Glu Ile Met Lys Ser His Thr
```

```
                            785                 790                 795                 800
Leu Gly Asn Pro Val Arg Leu Gly Ile Met Ile Tyr Leu Phe Pro Arg
                    805                 810                 815

Arg Arg Ala Pro Phe Ser His Ile Gln Lys Ala Leu Asp Leu Thr Pro
                820                 825                 830

Gly Asn Leu Asp Ser His Ile Lys Val Leu Glu Lys His Gly Phe Val
            835                 840                 845

Arg Thr Tyr Lys Val Ile Ala Asp Arg Pro Arg Thr Met Val Glu Ile
        850                 855                 860

Thr Asp Tyr Gly Met Glu Glu Thr Arg Lys Phe Leu Ser His Leu Lys
865                 870                 875                 880

Thr Val Ile Asp Ala Ile His Phe
                885

<210> SEQ ID NO 116
<211> LENGTH: 959
<212> TYPE: PRT
<213> ORGANISM: Artificial Sequence
<220> FEATURE:
<223> OTHER INFORMATION: Synthetic construct

<400> SEQUENCE: 116

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Thr Tyr Gly Val Ala Arg Met Leu Val Arg Phe Ile Lys Asp
        35                  40                  45

His Ile Ile Val Gly Lys Asp Tyr Val Ala Val Ala Phe Asp Lys Lys
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
        115                 120                 125

Asp Glu Ile Phe Ile Val Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205

Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
```

-continued

```
                260                 265                 270
Pro Leu Leu Lys Glu Leu Glu Phe Ala Ser Ile Met Lys Glu Leu Gln
            275                 280                 285
Leu Tyr Glu Glu Ser Glu Pro Val Gly Tyr Arg Ile Val Lys Asp Leu
            290                 295                 300
Val Glu Phe Glu Lys Leu Ile Glu Lys Leu Arg Glu Ser Pro Ser Phe
305                 310                 315                 320
Ala Ile Asp Leu Glu Thr Ser Ser Leu Asp Pro Phe Asp Cys Asp Ile
            325                 330                 335
Val Gly Ile Ser Val Ser Phe Lys Pro Lys Glu Ala Tyr Tyr Ile Pro
            340                 345                 350
Leu His His Arg Asn Ala Gln Asn Leu Asp Glu Lys Glu Val Leu Lys
            355                 360                 365
Lys Leu Lys Glu Ile Leu Glu Asp Pro Gly Ala Lys Ile Val Gly Gln
            370                 375                 380
Asn Leu Lys Phe Asp Tyr Lys Val Leu Met Val Lys Gly Val Glu Pro
385                 390                 395                 400
Val Pro Pro His Phe Asp Thr Met Ile Ala Ala Tyr Leu Leu Glu Pro
            405                 410                 415
Asn Glu Lys Lys Phe Asn Leu Asp Asp Leu Ala Leu Lys Phe Leu Gly
            420                 425                 430
Tyr Lys Met Thr Ser Tyr Gln Glu Leu Met Ser Phe Ser Ser Pro Leu
            435                 440                 445
Phe Gly Phe Ser Phe Ala Asp Val Pro Val Glu Lys Ala Ala Asn Tyr
            450                 455                 460
Ser Cys Glu Asp Ala Asp Ile Thr Tyr Arg Leu Tyr Lys Ile Leu Ser
465                 470                 475                 480
Leu Lys Leu His Glu Ala Asp Leu Glu Asn Val Phe Tyr Lys Ile Glu
            485                 490                 495
Met Pro Leu Val Ser Val Leu Ala Arg Met Glu Leu Asn Gly Val Tyr
            500                 505                 510
Val Asp Thr Glu Phe Leu Lys Lys Leu Ser Glu Glu Tyr Gly Lys Lys
            515                 520                 525
Leu Glu Glu Leu Ala Glu Glu Ile Tyr Arg Ile Ala Gly Glu Pro Phe
            530                 535                 540
Asn Ile Asn Ser Pro Lys Gln Val Ser Arg Ile Leu Phe Glu Lys Leu
545                 550                 555                 560
Gly Ile Lys Pro Arg Gly Lys Thr Thr Lys Thr Gly Asp Tyr Ser Thr
            565                 570                 575
Arg Ile Glu Val Leu Glu Glu Leu Ala Gly Glu His Glu Ile Ile Pro
            580                 585                 590
Leu Ile Leu Glu Tyr Arg Lys Ile Gln Lys Leu Lys Ser Thr Tyr Ile
            595                 600                 605
Asp Ala Leu Pro Lys Met Val Asn Pro Lys Thr Gly Arg Ile His Ala
            610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
            645                 650                 655
Arg Lys Ala Ile Val Pro Gln Asp Pro Asn Trp Trp Ile Val Ser Ala
            660                 665                 670
Asp Tyr Ser Gln Ile Glu Leu Arg Ile Leu Ala His Leu Ser Gly Asp
            675                 680                 685
```

-continued

Glu Asn Leu Leu Lys Ala Phe Glu Glu Gly Ile Asp Val His Thr Leu
    690                 695                 700

Thr Ala Ser Arg Ile Phe Asn Val Lys Pro Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
        835                 840                 845

His Asp Glu Leu Val Phe Glu Val Pro Asp Glu Glu Lys Asp Ala Leu
850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser Gly Thr Gly
                885                 890                 895

Gly Gly Gly Lys Arg Arg Pro Thr Ile Asn Asp Val Ala Lys Leu Ala
            900                 905                 910

Gly Val Ser Ile Ser Thr Val Ser Arg Tyr Leu Lys Asp Pro Ser Gln
        915                 920                 925

Val Ser Glu Lys Leu Gly Glu Arg Ile Arg Glu Ala Ile Lys Lys Leu
930                 935                 940

Gly Tyr Lys Pro Asn Lys Ile Ala Gln Gly Leu Arg Thr Gly Asp
945                 950                 955

<210> SEQ ID NO 117
<211> LENGTH: 848
<212> TYPE: PRT
<213> ORGANISM: Artificial Sequence
<220> FEATURE:
<223> OTHER INFORMATION: Synthetic construct

<400> SEQUENCE: 117

Met Ile Lys Ala Trp Leu Leu Asp Val Asp Tyr Val Thr Glu Asn Asp
1               5                   10                  15

Arg Ala Val Ile Arg Leu Trp Cys Lys Asp Asp Lys Gly Val Phe Val
                20                  25                  30

Ala Tyr Asp Arg Asn Phe Leu Pro Tyr Phe Tyr Val Ile Gly Cys Lys
            35                  40                  45

Ala Glu Asp Val Met Lys Val Lys Val Arg Thr Asn Glu Gly Ile Ile
        50                  55                  60

Thr Pro Leu Lys Val Glu Glu Ile Glu Ala Lys Ser Leu Gly Lys Pro
65                  70                  75                  80

Ile Lys Ala Leu Lys Val Tyr Thr Arg His Pro Gln His Val Pro Lys
                85                  90                  95

```
Leu Arg Glu Glu Ile Lys Lys Phe Ala Glu Val Arg Glu Ala Asp Ile
            100                 105                 110

Pro Phe Ala Tyr Arg Tyr Leu Ile Asp Lys Asp Leu Ala Cys Met Asp
            115                 120                 125

Gly Ile Glu Ile Glu Pro Ile Ala Val Lys Gly Val Leu Arg Ala
            130                 135                 140

Tyr Glu Val Arg Ser Val Arg Arg Val Glu Lys Lys Gly Phe Pro Asp
145                 150                 155                 160

Leu Lys Ile Leu Ala Phe Asp Cys Glu Met Leu Ala Gln Phe Met Pro
                        165                 170                 175

Asp Pro Glu Lys Asp Pro Ile Ile Ala Ile Ala Val Lys Cys Gly Asp
                    180                 185                 190

Phe Glu Glu Val Leu His Gly Asp Glu Arg Asp Ile Leu Arg Arg Phe
                195                 200                 205

Val Ser Ile Ile Lys Glu Gln Asp Pro Asp Ile Ile Val Gly Tyr Asn
    210                 215                 220

Gln Asp Asn Phe Asp Trp Pro Tyr Val Lys Lys Arg Ala Glu Lys Phe
225                 230                 235                 240

Gly Ile Arg Leu Asp Ile Gly Arg Asp Arg Ser Glu Ile Ser Phe Arg
                245                 250                 255

Gly Gly Arg Pro Lys Ile Ala Gly Arg Leu Asn Val Asp Leu Tyr Asp
            260                 265                 270

Ile Ala Leu Lys Ile Pro Asp Val Lys Ile Lys Thr Leu Lys Lys Val
                275                 280                 285

Ala Glu Phe Leu Gly Ala Lys Val Glu Glu Glu Asp Ile Glu Gly Arg
            290                 295                 300

Asp Ile Tyr Lys Cys Trp Met Arg Gly Glu Lys Glu Lys Val Phe Lys
305                 310                 315                 320

His Val Leu Asn Asp Val Leu Thr Thr Tyr Arg Leu Ala Leu Glu Leu
                    325                 330                 335

Leu Pro Met His Tyr Glu Leu Ser Arg Met Ile Arg Leu Pro Leu Asp
                340                 345                 350

Asp Val Ala Arg Leu Gly Arg Gly Lys Gln Val Asp Tyr Phe Leu Leu
            355                 360                 365

Ser Glu Ala Lys Lys Ile Asn Glu Ile Ala Pro Asn Pro Glu Ile
    370                 375                 380

Glu Glu Ser Tyr Glu Gly Ala Phe Val Leu Glu Pro Ala Arg Gly Leu
385                 390                 395                 400

His Glu Asn Val Ala Cys Leu Asp Phe Ala Ser Met Tyr Pro Ser Ile
                    405                 410                 415

Met Ile Asn Phe Asn Ile Ser Pro Asp Thr Leu Val Lys Gly Glu Cys
                420                 425                 430

Glu Asp Cys Tyr Val Ala Pro Glu Val Gly His Lys Phe Arg Lys Ser
            435                 440                 445

Pro Asp Gly Phe Phe Lys Arg Ile Leu Lys Met Leu Ile Glu Lys Arg
            450                 455                 460

Arg Glu Met Lys Arg Gln Met Lys Glu Leu Asp Pro Asp Ser Glu Asp
465                 470                 475                 480

Tyr Lys Leu Leu Asp Ile Lys Gln Gln Thr Leu Lys Val Leu Thr Asn
                    485                 490                 495

Ser Phe Tyr Gly Tyr Thr Gly Trp Asn Leu Ala Arg Trp Tyr Cys Arg
            500                 505                 510
```

```
Glu Cys Ala Glu Ala Thr Thr Ala Trp Gly Arg Tyr Phe Ile Lys Arg
            515                 520                 525

Ala Val Lys Ile Ala Glu Ser Met Gly Phe Glu Val Leu Tyr Gly Asp
530                 535                 540

Thr Asp Ser Leu Phe Ile Lys Lys Asn Lys Leu Asn Leu Lys Asp Leu
545                 550                 555                 560

Glu Lys Glu Cys Leu Lys Leu Ile Asp Val Ile Ser Lys Glu Leu Pro
                565                 570                 575

Ile Gln Leu Glu Ile Asp Glu Phe Tyr Lys Ala Ile Phe Phe Val Glu
            580                 585                 590

Lys Lys Arg Tyr Ala Gly Leu Thr Asp Asp Arg Ile Val Val Lys
        595                 600                 605

Gly Leu Glu Val Arg Arg Gly Asp Trp Cys Glu Leu Ala Lys Arg Val
610                 615                 620

Gln Arg Glu Val Ile Glu Ile Leu Arg Glu Arg Asn Pro Asp Lys
625                 630                 635                 640

Ala Leu Lys Phe Val Lys Asn Val Ile Glu Ile Lys Glu Gly Lys
                645                 650                 655

Phe Lys Leu Glu Asp Tyr Val Ile Tyr Lys Gly Leu Thr Lys Lys Pro
            660                 665                 670

Asp Lys Tyr Glu Ser Lys Gln Ala His Val Lys Ala Ala Leu Arg Ala
        675                 680                 685

Met Glu Met Gly Ile Tyr Tyr Pro Ile Gly Thr Lys Val Gly Phe Val
690                 695                 700

Ile Val Lys Gly Gly Ser Ile Ser Asp Arg Ala Tyr Pro Ile Glu
705                 710                 715                 720

Leu Ile Glu Glu Phe Asp Gly Glu Asn Leu Lys Ile Arg Thr Pro Ser
                725                 730                 735

Gly Ile Met Val Lys Lys Ile Asp Lys Asp Tyr Tyr Ile Asp His Gln
            740                 745                 750

Ile Ile Pro Ala Val Met Arg Ile Leu Glu Arg Phe Gly Tyr Thr Glu
        755                 760                 765

Ala Ser Leu Lys Thr Thr Ile Gln Lys Thr Leu Phe Asp Phe Thr Gly
770                 775                 780

Thr Gly Gly Gly Lys Ser Leu Gln Arg Phe Leu Arg Arg Asn Thr
785                 790                 795                 800

Thr Ser Ile Lys His Leu Ser Glu Ile Thr Gly Val Ala Arg Asn Arg
                805                 810                 815

Leu Ser Asp Ile Leu Asn Gly Lys Thr Gln Lys Ile Arg Gly Glu Thr
            820                 825                 830

Leu Arg Lys Ile Ala Lys Ala Phe Glu Lys Ser Asn Ile Leu Ser Phe
        835                 840                 845

<210> SEQ ID NO 118
<211> LENGTH: 998
<212> TYPE: PRT
<213> ORGANISM: Artificial Sequence
<220> FEATURE:
<223> OTHER INFORMATION: Synthetic construct

<400> SEQUENCE: 118

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30
```

-continued

Asn Ala Thr Tyr Gly Val Ala Arg Met Leu Val Arg Phe Ile Lys Asp
                35                  40                  45

His Ile Ile Val Gly Lys Asp Tyr Val Ala Val Ala Phe Asp Lys Lys
 50                  55                  60

Ala Ala Thr Phe Arg His Lys Leu Leu Glu Thr Tyr Lys Ala Gln Arg
 65                  70                  75                  80

Pro Lys Thr Pro Asp Leu Leu Ile Gln Gln Leu Pro Tyr Ile Lys Lys
                 85                  90                  95

Leu Val Glu Ala Leu Gly Met Lys Val Leu Val Glu Gly Tyr Glu
                100                 105                 110

Ala Asp Asp Ile Ile Ala Thr Leu Ala Val Lys Gly Leu Pro Leu Phe
                115                 120                 125

Asp Glu Ile Phe Ile Val Thr Gly Asp Lys Asp Met Leu Gln Leu Val
130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
                180                 185                 190

Ile Pro Gly Val Thr Gly Ile Gly Glu Lys Thr Ala Val Gln Leu Leu
                195                 200                 205

Glu Lys Tyr Lys Asp Leu Glu Asp Ile Leu Asn His Val Arg Glu Leu
                210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
                260                 265                 270

Pro Leu Leu Lys Glu Leu Glu Phe Ala Ser Ile Met Lys Glu Leu Gln
                275                 280                 285

Leu Tyr Glu Glu Ser Glu Pro Val Gly Tyr Arg Ile Val Lys Asp Leu
                290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
                340                 345                 350

Leu His His Arg Asn Ala Gln Asn Leu Asp Glu Lys Glu Val Leu Lys
                355                 360                 365

Lys Leu Lys Glu Ile Leu Glu Asp Pro Gly Ala Lys Ile Val Gly Gln
                370                 375                 380

Asn Leu Lys Phe Asp Tyr Lys Val Leu Met Val Lys Gly Val Glu Pro
385                 390                 395                 400

Val Pro Pro His Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Ser Pro Leu
                435                 440                 445

Phe Gly Phe Ser Phe Ala Asp Val Pro Val Glu Lys Ala Ala Asn Tyr

-continued

```
                450                 455                 460
Ser Cys Glu Asp Ala Asp Ile Thr Tyr Arg Leu Tyr Lys Ile Leu Ser
465                 470                 475                 480

Leu Lys Leu His Glu Ala Asp Leu Glu Asn Val Phe Tyr Lys Ile Glu
                485                 490                 495

Met Pro Leu Val Ser Val Leu Ala Arg Met Glu Leu Asn Gly Val Tyr
                500                 505                 510

Val Asp Thr Glu Phe Leu Lys Lys Leu Ser Glu Tyr Gly Lys Lys
                515                 520                 525

Leu Glu Glu Leu Ala Glu Ile Tyr Arg Ile Ala Gly Glu Pro Phe
                530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
                580                 585                 590

Leu Ile Leu Glu Tyr Arg Lys Ile Gln Lys Leu Lys Ser Thr Tyr Ile
                595                 600                 605

Asp Ala Leu Pro Lys Met Val Asn Pro Lys Thr Gly Arg Ile His Ala
                610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
                675                 680                 685

Glu Asn Leu Leu Lys Ala Phe Glu Gly Ile Asp Val His Thr Leu
                690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
                755                 760                 765

Tyr Ile Gln Arg Val Val Ser Glu Ala Lys Glu Lys Gly Tyr Val Arg
                770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
                835                 840                 845

His Asp Glu Leu Val Phe Glu Val Pro Asp Glu Glu Lys Asp Ala Leu
                850                 855                 860

Val Glu Leu Val Lys Asp Arg Met Thr Asn Val Val Lys Leu Ser Val
865                 870                 875                 880
```

```
Pro Leu Glu Val Asp Val Thr Ile Gly Lys Thr Trp Ser Gly Thr Gly
                885                 890                 895

Gly Gly Gly Glu Ile Lys Glu Ile Met Lys Ser His Thr Leu Gly
            900                 905                 910

Asn Pro Val Arg Leu Gly Ile Met Ile Tyr Leu Phe Pro Arg Arg Arg
            915                 920                 925

Ala Pro Phe Ser His Ile Gln Lys Ala Leu Asp Leu Thr Pro Gly Asn
        930                 935                 940

Leu Asp Ser His Ile Lys Val Leu Glu Lys His Gly Phe Val Arg Thr
945                 950                 955                 960

Tyr Lys Val Ile Ala Asp Arg Pro Arg Thr Met Val Glu Ile Thr Asp
                965                 970                 975

Tyr Gly Met Glu Glu Thr Arg Lys Phe Leu Ser His Leu Lys Thr Val
            980                 985                 990

Ile Asp Ala Ile His Phe
        995

<210> SEQ ID NO 119
<211> LENGTH: 851
<212> TYPE: PRT
<213> ORGANISM: Artificial Sequence
<220> FEATURE:
<223> OTHER INFORMATION: Synthetic construct

<400> SEQUENCE: 119

Met Glu Gly Trp Leu Leu Asp Ala Asp Tyr Ile Thr Ala Glu Asp Gly
1               5                   10                  15

Arg Ala Val Val Arg Leu Trp Cys Lys Asp Phe Asp Gly Asn Thr Phe
                20                  25                  30

Val Val Tyr Asp Arg Asn Phe Gln Pro Tyr Phe Tyr Ala Phe Lys Asn
            35                  40                  45

Gly Leu Ser Lys Glu Asp Ile Glu Lys Ile Val Val Lys Ser Arg Glu
        50                  55                  60

Gly Val Ile Lys Pro Phe Lys Val Glu Glu Val Arg Arg Lys Val Phe
65                  70                  75                  80

Gly Lys Glu Val Glu Val Phe Lys Ile Tyr Ala Tyr His Pro Gln His
                85                  90                  95

Val Pro Lys Leu Arg Glu Glu Leu Lys Lys Ile Thr Glu Val Arg Glu
            100                 105                 110

Ala Asp Ile Pro Phe Ala Tyr Arg Tyr Leu Ile Asp Lys Asp Leu Ala
        115                 120                 125

Cys Met Asp Gly Ile Arg Val Glu Gly Lys Val Arg Glu Glu Arg Gly
    130                 135                 140

Leu Lys Val Ile Asp Ala Glu His Val Glu Arg Phe Glu Ile Pro Leu
145                 150                 155                 160

Pro Glu Pro Lys Val Leu Ala Phe Asp Cys Glu Met Leu Thr Glu Leu
                165                 170                 175

Gly Met Pro Asp Pro Glu Lys Asp Lys Ile Ile Ile Gly Val Lys
            180                 185                 190

Cys Gly Asp Phe Glu Glu Ile Ile Thr Gly Asn Glu Arg Glu Ile Leu
        195                 200                 205

Leu Arg Phe Val Glu Ile Ile Lys Glu Gln Asp Pro Asp Val Ile Val
    210                 215                 220

Gly Tyr Asn Gln Asp Asn Phe Asp Trp Pro Tyr Ile Arg Lys Arg Ala
225                 230                 235                 240
```

```
Glu Lys Leu Ser Val Lys Leu Asn Ile Gly Arg Asp Gly Ser Glu Ile
                245                 250                 255

Ser Phe Arg Gly Gly Arg Pro Lys Ile Ala Gly Arg Leu Asn Val Asp
            260                 265                 270

Leu Tyr Asp Ile Ala Met Lys Leu Asp Val Lys Val Lys Thr Leu Glu
        275                 280                 285

Asn Val Ala Glu Phe Leu Gly Arg Lys Val Glu Leu Ala Asp Ile Glu
    290                 295                 300

Ala Lys Asp Ile Tyr Lys Arg Trp Thr Ser Gly Asp Lys Glu Ser Val
305                 310                 315                 320

Leu Lys Tyr Ser Lys Gln Asp Val Leu Asn Thr Tyr Phe Ile Ala Glu
                325                 330                 335

Glu Leu Leu Pro Met His Tyr Glu Leu Ser Arg Met Ile Arg Ile Pro
            340                 345                 350

Thr Asp Asp Val Ala Arg Ile Gly Arg Gly Lys Gln Val Asp Trp Phe
        355                 360                 365

Leu Leu Ser Glu Ala Tyr Lys Ile Gly Glu Ile Ala Pro Asn Pro Ala
    370                 375                 380

Glu Val Glu Glu Ser Tyr Glu Gly Ala Phe Val Leu Glu Pro Ser Arg
385                 390                 395                 400

Gly Leu His Lys Asn Val Val Cys Leu Asp Phe Ala Ser Met Tyr Pro
                405                 410                 415

Ser Ile Met Ile Ala Tyr Asn Ile Ser Pro Asp Thr Tyr Val Phe Gly
            420                 425                 430

Lys Cys Asp Asp Cys Tyr Val Ala Pro Glu Val Gly His Lys Phe Arg
        435                 440                 445

Lys His Pro Asp Gly Phe Phe Lys Arg Ile Leu Lys Met Leu Ile Glu
    450                 455                 460

Lys Arg Arg Glu Ile Lys Asn Gln Met Lys Ser Leu Asp Arg Asn Ser
465                 470                 475                 480

Arg Glu Tyr Leu Leu Leu Asn Ile Lys Gln Gln Thr Leu Lys Ile Leu
                485                 490                 495

Thr Asn Ser Phe Tyr Gly Tyr Thr Gly Trp Ser Gly Ala Arg Trp Tyr
            500                 505                 510

Cys Arg Gln Cys Ala Glu Ala Thr Thr Ala Trp Gly Arg His Leu Ile
        515                 520                 525

Lys Ser Ala Val Glu Ile Ala Lys Lys Leu Gly Phe Glu Val Leu Tyr
    530                 535                 540

Gly Asp Thr Asp Ser Ile Phe Val Lys Lys Gly Asn Leu Ser Leu Glu
545                 550                 555                 560

Lys Ile Arg Gly Glu Val Glu Lys Leu Ile Glu Ile Ser Glu Lys
                565                 570                 575

Phe Pro Val Gln Ile Glu Val Asp Glu Tyr Tyr Lys Thr Ile Phe Phe
            580                 585                 590

Val Glu Lys Lys Arg Tyr Ala Gly Leu Thr Glu Asp Gly Ile Leu Val
        595                 600                 605

Val Lys Gly Leu Glu Val Arg Arg Gly Asp Trp Cys Glu Leu Ala Lys
    610                 615                 620

Glu Val Gln Lys Lys Val Ile Glu Ile Ile Leu Lys Glu Glu Asn Pro
625                 630                 635                 640

Glu Lys Ala Ala Glu Tyr Val Arg Lys Val Ile Asn Asp Ile Lys Ser
                645                 650                 655
```

```
Gly Lys Val Lys Leu Glu Asp Val Val Ile Tyr Lys Gly Leu Thr Lys
            660                 665                 670

Arg Pro Asp Lys Tyr Glu Ser Lys Gln Ala His Val Lys Ala Ala Leu
        675                 680                 685

Arg Ala Met Glu Leu Gly Ile Val Tyr Asn Val Gly Ser Lys Val Gly
    690                 695                 700

Phe Val Val Val Glu Gly Ala Gly Asn Val Gly Asp Arg Ala Tyr Pro
705                 710                 715                 720

Ile Asp Leu Ile Glu Glu Phe Asp Gly Glu Asn Leu Val Ile Arg Thr
                725                 730                 735

Arg Ser Gly Ser Ile Val Lys Lys Leu Asp Lys Asp Tyr Tyr Ile Asn
            740                 745                 750

His Gln Ile Ile Pro Ser Val Leu Arg Ile Leu Glu Arg Phe Gly Tyr
        755                 760                 765

Asn Glu Ala Ser Leu Lys Gly Ala Thr Gln Lys Thr Leu Asp Ala Phe
    770                 775                 780

Trp Gly Thr Gly Gly Gly Lys Arg Arg Pro Thr Ile Asn Asp Val
785                 790                 795                 800

Ala Lys Leu Ala Gly Val Ser Ile Ser Thr Val Ser Arg Tyr Leu Lys
                805                 810                 815

Asp Pro Ser Gln Val Ser Glu Lys Leu Gly Glu Arg Ile Arg Glu Ala
            820                 825                 830

Ile Lys Lys Leu Gly Tyr Lys Pro Asn Lys Ile Ala Gln Gly Leu Arg
        835                 840                 845

Thr Gly Asp
    850

<210> SEQ ID NO 120
<211> LENGTH: 851
<212> TYPE: PRT
<213> ORGANISM: Artificial Sequence
<220> FEATURE:
<223> OTHER INFORMATION: Synthetic construct

<400> SEQUENCE: 120

Met Glu Gly Trp Leu Leu Asp Ala Asp Tyr Ile Thr Ala Glu Asp Gly
1               5                   10                  15

Arg Ala Val Val Arg Leu Trp Cys Lys Asp Phe Asp Gly Asn Thr Phe
                20                  25                  30

Val Val Tyr Asp Arg Asn Phe Gln Pro Tyr Phe Tyr Ala Phe Lys Asn
            35                  40                  45

Gly Leu Ser Lys Glu Asp Ile Glu Lys Ile Val Val Lys Ser Arg Glu
    50                  55                  60

Gly Val Ile Lys Pro Phe Lys Val Glu Glu Val Arg Arg Lys Val Phe
65                  70                  75                  80

Gly Lys Glu Val Glu Val Phe Lys Ile Tyr Ala Tyr His Pro Gln His
                85                  90                  95

Val Pro Lys Leu Arg Glu Glu Leu Lys Ile Thr Glu Val Arg Glu
            100                 105                 110

Ala Asp Ile Pro Phe Ala Tyr Arg Tyr Leu Ile Asp Lys Asp Leu Ala
        115                 120                 125

Cys Met Asp Gly Ile Arg Val Glu Gly Lys Val Arg Glu Glu Arg Gly
    130                 135                 140

Leu Lys Val Ile Asp Ala Glu His Val Glu Arg Phe Glu Ile Pro Leu
145                 150                 155                 160
```

-continued

```
Pro Glu Pro Lys Val Leu Ala Phe Asp Cys Glu Met Leu Thr Glu Leu
            165                 170                 175
Gly Met Pro Asp Pro Glu Lys Asp Lys Ile Ile Ile Ile Gly Val Lys
        180                 185                 190
Cys Gly Asp Phe Glu Glu Ile Ile Thr Gly Asn Glu Arg Glu Ile Leu
        195                 200                 205
Leu Arg Phe Val Glu Ile Ile Lys Glu Gln Asp Pro Asp Val Ile Val
    210                 215                 220
Gly Tyr Asn Gln Asp Asn Phe Asp Trp Pro Tyr Ile Arg Lys Arg Ala
225                 230                 235                 240
Glu Lys Leu Ser Val Lys Leu Asn Ile Gly Arg Asp Gly Ser Glu Ile
                245                 250                 255
Ser Phe Arg Gly Gly Arg Pro Lys Ile Ala Gly Arg Leu Asn Val Asp
            260                 265                 270
Leu Tyr Asp Ile Ala Met Lys Leu Asp Val Lys Val Lys Thr Leu Glu
    275                 280                 285
Asn Val Ala Glu Phe Leu Gly Arg Lys Val Glu Leu Ala Asp Ile Glu
    290                 295                 300
Ala Lys Asp Ile Tyr Lys Arg Trp Thr Ser Gly Asp Lys Glu Ser Val
305                 310                 315                 320
Leu Lys Tyr Ser Lys Gln Asp Val Leu Asn Thr Tyr Phe Ile Ala Glu
                325                 330                 335
Glu Leu Leu Pro Met His Tyr Glu Leu Ser Arg Met Ile Arg Ile Pro
            340                 345                 350
Thr Asp Asp Val Ala Arg Ile Gly Arg Gly Lys Gln Val Asp Trp Phe
    355                 360                 365
Leu Leu Ser Glu Ala Tyr Lys Ile Gly Glu Ile Ala Pro Asn Pro Ala
    370                 375                 380
Glu Val Glu Glu Ser Tyr Glu Gly Ala Phe Val Leu Glu Pro Ser Arg
385                 390                 395                 400
Gly Leu His Lys Asn Val Val Cys Leu Asp Phe Ala Ser Met Tyr Pro
                405                 410                 415
Ser Ile Met Ile Ala Tyr Asn Ile Ser Pro Asp Thr Tyr Val Phe Gly
            420                 425                 430
Lys Cys Asp Asp Cys Tyr Val Ala Pro Glu Val Gly His Lys Phe Arg
    435                 440                 445
Lys His Pro Asp Gly Phe Phe Lys Arg Ile Leu Lys Met Leu Ile Glu
    450                 455                 460
Lys Arg Arg Glu Ile Lys Asn Gln Met Lys Ser Leu Asp Arg Asn Ser
465                 470                 475                 480
Arg Glu Tyr Leu Leu Leu Asn Ile Lys Gln Gln Thr Leu Lys Ile Leu
                485                 490                 495
Thr Asn Ser Phe Tyr Gly Tyr Thr Gly Trp Ser Gly Ala Arg Trp Tyr
            500                 505                 510
Cys Arg Gln Cys Ala Glu Ala Thr Thr Ala Trp Gly Arg His Leu Ile
    515                 520                 525
Lys Ser Ala Val Glu Ile Ala Lys Lys Leu Gly Phe Glu Val Leu Tyr
    530                 535                 540
Gly Asp Thr Asp Ser Ile Phe Val Lys Lys Gly Asn Leu Ser Leu Glu
545                 550                 555                 560
Lys Ile Arg Gly Glu Val Glu Lys Leu Ile Glu Glu Ile Ser Glu Lys
                565                 570                 575
Phe Pro Val Gln Ile Glu Val Asp Glu Tyr Tyr Lys Thr Ile Phe Phe
```

```
                580             585             590
Val Glu Lys Lys Arg Tyr Ala Gly Leu Thr Glu Asp Gly Ile Leu Val
            595                 600                 605

Val Lys Gly Leu Glu Val Arg Arg Gly Asp Trp Cys Glu Leu Ala Lys
610                 615                 620

Glu Val Gln Lys Lys Val Ile Glu Ile Ile Leu Lys Glu Glu Asn Pro
625                 630                 635                 640

Glu Lys Ala Ala Glu Tyr Val Arg Lys Val Ile Asn Asp Ile Lys Ser
            645                 650                 655

Gly Lys Val Lys Leu Glu Asp Val Ile Tyr Lys Gly Leu Thr Lys
            660                 665                 670

Arg Pro Asp Lys Tyr Glu Ser Lys Gln Ala His Val Lys Ala Ala Leu
            675                 680                 685

Arg Ala Met Glu Leu Gly Ile Val Tyr Asn Val Gly Ser Lys Val Gly
            690                 695                 700

Phe Val Val Glu Gly Ala Gly Asn Val Gly Asp Arg Ala Tyr Pro
705                 710                 715                 720

Ile Asp Leu Ile Glu Glu Phe Asp Gly Glu Asn Leu Val Ile Arg Thr
                725                 730                 735

Arg Ser Gly Ser Ile Val Lys Lys Leu Asp Lys Asp Tyr Tyr Ile Asn
            740                 745                 750

His Gln Ile Ile Pro Ser Val Leu Arg Ile Leu Glu Arg Phe Gly Tyr
            755                 760                 765

Asn Glu Ala Ser Leu Lys Gly Ala Thr Gln Lys Thr Leu Asp Ala Phe
            770                 775                 780

Trp Gly Thr Gly Gly Gly Lys Lys Tyr Val Thr Ile Arg Asp
785                 790                 795                 800

Ile Ala Glu Lys Ala Gly Val Ser Ile Asn Thr Val Ser Arg Ala Leu
                805                 810                 815

Asn Asn Lys Pro Asp Ile Ser Glu Glu Thr Arg Arg Lys Ile Leu Lys
            820                 825                 830

Ile Ala Gln Glu Leu Gly Tyr Val Lys Asn Ala Thr Ala Ser Ser Leu
            835                 840                 845

Arg Ser Lys
    850

<210> SEQ ID NO 121
<211> LENGTH: 872
<212> TYPE: PRT
<213> ORGANISM: Artificial Sequence
<220> FEATURE:
<223> OTHER INFORMATION: Synthetic construct

<400> SEQUENCE: 121

Met Glu Gly Trp Leu Leu Asp Ala Asp Tyr Ile Thr Ala Glu Asp Gly
1               5                   10                  15

Arg Ala Val Val Arg Leu Trp Cys Lys Asp Phe Asp Gly Asn Thr Phe
            20                  25                  30

Val Val Tyr Asp Arg Asn Phe Gln Pro Tyr Phe Tyr Ala Phe Lys Asn
            35                  40                  45

Gly Leu Ser Lys Glu Asp Ile Glu Lys Ile Val Val Lys Ser Arg Glu
    50                  55                  60

Gly Val Ile Lys Pro Phe Lys Val Glu Glu Val Arg Arg Lys Val Phe
65                  70                  75                  80

Gly Lys Glu Val Glu Val Phe Lys Ile Tyr Ala Tyr His Pro Gln His
```

```
                    85                  90                  95
Val Pro Lys Leu Arg Glu Glu Leu Lys Lys Ile Thr Glu Val Arg Glu
                100                 105                 110
Ala Asp Ile Pro Phe Ala Tyr Arg Tyr Leu Ile Asp Lys Asp Leu Ala
                115                 120                 125
Cys Met Asp Gly Ile Arg Val Glu Gly Lys Val Arg Glu Glu Arg Gly
                130                 135                 140
Leu Lys Val Ile Asp Ala Glu His Val Glu Arg Phe Glu Ile Pro Leu
145                 150                 155                 160
Pro Glu Pro Lys Val Leu Ala Phe Asp Cys Glu Met Leu Thr Glu Leu
                165                 170                 175
Gly Met Pro Asp Pro Glu Lys Asp Lys Ile Ile Ile Gly Val Lys
                180                 185                 190
Cys Gly Asp Phe Glu Glu Ile Ile Thr Gly Asn Glu Arg Glu Ile Leu
                195                 200                 205
Leu Arg Phe Val Glu Ile Ile Lys Glu Gln Asp Pro Asp Val Ile Val
                210                 215                 220
Gly Tyr Asn Gln Asp Asn Phe Asp Trp Pro Tyr Ile Arg Lys Arg Ala
225                 230                 235                 240
Glu Lys Leu Ser Val Lys Leu Asn Ile Gly Arg Asp Gly Ser Glu Ile
                245                 250                 255
Ser Phe Arg Gly Gly Arg Pro Lys Ile Ala Gly Arg Leu Asn Val Asp
                260                 265                 270
Leu Tyr Asp Ile Ala Met Lys Leu Asp Val Lys Val Lys Thr Leu Glu
                275                 280                 285
Asn Val Ala Glu Phe Leu Gly Arg Lys Val Glu Leu Ala Asp Ile Glu
                290                 295                 300
Ala Lys Asp Ile Tyr Lys Arg Trp Thr Ser Gly Asp Lys Glu Ser Val
305                 310                 315                 320
Leu Lys Tyr Ser Lys Gln Asp Val Leu Asn Thr Tyr Phe Ile Ala Glu
                325                 330                 335
Glu Leu Leu Pro Met His Tyr Glu Leu Ser Arg Met Ile Arg Ile Pro
                340                 345                 350
Thr Asp Asp Val Ala Arg Ile Gly Arg Gly Lys Gln Val Asp Trp Phe
                355                 360                 365
Leu Leu Ser Glu Ala Tyr Lys Ile Gly Glu Ile Ala Pro Asn Pro Ala
                370                 375                 380
Glu Val Glu Glu Ser Tyr Glu Gly Ala Phe Val Leu Glu Pro Ser Arg
385                 390                 395                 400
Gly Leu His Lys Asn Val Val Cys Leu Asp Phe Ala Ser Met Tyr Pro
                405                 410                 415
Ser Ile Met Ile Ala Tyr Asn Ile Ser Pro Asp Thr Tyr Val Phe Gly
                420                 425                 430
Lys Cys Asp Asp Cys Tyr Val Ala Pro Glu Val Gly His Lys Phe Arg
                435                 440                 445
Lys His Pro Asp Gly Phe Phe Lys Arg Ile Leu Lys Met Leu Ile Glu
                450                 455                 460
Lys Arg Arg Glu Ile Lys Asn Gln Met Lys Ser Leu Asp Arg Asn Ser
465                 470                 475                 480
Arg Glu Tyr Leu Leu Leu Asn Ile Lys Gln Gln Thr Leu Lys Ile Leu
                485                 490                 495
Thr Asn Ser Phe Tyr Gly Tyr Thr Gly Trp Ser Gly Ala Arg Trp Tyr
                500                 505                 510
```

Cys Arg Gln Cys Ala Glu Ala Thr Thr Ala Trp Gly Arg His Leu Ile
            515                 520                 525

Lys Ser Ala Val Glu Ile Ala Lys Lys Leu Gly Phe Glu Val Leu Tyr
        530                 535                 540

Gly Asp Thr Asp Ser Ile Phe Val Lys Lys Gly Asn Leu Ser Leu Glu
545                 550                 555                 560

Lys Ile Arg Gly Glu Val Glu Lys Leu Ile Glu Glu Ile Ser Glu Lys
                565                 570                 575

Phe Pro Val Gln Ile Glu Val Asp Glu Tyr Tyr Lys Thr Ile Phe Phe
            580                 585                 590

Val Glu Lys Lys Arg Tyr Ala Gly Leu Thr Glu Asp Gly Ile Leu Val
        595                 600                 605

Val Lys Gly Leu Glu Val Arg Arg Gly Asp Trp Cys Glu Leu Ala Lys
        610                 615                 620

Glu Val Gln Lys Lys Val Ile Glu Ile Leu Lys Glu Glu Asn Pro
625                 630                 635                 640

Glu Lys Ala Ala Glu Tyr Val Arg Lys Val Ile Asn Asp Ile Lys Ser
                645                 650                 655

Gly Lys Val Lys Leu Glu Asp Val Val Ile Tyr Lys Gly Leu Thr Lys
            660                 665                 670

Arg Pro Asp Lys Tyr Glu Ser Lys Gln Ala His Val Lys Ala Ala Leu
        675                 680                 685

Arg Ala Met Glu Leu Gly Ile Val Tyr Asn Val Gly Ser Lys Val Gly
        690                 695                 700

Phe Val Val Glu Gly Ala Gly Asn Val Gly Asp Arg Ala Tyr Pro
705                 710                 715                 720

Ile Asp Leu Ile Glu Glu Phe Asp Gly Glu Asn Leu Val Ile Arg Thr
                725                 730                 735

Arg Ser Gly Ser Ile Val Lys Lys Leu Asp Lys Asp Tyr Tyr Ile Asn
            740                 745                 750

His Gln Ile Ile Pro Ser Val Leu Arg Ile Leu Glu Arg Phe Gly Tyr
        755                 760                 765

Asn Glu Ala Ser Leu Lys Gly Ala Thr Gln Lys Thr Leu Asp Ala Phe
        770                 775                 780

Trp Gly Thr Gly Gly Gly His Lys Lys Leu Asn Pro Lys Ser Met
785                 790                 795                 800

Lys Arg Glu Asn Lys Lys Met Val Leu Arg Tyr Leu Ile Glu Ser Gly
                805                 810                 815

Pro His Ser Arg Val Glu Ile Ala Arg Lys Thr Gly Leu Ala Gln Ser
            820                 825                 830

Ala Ile Trp Arg Ile Ile Glu Glu Leu Val Asn Glu Gly Leu Val Glu
        835                 840                 845

Glu Lys Gly Thr Ala Thr Gly Arg Arg Lys Ala Val Thr Tyr Gly
        850                 855                 860

Pro Thr Arg Ser Phe Ile Thr Ser
865                 870

<210> SEQ ID NO 122
<211> LENGTH: 862
<212> TYPE: PRT
<213> ORGANISM: Artificial Sequence
<220> FEATURE:
<223> OTHER INFORMATION: Synthetic construct

<400> SEQUENCE: 122

```
Met Glu Gly Trp Leu Leu Asp Ala Asp Tyr Ile Thr Ala Glu Asp Gly
1               5                   10                  15

Arg Ala Val Val Arg Leu Trp Cys Lys Asp Phe Asp Gly Asn Thr Phe
            20                  25                  30

Val Val Tyr Asp Arg Asn Phe Gln Pro Tyr Phe Ala Phe Lys Asn
        35                  40                  45

Gly Leu Ser Lys Glu Asp Ile Glu Lys Ile Val Val Lys Ser Arg Glu
        50                  55                  60

Gly Val Ile Lys Pro Phe Lys Val Glu Glu Val Arg Arg Lys Val Phe
65                  70                  75                  80

Gly Lys Glu Val Glu Val Phe Lys Ile Tyr Ala Tyr His Pro Gln His
                85                  90                  95

Val Pro Lys Leu Arg Glu Glu Leu Lys Lys Ile Thr Glu Val Arg Glu
                100                 105                 110

Ala Asp Ile Pro Phe Ala Tyr Arg Tyr Leu Ile Asp Lys Asp Leu Ala
            115                 120                 125

Cys Met Asp Gly Ile Arg Val Glu Gly Lys Val Arg Glu Glu Arg Gly
        130                 135                 140

Leu Lys Val Ile Asp Ala Glu His Val Glu Arg Phe Glu Ile Pro Leu
145                 150                 155                 160

Pro Glu Pro Lys Val Leu Ala Phe Asp Cys Glu Met Leu Thr Glu Leu
                165                 170                 175

Gly Met Pro Asp Pro Glu Lys Asp Lys Ile Ile Ile Gly Val Lys
                180                 185                 190

Cys Gly Asp Phe Glu Glu Ile Ile Thr Gly Asn Glu Arg Glu Ile Leu
            195                 200                 205

Leu Arg Phe Val Glu Ile Ile Lys Glu Gln Asp Pro Asp Val Ile Val
        210                 215                 220

Gly Tyr Asn Gln Asp Asn Phe Asp Trp Pro Tyr Ile Arg Lys Arg Ala
225                 230                 235                 240

Glu Lys Leu Ser Val Lys Leu Asn Ile Gly Arg Asp Gly Ser Glu Ile
            245                 250                 255

Ser Phe Arg Gly Gly Arg Pro Lys Ile Ala Gly Arg Leu Asn Val Asp
        260                 265                 270

Leu Tyr Asp Ile Ala Met Lys Leu Asp Val Lys Val Lys Thr Leu Glu
        275                 280                 285

Asn Val Ala Glu Phe Leu Gly Arg Lys Val Glu Leu Ala Asp Ile Glu
        290                 295                 300

Ala Lys Asp Ile Tyr Lys Arg Trp Thr Ser Gly Asp Lys Glu Ser Val
305                 310                 315                 320

Leu Lys Tyr Ser Lys Gln Asp Val Leu Asn Thr Tyr Phe Ile Ala Glu
            325                 330                 335

Glu Leu Leu Pro Met His Tyr Glu Leu Ser Arg Met Ile Arg Ile Pro
            340                 345                 350

Thr Asp Asp Val Ala Arg Ile Gly Arg Gly Lys Gln Val Asp Trp Phe
            355                 360                 365

Leu Leu Ser Glu Ala Tyr Lys Ile Gly Glu Ile Ala Pro Asn Pro Ala
        370                 375                 380

Glu Val Glu Glu Ser Tyr Glu Gly Ala Phe Val Leu Glu Pro Ser Arg
385                 390                 395                 400

Gly Leu His Lys Asn Val Val Cys Leu Asp Phe Ala Ser Met Tyr Pro
            405                 410                 415
```

```
Ser Ile Met Ile Ala Tyr Asn Ile Ser Pro Asp Thr Tyr Val Phe Gly
            420                 425                 430

Lys Cys Asp Asp Cys Tyr Val Ala Pro Glu Val Gly His Lys Phe Arg
            435                 440                 445

Lys His Pro Asp Gly Phe Phe Lys Arg Ile Leu Lys Met Leu Ile Glu
            450                 455                 460

Lys Arg Arg Glu Ile Lys Asn Gln Met Lys Ser Leu Asp Arg Asn Ser
465                 470                 475                 480

Arg Glu Tyr Leu Leu Leu Asn Ile Lys Gln Gln Thr Leu Lys Ile Leu
                    485                 490                 495

Thr Asn Ser Phe Tyr Gly Tyr Thr Gly Trp Ser Gly Ala Arg Trp Tyr
                500                 505                 510

Cys Arg Gln Cys Ala Glu Ala Thr Thr Ala Trp Gly Arg His Leu Ile
            515                 520                 525

Lys Ser Ala Val Glu Ile Ala Lys Lys Leu Gly Phe Glu Val Leu Tyr
            530                 535                 540

Gly Asp Thr Asp Ser Ile Phe Val Lys Lys Gly Asn Leu Ser Leu Glu
545                 550                 555                 560

Lys Ile Arg Gly Glu Val Glu Lys Leu Ile Glu Glu Ile Ser Glu Lys
                565                 570                 575

Phe Pro Val Gln Ile Glu Val Asp Glu Tyr Tyr Lys Thr Ile Phe Phe
                580                 585                 590

Val Glu Lys Lys Arg Tyr Ala Gly Leu Thr Glu Asp Gly Ile Leu Val
            595                 600                 605

Val Lys Gly Leu Glu Val Arg Arg Gly Asp Trp Cys Glu Leu Ala Lys
610                 615                 620

Glu Val Gln Lys Lys Val Ile Glu Ile Ile Leu Lys Glu Glu Asn Pro
625                 630                 635                 640

Glu Lys Ala Ala Glu Tyr Val Arg Lys Val Ile Asn Asp Ile Lys Ser
                645                 650                 655

Gly Lys Val Lys Leu Glu Asp Val Val Ile Tyr Lys Gly Leu Thr Lys
                660                 665                 670

Arg Pro Asp Lys Tyr Glu Ser Lys Gln Ala His Val Lys Ala Ala Leu
                675                 680                 685

Arg Ala Met Glu Leu Gly Ile Val Tyr Asn Val Gly Ser Lys Val Gly
690                 695                 700

Phe Val Val Glu Gly Ala Gly Asn Val Gly Asp Arg Ala Tyr Pro
705                 710                 715                 720

Ile Asp Leu Ile Glu Glu Phe Asp Gly Glu Asn Leu Val Ile Arg Thr
                725                 730                 735

Arg Ser Gly Ser Ile Val Lys Lys Leu Asp Lys Asp Tyr Tyr Ile Asn
                740                 745                 750

His Gln Ile Ile Pro Ser Val Leu Arg Ile Leu Glu Arg Phe Gly Tyr
            755                 760                 765

Asn Glu Ala Ser Leu Lys Gly Ala Thr Gln Lys Thr Leu Asp Ala Phe
770                 775                 780

Trp Gly Thr Gly Gly Gly Asn Thr Gly Ala Gln Gly Val Ser Glu
785                 790                 795                 800

Met Ser Arg Met Lys Ile Ser Val Gln Leu Pro Gln Ser Leu Ile
                805                 810                 815

His Gly Leu Asp Ala Leu Val Lys Arg Gly Ile Tyr Pro Asn Arg Ser
            820                 825                 830

Glu Ala Ile Arg Val Ala Ile Arg Glu Leu Leu Lys Lys Glu Leu Tyr
```

-continued

```
              835                 840                 845
Lys Glu Glu Ile Gln Glu Ile Pro Glu Tyr Val Val Lys
    850                 855                 860

<210> SEQ ID NO 123
<211> LENGTH: 866
<212> TYPE: PRT
<213> ORGANISM: Artificial Sequence
<220> FEATURE:
<223> OTHER INFORMATION: Synthetic construct

<400> SEQUENCE: 123

Met Glu Gly Trp Leu Leu Asp Ala Asp Tyr Ile Thr Ala Glu Asp Gly
1               5                   10                  15

Arg Ala Val Val Arg Leu Trp Cys Lys Asp Phe Asp Gly Asn Thr Phe
            20                  25                  30

Val Val Tyr Asp Arg Asn Phe Gln Pro Tyr Phe Tyr Ala Phe Lys Asn
        35                  40                  45

Gly Leu Ser Lys Glu Asp Ile Glu Lys Ile Val Val Lys Ser Arg Glu
    50                  55                  60

Gly Val Ile Lys Pro Phe Lys Val Glu Val Arg Arg Lys Val Phe
65                  70                  75                  80

Gly Lys Glu Val Glu Val Phe Lys Ile Tyr Ala Tyr His Pro Gln His
            85                  90                  95

Val Pro Lys Leu Arg Glu Glu Leu Lys Lys Ile Thr Glu Val Arg Glu
            100                 105                 110

Ala Asp Ile Pro Phe Ala Tyr Arg Tyr Leu Ile Asp Lys Asp Leu Ala
        115                 120                 125

Cys Met Asp Gly Ile Arg Val Glu Gly Lys Val Arg Glu Glu Arg Gly
    130                 135                 140

Leu Lys Val Ile Asp Ala Glu His Val Glu Arg Phe Glu Ile Pro Leu
145                 150                 155                 160

Pro Glu Pro Lys Val Leu Ala Phe Asp Cys Glu Met Leu Thr Glu Leu
            165                 170                 175

Gly Met Pro Asp Pro Glu Lys Asp Lys Ile Ile Ile Gly Val Lys
            180                 185                 190

Cys Gly Asp Phe Glu Glu Ile Ile Thr Gly Asn Glu Arg Glu Ile Leu
        195                 200                 205

Leu Arg Phe Val Glu Ile Ile Lys Glu Gln Asp Pro Asp Val Ile Val
    210                 215                 220

Gly Tyr Asn Gln Asp Asn Phe Asp Trp Pro Tyr Ile Arg Lys Arg Ala
225                 230                 235                 240

Glu Lys Leu Ser Val Lys Leu Asn Ile Gly Arg Asp Gly Ser Glu Ile
            245                 250                 255

Ser Phe Arg Gly Gly Arg Pro Lys Ile Ala Gly Arg Leu Asn Val Asp
            260                 265                 270

Leu Tyr Asp Ile Ala Met Lys Leu Asp Val Lys Val Lys Thr Leu Glu
        275                 280                 285

Asn Val Ala Glu Phe Leu Gly Arg Lys Val Glu Leu Ala Asp Ile Glu
    290                 295                 300

Ala Lys Asp Ile Tyr Lys Arg Trp Thr Ser Gly Asp Lys Glu Ser Val
305                 310                 315                 320

Leu Lys Tyr Ser Lys Gln Asp Val Leu Asn Thr Tyr Phe Ile Ala Glu
            325                 330                 335

Glu Leu Leu Pro Met His Tyr Glu Leu Ser Arg Met Ile Arg Ile Pro
```

-continued

```
                340                 345                 350
Thr Asp Asp Val Ala Arg Ile Gly Arg Gly Lys Gln Val Asp Trp Phe
            355                 360                 365

Leu Leu Ser Glu Ala Tyr Lys Ile Gly Glu Ile Ala Pro Asn Pro Ala
        370                 375                 380

Glu Val Glu Glu Ser Tyr Glu Gly Ala Phe Val Leu Pro Ser Arg
385                 390                 395                 400

Gly Leu His Lys Asn Val Val Cys Leu Asp Phe Ala Ser Met Tyr Pro
                405                 410                 415

Ser Ile Met Ile Ala Tyr Asn Ile Ser Pro Asp Thr Tyr Val Phe Gly
            420                 425                 430

Lys Cys Asp Cys Tyr Val Ala Pro Glu Val Gly His Lys Phe Arg
            435                 440                 445

Lys His Pro Asp Gly Phe Phe Lys Arg Ile Leu Lys Met Leu Ile Glu
        450                 455                 460

Lys Arg Arg Glu Ile Lys Asn Gln Met Lys Ser Leu Asp Arg Asn Ser
465                 470                 475                 480

Arg Glu Tyr Leu Leu Leu Asn Ile Lys Gln Gln Thr Leu Lys Ile Leu
                485                 490                 495

Thr Asn Ser Phe Tyr Gly Tyr Thr Gly Trp Ser Gly Ala Arg Trp Tyr
            500                 505                 510

Cys Arg Gln Cys Ala Glu Ala Thr Thr Ala Trp Gly Arg His Leu Ile
            515                 520                 525

Lys Ser Ala Val Glu Ile Ala Lys Lys Leu Gly Phe Glu Val Leu Tyr
        530                 535                 540

Gly Asp Thr Asp Ser Ile Phe Val Lys Lys Gly Asn Leu Ser Leu Glu
545                 550                 555                 560

Lys Ile Arg Gly Glu Val Glu Lys Leu Ile Glu Ile Ser Glu Lys
                565                 570                 575

Phe Pro Val Gln Ile Glu Val Asp Glu Tyr Tyr Lys Thr Ile Phe Phe
            580                 585                 590

Val Glu Lys Lys Arg Tyr Ala Gly Leu Thr Glu Asp Gly Ile Leu Val
            595                 600                 605

Val Lys Gly Leu Glu Val Arg Arg Gly Asp Trp Cys Glu Leu Ala Lys
        610                 615                 620

Glu Val Gln Lys Lys Val Ile Glu Ile Leu Lys Glu Glu Asn Pro
625                 630                 635                 640

Glu Lys Ala Ala Glu Tyr Val Arg Lys Val Ile Asn Asp Ile Lys Ser
                645                 650                 655

Gly Lys Val Lys Leu Glu Asp Val Val Ile Tyr Lys Gly Leu Thr Lys
            660                 665                 670

Arg Pro Asp Lys Tyr Glu Ser Lys Gln Ala His Val Lys Ala Ala Leu
        675                 680                 685

Arg Ala Met Glu Leu Gly Ile Val Tyr Asn Val Gly Ser Lys Val Gly
        690                 695                 700

Phe Val Val Glu Gly Ala Gly Asn Val Gly Asp Arg Ala Tyr Pro
705                 710                 715                 720

Ile Asp Leu Ile Glu Glu Phe Asp Gly Glu Asn Leu Val Ile Arg Thr
                725                 730                 735

Arg Ser Gly Ser Ile Val Lys Lys Leu Asp Lys Asp Tyr Tyr Ile Asn
            740                 745                 750

His Gln Ile Ile Pro Ser Val Leu Arg Ile Leu Glu Arg Phe Gly Tyr
        755                 760                 765
```

```
Asn Glu Ala Ser Leu Lys Gly Ala Thr Gln Lys Thr Leu Asp Ala Phe
    770                 775                 780

Trp Gly Thr Gly Gly Gly Ile Ile Asn Pro Gln Ala Arg Leu Thr
785                 790                 795                 800

Pro Leu Glu Leu Glu Ile Leu Glu Ile Ile Lys Gln Lys Lys Ser Ile
                805                 810                 815

Thr Ile Thr Glu Ile Lys Glu Ile Leu Ser Glu Arg Arg Lys Ser Glu
                820                 825                 830

Tyr Pro Leu Ser Leu Val Ser Glu Tyr Ile Ser Arg Leu Glu Arg Lys
            835                 840                 845

Gly Tyr Val Lys Lys Ile Ala Lys Gly Arg Lys Lys Phe Val Glu Ala
    850                 855                 860

Leu Ile
865
```

<210> SEQ ID NO 124
<211> LENGTH: 873
<212> TYPE: PRT
<213> ORGANISM: Artificial Sequence
<220> FEATURE:
<223> OTHER INFORMATION: Synthetic construct

<400> SEQUENCE: 124

```
Met Glu Gly Trp Leu Leu Asp Ala Asp Tyr Ile Thr Ala Glu Asp Gly
1               5                   10                  15

Arg Ala Val Val Arg Leu Trp Cys Lys Asp Phe Asp Gly Asn Thr Phe
                20                  25                  30

Val Val Tyr Asp Arg Asn Phe Gln Pro Tyr Phe Tyr Ala Phe Lys Asn
                35                  40                  45

Gly Leu Ser Lys Glu Asp Ile Glu Lys Ile Val Val Lys Ser Arg Glu
        50                  55                  60

Gly Val Ile Lys Pro Phe Lys Val Glu Val Arg Arg Lys Val Phe
65                  70                  75                  80

Gly Lys Glu Val Glu Val Phe Lys Ile Tyr Ala Tyr His Pro Gln His
                85                  90                  95

Val Pro Lys Leu Arg Glu Glu Leu Lys Lys Ile Thr Glu Val Arg Glu
                100                 105                 110

Ala Asp Ile Pro Phe Ala Tyr Arg Tyr Leu Ile Asp Lys Asp Leu Ala
            115                 120                 125

Cys Met Asp Gly Ile Arg Val Glu Gly Lys Val Arg Glu Glu Arg Gly
130                 135                 140

Leu Lys Val Ile Asp Ala Glu His Val Glu Arg Phe Glu Ile Pro Leu
145                 150                 155                 160

Pro Glu Pro Lys Val Leu Ala Phe Asp Cys Glu Met Leu Thr Glu Leu
                165                 170                 175

Gly Met Pro Asp Pro Glu Lys Asp Lys Ile Ile Ile Gly Val Lys
                180                 185                 190

Cys Gly Asp Phe Glu Glu Ile Ile Thr Gly Asn Glu Arg Glu Ile Leu
            195                 200                 205

Leu Arg Phe Val Glu Ile Ile Lys Glu Gln Asp Pro Asp Val Ile Val
        210                 215                 220

Gly Tyr Asn Gln Asp Asn Phe Asp Trp Pro Tyr Ile Arg Lys Arg Ala
225                 230                 235                 240

Glu Lys Leu Ser Val Lys Leu Asn Ile Gly Arg Asp Gly Ser Glu Ile
                245                 250                 255
```

```
Ser Phe Arg Gly Gly Arg Pro Lys Ile Ala Gly Arg Leu Asn Val Asp
            260                 265                 270

Leu Tyr Asp Ile Ala Met Lys Leu Asp Val Lys Val Lys Thr Leu Glu
        275                 280                 285

Asn Val Ala Glu Phe Leu Gly Arg Lys Val Glu Leu Ala Asp Ile Glu
    290                 295                 300

Ala Lys Asp Ile Tyr Lys Arg Trp Thr Ser Gly Asp Lys Glu Ser Val
305                 310                 315                 320

Leu Lys Tyr Ser Lys Gln Asp Val Leu Asn Thr Tyr Phe Ile Ala Glu
                325                 330                 335

Glu Leu Leu Pro Met His Tyr Glu Leu Ser Arg Met Ile Arg Ile Pro
            340                 345                 350

Thr Asp Asp Val Ala Arg Ile Gly Arg Gly Lys Gln Val Asp Trp Phe
        355                 360                 365

Leu Leu Ser Glu Ala Tyr Lys Ile Gly Glu Ile Ala Pro Asn Pro Ala
    370                 375                 380

Glu Val Glu Glu Ser Tyr Gly Ala Phe Val Leu Glu Pro Ser Arg
385                 390                 395                 400

Gly Leu His Lys Asn Val Val Cys Leu Asp Phe Ala Ser Met Tyr Pro
                405                 410                 415

Ser Ile Met Ile Ala Tyr Asn Ile Ser Pro Asp Thr Tyr Val Phe Gly
            420                 425                 430

Lys Cys Asp Asp Cys Tyr Val Ala Pro Glu Val Gly His Lys Phe Arg
        435                 440                 445

Lys His Pro Asp Gly Phe Phe Lys Arg Ile Leu Lys Met Leu Ile Glu
    450                 455                 460

Lys Arg Arg Glu Ile Lys Asn Gln Met Lys Ser Leu Asp Arg Asn Ser
465                 470                 475                 480

Arg Glu Tyr Leu Leu Leu Asn Ile Lys Gln Gln Thr Leu Lys Ile Leu
                485                 490                 495

Thr Asn Ser Phe Tyr Gly Tyr Thr Gly Trp Ser Gly Ala Arg Trp Tyr
            500                 505                 510

Cys Arg Gln Cys Ala Glu Ala Thr Thr Ala Trp Gly Arg His Leu Ile
        515                 520                 525

Lys Ser Ala Val Glu Ile Ala Lys Lys Leu Gly Phe Glu Val Leu Tyr
    530                 535                 540

Gly Asp Thr Asp Ser Ile Phe Val Lys Gly Asn Leu Ser Leu Glu
545                 550                 555                 560

Lys Ile Arg Gly Glu Val Lys Leu Ile Glu Ile Ser Glu Lys
                565                 570                 575

Phe Pro Val Gln Ile Glu Val Asp Glu Tyr Tyr Lys Thr Ile Phe Phe
            580                 585                 590

Val Glu Lys Lys Arg Tyr Ala Gly Leu Thr Glu Asp Gly Ile Leu Val
        595                 600                 605

Val Lys Gly Leu Glu Val Arg Arg Gly Asp Trp Cys Glu Leu Ala Lys
    610                 615                 620

Glu Val Gln Lys Val Ile Glu Ile Leu Lys Glu Glu Asn Pro
625                 630                 635                 640

Glu Lys Ala Ala Glu Tyr Val Arg Lys Val Ile Asn Asp Ile Lys Ser
                645                 650                 655

Gly Lys Val Lys Leu Glu Asp Val Ile Tyr Lys Gly Leu Thr Lys
            660                 665                 670
```

```
Arg Pro Asp Lys Tyr Glu Ser Lys Gln Ala His Val Lys Ala Ala Leu
            675                 680                 685

Arg Ala Met Glu Leu Gly Ile Val Tyr Asn Val Gly Ser Lys Val Gly
    690                 695                 700

Phe Val Val Glu Gly Ala Gly Asn Val Gly Asp Arg Ala Tyr Pro
705                 710                 715                 720

Ile Asp Leu Ile Glu Glu Phe Asp Gly Glu Asn Leu Val Ile Arg Thr
                725                 730                 735

Arg Ser Gly Ser Ile Val Lys Lys Leu Asp Lys Asp Tyr Tyr Ile Asn
        740                 745                 750

His Gln Ile Ile Pro Ser Val Leu Arg Ile Leu Glu Arg Phe Gly Tyr
        755                 760                 765

Asn Glu Ala Ser Leu Lys Gly Ala Thr Gln Lys Thr Leu Asp Ala Phe
    770                 775                 780

Trp Gly Thr Gly Gly Gly Gly Arg Lys Val Arg Thr Gln Gln Asn
785                 790                 795                 800

Glu Ile Leu Asn Leu Leu Asn Glu Lys Glu Lys Ala Val Leu Arg Ala
                805                 810                 815

Ile Leu Glu His Gly Gly Glu Ile Lys Gln Glu Asp Leu Pro Glu Leu
                820                 825                 830

Val Gly Tyr Ser Arg Pro Thr Ile Ser Lys Val Ile Gln Glu Leu Glu
                835                 840                 845

Asn Lys Gly Leu Ile Lys Arg Glu Lys Ser Gly Lys Thr Phe Val Val
    850                 855                 860

Lys Ile Glu Arg Lys Ile Lys Leu Asp
865                 870

<210> SEQ ID NO 125
<211> LENGTH: 841
<212> TYPE: PRT
<213> ORGANISM: Artificial Sequence
<220> FEATURE:
<223> OTHER INFORMATION: Synthetic construct

<400> SEQUENCE: 125

Met Ile Leu Asp Ala Asp Tyr Ile Thr Glu Asp Gly Lys Pro Ile Ile
1               5                   10                  15

Arg Leu Phe Lys Lys Glu Asn Gly Arg Phe Lys Val Glu Tyr Asp Arg
                20                  25                  30

Asn Phe Arg Pro Tyr Ile Tyr Ala Leu Leu Lys Asp Asp Ser Ala Ile
            35                  40                  45

Asp Asp Val Arg Lys Ile Thr Ser Glu Arg His Gly Lys Val Val Arg
    50                  55                  60

Val Ile Asp Val Glu Lys Val Lys Lys Phe Leu Gly Arg Pro Ile
65                  70                  75                  80

Glu Val Trp Lys Leu Tyr Phe Glu His Pro Gln Asp Val Pro Ala Met
                85                  90                  95

Arg Asp Lys Ile Arg Glu His Pro Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160
```

```
Ser Tyr Ala Asp Glu Glu Gly Ala Lys Val Ile Thr Trp Lys Lys Ile
            165                 170                 175
Asp Leu Pro Tyr Val Glu Val Val Ala Asn Glu Arg Glu Met Ile Lys
        180                 185                 190
Arg Leu Ile Lys Val Ile Arg Glu Lys Asp Pro Asp Val Ile Ile Thr
    195                 200                 205
Tyr Asn Gly Asp Asn Phe Asp Phe Pro Tyr Leu Leu Lys Arg Ala Glu
210                 215                 220
Lys Leu Gly Met Lys Leu Pro Leu Gly Arg Asp Asn Ser Glu Pro Lys
225                 230                 235                 240
Met Gln Arg Leu Gly Asp Ser Leu Ala Val Glu Ile Lys Gly Arg Ile
            245                 250                 255
His Phe Asp Leu Phe Pro Val Ile Arg Arg Thr Ile Asn Leu Pro Thr
        260                 265                 270
Tyr Thr Leu Glu Ala Val Tyr Glu Ala Ile Phe Gly Lys Gln Lys Glu
    275                 280                 285
Lys Val Tyr Pro His Glu Ile Ala Glu Ala Trp Glu Thr Gly Lys Gly
290                 295                 300
Leu Glu Arg Val Ala Lys Tyr Ser Met Glu Asp Ala Lys Val Thr Tyr
305                 310                 315                 320
Glu Leu Gly Lys Glu Phe Phe Pro Met Glu Ala Gln Leu Ala Arg Leu
            325                 330                 335
Val Gly Gln Pro Leu Trp Asp Val Ser Arg Ser Ser Thr Gly Asn Leu
        340                 345                 350
Val Glu Trp Tyr Leu Leu Arg Lys Ala Tyr Glu Arg Asn Glu Leu Ala
    355                 360                 365
Pro Asn Lys Pro Asp Glu Arg Glu Tyr Glu Arg Arg Leu Arg Glu Ser
370                 375                 380
Tyr Glu Gly Gly Tyr Val Lys Glu Pro Glu Arg Gly Leu Trp Glu Gly
385                 390                 395                 400
Ile Val Ser Leu Asp Phe Arg Ser Leu Tyr Pro Ser Ile Ile Ile Thr
            405                 410                 415
His Asn Val Ser Pro Asp Thr Leu Asn Lys Glu Gly Cys Gly Glu Tyr
        420                 425                 430
Asp Glu Ala Pro Glu Val Gly His Arg Phe Cys Lys Asp Phe Pro Gly
    435                 440                 445
Phe Ile Pro Ser Leu Leu Gly Ser Leu Leu Glu Glu Arg Gln Lys Ile
450                 455                 460
Lys Lys Arg Met Lys Glu Ser Lys Asp Pro Val Glu Arg Lys Leu Leu
465                 470                 475                 480
Asp Tyr Arg Gln Arg Ala Ile Lys Ile Leu Ala Asn Ser Phe Tyr Gly
            485                 490                 495
Tyr Tyr Gly Tyr Ala Lys Ala Arg Trp Tyr Cys Lys Glu Cys Ala Glu
        500                 505                 510
Ser Val Thr Ala Trp Gly Arg Gln Tyr Ile Glu Leu Val Arg Arg Glu
    515                 520                 525
Leu Glu Glu Arg Gly Phe Lys Val Leu Tyr Ile Asp Thr Asp Gly Leu
530                 535                 540
Tyr Ala Thr Ile Pro Gly Glu Lys Asn Trp Glu Ile Lys Arg Arg
545                 550                 555                 560
Ala Leu Glu Phe Val Asn Tyr Ile Asn Ser Lys Leu Pro Gly Ile Leu
            565                 570                 575
Glu Leu Glu Tyr Glu Gly Phe Tyr Thr Arg Gly Phe Phe Val Thr Lys
```

580                 585                 590
Lys Lys Tyr Ala Leu Ile Asp Glu Glu Gly Lys Ile Val Thr Arg Gly
            595                 600                 605

Leu Glu Ile Val Arg Arg Asp Trp Ser Glu Ile Ala Lys Glu Thr Gln
        610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Asn Tyr Glu Ile
                645                 650                 655

Pro Val Glu Lys Leu Val Ile Tyr Glu Gln Ile Thr Arg Pro Leu Asn
            660                 665                 670

Glu Tyr Lys Ala Ile Gly Pro His Val Ala Val Ala Lys Arg Leu Ala
        675                 680                 685

Ala Lys Gly Ile Lys Ile Lys Pro Gly Met Val Ile Gly Tyr Val Val
690                 695                 700

Leu Arg Gly Asp Gly Pro Ile Ser Lys Arg Ala Ile Ala Ile Glu Glu
705                 710                 715                 720

Phe Asp Gly Lys Lys His Lys Tyr Asp Ala Glu Tyr Tyr Ile Glu Asn
                725                 730                 735

Gln Val Leu Pro Ala Val Glu Arg Ile Leu Lys Ala Phe Gly Tyr Lys
            740                 745                 750

Arg Glu Asp Leu Arg Trp Gln Lys Thr Lys Gln Val Gly Leu Gly Ala
        755                 760                 765

Trp Leu Lys Val Lys Lys Ser Gly Thr Gly Gly Gly Lys Arg Arg
770                 775                 780

Pro Thr Ile Asn Asp Val Ala Lys Leu Ala Gly Val Ser Ile Ser Thr
785                 790                 795                 800

Val Ser Arg Tyr Leu Lys Asp Pro Ser Gln Val Ser Glu Lys Leu Gly
                805                 810                 815

Glu Arg Ile Arg Glu Ala Ile Lys Lys Leu Gly Tyr Lys Pro Asn Lys
            820                 825                 830

Ile Ala Gln Gly Leu Arg Thr Gly Asp
        835                 840

<210> SEQ ID NO 126
<211> LENGTH: 841
<212> TYPE: PRT
<213> ORGANISM: Artificial Sequence
<220> FEATURE:
<223> OTHER INFORMATION: Synthetic construct

<400> SEQUENCE: 126

Met Ile Leu Asp Ala Asp Tyr Ile Thr Glu Asp Gly Lys Pro Ile Ile
1               5                   10                  15

Arg Leu Phe Lys Lys Glu Asn Gly Arg Phe Lys Val Glu Tyr Asp Arg
            20                  25                  30

Asn Phe Arg Pro Tyr Ile Tyr Ala Leu Leu Lys Asp Asp Ser Ala Ile
        35                  40                  45

Asp Asp Val Arg Lys Ile Thr Ser Glu Arg His Gly Lys Val Val Arg
    50                  55                  60

Val Ile Asp Val Glu Lys Val Lys Lys Phe Leu Gly Arg Pro Ile
65                  70                  75                  80

Glu Val Trp Lys Leu Tyr Phe Glu His Pro Gln Asp Val Pro Ala Met
                85                  90                  95

Arg Asp Lys Ile Arg Glu His Pro Ala Val Ile Asp Ile Phe Glu Tyr

-continued

```
                100                 105                 110
Asp Ile Pro Phe Ala Lys Arg Tyr Leu Ile Asp Lys Gly Leu Ile Pro
            115                 120                 125
Met Glu Gly Asn Glu Glu Leu Thr Phe Leu Ala Val Asp Ile Glu Thr
            130                 135                 140
Leu Tyr His Glu Gly Glu Phe Gly Lys Gly Pro Ile Ile Met Ile
145                 150                 155                 160
Ser Tyr Ala Asp Glu Glu Gly Ala Lys Val Ile Thr Trp Lys Lys Ile
            165                 170                 175
Asp Leu Pro Tyr Val Glu Val Ala Asn Glu Arg Glu Met Ile Lys
            180                 185                 190
Arg Leu Ile Lys Val Ile Arg Glu Lys Asp Pro Asp Val Ile Ile Thr
            195                 200                 205
Tyr Asn Gly Asp Asn Phe Asp Phe Pro Tyr Leu Leu Lys Arg Ala Glu
            210                 215                 220
Lys Leu Gly Met Lys Leu Pro Leu Gly Arg Asp Asn Ser Glu Pro Lys
225                 230                 235                 240
Met Gln Arg Leu Gly Asp Ser Leu Ala Val Glu Ile Lys Gly Arg Ile
            245                 250                 255
His Phe Asp Leu Phe Pro Val Ile Arg Arg Thr Ile Asn Leu Pro Thr
            260                 265                 270
Tyr Thr Leu Glu Ala Val Tyr Glu Ala Ile Phe Gly Lys Gln Lys Glu
            275                 280                 285
Lys Val Tyr Pro His Glu Ile Ala Glu Ala Trp Glu Thr Gly Lys Gly
            290                 295                 300
Leu Glu Arg Val Ala Lys Tyr Ser Met Glu Asp Ala Lys Val Thr Tyr
305                 310                 315                 320
Glu Leu Gly Lys Glu Phe Phe Pro Met Glu Ala Gln Leu Ala Arg Leu
            325                 330                 335
Val Gly Gln Pro Leu Trp Asp Val Ser Arg Ser Ser Thr Gly Asn Leu
            340                 345                 350
Val Glu Trp Tyr Leu Leu Arg Lys Ala Tyr Glu Arg Asn Glu Leu Ala
            355                 360                 365
Pro Asn Lys Pro Asp Glu Arg Glu Tyr Glu Arg Arg Leu Arg Glu Ser
370                 375                 380
Tyr Glu Gly Gly Tyr Val Lys Glu Pro Glu Arg Gly Leu Trp Glu Gly
385                 390                 395                 400
Ile Val Ser Leu Asp Phe Arg Ser Leu Tyr Pro Ser Ile Ile Ile Thr
            405                 410                 415
His Asn Val Ser Pro Asp Thr Leu Asn Lys Glu Gly Cys Gly Glu Tyr
            420                 425                 430
Asp Glu Ala Pro Glu Val Gly His Arg Phe Cys Lys Asp Phe Pro Gly
            435                 440                 445
Phe Ile Pro Ser Leu Leu Gly Ser Leu Leu Glu Glu Arg Gln Lys Ile
            450                 455                 460
Lys Lys Arg Met Lys Glu Ser Lys Asp Pro Val Glu Arg Lys Leu Leu
465                 470                 475                 480
Asp Tyr Arg Gln Arg Ala Ile Lys Ile Leu Ala Asn Ser Phe Tyr Gly
            485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Gln Tyr Ile Glu Leu Val Arg Arg Glu
            515                 520                 525
```

Leu Glu Glu Arg Gly Phe Lys Val Leu Tyr Ile Asp Thr Asp Gly Leu
            530                 535                 540

Tyr Ala Thr Ile Pro Gly Glu Lys Asn Trp Glu Ile Lys Arg Arg
545                 550                 555                 560

Ala Leu Glu Phe Val Asn Tyr Ile Asn Ser Lys Leu Pro Gly Ile Leu
                565                 570                 575

Glu Leu Glu Tyr Glu Gly Phe Tyr Thr Arg Gly Phe Phe Val Thr Lys
            580                 585                 590

Lys Lys Tyr Ala Leu Ile Asp Glu Glu Gly Lys Ile Val Thr Arg Gly
595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Glu Ala
625                 630                 635                 640

Val Lys Ile Val Lys Glu Val Thr Glu Lys Leu Ser Asn Tyr Glu Ile
                645                 650                 655

Pro Val Glu Lys Leu Val Ile Tyr Glu Gln Ile Thr Arg Pro Leu Asn
            660                 665                 670

Glu Tyr Lys Ala Ile Gly Pro His Val Ala Val Ala Lys Arg Leu Ala
675                 680                 685

Ala Lys Gly Ile Lys Ile Lys Pro Gly Met Val Ile Gly Tyr Val Val
            690                 695                 700

Leu Arg Gly Asp Gly Pro Ile Ser Lys Arg Ala Ile Ala Ile Glu Glu
705                 710                 715                 720

Phe Asp Gly Lys Lys His Lys Tyr Asp Ala Glu Tyr Tyr Ile Glu Asn
                725                 730                 735

Gln Val Leu Pro Ala Val Glu Arg Ile Leu Lys Ala Phe Gly Tyr Lys
            740                 745                 750

Arg Glu Asp Leu Arg Trp Gln Lys Thr Lys Gln Val Gly Leu Gly Ala
            755                 760                 765

Trp Leu Lys Val Lys Ser Gly Thr Gly Gly Gly Lys Lys Lys
            770                 775                 780

Tyr Val Thr Ile Arg Asp Ile Ala Glu Lys Ala Gly Val Ser Ile Asn
785                 790                 795                 800

Thr Val Ser Arg Ala Leu Asn Asn Lys Pro Asp Ile Ser Glu Thr
            805                 810                 815

Arg Arg Lys Ile Leu Lys Ile Ala Gln Glu Leu Gly Tyr Val Lys Asn
            820                 825                 830

Ala Thr Ala Ser Ser Leu Arg Ser Lys
            835                 840

<210> SEQ ID NO 127
<211> LENGTH: 862
<212> TYPE: PRT
<213> ORGANISM: Artificial Sequence
<220> FEATURE:
<223> OTHER INFORMATION: Synthetic construct

<400> SEQUENCE: 127

Met Ile Leu Asp Ala Asp Tyr Ile Thr Glu Asp Gly Lys Pro Ile Ile
1               5                   10                  15

Arg Leu Phe Lys Lys Glu Asn Gly Arg Phe Lys Val Glu Tyr Asp Arg
            20                  25                  30

Asn Phe Arg Pro Tyr Ile Tyr Ala Leu Leu Lys Asp Asp Ser Ala Ile
        35                  40                  45

-continued

Asp Asp Val Arg Lys Ile Thr Ser Glu Arg His Gly Lys Val Val Arg
    50                  55                  60

Val Ile Asp Val Glu Lys Val Lys Lys Lys Phe Leu Gly Arg Pro Ile
65                  70                  75                  80

Glu Val Trp Lys Leu Tyr Phe Glu His Pro Gln Asp Val Pro Ala Met
                85                  90                  95

Arg Asp Lys Ile Arg Glu His Pro Ala Val Ile Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asn Glu Glu Leu Thr Phe Leu Ala Val Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ala Asn Glu Arg Glu Met Ile Lys
                180                 185                 190

Arg Leu Ile Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
        210                 215                 220

Lys Leu Gly Met Lys Leu Pro Leu Gly Arg Asp Asn Ser Glu Pro Lys
225                 230                 235                 240

Met Gln Arg Leu Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
                260                 265                 270

Tyr Thr Leu Glu Ala Val Tyr Glu Ala Ile Phe Gly Lys Gln Lys Glu
            275                 280                 285

Lys Val Tyr Pro His Glu Ile Ala Glu Ala Trp Glu Thr Gly Lys Gly
        290                 295                 300

Leu Glu Arg Val Ala Lys Tyr Ser Met Glu Asp Ala Lys Val Thr Tyr
305                 310                 315                 320

Glu Leu Gly Lys Glu Phe Phe Pro Met Glu Ala Gln Leu Ala Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Arg Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Lys Glu Gly Cys Gly Glu Tyr
            420                 425                 430

Asp Glu Ala Pro Glu Val Gly His Arg Phe Cys Lys Asp Phe Pro Gly
        435                 440                 445

Phe Ile Pro Ser Leu Leu Gly Ser Leu Leu Glu Glu Arg Gln Lys Ile
450                 455                 460

-continued

```
Lys Lys Arg Met Lys Glu Ser Lys Asp Pro Val Glu Arg Lys Leu Leu
465                 470                 475                 480

Asp Tyr Arg Gln Arg Ala Ile Lys Ile Leu Ala Asn Ser Phe Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Glu Leu Val Arg Arg Glu
            515                 520                 525

Leu Glu Glu Arg Gly Phe Lys Val Leu Tyr Ile Asp Thr Asp Gly Leu
530                 535                 540

Tyr Ala Thr Ile Pro Gly Glu Lys Asn Trp Glu Glu Ile Lys Arg Arg
545                 550                 555                 560

Ala Leu Glu Phe Val Asn Tyr Ile Asn Ser Lys Leu Pro Gly Ile Leu
            565                 570                 575

Glu Leu Glu Tyr Glu Gly Phe Tyr Thr Arg Gly Phe Phe Val Thr Lys
            580                 585                 590

Lys Lys Tyr Ala Leu Ile Asp Glu Glu Gly Lys Ile Val Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Asn Tyr Glu Ile
            645                 650                 655

Pro Val Glu Lys Leu Val Ile Tyr Glu Gln Ile Thr Arg Pro Leu Asn
            660                 665                 670

Glu Tyr Lys Ala Ile Gly Pro His Val Ala Val Ala Lys Arg Leu Ala
            675                 680                 685

Ala Lys Gly Ile Lys Ile Lys Pro Gly Met Val Ile Gly Tyr Val Val
            690                 695                 700

Leu Arg Gly Asp Gly Pro Ile Ser Lys Arg Ala Ile Ala Ile Glu Glu
705                 710                 715                 720

Phe Asp Gly Lys Lys His Lys Tyr Asp Ala Glu Tyr Tyr Ile Glu Asn
            725                 730                 735

Gln Val Leu Pro Ala Val Glu Arg Ile Leu Lys Ala Phe Gly Tyr Lys
            740                 745                 750

Arg Glu Asp Leu Arg Trp Gln Lys Thr Lys Gln Val Gly Leu Gly Ala
            755                 760                 765

Trp Leu Lys Val Lys Lys Ser Gly Thr Gly Gly His Lys Lys
770                 775                 780

Leu Asn Pro Lys Ser Met Lys Arg Glu Asn Lys Lys Met Val Leu Arg
785                 790                 795                 800

Tyr Leu Ile Glu Ser Gly Pro His Ser Arg Val Glu Ile Ala Arg Lys
            805                 810                 815

Thr Gly Leu Ala Gln Ser Ala Ile Trp Arg Ile Ile Glu Glu Leu Val
            820                 825                 830

Asn Glu Gly Leu Val Glu Glu Lys Gly Thr Ala Thr Gly Arg Arg Arg
            835                 840                 845

Lys Ala Val Thr Tyr Gly Pro Thr Arg Ser Phe Ile Thr Ser
            850                 855                 860

<210> SEQ ID NO 128
<211> LENGTH: 852
<212> TYPE: PRT
```

<213> ORGANISM: Artificial Sequence
<220> FEATURE:
<223> OTHER INFORMATION: Synthetic construct

<400> SEQUENCE: 128

| | | | | | | | | | | | | | | | |
|---|---|---|---|---|---|---|---|---|---|---|---|---|---|---|---|
| Met | Ile | Leu | Asp | Ala | Asp | Tyr | Ile | Thr | Glu | Asp | Gly | Lys | Pro | Ile | Ile |
| 1 | | | | 5 | | | | | 10 | | | | | 15 | |
| Arg | Leu | Phe | Lys | Lys | Glu | Asn | Gly | Arg | Phe | Lys | Val | Glu | Tyr | Asp | Arg |
| | | | 20 | | | | | 25 | | | | | 30 | | |
| Asn | Phe | Arg | Pro | Tyr | Ile | Tyr | Ala | Leu | Leu | Lys | Asp | Ser | Ala | Ile | |
| | | 35 | | | | | 40 | | | | | 45 | | | |
| Asp | Asp | Val | Arg | Lys | Ile | Thr | Ser | Glu | Arg | His | Gly | Lys | Val | Val | Arg |
| | 50 | | | | | 55 | | | | | 60 | | | | |
| Val | Ile | Asp | Val | Glu | Lys | Val | Lys | Lys | Phe | Leu | Gly | Arg | Pro | Ile | |
| 65 | | | | | 70 | | | | | 75 | | | | | 80 |
| Glu | Val | Trp | Lys | Leu | Tyr | Phe | Glu | His | Pro | Gln | Asp | Val | Pro | Ala | Met |
| | | | | 85 | | | | | 90 | | | | | 95 | |
| Arg | Asp | Lys | Ile | Arg | Glu | His | Pro | Ala | Val | Ile | Asp | Ile | Phe | Glu | Tyr |
| | | | 100 | | | | | 105 | | | | | 110 | | |
| Asp | Ile | Pro | Phe | Ala | Lys | Arg | Tyr | Leu | Ile | Asp | Lys | Gly | Leu | Ile | Pro |
| | | 115 | | | | | 120 | | | | | 125 | | | |
| Met | Glu | Gly | Asn | Glu | Glu | Leu | Thr | Phe | Leu | Ala | Val | Asp | Ile | Glu | Thr |
| | 130 | | | | | 135 | | | | | 140 | | | | |
| Leu | Tyr | His | Glu | Gly | Glu | Glu | Phe | Gly | Lys | Gly | Pro | Ile | Ile | Met | Ile |
| 145 | | | | | 150 | | | | | 155 | | | | | 160 |
| Ser | Tyr | Ala | Asp | Glu | Glu | Gly | Ala | Lys | Val | Ile | Thr | Trp | Lys | Lys | Ile |
| | | | | 165 | | | | | 170 | | | | | 175 | |
| Asp | Leu | Pro | Tyr | Val | Glu | Val | Val | Ala | Asn | Glu | Arg | Glu | Met | Ile | Lys |
| | | | 180 | | | | | 185 | | | | | 190 | | |
| Arg | Leu | Ile | Lys | Val | Ile | Arg | Glu | Lys | Asp | Pro | Asp | Val | Ile | Ile | Thr |
| | | 195 | | | | | 200 | | | | | 205 | | | |
| Tyr | Asn | Gly | Asp | Asn | Phe | Asp | Phe | Pro | Tyr | Leu | Leu | Lys | Arg | Ala | Glu |
| | 210 | | | | | 215 | | | | | 220 | | | | |
| Lys | Leu | Gly | Met | Lys | Leu | Pro | Leu | Gly | Arg | Asp | Asn | Ser | Glu | Pro | Lys |
| 225 | | | | | 230 | | | | | 235 | | | | | 240 |
| Met | Gln | Arg | Leu | Gly | Asp | Ser | Leu | Ala | Val | Glu | Ile | Lys | Gly | Arg | Ile |
| | | | | 245 | | | | | 250 | | | | | 255 | |
| His | Phe | Asp | Leu | Phe | Pro | Val | Ile | Arg | Arg | Thr | Ile | Asn | Leu | Pro | Thr |
| | | | 260 | | | | | 265 | | | | | 270 | | |
| Tyr | Thr | Leu | Glu | Ala | Val | Tyr | Glu | Ala | Ile | Phe | Gly | Lys | Gln | Lys | Glu |
| | | 275 | | | | | 280 | | | | | 285 | | | |
| Lys | Val | Tyr | Pro | His | Glu | Ile | Ala | Glu | Ala | Trp | Glu | Thr | Gly | Lys | Gly |
| | 290 | | | | | 295 | | | | | 300 | | | | |
| Leu | Glu | Arg | Val | Ala | Lys | Tyr | Ser | Met | Glu | Asp | Ala | Lys | Val | Thr | Tyr |
| 305 | | | | | 310 | | | | | 315 | | | | | 320 |
| Glu | Leu | Gly | Lys | Glu | Phe | Phe | Pro | Met | Glu | Ala | Gln | Leu | Ala | Arg | Leu |
| | | | | 325 | | | | | 330 | | | | | 335 | |
| Val | Gly | Gln | Pro | Leu | Trp | Asp | Val | Ser | Arg | Ser | Ser | Thr | Gly | Asn | Leu |
| | | | 340 | | | | | 345 | | | | | 350 | | |
| Val | Glu | Trp | Tyr | Leu | Leu | Arg | Lys | Ala | Tyr | Glu | Arg | Asn | Glu | Leu | Ala |
| | | 355 | | | | | 360 | | | | | 365 | | | |
| Pro | Asn | Lys | Pro | Asp | Glu | Arg | Glu | Tyr | Glu | Arg | Arg | Leu | Arg | Glu | Ser |
| | 370 | | | | | 375 | | | | | 380 | | | | |
| Tyr | Glu | Gly | Gly | Tyr | Val | Lys | Glu | Pro | Glu | Arg | Gly | Leu | Trp | Glu | Gly |

```
            385                 390                 395                 400
        Ile Val Ser Leu Asp Phe Arg Ser Leu Tyr Pro Ser Ile Ile Ile Thr
                        405                 410                 415
        His Asn Val Ser Pro Asp Thr Leu Asn Lys Glu Gly Cys Gly Glu Tyr
                        420                 425                 430
        Asp Glu Ala Pro Glu Val Gly His Arg Phe Cys Lys Asp Phe Pro Gly
                        435                 440                 445
        Phe Ile Pro Ser Leu Leu Gly Ser Leu Leu Glu Arg Gln Lys Ile
                    450                 455                 460
        Lys Lys Arg Met Lys Glu Ser Lys Asp Pro Val Glu Arg Lys Leu Leu
        465                 470                 475                 480
        Asp Tyr Arg Gln Arg Ala Ile Lys Ile Leu Ala Asn Ser Phe Tyr Gly
                            485                 490                 495
        Tyr Tyr Gly Tyr Ala Lys Ala Arg Trp Tyr Cys Lys Glu Cys Ala Glu
                        500                 505                 510
        Ser Val Thr Ala Trp Gly Arg Gln Tyr Ile Glu Leu Val Arg Arg Glu
                        515                 520                 525
        Leu Glu Glu Arg Gly Phe Lys Val Leu Tyr Ile Asp Thr Asp Gly Leu
                    530                 535                 540
        Tyr Ala Thr Ile Pro Gly Glu Lys Asn Trp Glu Glu Ile Lys Arg Arg
        545                 550                 555                 560
        Ala Leu Glu Phe Val Asn Tyr Ile Asn Ser Lys Leu Pro Gly Ile Leu
                        565                 570                 575
        Glu Leu Glu Tyr Glu Gly Phe Tyr Thr Arg Gly Phe Phe Val Thr Lys
                        580                 585                 590
        Lys Lys Tyr Ala Leu Ile Asp Glu Glu Gly Lys Ile Val Thr Arg Gly
                        595                 600                 605
        Leu Glu Ile Val Arg Arg Asp Trp Ser Glu Ile Ala Lys Glu Thr Gln
                    610                 615                 620
        Ala Lys Val Leu Glu Ala Ile Leu Lys His Gly Asn Val Glu Glu Ala
        625                 630                 635                 640
        Val Lys Ile Val Lys Glu Val Thr Glu Lys Leu Ser Asn Tyr Glu Ile
                        645                 650                 655
        Pro Val Glu Lys Leu Val Ile Tyr Glu Gln Ile Thr Arg Pro Leu Asn
                        660                 665                 670
        Glu Tyr Lys Ala Ile Gly Pro His Val Ala Val Ala Lys Arg Leu Ala
                    675                 680                 685
        Ala Lys Gly Ile Lys Ile Lys Pro Gly Met Val Ile Gly Tyr Val Val
        690                 695                 700
        Leu Arg Gly Asp Gly Pro Ile Ser Lys Arg Ala Ile Ala Ile Glu Glu
        705                 710                 715                 720
        Phe Asp Gly Lys Lys His Lys Tyr Asp Ala Glu Tyr Tyr Ile Glu Asn
                        725                 730                 735
        Gln Val Leu Pro Ala Val Glu Arg Ile Leu Lys Ala Phe Gly Tyr Lys
                    740                 745                 750
        Arg Glu Asp Leu Arg Trp Gln Lys Thr Lys Gln Val Gly Leu Gly Ala
                    755                 760                 765
        Trp Leu Lys Val Lys Ser Gly Thr Gly Gly Gly Asn Thr Gly
            770                 775                 780
        Ala Gln Gly Val Ser Glu Met Ser Arg Met Lys Ile Ile Ser Val Gln
        785                 790                 795                 800
        Leu Pro Gln Ser Leu Ile His Gly Leu Asp Ala Leu Val Lys Arg Gly
                        805                 810                 815
```

```
Ile Tyr Pro Asn Arg Ser Glu Ala Ile Arg Val Ala Ile Arg Glu Leu
            820                 825                 830

Leu Lys Lys Glu Leu Tyr Lys Glu Glu Ile Gln Glu Ile Pro Glu
        835                 840                 845

Tyr Val Val Lys
        850

<210> SEQ ID NO 129
<211> LENGTH: 856
<212> TYPE: PRT
<213> ORGANISM: Artificial Sequence
<220> FEATURE:
<223> OTHER INFORMATION: Synthetic construct

<400> SEQUENCE: 129

Met Ile Leu Asp Ala Asp Tyr Ile Thr Glu Asp Gly Lys Pro Ile Ile
1               5                   10                  15

Arg Leu Phe Lys Lys Glu Asn Gly Arg Phe Lys Val Glu Tyr Asp Arg
            20                  25                  30

Asn Phe Arg Pro Tyr Ile Tyr Ala Leu Leu Lys Asp Asp Ser Ala Ile
        35                  40                  45

Asp Asp Val Arg Lys Ile Thr Ser Glu Arg His Gly Lys Val Val Arg
    50                  55                  60

Val Ile Asp Val Glu Lys Val Lys Lys Phe Leu Gly Arg Pro Ile
65                  70                  75                  80

Glu Val Trp Lys Leu Tyr Phe Glu His Pro Gln Asp Val Pro Ala Met
                85                  90                  95

Arg Asp Lys Ile Arg Glu His Pro Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ala Asn Glu Arg Glu Met Ile Lys
            180                 185                 190

Arg Leu Ile Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Met Lys Leu Pro Leu Gly Arg Asp Asn Ser Glu Pro Lys
225                 230                 235                 240

Met Gln Arg Leu Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Gln Lys Glu
        275                 280                 285

Lys Val Tyr Pro His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320
```

-continued

Glu Leu Gly Lys Glu Phe Pro Met Glu Ala Gln Leu Ala Arg Leu
            325                 330                 335

Val Gly Gln Pro Leu Trp Asp Val Ser Arg Ser Ser Thr Gly Asn Leu
        340                 345                 350

Val Glu Trp Tyr Leu Leu Arg Lys Ala Tyr Glu Arg Asn Glu Leu Ala
    355                 360                 365

Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Arg Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Lys Glu Gly Cys Gly Glu Tyr
            420                 425                 430

Asp Glu Ala Pro Glu Val Gly His Arg Phe Cys Lys Asp Phe Pro Gly
        435                 440                 445

Phe Ile Pro Ser Leu Leu Gly Ser Leu Leu Glu Glu Arg Gln Lys Ile
    450                 455                 460

Lys Lys Arg Met Lys Glu Ser Lys Asp Pro Val Glu Arg Lys Leu Leu
465                 470                 475                 480

Asp Tyr Arg Gln Arg Ala Ile Lys Ile Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Glu Leu Val Arg Arg Glu
        515                 520                 525

Leu Glu Glu Arg Gly Phe Lys Val Leu Tyr Ile Asp Thr Asp Gly Leu
    530                 535                 540

Tyr Ala Thr Ile Pro Gly Glu Lys Asn Trp Glu Glu Ile Lys Arg Arg
545                 550                 555                 560

Ala Leu Glu Phe Val Asn Tyr Ile Asn Ser Lys Leu Pro Gly Ile Leu
                565                 570                 575

Glu Leu Glu Tyr Glu Gly Phe Tyr Thr Arg Gly Phe Phe Val Thr Lys
            580                 585                 590

Lys Lys Tyr Ala Leu Ile Asp Glu Glu Gly Lys Ile Val Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Asn Tyr Glu Ile
                645                 650                 655

Pro Val Glu Lys Leu Val Ile Tyr Glu Gln Ile Thr Arg Pro Leu Asn
            660                 665                 670

Glu Tyr Lys Ala Ile Gly Pro His Val Ala Val Ala Lys Arg Leu Ala
        675                 680                 685

Ala Lys Gly Ile Lys Ile Lys Pro Gly Met Val Ile Gly Tyr Val Val
    690                 695                 700

Leu Arg Gly Asp Gly Pro Ile Ser Lys Arg Ala Ile Ala Ile Glu Glu
705                 710                 715                 720

Phe Asp Gly Lys Lys His Lys Tyr Asp Ala Glu Tyr Tyr Ile Glu Asn
                725                 730                 735

```
Gln Val Leu Pro Ala Val Glu Arg Ile Leu Lys Ala Phe Gly Tyr Lys
                740                 745                 750

Arg Glu Asp Leu Arg Trp Gln Lys Thr Lys Gln Val Gly Leu Gly Ala
            755                 760                 765

Trp Leu Lys Val Lys Lys Ser Gly Thr Gly Gly Gly Ile Ile Asn
    770                 775                 780

Pro Gln Ala Arg Leu Thr Pro Leu Glu Leu Glu Ile Leu Glu Ile Ile
785                 790                 795                 800

Lys Gln Lys Lys Ser Ile Thr Ile Thr Glu Ile Lys Glu Ile Leu Ser
                805                 810                 815

Glu Arg Arg Lys Ser Glu Tyr Pro Leu Ser Leu Val Ser Glu Tyr Ile
            820                 825                 830

Ser Arg Leu Glu Arg Lys Gly Tyr Val Lys Lys Ile Ala Lys Gly Arg
        835                 840                 845

Lys Lys Phe Val Glu Ala Leu Ile
    850                 855

<210> SEQ ID NO 130
<211> LENGTH: 863
<212> TYPE: PRT
<213> ORGANISM: Artificial Sequence
<220> FEATURE:
<223> OTHER INFORMATION: Synthetic construct

<400> SEQUENCE: 130

Met Ile Leu Asp Ala Asp Tyr Ile Thr Glu Asp Gly Lys Pro Ile Ile
1               5                   10                  15

Arg Leu Phe Lys Lys Glu Asn Gly Arg Phe Lys Val Glu Tyr Asp Arg
            20                  25                  30

Asn Phe Arg Pro Tyr Ile Tyr Ala Leu Leu Lys Asp Asp Ser Ala Ile
        35                  40                  45

Asp Asp Val Arg Lys Ile Thr Ser Glu Arg His Gly Lys Val Val Arg
    50                  55                  60

Val Ile Asp Val Glu Lys Val Lys Lys Lys Phe Leu Gly Arg Pro Ile
65                  70                  75                  80

Glu Val Trp Lys Leu Tyr Phe Glu His Pro Gln Asp Val Pro Ala Met
                85                  90                  95

Arg Asp Lys Ile Arg Glu His Pro Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ala Asn Glu Arg Glu Met Ile Lys
            180                 185                 190

Arg Leu Ile Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Met Lys Leu Pro Leu Gly Arg Asp Asn Ser Glu Pro Lys
225                 230                 235                 240
```

```
Met Gln Arg Leu Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Gln Lys Glu
        275                 280                 285

Lys Val Tyr Pro His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Phe Pro Met Glu Ala Gln Leu Ala Arg Leu
                325                 330                 335

Val Gly Gln Pro Leu Trp Asp Val Ser Arg Ser Thr Gly Asn Leu
            340                 345                 350

Val Glu Trp Tyr Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Arg Gly Leu Trp Glu Gly
385                 390                 395                 400

Ile Val Ser Leu Asp Phe Arg Ser Leu Tyr Pro Ser Ile Ile Thr
            405                 410                 415

His Asn Val Ser Pro Asp Thr Leu Asn Lys Glu Gly Cys Gly Glu Tyr
            420                 425                 430

Asp Glu Ala Pro Glu Val Gly His Arg Phe Cys Lys Asp Phe Pro Gly
            435                 440                 445

Phe Ile Pro Ser Leu Leu Gly Ser Leu Leu Glu Glu Arg Gln Lys Ile
    450                 455                 460

Lys Lys Arg Met Lys Glu Ser Lys Asp Pro Val Glu Arg Lys Leu Leu
465                 470                 475                 480

Asp Tyr Arg Gln Arg Ala Ile Lys Ile Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Glu Leu Val Arg Arg Glu
        515                 520                 525

Leu Glu Glu Arg Gly Phe Lys Val Leu Tyr Ile Asp Thr Asp Gly Leu
    530                 535                 540

Tyr Ala Thr Ile Pro Gly Glu Lys Asn Trp Glu Glu Ile Lys Arg Arg
545                 550                 555                 560

Ala Leu Glu Phe Val Asn Tyr Ile Asn Ser Lys Leu Pro Gly Ile Leu
                565                 570                 575

Glu Leu Glu Tyr Glu Gly Phe Tyr Thr Arg Gly Phe Phe Val Thr Lys
            580                 585                 590

Lys Lys Tyr Ala Leu Ile Asp Glu Glu Gly Lys Ile Val Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Asn Tyr Glu Ile
                645                 650                 655

Pro Val Glu Lys Leu Val Ile Tyr Glu Gln Ile Thr Arg Pro Leu Asn
```

-continued

```
                660                 665                 670
Glu Tyr Lys Ala Ile Gly Pro His Val Ala Val Ala Lys Arg Leu Ala
        675                 680                 685

Ala Lys Gly Ile Lys Ile Lys Pro Gly Met Val Ile Gly Tyr Val Val
        690                 695             700

Leu Arg Gly Asp Gly Pro Ile Ser Lys Arg Ala Ile Ala Ile Glu Glu
705                     710                 715                 720

Phe Asp Gly Lys Lys His Lys Tyr Asp Ala Glu Tyr Tyr Ile Glu Asn
                725                 730                 735

Gln Val Leu Pro Ala Val Glu Arg Ile Leu Lys Ala Phe Gly Tyr Lys
                740                 745             750

Arg Glu Asp Leu Arg Trp Gln Lys Thr Lys Gln Val Gly Leu Gly Ala
        755                 760                 765

Trp Leu Lys Val Lys Lys Ser Gly Thr Gly Gly Gly Gly Arg Lys
        770                 775             780

Val Arg Thr Gln Gln Asn Glu Ile Leu Asn Leu Leu Asn Glu Lys Glu
785                     790                 795                 800

Lys Ala Val Leu Arg Ala Ile Leu Glu His Gly Gly Glu Ile Lys Gln
                805                 810                 815

Glu Asp Leu Pro Glu Leu Val Gly Tyr Ser Arg Pro Thr Ile Ser Lys
                820                 825             830

Val Ile Gln Glu Leu Glu Asn Lys Gly Leu Ile Lys Arg Glu Lys Ser
        835                 840                 845

Gly Lys Thr Phe Val Val Lys Ile Glu Arg Lys Ile Lys Leu Asp
        850                 855             860
```